United States Patent
Yan et al.

(10) Patent No.: US 11,660,335 B2
(45) Date of Patent: May 30, 2023

(54) VACCINES AGAINST CORONAVIRUS AND METHODS OF USE

(71) Applicants: Inovio Pharmaceuticals, Inc., Plymouth Meeting, PA (US); The Wistar Institute of Anatomy and Biology, Philadelphia, PA (US)

(72) Inventors: Jian Yan, Wallingford, PA (US); Kate Broderick, San Diego, CA (US); David Weiner, Merion, PA (US); Kar Muthumani, Cherry Hill, NJ (US); Ami Patel, Philadelphia, PA (US)

(73) Assignees: Inovio Pharmaceuticals, Inc., Plymouth Meeting, PA (US); The Wistar Institute of Anatomy and Biology, Philadelphia, PA (US)

( * ) Notice: Subject to any disclaimer, the term of this patent is extended or adjusted under 35 U.S.C. 154(b) by 0 days.

(21) Appl. No.: 17/185,458

(22) Filed: Feb. 25, 2021

(65) Prior Publication Data

US 2021/0268102 A1 Sep. 2, 2021

Related U.S. Application Data

(60) Provisional application No. 63/136,973, filed on Jan. 13, 2021, provisional application No. 63/130,593, filed on Dec. 24, 2020, provisional application No. 63/114,858, filed on Nov. 17, 2020, provisional application No. 63/063,157, filed on Aug. 7, 2020, provisional application No. 63/062,762, filed on Aug. 7, 2020, provisional application No. 63/056,996, filed on Jul. 27, 2020, provisional application No. (Continued)

(51) Int. Cl.
 *A61K 39/215* (2006.01)
 *C12N 15/86* (2006.01)
 *A61K 39/00* (2006.01)

(52) U.S. Cl.
 CPC ........... *A61K 39/215* (2013.01); *C12N 15/86* (2013.01); *A61K 2039/545* (2013.01); *C12N 2770/20034* (2013.01); *C12N 2770/20044* (2013.01)

(58) Field of Classification Search
None
See application file for complete search history.

(56) References Cited

U.S. PATENT DOCUMENTS 3,805,783 A 4/1974 Ismach
4,342,310 A 8/1982 Lindmayer et al.
(Continued)

FOREIGN PATENT DOCUMENTS

WO 93/24640 A2 12/1993
WO 2021/155323 A1 8/2021

OTHER PUBLICATIONS

ISA/220—Notification of Transmittal or Search Report and Written Opinion of the ISA, or the Declaration dated Jun. 8, 2021 for WO Application No. PCT/US21/019662.
(Continued)

*Primary Examiner* — M Franco G Salvoza
(74) *Attorney, Agent, or Firm* — BakerHostetler

(57) ABSTRACT

Disclosed herein are nucleic acid molecules encoding a SARS-CoV-2 spike antigen, SARS-CoV-2 spike antigens, immunogenic compositions, and vaccines and their use in inducing immune responses and protecting against or treating a Severe Acute Respiratory Syndrome coronavirus 2 (SARS-CoV-2) infection in a subject.

21 Claims, 68 Drawing Sheets

Specification includes a Sequence Listing.

Related U.S. Application Data

63/046,415, filed on Jun. 30, 2020, provisional application No. 63/040,865, filed on Jun. 18, 2020, provisional application No. 63/033,349, filed on Jun. 2, 2020, provisional application No. 63/028,404, filed on May 21, 2020, provisional application No. 63/022,032, filed on May 8, 2020, provisional application No. 63/004,380, filed on Apr. 2, 2020, provisional application No. 62/981,168, filed on Feb. 25, 2020, provisional application No. 62/981,451, filed on Feb. 25, 2020.

(56) References Cited

U.S. PATENT DOCUMENTS

| | | | |
|---|---|---|---|
| 4,447,223 | A | 5/1984 | Kaye et al. |
| 5,505,697 | A | 4/1996 | McKinnon et al. |
| 5,580,859 | A | 12/1996 | Felgner et al. |
| 5,676,646 | A | 10/1997 | Hofmann et al. |
| 5,679,547 | A | 10/1997 | Krivan et al. |
| 5,679,647 | A | 10/1997 | Carson et al. |
| 5,702,359 | A | 12/1997 | Hofmann et al. |
| 5,703,055 | A | 12/1997 | Felgner et al. |
| 6,009,347 | A | 12/1999 | Hofmann |
| 6,068,650 | A | 5/2000 | Hofmann et al. |
| 6,096,020 | A | 8/2000 | Hofmann |
| 6,120,493 | A | 9/2000 | Hofmann |
| 6,150,148 | A | 11/2000 | Nanda et al. |
| 6,181,964 | B1 | 1/2001 | Hofmann et al. |
| 6,192,270 | B1 | 2/2001 | Hofmann et al. |
| 6,208,893 | B1 | 3/2001 | Hofmann |
| 6,216,034 | B1 | 4/2001 | Hofmann et al. |
| 6,233,482 | B1 | 5/2001 | Hofmann et al. |
| 6,241,701 | B1 | 6/2001 | Hofmann |
| 6,302,874 | B1 | 10/2001 | Zhang et al. |
| 6,520,950 | B1 | 2/2003 | Hofmann et al. |
| 6,763,264 | B2 | 7/2004 | Hofmann |
| 7,171,264 | B1 | 1/2007 | Hofmann et al. |
| 7,245,963 | B2 | 7/2007 | Draghia-Akli et al. |
| 7,328,064 | B2 | 2/2008 | Mathiesen et al. |
| 7,664,545 | B2 | 2/2010 | Westersten et al. |
| 10,953,089 | B1 | 3/2021 | Smith et al. |
| 2008/0234655 | A1 | 9/2008 | Mathiesen et al. |
| 2020/0222527 | A1 | 7/2020 | Weiner et al. |
| 2020/0407402 | A1 | 12/2020 | He et al. |

OTHER PUBLICATIONS

Modjarrad et al.; "Safety and immunogenicity of an anti-Middle East respiratory syndrome coronavirus DNA vaccine: a phase 1, open-label, single-arm, dose-escalation trial"; The Lancet Infectious Diseases; vol. 19; Sep. 2019; p. 1013-1022.

Muthamani et al.; "A synthetic consensus anti-spike protein DNA vaccine induces protective immunity against Middle East respiratory syndrome coronavirus in nonhuman primates"; Science Translational Medicine; vol. 7; Aug. 2015; 14 pages.

Smith et al.; "Immunogenicity of a DNA vaccine candidate for COVID-19"; Nature Communications; vol. 11; May 2020; 13 pages.

Wu et al.; "Genome Composition and Divergence of the Novel Coronavirus (2019-nCoV) Originating in China"; Cell Host & Microbe; vol. 27; Mar. 2020; p. 325-328.

"Severe acute respiratory syndrome coronavirus 2 isolate Wuhan-Hu-1, complete genome," NCBI Reference Sequence: NC_045512.2, 36 pages.

Bagarazzi et al., "Immunotherapy against HPV16/18 generates potent TH1 and cytotoxic cellular immune responses," Sci. Transl. Med., vol. 4(155), Oct. 2012, 33 pages.

Bewley et al., "Immunological and pathological outcomes of SARS-CoV-2 challenge after formalin-inactivated vaccine immunization of ferrets and rhesus macaques," bioRxiv, 2020, 54 pages.

Bolles et al., "A double-inactivated severe acute respiratory syndrome coronavirus provides incomplete protection in mice and induces increased eosinophilic proinflammatory pulmonary response upon challenge," Journal of Virology, vol. 85(23), Dec. 2011, pp. 12201-12215.

Caly et al., "Isolation and rapid sharing of the 2019 novel coronavirus (SARS-CoV-2) from the patient diagnosed with COVID-19 Australia," The Medical Journal of Australia, vol. 212(10), Jun. 2020, pp. 459-462.

Carter et al., "The adjuvant GLA-AF enhances human intradermal vaccine responses," Science Advances, vol. 4, Sep. 2018, 8 pages.

Chandrashekar et al., "SARS-CoV-2 infection protects against rechallenge in rhesus macaques," Science, vol. 369, Aug. 2020, pp. 812-817.

Corbett et al., "Evaluation of the mRNA-1273 Vaccine against SARS-CoV-2 in Nonhuman Primates," New England Journal of Medicine, vol. 383(16), Oct. 2020, pp. 1544-1555.

Doremalen et al., "ChAdOx1 nCoV-19 vaccination prevents SARS-CoV-2 pneumonia in rhesus macaques," bioRxiv, 2020, 23 pages.

Doremalen et al., "ChAdOx1nCoV-19 vaccine prevents SARS-CoV-2 pneumonia in rhesus macaques," Nature, vol. 586, Oct. 2020, pp. 578-582.

Durudas et al., "Differential Innate Immune Responses to Low or High Dose Oral SIV Challenge in Rhesus Macaques," Curr. HIV Res., vol. 9, 2011, pp. 276-288.

Gao et al., "Development of an inactivated vaccine candidate for SARS-CoV-2," Science, vol. 369, Jul. 2020, pp. 77-81.

Hu et al., "The D614G mutation of SARS-CoV-2 spike protein enhances viral infectivity," 2020, bioRxiv, 2020, 33 pages.

Huang et al., "Clinical features of patients infected with 2019 novel coronavirus in Wuhan," China; Lancet, vol. 395, Feb. 2020, pp. 497-506.

Innis et al., "Convening on the influenza human viral challenge model for universal influenza vaccines, Part 2: Methodologic considerations," Vaccine, vol. 37, 2019, p. 4830-4834.

Korber et al., "Tracking Changes in SARS-CoV-2 Spike: Evidence that D614G Increases Infectivity of the COVID-19 Virus," Cell, vol. 182, 2020, pp. 812-827.

Lewandowski et al., "Metagenomic Nanopore Sequencing of Influenza Virus Direct from Clinical Respiratory Samples," Journal of Clinical Microbiology, vol. 58(1), Jan. 2020, 15 pages.

Mohammadi et al., "SARS-CoV-2 detection in different respiratory sites: A systematic review and meta-analysis," EBioMedicine, vol. 59, 2020, 6 pages.

Moore et al., "SARS-CoV-2 Vaccines and the Growing Threat of Viral Variants," JAMA, vol. 325, Mar. 2021, pp. 821-822.

Munoz-Fontela et al., "Animal models for COVID-19," Nature, vol. 586, Oct. 2020, pp. 509-515.

Ni et al., "Detection of SARS-CoV-2-Specific Humoral and Cellular Immunity in COVID-19 Convalescent Individuals," Immunity, vol. 52, Jun. 2020, pp. 971-977.

Ozono et al., "Naturally mutated spike proteins of SARS-CoV-2 variants show differential levels of cell entry," Nature Communications, 2020, 23 pages.

Qin et al., "An animal model of SARS produced by infection of Macaca mulatta with SARS coronavirus," Journal of Pathology, vol. 206, 2005, pp. 251-259.

Robbiani et al., "Convergent Antibody Responses to SARS-CoV-2 in Convalescent Individuals," Nature, vol. 584, Aug. 2020, pp. 437-442.

Salguero et al., "Comparison of Rhesus and Cynomolgus macaques as an authentic model for COVID 19," bioRxiv, 2020, 52 pages.

Sardesai et al., "Electroporation Delivery of DNA Vaccines: Prospects for Success," Curr. Opin. Immunol., vol. 23, Jun. 2011, pp. 421-429.

Schultheis et al., "Characterization of guinea pig T cell responses elicited after EP-assisted delivery of DNA vaccines to skin," Vaccine, vol. 35(1), Jan. 2017, pp. 61-70.

Sibley et al., "ELISPOT Refinement Using Spot Morphology for Assessing Host Responses to Tuberculosis," Cells, vol. 1, 2012, pp. 5-14.

(56) References Cited

OTHER PUBLICATIONS

Tian et al., "Potent binding of 2019 novel coronavirus spike protein by a SARS coronavirus specific human monoclonal antibody," Emerging Microbes & Infections, vol. 9, 2020, pp. 382-385.

Wibmer et al., "SARS-CoV-2 501Y.V2 escapes neutralization by South African COVID-19 donor plasma," Nature Medicine, 2021, 9 pages.

Wolfel et al., "Virological assessment of hospitalized patients with COVID-2019," Nature, vol. 581, May 2020, pp. 465-469.

Wu et al., "A new coronavirus associated with human respiratory disease in China," Nature, vol. 579, Mar. 2020, pp. 265-269.

Yan et al., "Enhanced cellular immune responses elicited by an engineering HIV-1 subtype B consensus-based envelope DNA vaccine," Molecular Therapy, vol. 15, Feb. 2007, pp. 411-421.

Yao et al., "An Animal Model of MERS Produced by Infection of Rhesus Macaques With MERS Coronavirus," J. Infect. Dis., vol. 209, Jan. 2014, pp. 236-242.

Yasui et al., "Prior Immunization with Severe Acute Respiratory Syndrome (SARS)-Associated Coronavirus (SARS-CoV) Nucleocapsid Protein Causes Severe Pneumonia in Mice Infected with SARS-CoV," The Journal Immunology, vol. 181(9), 2018, pp. 6337-6348.

Yu et al., "DNA vaccine protection against SARS-CoV-2 in rhesus macaques," Science, vol. 369, Aug. 2020, pp. 806-811.

Zhu et al., "A Novel Coronavirus from Patients with Pneumonia in China, 2019," The New England Journal of Medicine; vol. 382, Feb. 2020, pp. 727-733.

Andrade. V.M. et al., "INO-4800 DNA vaccine induces neutralizing antibodies and T cell activity against global SARS-CoV-2 variants," NPJ Vaccines, vol. 6 Article 121, 2021, pp. 4.

Baum. A. et al., "REGN-COV2 antibodies prevent and treat SARS-CoV-2 infection in rhesus macaques and hamsters," Science, vol. 370, 2020, pp. 1110-1115.

Bewley et al., "Immunological and pathological outcomes of SARS-CoV-2 challenge after formalin-inactivated vaccine immunisation of ferrets and rhesus macaques," bioRxiv, 2020.

Bolles et al., "A Double-Inactivated Severe Acute Respiratory Syndrome Coronavirus Vaccine Provides Incomplete Protection in Mice and Induces Increased Eosinophilic Proinflammatory Pulmonary Response upon Challenge," Journal of Virology, vol. 85, No. 23, 2011, pp. 12201-12215.

Caly et al., "Isolation and rapid sharing of the 2019 novel coronavirus (SARS-CoV-2) from the first patient diagnosed with COVID-19 in Australia," Medical Journal of Australia, vol. 212, 2020, pp. 24.

Carter et al., "The adjuvant GLA-AF enhances human intradermal vaccine responses," Science Advances, vol. 4, 2018, pp. 9.

Chan. J.F.W et al., "Simulation of the Clinical and Pathological Manifestations of Coronavirus Disease 2019 (COVID-19) in a Golden Syrian Hamster Model: Implications for Disease Pathogenesis and Transmissibility," Clinical Infectious Diseases, vol. 71, Issue 9, 2020, pp. 2428-2446.

Channappanavar et al., "T cell-mediated immune response to respiratory coronaviruses"; Immunologic Research; vol. 59; 2014; pp. 118-128.

Chen et al., "Resistance of SARS-CoV-2 variants to neutralization by monoclonal and serum-derived polyclonal antibodies"; Nature Medicine; vol. 27; Apr. 2021; pp. 717-726.

Collier. D.A et al, "Sensitivity of SARS-CoV-2 B.1.1.7 to mRNA vaccine-elicited antibodies," Nature, vol. 593, 2021 pp. 136-141.

Crotty. S et al., "T Follicular Helper Cell Biology: A Decade of Discovery and Diseases," Immunity, vol. 50, 2019, pp. 1132-1148.

Davies et al.; "Estimated transmissibility and impact of SARS-CoV-2 lineage B.1.1.7 in England"; Science; vol. 372 No. 6538; Apr. 2021; 9 pages.

Davies et al.; "Increased mortality in community-tested cases of SARS-CoV-2 lineage B.1.1.7"; Nature; vol. 593 May 2021; p. 270-274 (total of 19 pages).

Dejnirattisai et al.; "Antibody evasion by the P.1 strain of SARS-CoV-2"; Cell; vol. 184; May 2021; pp. 2939-2954 (total 26 pages).

Donnelly. J et al., "DNA Vaccines," Annual Review Immunology, vol. 15, 1997, pp. 617-648.

Durudas et al., "Differential Innate Immune Responses to Low or High Dose Oral SIV Challenge in Rhesus Macaques," Current HIV Research, vol. 9, No. 5, 2011, pp. 276-288.

Edara et al.; "Reduced binding and neutralization of infection- and vaccine-induced antibodies to the B.1.351 (South African) SARS-CoV-2 variant"; bioRxiv; 2021; 26 pages.

Funk. T et al., "Characteristics of SARS-CoV-2 variants of concern B.1.1.7, B.1.351 or P.1: data from seven EU/EEA countries, weeks 38/2020 to Oct. 2021," Eurosurveillance, vol. 26, 2021, pp. 10.

Garcia-Beltran et al., "Multiple SARS-CoV-2 variants escape neutralization by vaccine-induced humoral immunity"; Cell; vol. 184; Apr. 2021; p. 2372-2383 (total 22 pages).

Gary et al., "DNA vaccines: prime time is now," Current Opinion in Immunology, vol. 65, 2020, pp. 21-27.

Gomez. C.E. et al., "Emerging SARS-CoV-2 Variants and Impact in Global Vaccination Programs against SARS-CoV-2/COVID-19," Vaccines, vol. 9, No. 243, 2021, pp. 13.

Hacisuleyman. E. et al., "Vaccine Breakthrough Infections with SARS-CoV-2 Variants," New England Journal of Medicine, vol. 384, 2021, pp. 2212-2218.

Hodgson. S.H. et al., "What defines an efficacious COVID-19 vaccine? A review of the challenges assessing the clinical efficacy of vaccines against SARS-CoV-2," Lancet, vol. 21, 2021, pp. e26-e35.

Hu et al., "D614G mutation of SARS-CoV-2 spike protein enhances viral infectivity," BioRxiv, 2020, pp. 37.

Huang et al., "Clinical features of patients infected with 2019 novel coronavirus in Wuhan, China," The Lancet, vol. 395, 2020, pp. 497-506.

Innis et al., "Convening on the influenza human viral challenge model for universal influenza vaccines, Part 2: Methodologic considerations," Vaccine, vol. 37, 2019, pp. 4830-4834.

ISA/220—Notification of Transmittal or Search Report and Written Opinion of the ISA, or the Declaration dated Jul. 5, 2022 for WO Application No. PCT/US22/071691.

Karim. S.S.A et al, "New SARS-CoV-2 Variants—Clinical, Public Health, and Vaccine Implications," New England Journal of Medicine, vol. 384, 2021, pp. 1866-1868.

Kirchdoerfer. R.N et al, "Stabilized coronavirus spikes are resistant to conformational changes induced by receptor recognition or proteolysis," Scientific Reports, vol. 8, No. 15701, 2018, pp. 11.

Kustin. T. et al, "Evidence for increased breakthrough rates of SARS-CoV-2 variants of concern in BNT162b2-mRNA-vaccinated individuals," Nature, vol. 27, 2021, pp. 1379-1384.

Kyte. J et al, "A Simple Method for Displaying the Hydropathic Character of a Protein," J. Mol. Biol, vol. 157, 1982, pp. 105-132.

Liu. J. et al., "BNT162b2-elicited neutralization of B.1.617 and other SARS-CoV-2 variants," Nature, vol. 596, 2021, pp. 273-275.

Locci. M et al, "Human Circulating PD-1+CXCR3-CXCR5+ Memory Tfh Cells Are Highly Functional and Correlate with Broadly Neutralizing HIV Antibody Responses," Immunity, vol. 39, 2013, pp. 758-769.

Madhi et al.; "Efficacy of the ChAdOx1 nCoV-19 Covid-19 Vaccine against the B.1.351 Variant"; The New England Journal of Medicine; vol. 384 No. 20; May 20, 2021; pp. 1885-1898.

Mahase E., "Covid-19: Novavax vaccine efficacy is 86% against UK variant and 60% against South African variant" BMJ; vol. 372; 2021; 1 Page.

Mallapaty S, "India's massive COVID surge puzzles scientists," Nature, vol. 592, 2021, pp. 667-668.

Mammen et al., "Safety and immunogenicity of INO-4800 DNA vaccine against SARS-CoV-2: a preliminary report of a randomized, blinded, placebo-controlled, Phase 2 clinical trial in adults at high risk of viral exposure"; medRxiv 2021; 37 pages.

McCallum. M et al, "N-terminal domain antigenic mapping reveals a site of vulnerability for SARS-CoV-2," Cell, vol. 184, 2021, pp. 2332-2347.

McMahan et al., "Correlates of protection against SARS-CoV-2 in rhesus macaques"; Nature; vol. 590; Feb. 2021; pp. 630-634 (total 20 pages).

Meyer. M et al, "mRNA-1273 efficacy in a severe COVID-19 model: attenuated activation of pulmonary immune cells after challenge," bioRxiv, 2021, pp. 62.

(56) References Cited

OTHER PUBLICATIONS

Moore et al, "SARS-CoV-2 Vaccines and the Growing Threat of Viral Variants," JAMA, vol. 325, No. 9, 2021, pp. 821-822.
Ozono et al, "Naturally mutated spike proteins of SARS-CoV-2 variants show differential levels of cell entry," bioRxiv, 2020, pp. 23.
Pallesen. J et al, "Immunogenicity and structures of a rationally designed prefusion MERS-CoV spike antigen," PNAS, vol. 114, No. 35, 2017, pp. e7348-e7357.
Patel. A et al, "Intradermal delivery of a synthetic DNA vaccine protects macaques from Middle East respiratory syndrome coronavirus," JCI Insight, vol. 6, 2021, pp. 11.
Qin et al, "An animal model of SARS produced by infection of Macaca mulatta with SARS coronavirus," The Journal of Pathology, vol. 206, 2005, pp. 251-259.
Rambaut. A et al, "A dynamic nomenclature proposal for SARS-CoV-2 lineages to assist genomic epidemiology," Nature Microbiology, vol. 5, 2020, pp. 1403-1407.
Sariol et al., "Lessons for COVID-19 Immunity from Other Coronavirus Infections"; Immunity; vol. 53; Aug. 2020 p. 248-263.
Schultheis et al, "Characterization of guinea pig T cell responses elicited after EP-assisted delivery of DNA vaccines to the skin," Vaccine, vol. 35, 2017, pp. 61-70.
Sekine. T et al, "Robust T Cell Immunity in Convalescent Individuals with Asymptomatic or Mild COVID-19," Cell, vol. 183, 2020, pp. 158-168.
Shinde. V et al, "Efficacy of NVX-CoV2373 Covid-19 Vaccine against the B.1.351 Variant," New England Journal of Medicine, 2021, pp. 1899-1909.
Stephenson et al.; "Immunogenicity of the Ad26.COV2.S Vaccine for COVID-19"; JAMA; vol. 325(15); Mar. 2021; pp. 1535-1544.
Sun. J. et al, "Generation of a Broadly Useful Model for COVID-19 Pathogenesis, Vaccination, and Treatment," Cell, vol. 182, 2020, pp. 734-743.
Tarke et al.; "SARS-CoV-2 vaccination induces immunological T cell memory able to cross-recognize variants from Alpha to Omicron"; Cell; vol. 185 Issue 5; Mar. 2022; pp. 847-859 (total 25 pages).
Tarke. A et al, "Negligible impact of SARS-CoV-2 variants on CD4+ and CD8+ T cell reactivity in COVID-19 exposed donors and vaccinees," bioRxiv, 2021, pp. 35.
Tebas et al.; "Safety and immunogenicity of INO-4800 DNA vaccine against SARS-CoV-2: A preliminary report of an open-label, Phase 1 clinical trial"; eClinicalMedicine; vol. 31; 2021; 9 pages.
Tegally. H et al, "Emergence and rapid spread of a new severe acute respiratory syndrome-related coronavirus 2 (SARS-CoV-2) lineage with multiple spike mutations in South Africa," medRxiv, 2020, pp. 19.
Tostanoski. L.H et al, "Ad26 vaccine protects against SARS-CoV-2 severe clinical disease in hamsters," Nature Medicine, vol. 26, 2020, pp. 1694-1700.
Vogel. AB et al, "BNT162b vaccines protect rhesus macaques from SARS-CoV-2," Nature, vol. 592, 2021, pp. 283-289.
Volz. E et al, "Assessing transmissibility of SARS-CoV-2 lineage B.1.1.7 in England," Nature, vol. 593, 2021, pp. 266-269.
Wang et al., "Increased resistance of SARS-CoV-2 variant p. 1 to antibody neutralization"; Cell Host & Microbe; vol. 29 Issue 5; May 2021; pp. 747-751(total 10 pages).
Wang et al.; "Increased Resistance of SARS-CoV-2 Variants B.1.351 and B.1.1.7 to Antibody Neutralization" bioRxiv; 2021; 30 pages.
Wang et al.; "mRNA vaccine-elicited antibodies to SARS-CoV-2 and circulating variants"; Nature; vol. 592; Apr. 2021; p. 616-622 (total 23 pages).
Wibmer et al., "SARS-CoV-2 501Y.V2 escapes neutralization by South African COVID-19 donor plasma"; Nature Medicine; vol. 27; 2021; p. 622-625 (total 9 pages).
Wu et al.; "mRNA-1273 vaccine induces neutralizing antibodies against spike mutants from global SARS-CoV-2 variants"; bioRxiv; 2021; 20 pages.
Wu. K. et al, "Variant SARS-CoV-2 mRNA vaccines confer broad neutralization as primary or booster series in mice," Vaccine, vol. 39, 2021, pp. 7394-7400.
Xia. X, "Domains and Functions of Spike Protein in SARS-Cov-2 in the Context of Vaccine Design," Viruses, vol. 13, 2021, pp. 16.
Xie et al., "Neutralization of SARS-CoV-2 spike 69/70 deletion, E484K and N501Y variants by BNT162b2 vaccine-elicited sera"; Nature Medicine; vol. 27; Apr. 2021; pp. 620-621 (total 6 pages).
Yan et al, "Enhanced Cellular Immune Responses Elicited by an Engineered HIV-1 Subtype B Consensus-based Envelope DNA Vaccine," Molecular Therapy, vol. 15, 2007, pp. 411-421.
Yao et al, "An Animal Model of MERS Produced by Infection of Rhesus Macaques With MERS Coronavirus," The Journal of Infectious Diseases, vol. 209, 2014, pp. 236-242.
Yasui et al, "Prior Immunization with Severe Acute Respiratory Syndrome (SARS)-Associated Coronavirus (SARS-CoV) Nucleocapsid Protein Causes Severe Pneumonia in Mice Infected with SARS-CoV," Journal of Immunology, vol. 181, 2008, pp. 6337-6348.
Zhou. D et al, "Evidence of escape of SARS-CoV-2 variant B.1.351 from natural and vaccine-induced sera," Cell, vol. 184, 2021, pp. 2348-2361.
Zhu et al, "A Novel Coronavirus from Patients with Pneumonia in China 2019," New England Journal of Medicine, vol. 382, 2020, pp. 727-733.
Furtado et al.; "Azithromycin in addition to standard of care versus standard of care alone in the treatment of patients admitted to the hospital with severe COVID-19 in Brazil (Coalition II): a randomised clinical trial"; The Lancet; vol. 396; Oct. 2020; p. 959-967.
International Patent Application No. PCT/US2022/072135; Int'l Search Report and the Written Opinion; dated Sep. 8, 2022; 12 pages.
ISA/220—Notification of Transmittal or Search Report and Written Opinion of the ISA, or the Declaration dated Oct. 5, 2022 for WO Application No. PCT/US22/071855.
Prompetchara et al.; "DNA vaccine candidate encoding SARS-CoV-2 spike proteins elicited potent humoral and Th1 cell-mediated immune responses in mice"; PLOS One; Mar. 2021; 16 pages.
Ravichandran et al.; "Antibody signature induced by SARS-CoV-2 spike protein immunogens in rabbits"; Science Translational Medicine; vol. 12; Jul. 2020; 7 pages.
Watanabe et al.; "Native-like SARS-CoV-2 spike glycoprotein expressed by ChAdOx1 nCoV-19/AZD1222 vaccine" ACS Cent. Sci.; vol. 7; 2021; 26 pages.
"Wuhan seafood market pneumonia virus isolate Wuhan-Hu-1, complete genome"; GenBank: MN908947.02; https://www.ncbi.nlm.nih.gov/nuccore/MN908947.2; Jan. 2020; 11 pages.

Updated:

2.0mg Dose Cohort

| Subject ID | Pool 1 | Pool 2 | Pool 3 | Pool 4 | Pool 5 |
|---|---|---|---|---|---|
| 4801-0027 | 33.0% | 4.1% | 27.0% | 29.4% | 6.5% |
| 4801-0028 | 3.3% | 95.7% | 0.0% | 0.8% | 0.0% |
| 4801-0029 | 20.0% | 0.0% | 80.0% | 0.0% | 0.0% |
| 4802-0013 | 4.7% | 57.8% | 4.7% | 23.4% | 9.4% |
| 4802-0014 | 27.3% | 31.8% | 11.4% | 13.6% | 15.9% |
| 4802-0015 | 5.1% | 70.9% | 1.7% | 20.6% | 1.7% |
| 4801-0011 | 9.2% | 62.2% | 5.0% | 20.2% | 3.4% |
| 4801-0016 | 24.2% | 29.3% | 3.0% | 19.2% | 24.2% |
| 4801-0017 | 22.6% | 17.0% | 5.7% | 30.2% | 24.5% |
| 4801-0026 | 31.3% | 18.7% | 18.7% | 31.3% | 0.0% |
| 4802-0005 | 26.1% | 34.8% | 0.0% | 26.1% | 13.0% |
| 4802-0012 | 10.3% | 10.3% | 37.9% | 20.7% | 20.7% |
| 4802-0019 | 0.0% | 50.0% | 50.0% | 0.0% | 0.0% |
| 4802-0018 | 11.5% | 9.6% | 3.2% | 3.8% | 71.9% |
| 4802-0020 | 8.0% | 6.1% | 36.0% | 5.3% | 44.7% |
| 4802-0021 | 0.0% | 11.5% | 53.8% | 23.1% | 11.5% |
| 4802-0008 | 6.7% | 34.7% | 6.7% | 31.4% | 20.6% |
| 4802-0016 | 16.3% | 16.9% | 10.2% | 13.3% | 43.4% |
| | Pool 1 | Pool 2 | Pool 3 | Pool 4 | Pool 5 |

100.00% Highest
75.00%
50.00% Middle
25.00%
0.00% Lowest

Day 4

Day 7

Day 10

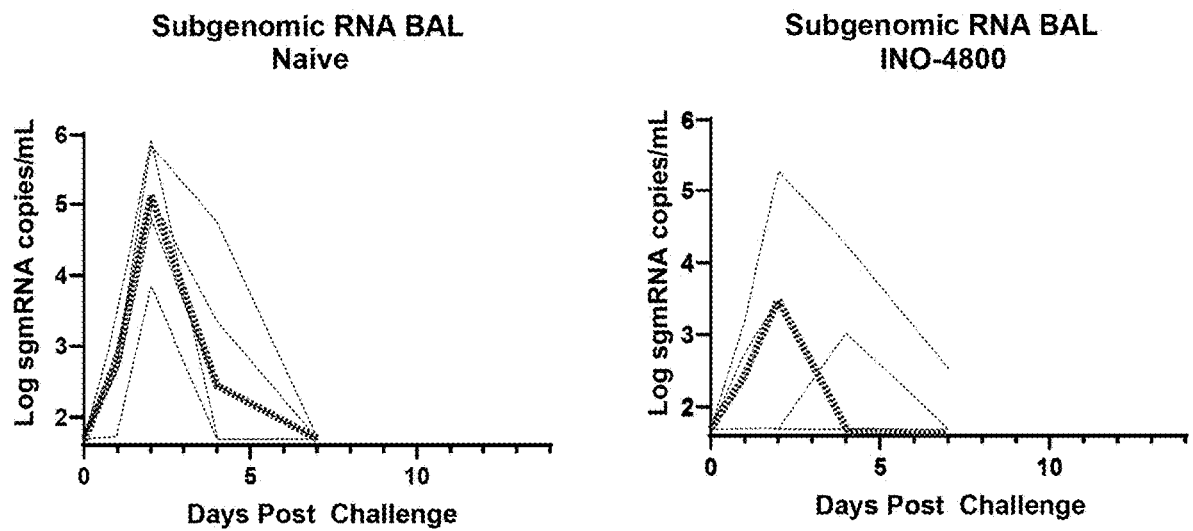
FIG. 40A
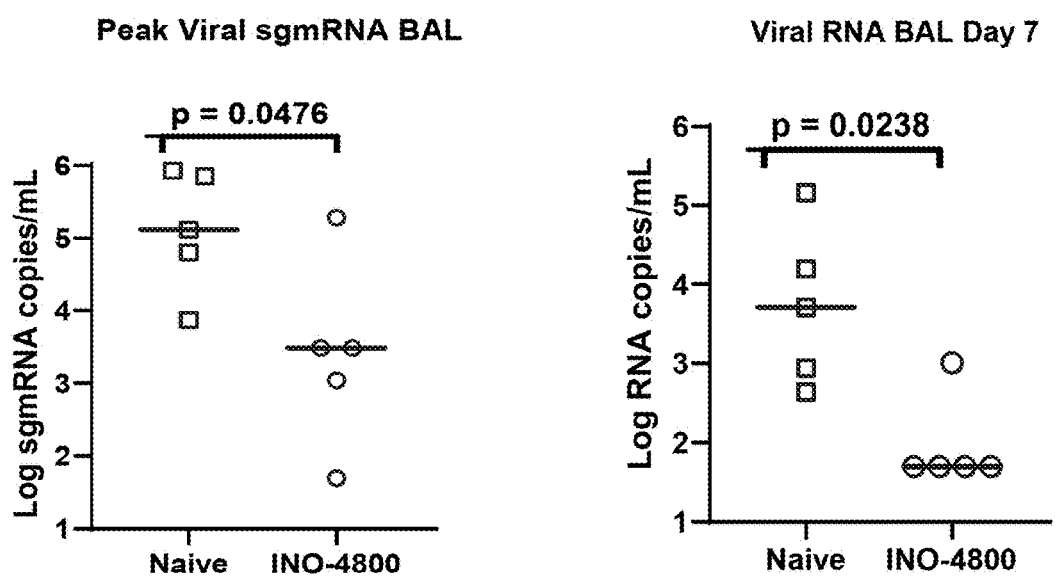
FIG. 40B
FIG. 40C

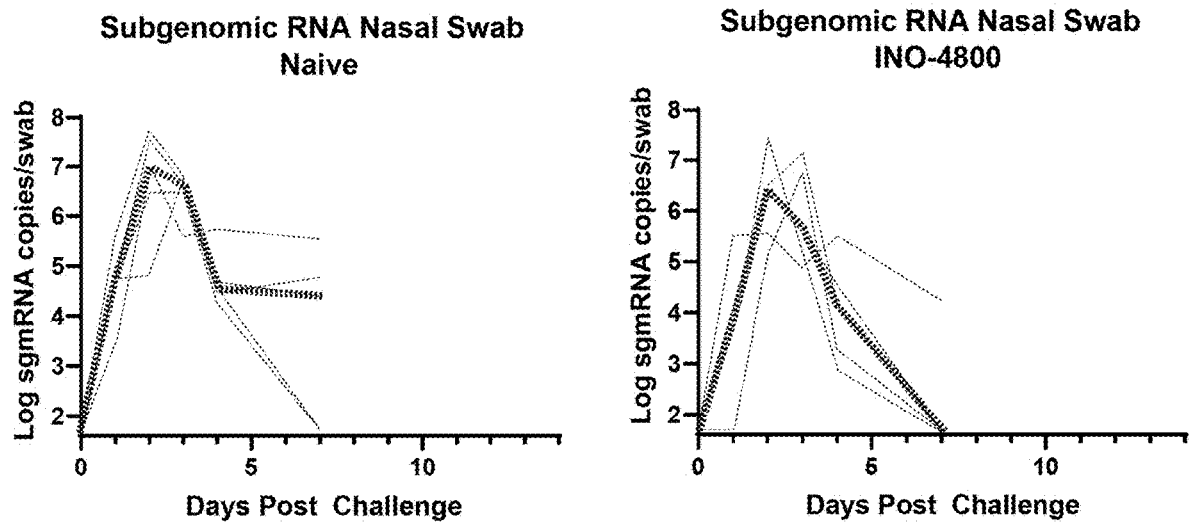
FIG. 40D
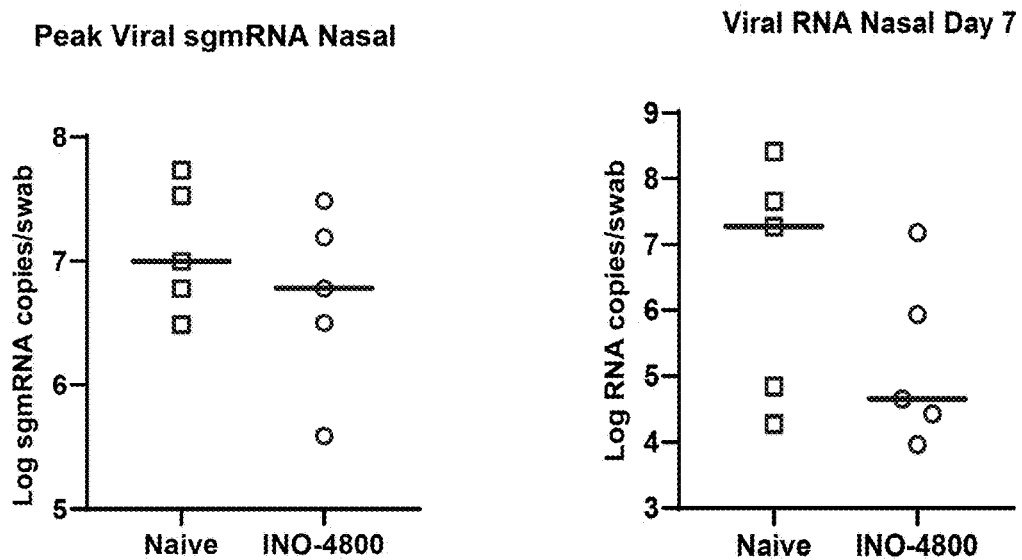
FIG. 40E
FIG. 40F

SEQUENCE LISTING

<160> NUMBER OF SEQ ID NOS: 35

<210> SEQ ID NO 1
<211> LENGTH: 1279
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

| | | | | | | | | | | | | | | |
|---|---|---|---|---|---|---|---|---|---|---|---|---|---|---|
| Met | Asp | Trp | Thr | Trp | Ile | Leu | Phe | Leu | Val | Ala | Ala | Thr | Arg | Val |
| 1 | | | | 5 | | | | | 10 | | | | | 15 |
| His | Ser | Ser | Gln | Cys | Val | Asn | Leu | Thr | Thr | Arg | Thr | Gln | Leu | Pro | Pro |
| | | | 20 | | | | | 25 | | | | | 30 | | |
| Ala | Tyr | Thr | Asn | Ser | Phe | Thr | Arg | Gly | Val | Tyr | Tyr | Pro | Asp | Lys | Val |
| | | | 35 | | | | 40 | | | | | 45 | | | |
| Phe | Arg | Ser | Ser | Val | Leu | His | Ser | Thr | Gln | Asp | Leu | Phe | Leu | Pro | Phe |
| | 50 | | | | | 55 | | | | | 60 | | | | |
| Phe | Ser | Asn | Val | Thr | Trp | Phe | His | Ala | Ile | His | Val | Ser | Gly | Thr | Asn |
| 65 | | | | | 70 | | | | | 75 | | | | | 80 |
| Gly | Thr | Lys | Arg | Phe | Asp | Asn | Pro | Val | Leu | Pro | Phe | Asn | Asp | Gly | Val |
| | | | | 85 | | | | | 90 | | | | | 95 | |
| Tyr | Phe | Ala | Ser | Thr | Glu | Lys | Ser | Asn | Ile | Ile | Arg | Gly | Trp | Ile | Phe |
| | | | | 100 | | | | | 105 | | | | | 110 | |
| Gly | Thr | Thr | Leu | Asp | Ser | Lys | Thr | Gln | Ser | Leu | Leu | Ile | Val | Asn | Asn |
| | | | | 115 | | | | | 120 | | | | | 125 | |
| Ala | Thr | Asn | Val | Val | Ile | Lys | Val | Cys | Glu | Phe | Gln | Phe | Cys | Asn | Asp |
| | | | 130 | | | | | 135 | | | | | 140 | | |
| Pro | Phe | Leu | Gly | Val | Tyr | Tyr | His | Lys | Asn | Asn | Lys | Ser | Trp | Met | Glu |
| 145 | | | | | 150 | | | | | 155 | | | | | 160 |
| Ser | Glu | Phe | Arg | Val | Tyr | Ser | Ser | Ala | Asn | Asn | Cys | Thr | Phe | Glu | Tyr |
| | | | | 165 | | | | | 170 | | | | | 175 | |
| Val | Ser | Gln | Pro | Phe | Leu | Met | Asp | Leu | Glu | Gly | Lys | Gln | Gly | Asn | Phe |
| | | | 180 | | | | | 185 | | | | | 190 | | |
| Lys | Asn | Leu | Arg | Glu | Phe | Val | Phe | Lys | Asn | Ile | Asp | Gly | Tyr | Phe | Lys |
| | | | 195 | | | | | 200 | | | | | 205 | | |
| Ile | Tyr | Ser | Lys | His | Thr | Pro | Ile | Asn | Leu | Val | Arg | Asp | Leu | Pro | Gln |
| | | 210 | | | | | 215 | | | | | 220 | | | |
| Gly | Phe | Ser | Ala | Leu | Glu | Pro | Leu | Val | Asp | Leu | Pro | Ile | Gly | Ile | Asn |
| 225 | | | | | 230 | | | | | 235 | | | | | 240 |
| Ile | Thr | Arg | Phe | Gln | Thr | Leu | Leu | Ala | Leu | His | Arg | Ser | Tyr | Leu | Thr |
| | | | | 245 | | | | | 250 | | | | | 255 | |
| Pro | Gly | Asp | Ser | Ser | Ser | Gly | Trp | Thr | Ala | Gly | Ala | Ala | Ala | Tyr | Tyr |
| | | | 260 | | | | | 265 | | | | | 270 | | |
| Val | Gly | Tyr | Leu | Gln | Pro | Arg | Thr | Phe | Leu | Leu | Lys | Tyr | Asn | Glu | Asn |
| | | | 275 | | | | | 280 | | | | | 285 | | |
| Gly | Thr | Ile | Thr | Asp | Ala | Val | Asp | Cys | Ala | Leu | Asp | Pro | Leu | Ser | Glu |
| | 290 | | | | | 295 | | | | | 300 | | | | |
| Thr | Lys | Cys | Thr | Leu | Lys | Ser | Phe | Thr | Val | Glu | Lys | Gly | Ile | Tyr | Gln |
| 305 | | | | | 310 | | | | | 315 | | | | | 320 |
| Thr | Ser | Asn | Phe | Arg | Val | Gln | Pro | Thr | Glu | Ser | Ile | Val | Arg | Phe | Pro |
| | | | | 325 | | | | | 330 | | | | | 335 | |
| Asn | Ile | Thr | Asn | Leu | Cys | Pro | Phe | Gly | Glu | Val | Phe | Asn | Ala | Thr | Arg |
| | | | 340 | | | | | 345 | | | | | 350 | | |
| Phe | Ala | Ser | Val | Tyr | Ala | Trp | Asn | Arg | Lys | Arg | Ile | Ser | Asn | Cys | Val |
| | | | 355 | | | | | 360 | | | | | 365 | | |
| Ala | Asp | Tyr | Ser | Val | Leu | Tyr | Asn | Ser | Ala | Ser | Phe | Ser | Thr | Phe | Lys |
| | 370 | | | | | 375 | | | | | 380 | | | | |
| Cys | Tyr | Gly | Val | Ser | Pro | Thr | Lys | Leu | Asn | Asp | Leu | Cys | Phe | Thr | Asn |
| 385 | | | | | 390 | | | | | 395 | | | | | 400 |

```
Val Tyr Ala Asp Ser Phe Val Ile Arg Gly Asp Glu Val Arg Gln Ile
                405                 410                 415

Ala Pro Gly Gln Thr Gly Lys Ile Ala Asp Tyr Asn Tyr Lys Leu Pro
            420                 425                 430

Asp Asp Phe Thr Gly Cys Val Ile Ala Trp Asn Ser Asn Asn Leu Asp
        435                 440                 445

Ser Lys Val Gly Gly Asn Tyr Asn Tyr Leu Tyr Arg Leu Phe Arg Lys
    450                 455                 460

Ser Asn Leu Lys Pro Phe Glu Arg Asp Ile Ser Thr Glu Ile Tyr Gln
465                 470                 475                 480

Ala Gly Ser Thr Pro Cys Asn Gly Val Glu Gly Phe Asn Cys Tyr Phe
                485                 490                 495

Pro Leu Gln Ser Tyr Gly Phe Gln Pro Thr Asn Gly Val Gly Tyr Gln
            500                 505                 510

Pro Tyr Arg Val Val Val Leu Ser Phe Glu Leu Leu His Ala Pro Ala
        515                 520                 525

Thr Val Cys Gly Pro Lys Lys Ser Thr Asn Leu Val Lys Asn Lys Cys
    530                 535                 540

Val Asn Phe Asn Phe Asn Gly Leu Thr Gly Thr Gly Val Leu Thr Glu
545                 550                 555                 560

Ser Asn Lys Lys Phe Leu Pro Phe Gln Gln Phe Gly Arg Asp Ile Ala
                565                 570                 575

Asp Thr Thr Asp Ala Val Arg Asp Pro Gln Thr Leu Glu Ile Leu Asp
            580                 585                 590

Ile Thr Pro Cys Ser Phe Gly Gly Val Ser Val Ile Thr Pro Gly Thr
        595                 600                 605

Asn Thr Ser Asn Gln Val Ala Val Leu Tyr Gln Asp Val Asn Cys Thr
    610                 615                 620

Glu Val Pro Val Ala Ile His Ala Asp Gln Leu Thr Pro Thr Trp Arg
625                 630                 635                 640

Val Tyr Ser Thr Gly Ser Asn Val Phe Gln Thr Arg Ala Gly Cys Leu
                645                 650                 655

Ile Gly Ala Glu His Val Asn Asn Ser Tyr Glu Cys Asp Ile Pro Ile
            660                 665                 670

Gly Ala Gly Ile Cys Ala Ser Tyr Gln Thr Gln Thr Asn Ser Pro Arg
        675                 680                 685

Arg Ala Arg Ser Val Ala Ser Gln Ser Ile Ile Ala Tyr Thr Met Ser
    690                 695                 700

Leu Gly Ala Glu Asn Ser Val Ala Tyr Ser Asn Asn Ser Ile Ala Ile
705                 710                 715                 720

Pro Thr Asn Phe Thr Ile Ser Val Thr Thr Glu Ile Leu Pro Val Ser
                725                 730                 735

Met Thr Lys Thr Ser Val Asp Cys Thr Met Tyr Ile Cys Gly Asp Ser
            740                 745                 750

Thr Glu Cys Ser Asn Leu Leu Leu Gln Tyr Gly Ser Phe Cys Thr Gln
        755                 760                 765

Leu Asn Arg Ala Leu Thr Gly Ile Ala Val Glu Gln Asp Lys Asn Thr
    770                 775                 780

Gln Glu Val Phe Ala Gln Val Lys Gln Ile Tyr Lys Thr Pro Pro Ile
785                 790                 795                 800

Lys Asp Phe Gly Gly Phe Asn Phe Ser Gln Ile Leu Pro Asp Pro Ser
                805                 810                 815
```

-continued

Lys Pro Ser Lys Arg Ser Phe Ile Glu Asp Leu Leu Phe Asn Lys Val
              820                 825                 830

Thr Leu Ala Asp Ala Gly Phe Ile Lys Gln Tyr Gly Asp Cys Leu Gly
              835                 840                 845

Asp Ile Ala Ala Arg Asp Leu Ile Cys Ala Gln Lys Phe Asn Gly Leu
              850                 855                 860

Thr Val Leu Pro Pro Leu Leu Thr Asp Glu Met Ile Ala Gln Tyr Thr
865                 870                 875                 880

Ser Ala Leu Leu Ala Gly Thr Ile Thr Ser Gly Trp Thr Phe Gly Ala
              885                 890                 895

Gly Ala Ala Leu Gln Ile Pro Phe Ala Met Gln Met Ala Tyr Arg Phe
              900                 905                 910

Asn Gly Ile Gly Val Thr Gln Asn Val Leu Tyr Glu Asn Gln Lys Leu
              915                 920                 925

Ile Ala Asn Gln Phe Asn Ser Ala Ile Gly Lys Ile Gln Asp Ser Leu
              930                 935                 940

Ser Ser Thr Ala Ser Ala Leu Gly Lys Leu Gln Asp Val Val Asn Gln
945                 950                 955                 960

Asn Ala Gln Ala Leu Asn Thr Leu Val Lys Gln Leu Ser Ser Asn Phe
              965                 970                 975

Gly Ala Ile Ser Ser Val Leu Asn Asp Ile Leu Ser Arg Leu Asp Lys
              980                 985                 990

Val Glu Ala Glu Val Gln Ile Asp Arg Leu Ile Thr Gly Arg Leu Gln
              995                 1000                1005

Ser Leu Gln Thr Tyr Val Thr Gln Gln Leu Ile Arg Ala Ala Glu
     1010                1015                1020

Ile Arg Ala Ser Ala Asn Leu Ala Ala Thr Lys Met Ser Glu Cys
     1025                1030                1035

Val Leu Gly Gln Ser Lys Arg Val Asp Phe Cys Gly Lys Gly Tyr
     1040                1045                1050

His Leu Met Ser Phe Pro Gln Ser Ala Pro His Gly Val Val Phe
     1055                1060                1065

Leu His Val Thr Tyr Val Pro Ala Gln Glu Lys Asn Phe Thr Thr
     1070                1075                1080

Ala Pro Ala Ile Cys His Asp Gly Lys Ala His Phe Pro Arg Glu
     1085                1090                1095

Gly Val Phe Val Ser Asn Gly Thr His Trp Phe Val Thr Gln Arg
     1100                1105                1110

Asn Phe Tyr Glu Pro Gln Ile Ile Thr Thr Asp Asn Thr Phe Val
     1115                1120                1125

Ser Gly Asn Cys Asp Val Val Ile Gly Ile Val Asn Asn Thr Val
     1130                1135                1140

Tyr Asp Pro Leu Gln Pro Glu Leu Asp Ser Phe Lys Glu Glu Leu
     1145                1150                1155

Asp Lys Tyr Phe Lys Asn His Thr Ser Pro Asp Val Asp Leu Gly
     1160                1165                1170

Asp Ile Ser Gly Ile Asn Ala Ser Val Val Asn Ile Gln Lys Glu
     1175                1180                1185

Ile Asp Arg Leu Asn Glu Val Ala Lys Asn Leu Asn Glu Ser Leu
     1190                1195                1200

Ile Asp Leu Gln Glu Leu Gly Lys Tyr Glu Gln Tyr Ile Lys Trp
     1205                1210                1215

```
Pro Trp Tyr Ile Trp Leu Gly Phe Ile Ala Gly Leu Ile Ala Ile
    1220             1225                 1230

Val Met Val Thr Ile Met Leu Cys Cys Met Thr Ser Cys Cys Ser
    1235             1240                 1245

Cys Leu Lys Gly Cys Cys Ser Cys Gly Ser Cys Cys Lys Phe Asp
    1250             1255                 1260

Glu Asp Asp Ser Glu Pro Val Leu Lys Gly Val Lys Leu His Tyr
    1265             1270                 1275

Thr

<210> SEQ ID NO 2
<211> LENGTH: 3837
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
atggattgga cttggattct ctttctcgtt gctgcagcca cacgcgttca tagcagccag      60
tgtgtgaacc tgaccaccag aacacagctg cctcctgcct acaccaacag cttcaccaga     120
ggagtctact acccagacaa agtcttcaga agctctgtgc tgcacagcac ccaggacctg     180
ttcctgcctt tcttcagcaa cgtgacctgg ttccacgcca tccacgtgtc tggcaccaac     240
ggcaccaaga gatttgacaa ccctgttctt cctttcaatg atggcgtgta ctttgccagc     300
acagagaaga gcaacatcat ccgaggctgg atctttggca ccaccctgga cagcaaaacc     360
cagagcctgc tgatcgtgaa caacgccacc aacgtggtca tcaaggtgtg tgagttccag     420
ttctgcaatg acccttttcct gggcgtgtac taccacaaga caacaagtc ctggatggag     480 tctgagttca gagtctacag ctctgccaac aactgcacat ttgaatatgt gtcccagcct     540
ttcctgatgg acctggaggg caagcagggc aactttaaga acctgagaga atttgtgttc     600
aagaacatcg atggctactt caagatctac agcaagcaca cacccatcaa cctggtgaga     660
gacctgcctc agggcttctc tgccctggag cctctggtgg acctgcccat cggcatcaac     720
atcaccagat ccagaccct gctggccctg cacagaagct acctgacccc aggagacagc     780
agcagcggct ggacagctgg agctgctgcc tactacgtgg gctacctgca gccaggacc     840 ttcctgctga agtacaacga aaatggcacc atcacagatg ctgttgactg tgccctggac     900
cctcttagcg agaccaagtg caccctgaag tccttcacag tggagaaagg catctaccag     960
accagcaact tccgagtgca gccaacagag agcatcgtga gatttccaaa catcaccaac    1020
ctgtgccctt ttggagaagt cttcaatgcc accagatttg cttctgtgta cgcctggaac    1080
agaaaaagaa tcagcaactg tgtggctgac tactctgtgc tgtacaactc tgcctccttc    1140
tccaccttca gtgctatgg agtctctcca accaagctga atgacctgtg cttcaccaac    1200
gtgtatgctg acagctttgt gatcagagga gatgaagtgc ggcagattgc tcctggccag    1260
acaggcaaga ttgctgacta caactacaag ctgcctgatg acttcacagg ctgtgtcatc    1320
gcctggaaca gcaacaacct ggacagcaag gtgggcggca actacaacta cctgtacaga    1380
cttttcagga gagcaacct gaagcctttt gaaagagaca tctccacaga gatctaccag    1440
gctggcagca cacctgcaa tggtgtggaa ggcttcaact gctacttccc tctgcagagc    1500
tacggcttcc agccaacaaa tggcgtgggc taccagcctt acagagtggt ggtgctgtcc    1560
tttgagctgc tgcacgcccc tgccacagtg tgtggcccca gaagagcac caacctggtg    1620
```

-continued

```
aagaacaaat gtgtgaactt caatttcaat ggcctgacag gcacaggagt gctgacagag    1680
agcaacaaga agtttcttcc tttccagcag tttggaagag acattgctga caccacagat    1740
gctgtgagag atcctcagac cctggagatc ctggatatca caccctgctc ctttggagga    1800
gtttctgtca tcacacctgg caccaatacc agcaaccaag tggctgtgct gtaccaagat    1860
gtgaattgca cagaagtgcc tgtggccatc cacgctgacc agctgacacc cacctggaga    1920
gtgtacagca caggcagcaa tgttttccag acaagagctg gctgcctgat tggagcagag    1980
cacgtgaaca acagctatga atgtgacatc cctattggag ctggcatctg tgccagctac    2040
cagacccaaa ccaacagccc aagaagagcc agatctgtgg ccagccagag catcatcgcc    2100
tacaccatga gcctgggagc tgagaactct gtggcctaca gcaacaacag catcgccatc    2160
cccaccaact tcaccatctc tgtgaccaca gagatcctgc ctgtgtccat gaccaagaca    2220
tctgtggact gcaccatgta catctgtgga gacagcacag aatgcagcaa cctgctgctg    2280
cagtacggct ccttctgcac ccagctgaac agagccctga caggcatcgc tgtggagcag    2340
gacaagaaca cacaggaagt gtttgcccag gtgaagcaga tctacaaaac caccccatc    2400 aaggactttg gaggcttcaa tttctcccaa atcctgcctg accccagcaa gccttccaag    2460
agaagcttca ttgaagacct gctgttcaac aaagtgaccc tggctgatgc tggcttcatc    2520
aagcagtatg gagactgcct gggagacatt gctgccagag acctgatctg tgcccagaag    2580
tttaatggcc tgactgtgct gcctcctctg ctgacagatg aaatgatcgc ccagtacaca    2640
tctgccctgc tggctggcac catcaccagt ggctggacat ttggagctgg agctgccctg    2700
cagatccctt ttgccatgca gatggcctac agatttaatg gcatcggcgt gacccagaac    2760
gtgctgtacg agaaccagaa gctgatcgcc aaccagttca actctgccat cggcaagatc    2820
caggacagcc tgagcagcac agcctctgcc ctgggcaagc tgcaggatgt ggtgaaccaa    2880
aacgcccagg ccctgaacac cctggtgaag cagctgagca gcaactttgg agccatctcc    2940
tctgtgctga atgacatcct gagccggctg gacaaggtgg aagcagaagt gcagatcgac    3000
agactcatca caggccgcct gcagagcctg cagacctacg tgacccagca gctgatcaga    3060
gctgctgaga tccgggcctc tgccaacctg gctgccacca gatgtcaga atgtgtgctg    3120 ggccagagca aaagagtgga cttctgtggc aaaggctacc acctgatgtc cttccctcag    3180
tctgctcctc acggcgtggt gttcctgcac gtgacctacg tgcctgccca ggagaagaac    3240
ttcaccacag ctcctgccat ctgccacgat ggcaaggccc acttcccaag agaaggtgtc    3300
tttgtgtcca atggcaccca ctggttcgtg acccagagaa acttctacga gcctcagatc    3360
atcaccacag acaacacatt tgtgtctggc aactgtgatg tggtcatcgg catcgtgaac    3420
aacacagttt atgaccctct gcagcctgag ctggacagct tcaaagaaga gctggacaag    3480
tacttcaaga accacacatc tccagatgtg gacctgggag acatctctgg catcaatgcc    3540
tctgtggtga acatccagaa ggaaattgac aggctgaacg aagtggccaa gaacctgaac    3600
gaaagcctca tcgacctgca ggagctgggc aagtacgagc agtacatcaa gtggccttgg    3660
tacatctggc tgggcttcat cgctggcctc atcgccatcg tgatggtgac catcatgctg    3720
tgctgcatga ccagctgctg ctcttgcctg aagggctgct gcagctgtgg cagctgctgc    3780
aagtttgatg aagatgactc tgagcctgtg ctgaagggcg tgaagctgca ctacaca       3837
```

```
<210> SEQ ID NO 3
<211> LENGTH: 6797
<212> TYPE: DNA
```

<213> ORGANISM: Artificial Sequence
<220> FEATURE:
<223> OTHER INFORMATION: Description of Artificial Sequence: Synthetic polynucleotide

<400> SEQUENCE: 3

```
gctgcttcgc gatgtacggg ccagatatac gcgttgacat tgattattga ctagttatta      60
atagtaatca attacggggt cattagttca tagcccatat atggagttcc gcgttacata     120
acttacggta aatggcccgc ctggctgacc gcccaacgac ccccgcccat tgacgtcaat     180
aatgacgtat gttcccatag taacgccaat agggactttc cattgacgtc aatgggtgga     240
gtatttacgg taaactgccc acttggcagt acatcaagtg tatcatatgc caagtacgcc     300
ccctattgac gtcaatgacg gtaaatggcc cgcctggcat tatgcccagt acatgacctt     360
atgggacttt cctacttggc agtacatcta cgtattagtc atcgctatta ccatggtgat     420
gcggttttgg cagtacatca atgggcgtgg atagcggttt gactcacggg gatttccaag     480
tctccacccc attgacgtca atgggagttt gttttggcac caaaatcaac gggactttcc     540
aaaatgtcgt aacaactccg ccccattgac gcaaatgggc ggtaggcgtg tacggtggga     600
ggtctatata agcagagctc tctggctaac tagagaaccc actgcttact ggcttatcga     660
aattaatacg actcactata gggagaccca agctggctag cgtttaaact taagcttggt     720
accgagctcg gatccgccac catggattgg acttggattc tctttctcgt tgctgcagcc     780
acacgcgttc atagcagcca gtgtgtgaac ctgaccacca gaacacagct gcctcctgcc     840
tacaccaaca gcttcaccag aggagtctac tacccagaca agtcttcag aagctctgtg     900
ctgcacagca cccaggacct gttcctgcct tcttcagca acgtgacctg gttccacgcc     960
atccacgtgt ctggcaccaa cggcaccaag agatttgaca accctgttct tcctttcaat    1020
gatggcgtgt actttgccag cacagagaag agcaacatca tccgaggctg gatctttggc    1080
accaccctgg acagcaaaac ccagagcctg ctgatcgtga caacgccac caacgtggtc    1140
atcaaggtgt gtgagttcca gttctgcaat gacccttttc tgggcgtgta ctaccacaag    1200
aacaacaagt cctggatgga gtctgagttc agagtctaca gctctgccaa caactgcaca    1260
tttgaatatg tgtcccagcc tttcctgatg gacctggagg gcaagcaggg caactttaag    1320
aacctgagag aatttgtgtt caagaacatc gatggctact tcaagatcta cagcaagcac    1380
acacccatca acctggtgag agacctgcct caggggcttct ctgccctgga gcctctggtg    1440
gacctgccca tcggcatcaa catcaccaga ttccagaccc tgctggccct gcacagaagc    1500
tacctgaccc caggagacag cagcagcggc tggacagctg gagctgctgc ctactacgtg    1560
ggctacctgc agcccaggac cttcctgctg aagtacaacg aaaatggcac catcacagat    1620
gctgttgact gtgccctgga ccctctagc gagaccaagt gcaccctgaa gtccttcaca    1680
gtggagaaag gcatctacca gaccagcaac ttccgagtgc agccaacaga gagcatcgtg    1740
agatttccaa acatcaccaa cctgtgccct tttggagaag tcttcaatgc caccagattt    1800
gcttctgtgt acgcctggaa cagaaaaaga atcagcaact gtgtggctga ctactctgtg    1860
ctgtacaact ctgcctcctt ctccaccttc aagtgctatg gagtctctcc aaccaagctg    1920
aatgacctgt gcttccacaa cgtgtatgct gacagctttg tgatcagagg agatgaagtg    1980
cggcagattg ctcctggcca gacaggcaag attgctgact acaactacaa gctgcctgat    2040
gacttcacag gctgtgtcat cgcctggaac agcaacaacc tggacagcaa ggtgggcggc    2100
aactacaact acctgtacag acttttcagg aagagcaacc tgaagccttt tgaaagagac    2160
```

```
atctccacag agatctacca ggctggcagc acaccctgca atggtgtgga aggcttcaac    2220
tgctacttcc ctctgcagag ctacggcttc cagccaacaa atggcgtggg ctaccagcct    2280
tacagagtgg tggtgctgtc ctttgagctg ctgcacgccc ctgccacagt gtgtggcccc    2340
aagaagagca ccaacctggt gaagaacaaa tgtgtgaact tcaatttcaa tggcctgaca    2400
ggcacaggag tgctgacaga gagcaacaag aagtttcttc ctttccagca gtttggaaga    2460
gacattgctg acaccacaga tgctgtgaga gatcctcaga ccctggagat cctggatatc    2520
acaccctgct cctttggagg agtttctgtc atcacacctg gcaccaatac cagcaaccaa    2580
gtggctgtgc tgtaccaaga tgtgaattgc acagaagtgc ctgtggccat ccacgctgac    2640
cagctgacac ccacctggag agtgtacagc acaggcagca atgttttcca gacaagagct    2700
ggctgcctga ttggagcaga gcacgtgaac aacagctatg aatgtgacat ccctattgga    2760
gctggcatct gtgccagcta ccagacccaa accaacagcc aagaagagc cagatctgtg    2820
gccagccaga gcatcatcgc ctacaccatg agcctgggag ctgagaactc tgtggcctac    2880
agcaacaaca gcatcgccat ccccaccaac ttcaccatct ctgtgaccac agagatcctg    2940
cctgtgtcca tgaccaagac atctgtggac tgcaccatgt acatctgtgg agacagcaca    3000
gaatgcagca acctgctgct gcagtacggc tccttctgca cccagctgaa cagagccctg    3060
acaggcatcg ctgtggagca ggacaagaac acacaggaag tgtttgccca ggtgaagcag    3120
atctacaaaa caccacccat caaggacttt ggaggcttca ttttctccca aatcctgcct    3180
gaccccagca agccttccaa gagaagcttc attgaagacc tgctgttcaa caaagtgacc    3240
ctggctgatg ctggcttcat caagcagtat ggagactgcc tgggagacat tgctgccaga    3300
gacctgatct gtgcccagaa gtttaatggc ctgactgtgc tgcctcctct gctgacagat    3360
gaaatgatcg cccagtacac atctgccctg ctggctggca ccatcaccag tggctggaca    3420
tttggagctg gagctgccct gcagatccct tttgccatgc agatggccta cagatttaat    3480
ggcatcggcg tgacccagaa cgtgctgtac gagaaccaga gctgatcgc caaccagttc    3540
aactctgcca tcggcaagat ccaggacagc ctgagcagca cagcctctgc cctgggcaag    3600
ctgcaggatg tggtgaacca aaacgcccag gccctgaaca cccctggtgaa gcagctgagc    3660
agcaactttg gagccatctc ctctgtgctg aatgacatcc tgagccggct ggacaaggtg    3720
gaagcagaag tgcagatcga cagactcatc acaggccgcc tgcagagcct gcagacctac    3780
gtgacccagc agctgatcag agctgctgag atccgggcct ctgccaacct ggctgccacc    3840
aagatgtcag aatgtgtgct gggccagagc aaaagagtgg acttctgtgg caaaggctac    3900
cacctgatgt ccttccctca gtctgctcct cacggcgtgg tgttcctgca cgtgacctac    3960
gtgcctgccc aggagaagaa cttcaccaca gctcctgcca tctgccacga tggcaaggcc    4020
cacttcccaa gagaaggtgt ctttgtgtcc aatggcaccc actggttcgt gacccagaga    4080
aacttctacg agcctcagat catcaccaca gacaacacat tgtgtctgg caactgtgat    4140
gtggtcatcg gcatcgtgaa caacacagtt tatgaccctc tgcagcctga gctggacagc    4200
ttcaaagaag agctggacaa gtacttcaag aaccacacat ctccagatgt ggacctggga    4260
gacatctctg gcatcaatgc ctctgtggtg aacatccaga ggaaattga caggctgaac    4320
gaagtggcca agaacctgaa cgaaagcctc atcgacctgc aggagctggg caagtacgag    4380
cagtacatca gtggcctg gtacatctgg ctgggcttca tcgctggcct catcgccatc    4440
gtgatggtga ccatcatgct gtgctgcatg accagctgct gctcttgcct gaagggctgc    4500
tgcagctgtg gcagctgctg caagtttgat gaagatgact ctgagcctgt gctgaagggc    4560
```

```
gtgaagctgc actacacatg ataactcgag tctagagggc ccgtttaaac ccgctgatca    4620
gcctcgactg tgccttctag ttgccagcca tctgttgttt gcccctcccc cgtgccttcc    4680
ttgaccctgg aaggtgccac tcccactgtc ctttcctaat aaaatgagga aattgcatcg    4740
cattgtctga gtaggtgtca ttctattctg ggggtgggg tggggcagga cagcaagggg     4800
gaggattggg aagacaatag caggcatgct ggggatgcgg tgggctctat ggcttctact    4860
gggcggtttt atggacagca agcgaaccgg aattgccagc tggggcgccc tctggtaagg    4920
ttgggaagcc ctgcaaagta aactggatgg cttttcttgcc gccaaggatc tgatggcgca   4980
ggggatcaag ctctgatcaa gagacaggat gaggatcgtt tcgcatgatt gaacaagatg    5040
gattgcacgc aggttctccg gccgcttggg tggagaggct attcggctat gactgggcac    5100
aacagacaat cggctgctct gatgccgccg tgttccggct gtcagcgcag gggcgcccgg    5160 ttcttttttgt caagaccgac ctgtccggtg ccctgaatga actgcaagac gaggcagcgc   5220
ggctatcgtg gctggccacg acgggcgttc cttgcgcagc tgtgctcgac gttgtcactg    5280
aagcgggaag ggactggctg ctattgggcg aagtgccggg gcaggatctc ctgtcatctc    5340
accttgctcc tgccgagaaa gtatccatca tggctgatgc aatgcggcgg ctgcatacgc    5400
ttgatccggc tacctgccca ttcgaccacc aagcgaaaca tcgcatcgag cgagcacgta    5460
ctcggatgga agccggtctt gtcgatcagg atgatctgga cgaagagcat caggggctcg    5520
cgccagccga actgttcgcc aggctcaagg cgagcatgcc cgacggcgag gatctcgtcg    5580
tgacccatgg cgatgcctgc ttgccgaata tcatggtgga aaatggccgc ttttctggat    5640
tcatcgactg tggccggctg ggtgtggcgg accgctatca ggacatagcg ttggctaccc    5700
gtgatattgc tgaagagctt ggcggcgaat gggctgaccg cttcctcgtg ctttacggta    5760
tcgccgctcc cgattcgcag cgcatcgcct tctatcgcct tcttgacgag ttcttctgaa    5820
ttattaacgc ttacaatttc ctgatgcggt attttctcct tacgcatctg tgcggtattt    5880
cacaccgcat caggtggcac ttttcgggga atgtgcgcg gaacccctat ttgtttattt     5940
ttctaaatac attcaaatat gtatccgctc atgagacaat aaccctgata aatgcttcaa    6000
taatagcacg tgctaaaact tcattttaa tttaaaagga tctaggtgaa gatcctttt     6060 gataatctca tgaccaaaat cccttaacgt gagttttcgt tccactgagc gtcagacccc    6120
gtagaaaaga tcaaaggatc ttcttgagat cctttttttc tgcgcgtaat ctgctgcttg    6180
caaacaaaaa aaccaccgct accagcggtg gtttgtttgc cggatcaaga gctaccaact    6240
ctttttccga aggtaactgg cttcagcaga gcgcagatac caaatactgt tcttctagtg    6300
tagccgtagt taggccacca cttcaagaac tctgtagcac cgcctacata cctcgctctg    6360
ctaatcctgt taccagtggc tgctgccagt ggcgataagt cgtgtcttac cgggttggac    6420
tcaagacgat agttaccgga taaggcgcag cggtcgggct gaacggggg ttcgtgcaca    6480 cagcccagct tggagcgaac gacctacacc gaactgagat acctacagcg tgagctatga    6540
gaaagcgcca cgcttcccga agggagaaag gcggacaggt atccggtaag cggcagggtc    6600
ggaacaggag agcgcacgag ggagcttcca gggggaaacg cctggtatct ttatagtcct    6660
gtcgggtttc gccacctctg acttgagcgt cgatttttgt gatgctcgtc aggggggcgg    6720
agcctatgga aaaacgccag caacgcggcc ttttacggtt cctggccttt tgctggcct    6780 tttgctcaca tgttctt                                                   6797
```

<210> SEQ ID NO 4

```
<211> LENGTH: 1279
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4
```

Met Asp Trp Thr Trp Ile Leu Phe Leu Val Ala Ala Thr Arg Val
1               5                   10                  15

His Ser Ser Gln Cys Val Asn Leu Thr Arg Thr Gln Leu Pro Pro
            20                  25                  30

Ala Tyr Thr Asn Ser Phe Thr Arg Gly Val Tyr Tyr Pro Asp Lys Val
        35                  40                  45

Phe Arg Ser Ser Val Leu His Ser Thr Gln Asp Leu Phe Leu Pro Phe
    50                  55                  60

Phe Ser Asn Val Thr Trp Phe His Ala Ile His Val Ser Gly Thr Asn
65                  70                  75                  80

Gly Thr Lys Arg Phe Asp Asn Pro Val Leu Pro Phe Asn Asp Gly Val
                85                  90                  95

Tyr Phe Ala Ser Thr Glu Lys Ser Asn Ile Ile Arg Gly Trp Ile Phe
            100                 105                 110

Gly Thr Thr Leu Asp Ser Lys Thr Gln Ser Leu Leu Ile Val Asn Asn
        115                 120                 125

Ala Thr Asn Val Val Ile Lys Val Cys Glu Phe Gln Phe Cys Asn Asp
    130                 135                 140

Pro Phe Leu Gly Val Tyr Tyr His Lys Asn Asn Lys Ser Trp Met Glu
145                 150                 155                 160

Ser Glu Phe Arg Val Tyr Ser Ser Ala Asn Asn Cys Thr Phe Glu Tyr
                165                 170                 175

Val Ser Gln Pro Phe Leu Met Asp Leu Glu Gly Lys Gln Gly Asn Phe
            180                 185                 190

Lys Asn Leu Arg Glu Phe Val Phe Lys Asn Ile Asp Gly Tyr Phe Lys
        195                 200                 205

Ile Tyr Ser Lys His Thr Pro Ile Asn Leu Val Arg Asp Leu Pro Gln
    210                 215                 220

Gly Phe Ser Ala Leu Glu Pro Leu Val Asp Leu Pro Ile Gly Ile Asn
225                 230                 235                 240

Ile Thr Arg Phe Gln Thr Leu Leu Ala Leu His Arg Ser Tyr Leu Thr
                245                 250                 255

Pro Gly Asp Ser Ser Ser Gly Trp Thr Ala Gly Ala Ala Ala Tyr Tyr
            260                 265                 270

Val Gly Tyr Leu Gln Pro Arg Thr Phe Leu Leu Lys Tyr Asn Glu Asn
        275                 280                 285

Gly Thr Ile Thr Val Ala Val Ala Cys Ala Leu Asp Pro Leu Ser Glu
    290                 295                 300

Thr Lys Cys Thr Leu Lys Ser Phe Thr Val Glu Lys Gly Ile Tyr Gln
305                 310                 315                 320

Thr Ser Asn Phe Arg Val Gln Pro Thr Glu Ser Ile Val Arg Phe Pro
                325                 330                 335

Asn Ile Thr Asn Leu Cys Pro Phe Gly Glu Val Phe Asn Ala Thr Arg
            340                 345                 350

Phe Ala Ser Val Tyr Ala Trp Asn Arg Lys Arg Ile Ser Asn Cys Val
        355                 360                 365

```
Ala Asp Tyr Ser Val Leu Tyr Asn Ser Ala Ser Phe Ser Thr Phe Lys
    370                 375                 380

Cys Tyr Gly Val Ser Pro Thr Lys Leu Asn Asp Leu Cys Phe Thr Asn
385                 390                 395                 400

Val Tyr Ala Asp Ser Phe Val Ile Arg Gly Asp Glu Val Arg Gln Ile
                405                 410                 415

Ala Pro Gly Gln Thr Gly Lys Ile Ala Asp Tyr Asn Tyr Lys Leu Pro
            420                 425                 430

Asp Asp Phe Thr Gly Cys Val Ile Ala Trp Asn Ser Asn Asn Leu Asp
        435                 440                 445

Ser Lys Val Gly Gly Asn Tyr Asn Tyr Leu Tyr Arg Leu Phe Arg Lys
    450                 455                 460

Ser Asn Leu Lys Pro Phe Glu Arg Asp Ile Ser Thr Glu Ile Tyr Gln
465                 470                 475                 480

Ala Gly Ser Thr Pro Cys Asn Gly Val Glu Gly Phe Asn Cys Tyr Phe
                485                 490                 495

Pro Leu Gln Ser Tyr Gly Phe Gln Pro Thr Asn Gly Val Gly Tyr Gln
            500                 505                 510

Pro Tyr Arg Val Val Val Leu Ser Phe Glu Leu Leu His Ala Pro Ala
        515                 520                 525

Thr Val Cys Gly Pro Lys Lys Ser Thr Asn Leu Val Lys Asn Lys Cys
    530                 535                 540

Val Asn Phe Asn Phe Asn Gly Leu Thr Gly Thr Gly Val Leu Thr Glu
545                 550                 555                 560

Ser Asn Lys Lys Phe Leu Pro Phe Gln Gln Phe Gly Arg Asp Ile Ala
                565                 570                 575

Asp Thr Thr Asp Ala Val Arg Asp Pro Gln Thr Leu Glu Ile Leu Asp
            580                 585                 590

Ile Thr Pro Cys Ser Phe Gly Gly Val Ser Val Ile Thr Pro Gly Ala
        595                 600                 605

Asn Thr Ser Asn Gln Val Thr Val Leu Tyr Gln Asp Val Asn Cys Thr
    610                 615                 620

Glu Val Pro Val Ala Ile His Ala Asp Gln Leu Thr Pro Thr Trp Arg
625                 630                 635                 640

Val Tyr Ser Thr Gly Ser Asn Val Phe Lys Thr Arg Ala Gly Cys Leu
                645                 650                 655

Ile Gly Ala Glu His Val Asn Asn Ser Tyr Glu Cys Asp Ile Pro Ile
            660                 665                 670

Gly Ala Gly Ile Cys Ala Ser Tyr Gln Thr Gln Thr Asn Ser Pro Arg
        675                 680                 685

Arg Ala Arg Ser Thr Ala Ser Gln Ser Ile Ile Ala Tyr Thr Met Ser
    690                 695                 700

Leu Gly Ala Glu Asn Ser Val Ala Tyr Ser Asn Asn Ser Ile Val Ile
705                 710                 715                 720

Pro Thr Asn Phe Thr Ile Ser Val Thr Thr Glu Ile Leu Pro Val Ser
                725                 730                 735

Met Thr Lys Thr Ser Val Asp Cys Thr Met Tyr Ile Cys Ser Asp Ser
            740                 745                 750

Thr Glu Cys Ser Asn Pro Leu Leu Gln Tyr Gly Ser Phe Cys Thr Gln
        755                 760                 765

Leu Asn Arg Ala Leu Thr Gly Ile Ala Val Glu Gln Asp Lys Asn Thr
    770                 775                 780
```

```
Gln Glu Val Phe Ala Gln Val Lys Gln Ile Tyr Lys Thr Pro Pro Ile
785                 790                 795                 800

Lys Asp Phe Gly Gly Phe Asn Phe Ser Gln Ile Leu Pro Asp Pro Ser
            805                 810                 815

Lys Pro Ser Lys Arg Ser Phe Ile Glu Asp Leu Leu Phe Asn Lys Val
        820                 825                 830

Thr Leu Ala Asp Ala Gly Phe Ile Lys Gln Tyr Gly Asp Cys Leu Gly
    835                 840                 845

Asp Ile Ala Ala Arg Asp Leu Ile Cys Ala Gln Lys Phe Asn Gly Leu
850                 855                 860

Thr Val Leu Pro Pro Leu Leu Thr Asp Glu Met Ile Ala Gln Tyr Thr
865                 870                 875                 880

Ser Ala Leu Leu Ala Gly Thr Ile Thr Ser Gly Trp Thr Phe Gly Ala
            885                 890                 895

Gly Ala Ala Leu Gln Ile Pro Phe Ala Met Gln Met Ala Tyr Arg Phe
            900                 905                 910

Asn Gly Ile Arg Val Thr Gln Asn Val Leu Tyr Glu Asn Gln Lys Leu
            915                 920                 925

Ile Ala Asn Gln Phe Asn Ser Ala Ile Gly Lys Ile Gln Asp Ser Leu
930                 935                 940

Ser Ser Thr Ala Ser Ala Leu Gly Lys Leu Gln Asp Val Val Asn Gln
945                 950                 955                 960

Asn Ala Gln Ala Leu Asn Thr Leu Val Lys Gln Leu Ser Ser Thr Phe
            965                 970                 975

Ser Thr Ile Ser Ser Val Leu Asn Asp Ile Leu Ser Arg Leu Asp Lys
        980                 985                 990

Val Glu Ala Glu Val Gln Ile Asp Arg Leu Ile Thr Gly Arg Leu Gln
            995                 1000                1005

Ser Leu Gln Thr Tyr Val Thr Gln Gln Leu Ile Arg Ala Ala Glu
    1010                1015                1020

Ile Arg Ala Ser Ala Asn Leu Lys Ala Thr Lys Met Ser Glu Cys
    1025                1030                1035

Val Leu Gly Gln Ser Lys Arg Val Asp Phe Cys Gly Lys Gly Tyr
    1040                1045                1050

His Leu Met Ser Phe Pro Gln Ser Ala Pro His Gly Val Val Phe
    1055                1060                1065

Leu His Val Thr Tyr Val Pro Ala Gln Glu Lys Asn Phe Thr Thr
    1070                1075                1080

Ala Pro Ala Thr Cys His Asp Gly Lys Ala His Phe Pro Arg Glu
    1085                1090                1095

Gly Val Phe Val Ser Asn Gly Thr His Trp Phe Val Thr Gln Arg
    1100                1105                1110

Asn Phe Asp Glu Pro Gln Ile Ile Thr Thr Asp Asn Thr Phe Val
    1115                1120                1125

Ser Gly Asn Cys Asp Val Val Ile Gly Ile Val Asn Asn Thr Val
    1130                1135                1140

Tyr Asp Pro Leu Gln Pro Glu Leu Asp Ser Phe Lys Glu Glu Leu
    1145                1150                1155

Asp Lys Tyr Phe Lys Asn His Thr Ser Pro Asp Val Asp Leu Gly
    1160                1165                1170

Asp Ile Ser Gly Ile Asn Ala Ser Val Val Asn Ile Gln Lys Glu
    1175                1180                1185
```

| | | | | | | | | | | |
|---|---|---|---|---|---|---|---|---|---|---|
| Ile | Asp | Arg | Leu | Asn | Glu | Val | Ala | Lys | Asn | Leu | Asn | Glu | Ser | Leu |
| | 1190 | | | | 1195 | | | | 1200 | |

| Ile | Asp | Leu | Gln | Glu | Leu | Gly | Lys | Tyr | Glu | Gln | Tyr | Ile | Lys | Trp |
|---|---|---|---|---|---|---|---|---|---|---|---|---|---|---|
| | 1205 | | | | 1210 | | | | 1215 | |

| Pro | Trp | Tyr | Ile | Trp | Leu | Gly | Phe | Ile | Ala | Gly | Leu | Ile | Ala | Ile |
|---|---|---|---|---|---|---|---|---|---|---|---|---|---|---|
| | 1220 | | | | 1225 | | | | 1230 | |

| Val | Met | Val | Thr | Ile | Met | Leu | Cys | Cys | Met | Thr | Ser | Cys | Cys | Ser |
|---|---|---|---|---|---|---|---|---|---|---|---|---|---|---|
| | 1235 | | | | 1240 | | | | 1245 | |

| Cys | Leu | Lys | Gly | Cys | Cys | Ser | Cys | Gly | Ser | Cys | Cys | Lys | Phe | Asp |
|---|---|---|---|---|---|---|---|---|---|---|---|---|---|---|
| | 1250 | | | | 1255 | | | | 1260 | |

| Glu | Asp | Asp | Ser | Glu | Pro | Val | Leu | Lys | Gly | Val | Lys | Leu | His | Tyr |
|---|---|---|---|---|---|---|---|---|---|---|---|---|---|---|
| | 1265 | | | | 1270 | | | | 1275 | |

Thr

<210> SEQ ID NO 5
<211> LENGTH: 3837
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 5

```
atggattgga cctggattct ttttctcgtt gcagctgcta cacgcgttca tagcagccag      60
tgtgtgaacc tgaccaccag aacacagctg cctcctgcct acaccaacag cttcaccaga     120
ggagtctact acccagacaa ggtgttcaga agctctgtgc tgcacagcac ccaggacctc     180
ttcctgcctt tcttcagcaa cgtgacctgg ttccacgcca tccacgtgtc tggcaccaac     240
ggcaccaaga gatttgacaa ccctgtgctg cctttcaatg atggtgtgta ctttgccagc     300
acagagaaga gcaacatcat ccgaggctgg atctttggca ccaccctgga cagcaaaaca     360
cagagcctgc tgatcgtgaa taatgccacc aacgtggtca tcaaggtgtg tgagttccag     420
ttctgcaatg acccttttct gggcgtgtac taccacaaga caacaagtc ctggatggag     480
tctgagttcc gagtgtacag ctctgccaac aactgcacat tgaatatgt gtcccagcct     540
ttcctgatgg acctggaggg caagcagggc aatttcaaga acctgagaga atttgtgttc     600
aagaacatcg atggctactt caagatctac agcaagcaca cacccatcaa cctggtgaga     660
gatcttcctc agggcttctc tgccctggag cctctggtgg acctgcccat cggcatcaac     720
atcacccgct ttcagaccct gctggccctg cacagaagct acctgacccc aggagacagc     780
agcagcggct ggacagctgg agctgctgcc tactacgtgg gctacctgca gccaagaacc     840
ttcctgctga gtacaacga aaatggcacc atcactgtgg ctgtggcctg tgccctggac     900
cctctttctg agaccaagtg caccctgaag tccttcacag tggagaaagg catctaccag     960
accagcaact tcagagttca gccaacagag agcatcgtga gatttccaaa catcaccaac    1020
ctgtgtcctt ttggagaagt cttcaatgcc accagatttg cttctgtgta cgcctggaac    1080
agaaaaagaa tcagcaactg tgtggctgac tactctgtgc tgtacaactc tgcctccttc    1140
tccaccttca gtgctacgg tgtgtctcct accaagctga atgacctgtg cttcaccaac    1200
gtgtatgctg acagctttgt catcagagga gatgaagtgc ggcagatcgc ccctggccag    1260
acaggcaaga ttgctgacta caactacaag ctgcctgatg acttcacagg ctgtgtcatc    1320
gcctggaaca gcaacaacct ggacagcaag gtgggcggca actacaacta cctgtacaga    1380
cttttcagga agagcaacct gaagcctttt gaaagagaca tctccacaga gatctaccag    1440
```

-continued

```
gctggcagca caccctgcaa tggagtggaa ggcttcaact gctacttccc tctgcagagc   1500
tacggcttcc agcccaccaa tggcgtgggc taccagcctt acagagtggt ggtgctgtcc   1560
tttgagctgc tgcacgcccc tgccacagtg tgtggcccca agaagagcac caacctggtg   1620
aagaacaaat gtgtgaactt caatttcaat ggcctgacag gcacaggagt gctgacagag   1680
agcaacaaga agttcctgcc tttccagcag tttggaagag acattgctga caccacagat   1740
gctgtgagag atcctcagac cctggagatc ctggacatca cccctgctc ctttggagga   1800 gtttctgtca tcacacctgg agccaacacc agcaaccaag tgacagtgct gtaccaagat   1860
gtgaactgca cagaagttcc tgtggccatc cacgctgacc agctgacccc aacctggaga   1920
gtctacagca caggcagcaa cgtgtttaaa acaagagctg gctgcctgat ggagcagag   1980 cacgtgaaca cagctatga atgtgacatc cctattggag ctggcatctg tgccagctac   2040
cagacccaaa ccaacagccc aagaagagcc aggagcacag ccagccagag catcatcgcc   2100
tacaccatga gcctgggagc agagaactct gtggcctaca gcaacaacag catcgtcatc   2160
cccaccaact tcaccatctc tgtgaccaca gagatcctgc ctgtgtccat gaccaagaca   2220
tctgtggact gcaccatgta catctgcagt gacagcacag aatgcagcaa ccctctgctg   2280
cagtacggct ccttctgcac ccagctgaac agagccctga caggcatcgc tgtggagcag   2340
gacaagaaca cacaggaagt gtttgcccag gtgaagcaga tctacaaaac caccccatc   2400 aaggactttg gaggcttcaa cttctcccag atcctgcctg accccagcaa gcccagcaag   2460
agaagcttca ttgaagacct gctgttcaac aaagtgaccc tggctgatgc tggcttcatc   2520
aaacaatatg gagactgcct gggagacatt gctgccagag acctgatctg tgcccagaag   2580
tttaatggcc tgactgtgct gcctcctctg ctgacagatg aaatgatcgc ccagtacaca   2640
tctgccctgc tggctggcac catcacatct ggctggacat ttggagctgg agctgccctg   2700 cagatcccctt ttgccatgca gatggcctac agatttaatg gcatcagagt gacccagaac   2760
gtgctgtatg aaaaccagaa gctgatcgcc aaccagttca actctgccat cggcaagatc   2820
caggacagcc tgagcagcac agcctctgcc ctgggcaagc tgcaggatgt ggtgaaccaa   2880
aatgcccagg ccctgaacac cctggtgaag cagctgagca gcaccttctc caccatctcc   2940
agcgtgctga atgacatcct gagccggctg gacaaggtgg aagctgaggt gcagatcgac   3000
agactcatca caggccggct gcagagcctg cagacctacg tgacccagca gctgatcaga   3060
gctgctgaga tcagagcttc tgccaacctg aaggccacca gatgtcaga atgtgtgctg   3120 ggccagagca gagagtgga cttctgtggc aaaggctacc acctgatgtc cttccctcag   3180
tctgctcctc acggcgtggt gttcctgcac gtgacctacg tgcctgccca ggagaagaac   3240
ttcaccacag ctcctgccac ctgccacgat ggcaaagccc acttcccaag agaaggcgtc   3300
tttgtgtcca atggcaccca ctggttcgtg acccagagaa actttgatga gcctcagatc   3360
atcaccacag acaacacatt tgtttctggc aactgtgatg tggtcatcgg catcgtgaac   3420
aacacagttt atgaccctct gcagcctgag ctggacagct tcaaagaaga gctgacaag   3480 tacttcaaga accacacatc tccagatgtg gacctgggag acatctctgg catcaatgcc   3540
tctgtggtga acatccagaa ggaaattgac aggctgaacg aagtggccaa gaacctgaac   3600
gaaagcctca tcgacctgca ggagctgggc aagtacgagc agtacatcaa gtggccttgg   3660
tacatctggc tgggcttcat tgctggcctc atcgccatcg tgatggtgac catcatgctg   3720
```

```
tgctgcatga ccagctgctg ctcttgcctg aagggctgct gcagctgtgg cagctgctgc    3780
aagtttgatg aagatgactc tgagcctgtg ctgaagggcg tgaagctgca ctacaca       3837

<210> SEQ ID NO 6
<211> LENGTH: 6797
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
gctgcttcgc gatgtacggg ccagatatac gcgttgacat tgattattga ctagttatta     60
atagtaatca attacggggt cattagttca tagcccatat atggagttcc gcgttacata    120
acttacggta aatggcccgc ctggctgacc gcccaacgac ccccgcccat tgacgtcaat    180
aatgacgtat gttcccatag taacgccaat agggactttc cattgacgtc aatgggtgga    240
gtatttacgg taaactgccc acttggcagt acatcaagtg tatcatatgc caagtacgcc    300
ccctattgac gtcaatgacg gtaaatggcc cgcctggcat tatgcccagt acatgacctt    360
atgggacttt cctacttggc agtacatcta cgtattagtc atcgctatta ccatggtgat    420
gcggttttgg cagtacatca atgggcgtgg atagcggttt gactcacggg gatttccaag    480
tctccacccc attgacgtca atgggagttt gttttggcac caaaatcaac gggactttcc    540
aaaatgtcgt aacaactccg ccccattgac gcaaatgggc ggtaggcgtg tacggtggga    600
ggtctatata agcagagctc tctggctaac tagagaaccc actgcttact ggcttatcga    660
aattaatacg actcactata gggagaccca gctggctag cgtttaaact taagcttggt     720
accgagctcg gatccgccac catggattgg acctggattc tttttctcgt tgcagctgct    780
acacgcgttc atagcagcca gtgtgtgaac ctgaccacca gaacacagct gcctcctgcc    840
tacaccaaca gcttcaccag aggagtctac tacccagaca aggtgttcag aagctctgtg    900
ctgcacagca cccaggacct cttcctgcct tcttcagca acgtgacctg gttccacgcc    960
atccacgtgt ctggcaccaa cggcaccaag agatttgaca accctgtgct gcctttcaat   1020
gatggtgtgt actttgccag cacagagaag agcaacatca tccgaggctg gatctttggc   1080
accaccctgg acagcaaaac acagagcctg ctgatcgtga ataatgccac caacgtggtc   1140
atcaaggtgt gtgagttcca gttctgcaat gacccttttc tgggcgtgta ctaccacaag   1200
aacaacaagt cctggatgga gtctgagttc cgagtgtaca gctctgccaa caactgcaca   1260
tttgaatatg tgtcccagcc tttcctgatg gacctggagg gcaagcaggg caatttcaag   1320
aacctgagag aatttgtgtt caagaacatc gatggctact tcaagatcta cagcaagcac   1380
acacccatca acctggtgag agatcttcct cagggcttct ctgccctgga gcctctggtg   1440
gacctgccca tcggcatcaa catcacccgc tttcagaccc tgctggccct gcacagaagc   1500
tacctgaccc caggagacag cagcagcggc tggacagctg agctgctgc ctactacgtg   1560 ggctacctgc agccaagaac cttcctgctg aagtacaacg aaaatggcac catcactgtg   1620
gctgtggcct gtcccctgga ccctcttttct gagaccaagt gcaccctgaa gtccttcaca   1680
gtggagaaag gcatctacca gaccagcaac ttcagagttc agccaacaga gagcatcgtg   1740
agatttccaa acatcaccaa cctgtgtcct tttggagaag tcttcaatgc caccagattt   1800
gcttctgtgt acgcctggaa cagaaaaaga atcagcaact gtgtggctga ctactctgtg   1860
ctgtacaact ctgcctcctt ctccaccttc aagtgctacg gtgtgtctcc taccaagctg   1920
```

```
aatgacctgt gcttcaccaa cgtgtatgct gacagctttg tcatcagagg agatgaagtg    1980
cggcagatcg cccctggcca gacaggcaag attgctgact acaactacaa gctgcctgat    2040
gacttcacag gctgtgtcat cgcctggaac agcaacaacc tggacagcaa ggtgggcggc    2100
aactacaact acctgtacag acttttcagg aagagcaacc tgaagccttt tgaaagagac    2160
atctccacag agatctacca ggctggcagc acaccctgca atggagtgga aggcttcaac    2220
tgctacttcc ctctgcagag ctacggcttc cagcccacca tggcgtggg  ctaccagcct    2280 tacagagtgg tggtgctgtc ctttgagctg ctgcacgccc ctgccacagt gtgtggcccc    2340
aagaagagca ccaacctggt gaagaacaaa tgtgtgaact tcaatttcaa tggcctgaca    2400
ggcacaggag tgctgacaga gagcaacaag aagttcctgc ctttccagca gtttggaaga    2460
gacattgctg acaccacaga tgctgtgaga gatcctcaga ccctggagat cctggacatc    2520
acaccctgct cctttggagg agtttctgtc atcacacctg agccaacac  cagcaaccaa    2580 gtgacagtgc tgtaccaaga tgtgaactgc acagaagttc ctgtgccat ccacgctgac    2640 cagctgaccc caacctggag agtctacagc acaggcagca acgtgtttaa acaagagct    2700 ggctgcctga ttggagcaga gcacgtgaac aacagctatg aatgtgacat ccctattgga    2760
gctggcatct gtgccagcta ccagacccaa accaacagcc aagaagagc  caggagcaca    2820 gccagccaga gcatcatcgc ctacaccatg agcctgggag cagagaactc tgtggcctac    2880
agcaacaaca gcatcgtcat ccccaccaac ttcaccatct ctgtgaccac agagatcctg    2940
cctgtgtcca tgaccaagac atctgtggac tgcaccatgt acatctgcag tgacagcaca    3000
gaatgcagca accctctgct gcagtacggc tccttctgca cccagctgaa cagagccctg    3060
acaggcatcg ctgtggagca ggacaagaac acacaggaag tgtttgccca ggtgaagcag    3120
atctacaaaa caccacccat caaggacttt ggaggcttca acttctccca gatcctgcct    3180
gaccccagca agcccagcaa gagaagcttc attgaagacc tgctgttcaa caaagtgacc    3240
ctggctgatg ctggcttcat caaacaatat ggagactgcc tgggagacat tgctgccaga    3300
gacctgatct gtgcccagaa gtttaatggc ctgactgtgc tgcctcctct gctgacagat    3360
gaaatgatcg cccagtacac atctgccctg ctggctggac ccatcacatc tggctggaca    3420
tttggagctg gagctgccct gcagatccct tttgccatgc agatggccta cagatttaat    3480
ggcatcagag tgacccagaa cgtgctgtat gaaaaccaga gctgatcgc  aaccagttc    3540 aactctgcca tcggcaagat ccaggacagc ctgagcagca cagcctctgc cctgggcaag    3600
ctgcaggatg tggtgaacca aaatgcccag gccctgaaca cctggtgaa  gcagctgagc    3660 agcaccttct ccaccatctc cagcgtgctg aatgacatcc tgagccggct ggacaaggtg    3720
gaagctgagg tgcagatcga cagactcatc acaggccggc tgcagagcct gcagacctac    3780
gtgacccagc agctgatcag agctgctgag atcagagctt ctgccaacct gaaggccacc    3840
aagatgtcag aatgtgtgct gggccagagc aagagagtgg acttctgtgg caaaggctac    3900
cacctgatgt ccttccctca gtctgctcct cacggcgtgg tgttcctgca cgtgacctac    3960
gtgcctgccc aggagaagaa cttcaccaca gctcctgcca cctgccacga tggcaaagcc    4020
cacttcccaa gagaaggcgt cttgtgtcc aatggcaccc actggttcgt gacccagaga    4080
aactttgatg agcctcagat catcaccaca gacaacacat ttgtttctgg caactgtgat    4140
gtggtcatcg gcatcgtgaa caacacagtt tatgaccctc tgcagcctga gctgacagc     4200 ttcaaagaag agctggacaa gtacttcaag aaccacacat ctccagatgt ggacctggga    4260
```

```
gacatctctg gcatcaatgc ctctgtggtg aacatccaga aggaaattga caggctgaac    4320
gaagtggcca agaacctgaa cgaaagcctc atcgacctgc aggagctggg caagtacgag    4380
cagtacatca agtggccttg gtacatctgg ctgggcttca ttgctggcct catcgccatc    4440
gtgatggtga ccatcatgct gtgctgcatg accagctgct gctcttgcct gaagggctgc    4500
tgcagctgtg gcagctgctg caagtttgat gaagatgact ctgagcctgt gctgaagggc    4560
gtgaagctgc actacacatg ataactcgag tctagagggc ccgtttaaac ccgctgatca    4620
gcctcgactg tgccttctag ttgccagcca tctgttgttt gcccctcccc cgtgccttcc    4680
ttgaccctgg aaggtgccac tcccactgtc ctttcctaat aaaatgagga aattgcatcg    4740
cattgtctga gtaggtgtca ttctattctg ggggtgggg tggggcagga cagcaagggg    4800
gaggattggg aagacaatag caggcatgct ggggatgcgg tgggctctat ggcttctact    4860
gggcggtttt atggacagca agcgaaccgg aattgccagc tggggcgccc tctggtaagg    4920
ttgggaagcc ctgcaaagta aactggatgg cttcttgcc gccaaggatc tgatggcgca    4980
ggggatcaag ctctgatcaa gagacaggat gaggatcgtt tcgcatgatt gaacaagatg    5040
gattgcacgc aggttctccg gccgcttggg tggagaggct attcggctat gactgggcac    5100
aacagacaat cggctgctct gatgccgccg tgttccggct gtcagcgcag gggcgcccgg    5160 ttcttttgt caagaccgac ctgtccggtg ccctgaatga actgcaagac gaggcagcgc    5220
ggctatcgtg gctggccacg acgggcgttc cttgcgcagc tgtgctcgac gttgtcactg    5280
aagcgggaag ggactggctg ctattgggcg aagtgccggg gcaggatctc ctgtcatctc    5340
accttgctcc tgccgagaaa gtatccatca tggctgatgc aatgcggcgg ctgcatacgc    5400
ttgatccggc tacctgccca ttcgaccacc aagcgaaaca tcgcatcgag cgagcacgta    5460
ctcggatgga agccggtctt gtcgatcagg atgatctgga cgaagagcat caggggctcg    5520
cgccagccga actgttcgcc aggctcaagg cgagcatgcc cgacggcgag gatctcgtcg    5580
tgacccatgg cgatgcctgc ttgccgaata tcatggtgga aaatggccgc ttttctggat    5640
tcatcgactg tggccggctg ggtgtggcgg accgctatca ggacatagcg ttggctaccc    5700
gtgatattgc tgaagagctt ggcggcgaat gggctgaccg cttcctcgtg ctttacggta    5760
tcgccgctcc cgattcgcag cgcatcgcct tctatcgcct tcttgacgag ttcttctgaa    5820
ttattaacgc ttacaatttc ctgatgcggt attttctcct tacgcatctg tgcggtattt    5880
cacaccgcat caggtggcac ttttcgggga atgtgcgcg aacccctat tgtttatt    5940 ttctaaatac attcaaatat gtatccgctc atgagacaat aaccctgata atgcttcaa    6000 taatagcacg tgctaaaact tcattttaa tttaaaagga tctaggtgaa gatcctttt    6060 gataatctca tgaccaaaat cccttaacgt gagttttcgt tccactgagc gtcagacccc    6120
gtagaaaaga tcaaaggatc ttcttgagat cctttttttc tgcgcgtaat ctgctgcttg    6180
caaacaaaaa aaccaccgct accagcggtg gtttgtttgc cggatcaaga gctaccaact    6240 cttttccga aggtaactgg cttcagcaga gcgcagatac caaatactgt tcttctagtg    6300
tagccgtagt taggccacca cttcaagaac tctgtagcac cgcctacata cctcgctctg    6360
ctaatcctgt taccagtggc tgctgccagt ggcgataagt cgtgtcttac cgggttggac    6420
tcaagacgat agttaccgga taaggcgcag cggtcgggct gaacggggg ttcgtgcaca    6480 cagcccagct tggagcgaac gacctacacc gaactgagat acctacagcg tgagctatga    6540
gaaagcgcca cgcttcccga agggagaaag gcggacaggt atccggtaag cggcagggtc    6600
ggaacaggag agcgcacgag ggagcttcca gggggaaacg cctggtatct ttatagtcct    6660
```

```
gtcgggtttc gccacctctg acttgagcgt cgattttttgt gatgctcgtc aggggggcgg    6720
agcctatgga aaaacgccag caacgcggcc tttttacggt tcctggcctt ttgctggcct    6780
tttgctcaca tgttctt                                                    6797
```

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
caggacaaga acacacagga a                                               21

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 8
caggcaggat ttgggagaaa                                                 20

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic probe

<400> SEQUENCE: 9
acccatcaag gactttggag g                                               21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 10
aggacaagaa cacacaggaa g                                               21

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
caggatctgg gagaagttga ag                                              22

<210> SEQ ID NO 12
<211> LENGTH: 24
<212> TYPE: DNA
<213> ORGANISM: Artificial Sequence
<220> FEATURE:

<223> OTHER INFORMATION: Description of Artificial Sequence: Synthetic
      probe

<400> SEQUENCE: 12
acaccaccca tcaaggactt tgga                                          24

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gtgacgtgga catccgtaaa                                               20

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cagggcagta atctccttct g                                             21

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15
taccctggca ttgctgacag gatg                                          24

<210> SEQ ID NO 16
<211> LENGTH: 9
<212> TYPE: PRT
<213> ORGANISM: Severe acute respiratory syndrome coronavirus 2

<400> SEQUENCE: 16

Pro His Gly Val Val Phe Leu His Val
1               5

<210> SEQ ID NO 17
<211> LENGTH: 10
<212> TYPE: PRT
<213> ORGANISM: Severe acute respiratory syndrome coronavirus 2

<400> SEQUENCE: 17

Val Val Phe Leu His Val Thr Val Tyr Val
1               5                   10

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gaccccaaaa tcagcgaaat                                              20

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tctggttact gccagttgaa tctg                                         24

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 20
accccgcatt acgtttggtg gacc                                         24

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cgatctcttg tagatctgtt ctc                                          23

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
atattgcagc agtacgcaca ca                                           22

<210> SEQ ID NO 23
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 23
acactagcca tccttactgc gcttcg                                       26

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
      10xHis tag

```
<400> SEQUENCE: 24

His His His His His His His His His
1               5                   10

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 25

His His His His His His
1               5

<210> SEQ ID NO 26
<211> LENGTH: 15
<212> TYPE: PRT
<213> ORGANISM: Severe acute respiratory syndrome coronavirus 2

<400> SEQUENCE: 26

Tyr Asn Tyr Lys Leu Pro Asp Asp Phe Thr Gly Cys Val Ile Ala
1               5                   10                  15

<210> SEQ ID NO 27
<211> LENGTH: 15
<212> TYPE: PRT
<213> ORGANISM: Severe acute respiratory syndrome coronavirus 2

<400> SEQUENCE: 27

Asp Asp Phe Thr Gly Cys Val Ile Ala Trp Asn Ser Asn Asn Leu
1               5                   10                  15

<210> SEQ ID NO 28
<211> LENGTH: 15
<212> TYPE: PRT
<213> ORGANISM: Severe acute respiratory syndrome coronavirus 2

<400> SEQUENCE: 28

Val Gly Gly Asn Tyr Asn Tyr Leu Tyr Arg Leu Phe Arg Lys Ser
1               5                   10                  15

<210> SEQ ID NO 29
<211> LENGTH: 15
<212> TYPE: PRT
<213> ORGANISM: Severe acute respiratory syndrome coronavirus 2

<400> SEQUENCE: 29

Val Val Leu Ser Phe Glu Leu Leu His Ala Pro Ala Thr Val Cys
1               5                   10                  15

<210> SEQ ID NO 30
<211> LENGTH: 15
<212> TYPE: PRT
<213> ORGANISM: Severe acute respiratory syndrome coronavirus 2

<400> SEQUENCE: 30

Leu Leu His Ala Pro Ala Thr Val Cys Gly Pro Lys Lys Ser Thr
1               5                   10                  15

<210> SEQ ID NO 31
<211> LENGTH: 15
<212> TYPE: PRT
<213> ORGANISM: Severe acute respiratory syndrome coronavirus 2
```

```
<400> SEQUENCE: 31

Lys Asn Lys Cys Val Asn Phe Asn Phe Asn Gly Leu Thr Gly Thr
1               5                   10                  15

<210> SEQ ID NO 32
<211> LENGTH: 15
<212> TYPE: PRT
<213> ORGANISM: Severe acute respiratory syndrome coronavirus 2

<400> SEQUENCE: 32

Ser Phe Pro Gln Ser Ala Pro His Gly Val Val Phe Leu His Val
1               5                   10                  15

<210> SEQ ID NO 33
<211> LENGTH: 15
<212> TYPE: PRT
<213> ORGANISM: Severe acute respiratory syndrome coronavirus 2

<400> SEQUENCE: 33

Pro His Gly Val Val Phe Leu His Val Thr Tyr Val Pro Ala Gln
1               5                   10                  15

<210> SEQ ID NO 34
<211> LENGTH: 15
<212> TYPE: PRT
<213> ORGANISM: Severe acute respiratory syndrome coronavirus 2

<400> SEQUENCE: 34

Phe Thr Thr Ala Pro Ala Ile Cys His Asp Gly Lys Ala His Phe
1               5                   10                  15

<210> SEQ ID NO 35
<211> LENGTH: 9
<212> TYPE: PRT
<213> ORGANISM: Severe acute respiratory syndrome coronavirus 2

<400> SEQUENCE: 35

Val Val Phe Leu His Val Thr Tyr Val
1               5
```

VACCINES AGAINST CORONAVIRUS AND METHODS OF USE

CROSS-REFERENCE TO RELATED APPLICATIONS

The present application claims the benefit of U.S. Provisional Appl. No. 62/981,451, filed Feb. 25, 2020; U.S. Provisional Appl. No. 63/004,380, filed Apr. 2, 2020; U.S. Provisional Appl. No. 63/028,404, filed May 21, 2020; U.S. Provisional Appl. No. 63/033,349, filed Jun. 2, 2020; U.S. Provisional Appl. No. 63/040,865, filed Jun. 18, 2020; U.S. Provisional Appl. No. 63/046,415, filed Jun. 30, 2020; U.S. Provisional Appl. No. 63/062,762, filed Aug. 7, 2020; U.S. Provisional Appl. No. 63/114,858, filed Nov. 17, 2020; U.S. Provisional Appl. No. 63/130,593 filed Dec. 24, 2020; U.S. Provisional Appl. No. 63/136,973 filed Jan. 13, 2021; U.S. Provisional Appl. No. 62/981,168, filed Feb. 25, 2020; U.S. Provisional Appl. No. 63/022,032, filed May 8, 2020; U.S. Provisional Appl. No. 63/056,996, filed Jul. 27, 2020; and U.S. Provisional Appl. No. 63/063,157, filed Aug. 7, 2020. The contents of each of these applications are incorporated herein by reference in the entirety.

SEQUENCE LISTING

This application includes a Sequence Listing submitted electronically as a text file named "104409_000605_SL.txt", created on Feb. 24, 2021 with a size of 57,904 bytes. The Sequence Listing is incorporated by reference herein.

TECHNICAL FIELD

The present invention relates to a vaccine for Severe Acute Respiratory Syndrome coronavirus 2 (SARS-CoV-2) and methods of administering the vaccine.

BACKGROUND

COVID-19, known previously as 2019-nCoV pneumonia or disease, has rapidly emerged as a global threat to public health, joining severe acute respiratory syndrome (SARS) and Middle East respiratory syndrome (MERS) in a growing number of coronavirus-associated illnesses which have jumped from animals to people. There is an imminent need for medical countermeasures such as vaccines to combat the spread of such emerging coronaviruses. There are at least seven identified coronaviruses that infect humans, including MERS-CoV and SARS-CoV.

In December 2019, the city of Wuhan in China became the epicenter for a global outbreak of a novel coronavirus. This coronavirus, SARS-CoV-2, was isolated and sequenced from human airway epithelial cells from infected patients (Zhu, et al. A Novel Coronavirus from Patients with Pneumonia in China, 2019. *N Engl J Med.* 2020; Wu, et al. A new coronavirus associated with human respiratory disease in China. *Nature.* 2020). Disease symptoms can range from mild flu-like to severe cases with life-threatening pneumonia (Huang, et al. Clinical features of patients infected with 2019 novel coronavirus in Wuhan, China. *Lancet.* 2020). The global situation is dynamically evolving, and on Jan. 30, 2020 the World Health Organization declared COVID-19 as a public health emergency of international concern (PHEIC).

SUMMARY

Provided herein are nucleic acid molecules encoding a SARS-CoV-2 spike antigen. According to some embodiments, the encoded SARS-CoV-2 spike antigen is a consensus antigen. In some embodiments, the nucleic acid molecule comprises: a nucleic acid sequence having at least about 90% identity over an entire length of the nucleic acid sequence set forth in nucleotides 55 to 3837 of SEQ ID NO: 2; a nucleic acid sequence having at least about 90% identity over an entire length of SEQ ID NO: 2; the nucleic acid sequence of nucleotides 55 to 3837 of SEQ ID NO: 2; the nucleic acid sequence of SEQ ID NO: 2; a nucleic acid sequence having at least about 90% identity over an entire length of SEQ ID NO: 3; the nucleic acid sequence of SEQ ID NO: 3; a nucleic acid sequence having at least about 90% identity over an entire length of nucleotides 55 to 3837 of SEQ ID NO: 5; a nucleic acid sequence having at least about 90% identity over an entire length of SEQ ID NO: 5; the nucleic acid sequence of nucleotides 55 to 3837 of SEQ ID NO: 5; the nucleic acid sequence of SEQ ID NO: 5; a nucleic acid sequence having at least about 90% identity over an entire length of SEQ ID NO: 6; or the nucleic acid sequence of SEQ ID NO: 6. Also provided herein are nucleic acid molecules encoding a SARS-CoV-2 spike antigen, wherein the SARS-CoV-2 spike antigen comprises: an amino acid sequence having at least about 90% identity over an entire length of residues 19 to 1279 of SEQ ID NO: 1; the amino acid sequence set forth in residues 19 to 1279 of SEQ ID NO: 1; an amino acid sequence having at least about 90% identity over an entire length of SEQ ID NO: 1; the amino acid sequence of SEQ ID NO: 1; an amino acid sequence having at least about 90% identity over an entire length of residues 19 to 1279 of SEQ ID NO: 4; an amino acid sequence having at least about 90% identity over an entire length of SEQ ID NO: 4; the amino acid sequence set forth in residues 19 to 1279 of SEQ ID NO: 4, or the amino acid sequence of SEQ ID NO: 4.

In some embodiments, the nucleic acid molecule encoding the SARS-CoV-2 antigen is incorporated into a viral particle.

Further provided are vectors comprising the nucleic acid molecule encoding the SARS-CoV-2 antigen. In some embodiments, the vector is an expression vector. The nucleic acid molecule may be operably linked to a regulatory element selected from a promoter and a poly-adenylation signal. The expression vector may be a plasmid or viral vector.

Immunogenic compositions comprising an effective amount of the vector or viral particle are disclosed. The immunogenic composition may comprise a pharmaceutically acceptable excipient, such as but not limited to, a buffer. The buffer may optionally be saline-sodium citrate buffer. In some embodiments, the immunogenic compositions comprise an adjuvant.

Also provided herein are SARS-CoV-2 spike antigens. According to some embodiments, the SARS-CoV-2 spike antigen is a consensus antigen. In some embodiments, the SARS-CoV-2 spike antigen comprises: an amino acid sequence having at least about 90% identity over an entire length of residues 19 to 1279 of SEQ ID NO: 1; the amino acid sequence set forth in residues 19 to 1279 of SEQ ID NO: 1; an amino acid sequence having at least about 90% identity over an entire length of SEQ ID NO: 1; the amino acid sequence of SEQ ID NO: 1; an amino acid sequence having at least about 90% identity over an entire length of residues 19 to 1279 of SEQ ID NO: 4; an amino acid sequence having at least about 90% identity over an entire length of SEQ ID NO: 4; the amino acid sequence set forth in residues 19 to 1279 of SEQ ID NO: 4; or the amino acid sequence of SEQ ID NO: 4.

Further provided herein are vaccines for the prevention or treatment of Severe Acute Respiratory Syndrome coronavirus 2 (SARS-CoV-2) infection. The vaccines comprising an effective amount of any one or combination of the aforementioned nucleic acid molecules, vectors, or antigens. According to some embodiments, the vaccine further comprises a pharmaceutically acceptable excipient. The pharmaceutically acceptable excipient may be a buffer, optionally saline-sodium citrate buffer. According to some embodiments, the vaccine further comprises an adjuvant.

Methods of inducing an immune response against Severe Acute Respiratory Syndrome coronavirus 2 (SARS-CoV-2) in a subject in need thereof are further provided. In come embodiments, the methods of inducing an immune response comprise administering an effective amount of any one or combination of the aforementioned nucleic acid molecules, vectors, immunogenic compositions, antigens, or vaccines to the subject. Also provided herein are methods of protecting a subject in need thereof from infection with SARS-CoV-2, the method comprising administering an effective amount of any one or combination of the aforementioned nucleic acid molecules, vectors, immunogenic compositions, antigens, or vaccines to the subject. Further provided are methods of treating SARS-CoV-2 infection in a subject in need thereof, the method comprising administering an effective amount of any one or combination of the aforementioned nucleic acid molecules, vectors, immunogenic compositions, antigens, or vaccines to the subject. In any of these methods, the administering may include at least one of electroporation and injection. According to some embodiments, the administering comprises parenteral administration, for example by intradermal, intramuscular, or subcutaneous injection, optionally followed by electroporation. In some embodiments of the disclosed methods, an initial dose of about 0.5 mg to about 2.0 mg of the nucleic acid molecule is administered to the subject, optionally the initial dose is 0.5 mg, 1.0 mg or 2.0 mg of the nucleic acid molecule. The methods may further involve administration of a subsequent dose of about 0.5 mg to about 2.0 mg of the nucleic acid molecule to the subject about four weeks after the initial dose, optionally wherein the subsequent dose is 0.5 mg, 1.0 mg or 2.0 mg of the nucleic acid molecule. In still further embodiments, the methods involve administration of one or more further subsequent doses of about 0.5 mg to about 2.0 mg of the nucleic acid molecule to the subject at least twelve weeks after the initial dose, optionally wherein the further subsequent dose is 0.5 mg, 1.0 mg, or 2.0 mg of the nucleic acid molecule. In any of these embodiments, INO-4800 or a biosimilar thereof is administered.

Also provided herein are uses of any one or combination of the disclosed nucleic acid molecules, vectors, immunogenic compositions, antigens, or vaccines in a method of inducing an immune response against Severe Acute Respiratory Syndrome coronavirus 2 (SARS-CoV-2) in a subject in need thereof. Further provided are uses of any one or combination of the disclosed nucleic acid molecules, vectors, immunogenic compositions, antigens, or vaccines in a method of protecting a subject from infection with Severe Acute Respiratory Syndrome coronavirus 2 (SARS-CoV-2). Also provided herein are uses of any one or combination of the disclosed nucleic acid molecules, vectors, immunogenic compositions, antigens, or vaccines in a method of treating a subject in need thereof against SARS-CoV-2 infection. In accordance with any of these uses, the nucleic acid molecule, the vector, the immunogenic composition, the antigen, or the vaccine may be administered to the subject by at least one of electroporation and injection. In some embodiments, the nucleic acid molecule, the vector, the immunogenic composition, the antigen, or the vaccine is parenterally administered to the subject, for example by intradermal, intramuscular, or subcutaneous injection, optionally followed by electroporation. In some embodiments of the disclosed uses, an initial dose of about 0.5 mg to about 2.0 mg of the nucleic acid molecule is administered to the subject, optionally the initial dose is 0.5 mg, 1.0 mg or 2.0 mg of the nucleic acid molecule. The uses may further involve administration of a subsequent dose of about 0.5 mg to about 2.0 mg of the nucleic acid molecule to the subject about four weeks after the initial dose, optionally wherein the subsequent dose is 0.5 mg, 1.0 mg or 2.0 mg of the nucleic acid molecule. In still further embodiments, the uses involve administration of one or more further subsequent doses of about 0.5 mg to about 2.0 mg of the nucleic acid molecule to the subject at least twelve weeks after the initial dose, optionally wherein the further subsequent dose is 0.5 mg, 1.0 mg, or 2.0 mg of the nucleic acid molecule. In any of these embodiments, INO-4800 or a biosimilar thereof is administered.

Further provided herein are uses of any one or combination of the disclosed nucleic acid molecules, vectors, immunogenic compositions, antigens, or vaccines in the preparation of a medicament. In some embodiments, the medicament is for treating or protecting against infection with Severe Acute Respiratory Syndrome coronavirus 2 (SARS-CoV-2). In some embodiments, the medicament is for treating or protecting against a disease or disorder associated with SARS-CoV-2 infection. In some embodiments, the medicament is for treating or protecting against Coronavirus Disease 2019 (COVID-19), Multisystem inflammatory syndrome in adults (MIS-A), or Multisystem inflammatory syndrome in children (MIS-C).

The invention further relates to a method of detecting a persistent cellular immune response in a subject, the method comprising the steps of: administering an immunogenic composition for inducing an immune response against a SARS-CoV-2 antigen to a subject in need thereof; isolating peripheral mononuclear cells (PBMCs) from the subject; stimulating the isolated PBMCs with a spike antigen comprising an amino acid sequence selected from the group consisting of: the amino acid sequence set forth in residues 19 to 1279 of SEQ ID NO: 1 the amino acid sequence of SEQ ID NO: 1; the amino acid sequence set forth in residues 19 to 1279 of SEQ ID NO: 4; or the amino acid sequence of SEQ ID NO: 4; or a fragment thereof comprising at least 20 amino acids; and detecting at least one of the number of cytokine expressing cells and the level of cytokine expression. In one embodiment, the step of detecting at least one of the number of cytokine expressing cells and the level of cytokine expression is performed using Enzyme-linked immunospot (ELISpot) or Intracellular Cytokine Staining (ICS) analysis using flow cytometry.

In one embodiment, the subject is administered an immunogenic composition comprising a nucleic acid molecule, wherein the nucleic acid molecule comprises a nucleotide sequence encoding a peptide comprising: an amino acid sequence having at least about 90% identity over an entire length of residues 19 to 1279 of SEQ ID NO: 1; the amino acid sequence set forth in residues 19 to 1279 of SEQ ID NO: 1; an amino acid sequence having at least about 90% identity over an entire length of SEQ ID NO: 1; the amino acid sequence of SEQ ID NO: 1; an amino acid sequence having at least about 90% identity over an entire length of residues 19 to 1279 of SEQ ID NO: 4; an amino acid sequence having at least about 90% identity over an entire length of SEQ ID NO: 4; the amino acid sequence set forth in residues 19 to 1279 of SEQ ID NO: 4; or the amino acid sequence of SEQ ID NO: 4.

BRIEF DESCRIPTION OF THE DRAWINGS

FIG. 1A shows a schematic diagram of SARS-CoV-2 synthetic DNA vaccine constructs, pGX9501 (matched) and pGX9503 (outlier (OL)) containing the IgE leader sequence and SARS-CoV-2 spike protein insert ("Covid-19 spike antigen" or "Covid-19 spike-OL antigen"). FIG. 1B shows results of an RT-PCR assay of RNA extract from COS-7 cells transfected in duplicate with pGX9501 or pGX9503. Extracted RNA was analyzed by RT-PCR using PCR assays designed for each target and for COS-7 β-Actin mRNA, used as an internal expression normalization gene. Delta $C_T$ ($\Delta C_T$) was calculated as the $C_T$ of the target minus the $C_T$ of β-Actin for each transfection concentration and is plotted against the log of the mass of pDNA transfected (Plotted as mean±SD). FIG. 1C shows analysis of in vitro expression of Spike protein after transfection of 293T cells with pGX9501, pGX9503 or MOCK plasmid by Western blot. 293T cell lysates were resolved on a gel and probed with a polyclonal anti-SARS Spike Protein. Blots were stripped then probed with an anti-β-actin loading control. FIG. 1D shows in vitro immunofluorescent staining of 293T cells transfected with 3 µg/well of pGX9501, pGX9503 or pVax (empty control vector). Expression of Spike protein was measured with polyclonal anti-SARS Spike Protein IgG and anti-IgG secondary. Cell nuclei were counterstained with DAPI. Images were captured using IMAGEXPRESS™ Pico automated cell imaging system.

FIG. 4A shows neutralization ID50 (mean±SD) in naïve and INO-4800 immunized mice. FIG. 4B shows relative luminescence units (RLU) for sera from naïve mice and mice vaccinated with INO-4800 as described in methods.

FIG. 5A shows SARS-CoV-2 S protein antigen binding of IgG in serial serum dilutions at day 0 and 14. Data shown represent mean OD450 nm values (mean+SD) for the 5 guinea pigs. FIG. 5B shows serum IgG binding titers (mean±SD) to SARS-CoV-2 S protein at day 14. P values determined by Mann-Whitney test.

FIG. 6A illustrates that soluble ACE2 receptor binds to CoV-2 full-length spike with an EC50 of 0.025 µg/ml. FIG. 6B illustrates that purified serum IgG from BALB/c mice (n of 5 per group) after second immunization with INO-4800 yields significant competition against ACE2 receptor. Serum IgG samples from the animals were run in triplicate. FIG. 6C illustrates that IgGs purified from n=5 mice day 7 post second immunization with INO-4800 show significant competition against ACE2 receptor binding to SARS-CoV-2 S 1+2 protein. The soluble ACE2 concentration for the competition assay is ~0.1 µg/ml. Bars represent the mean and standard deviation of AUC. FIG. 6D illustrates Hartley guinea pigs immunized on Day 0 and 14 with 100 µg INO-4800 or pVAX-empty vector as described in the methods. Day 28 collected sera (diluted 1:20) was added to SARS-CoV-2 coated wells prior to the addition of serial dilutions of ACE2 protein. Detection of ACE2 binding to SARS-CoV-2 S protein was measured. Sera collected from 5 INO-4800-treated and 3 pVAX-treated animals were used in this experiment. FIG. 6E illustrates serial dilutions of guinea pig sera collected on day 21 were added to SARS-CoV-2 coated wells prior to the addition of ACE2 protein. Detection of ACE2 binding to SARS-CoV-2 S protein was measured. Sera collected from 4 INO-4800-treated and 5 pVAX-treated guinea pigs were used in this experiment. FIG. 6F depicts IgGs purified from n=5 mice day 14 post second immunization with INO-4800 show competition against ACE2 receptor binding to SARS-CoV-2 Spike protein compared to pooled naïve mice IgGs. Naïve mice were run in a single column. Vaccinated mice were run in duplicate. If error bars are not visible, error is smaller than the data point.

In FIGS. 7A and 7C, bars represent the average of each group and error bars the standard deviation. **$p<0.01$ by Mann-Whitney U test.

(FIG. 12A-12G; left panel, 1 mg INO-4800; right panel, 2 mg INO-4800).

FIG. 14A demonstrates T cell responses following stimulation with matrix mapping SARS-CoV-2 peptide pools. Bars represent the mean+SD of 5 mice. FIG. 14B shows the map of the SARS-CoV-2 Spike protein and identification of immunodominant peptides in BALB/c mice. A known immunodominant SARS-CoV HLA-A2 epitope is included for comparison. FIG. 14B discloses SEQ ID NOS 26-35, respectively, in order of appearance.

(FIGS. 15A-15D) Correlation of throat viral load Log 10 cDNA copies mL-1 at day 1 (FIGS. 15A, 15B) and day 3 (FIGS. 15C, 15D) post SARS-CoV-2 challenge with microneutralization titers (FIGS. 15A, 15C) and RBD IgG binding endpoint titers (FIGS. 15B, 15D). (FIGS. 15E-15H) Same analysis for nasal viral loads. P and R values provided for two-sided non-parametric Spearman rank-correlation analyses. Control animals—red filled circles, INO-4800 X1—green filled circles and INO-4800 X2—blue filled circles.

In FIG. 17D, the humoral response in the 1.0 mg dose group and 2.0 mg dose group was assessed for the ability to bind whole spike protein (S1 and S2) (n=19, 1.0 mg; n=19, 2.0 mg). End point titers were calculated as the titer that exhibited an OD 3.0 SD above baseline, titers at baseline were set at 1. A response to live virus neutralization was a PRNT IC50≥10. In all graphs horizontal lines represent the Median and bars represent the Interquartile Range.

As shown in FIG. 18B, peptides spanning the entirety of the spike antigen were divided into pools and tested individually in ELISpot, with pools mapped to specific regions of the antigen. Three subjects are shown exemplifying the diversity of pool responses and associated magnitude across subjects. The pie chart represents the diversity of entirety of the 2.0 mg dose group. As illustrated in FIG. 18C, SARS-CoV-2 spike specific cytokine production was measured from CD4+ and CD8+ T cells via flow cytometry. Bars represent Mean response. Cytokine production is additionally broken out in FIG. 18D using CCR7 and CD45RA into Central Memory (CM), Effector Memory (EM) or Effector (E) differentiation status with data conveying what percentage of the overall cytokine response originates from what differentiated group. Pie charts represent the polyfunctionality of CD4+ and CD8+ T cells for each dose cohort are provided in FIG. 18E. IL-4 production by CD4+ T cells for each dose cohort is illustrated in FIG. 18F. Horizontal lines represent Mean response. Graphs represent all evaluable subjects. Statistical analyses were performed on all paired datasets. Those that were significant are noted within the figure, lack of notation in the figure represents lack of statistical significance. FIG. 18G provides a heat map of each subject in the 2.0 mg dose group and the percentage of their ELISpot response dedicated to each pool covering the SARS-CoV-2 spike antigen.

(FIGS. 24A&24D) Lines represent group geometric means with 95% CI. Area under the curve (AUC) of viral loads for throat swabs (FIG. 24B) and nasal swabs (FIG. 24E) for each experimental group. Peak viral loads measured in each animal during the challenge period for throat swabs (FIG. 24C) and nasal swabs (FIG. 24F). LLOQ (lower limit of quantification, 3.80 log copies/ml) and LLOD (lower limit of detection, 3.47 log copies/ml). Positive samples detected below the LLOQ were assigned the value of 3.80 log copies/ml. *p≤0.05 with Mann-Whitney t test.

(FIGS. 25A and 25D) Lines represent group geometric means with 95% CI. Area under the curve (AUC) of viral loads for throat swabs (FIG. 25B) and nasal swabs (FIG. 25E) for each experimental group. Peak viral loads measured in each animal during the challenge period for throat swabs (FIG. 25C) and nasal swabs (FIG. 25F). LLOQ (4.11 log copies/mL) and LLOD (3.06 log copies/mL). Positive samples detected below the LLOQ were assigned the value of 3.81 log copies/ml.

FIG. 29C provides a heat map illustration of histopathology scoring for each parameter for individual animals. Total CT score (FIG. 29E). CT radiology scores for individual animals (FIGS. 29D-29G). FIG. 29D: The extent of abnormality as a percentage of the lung affected. (FIG. 29E: COVID disease pattern with scoring based on presence of nodules, ground glass opacity, and consolidation. FIG. 29F: Zone classification (lung is divided into 12 zones and each zone showing abnormalities is attributed 1 point). FIG. 29G: Total cumulative CT score (Pattern+Zone scores). Line on graphs represent median value of group. *p≤0.05 with Mann-Whitney t test.

FIG. 32A: CD4+ and CD8+ T cell gating strategy; singlets were gated on (i), then lymphocytes (ii) followed by live CD45+ cells (iii). Next CD3+ cells were gated (iv) and from that population CD4+ (v) and CD8+ (vi) T-cells were gated. IFNγ+ cells were gated from each of the CD4+ (vii) and CD8+ (viii) T-cell populations. FIG. 32B: The percentage of CD4+ and CD8+ T cells producing IFNγ is depicted. Bars represent mean+SD. 4 BALB/c and 4 C57BL/6 mice were used in this study. *p<0.05, Mann Whitney test.

FIG. 33A: The study outline showing the vaccination regimen and blood collection timepoints. FIG. 33B: Schematic of SARS-CoV-2 spike protein. FIG. 33C: SARS-CoV-2 S1+S2 ECD, S1, RBD and S2 protein antigen binding of IgG in serially diluted NHP sera collected on Week 0, 2, 6, 12 and 15. Data represents the mean endpoint titers for each individual NHP. (FIGS. 33D and 33E) Pseudoneutralization assay using NHP sera, showing the presence of SARS-CoV-2 specific neutralizing antibodies against the D614 (FIG. 33D) and G614 (FIG. 33E) variants of SARS-CoV-2. FIG. 33F and FIG. 33G: Serum collected at Week 6 from INO-4800 vaccinated NHPs inhibited ACE2 binding. FIG. 33F: Plate-based ACE2 competition assay. FIG. 33G: Flow-based ACE2 inhibition assay showing that inhibition of ACE2 binding in serially diluted NHP sera. FIG. 33H: T cell responses were measured by IFN-γ ELISpot in PB; ICs harvested at weeks 0, 2, 6 and 15, and stimulated for 20 h with overlapping peptide pools spanning the SARS-CoV-2 Spike protein. Bars represent the mean+SD.

FIG. 37A: Study outline. FIG. 37B: IgG binding ELISA. SARS-CoV-2 S1+S2 and SARS-CoV-2 RBD protein antigen binding of IgG in diluted NHP sera collected prior to challenge, during challenge and post challenge. FIG. 37C: Pseudo-neutralization assay using NHP sera, showing the presence of SARS-CoV-2 specific neutralizing antibodies against the D614 and G614 variants of SARS-CoV-2 before and after viral challenge in INO-4800 vaccinated (top panels) and naïve animals (bottom panels).

FIGS. 40A through 40F depict viral loads in the BAL fluid and Nasal swabs after viral challenge. At week 17 naïve and INO-4800 immunized (5 per group) rhesus macaques were challenged by intranasal and intracheal administration of $1.1 \times 10^4$ PFU SARS-CoV-2 (US-WA1 isolate). FIG. 40A and FIG. 40D: Log sgmRNA copies/ml (FIG. 40A) in BAL (FIG. 40A), and NS copies/swab (FIG. 40D) were measured at multiple timepoints following challenge in naïve (left panels) and INO-4800 vaccinated (right panels) animals. FIG. 40B and FIG. 40E: Peak viral loads (Between days 1 to 7) in BAL (FIG. 40B) and NS (FIG. 40E) following challenge. FIG. 40C and FIG. 40F: Viral RNA in BAL and NS at day 7 after challenge. Blue and Red lines reflect median viral loads. Mann-Whitney test P values are provided (FIG. 40B and FIG. 40C).

DETAILED DESCRIPTION OF ILLUSTRATIVE EMBODIMENTS

Definitions

Figure 1A:
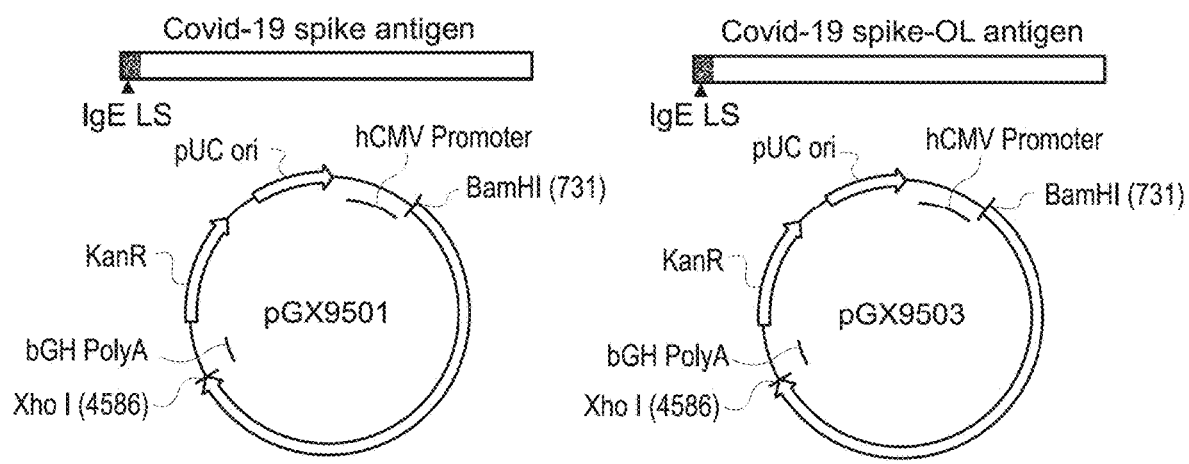
FIGS. 1A, 1B, 1C, and 1D illustrate the design and expression of SARS-CoV-2 synthetic DNA vaccine constructs.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The term "comprising" is intended to include examples encompassed by the terms "consisting essentially of" and "consisting of"; similarly, the term "consisting essentially of" is intended to include examples encompassed by the term "consisting of" The present disclosure also contemplates other embodiments "comprising," "consisting of" and "consisting essentially of" the embodiments or elements presented herein, whether explicitly set forth or not.

It is to be appreciated that certain features of the disclosed materials and methods which are, for clarity, described herein in the context of separate embodiments, may also be provided in combination in a single embodiment. Conversely, various features of the disclosed materials and methods that are, for brevity, described in the context of a single embodiment, may also be provided separately or in any subcombination.

The singular forms "a," "and" and "the" include plural references unless the context clearly dictates otherwise.

The term "about" when used in reference to numerical ranges, cutoffs, or specific values is used to indicate that the recited values may vary by up to as much as 10% from the listed value. Thus, the term "about" is used to encompass variations of ±10% or less, variations of ±5% or less, variations of ±1% or less, variations of ±0.5% or less, or variations of ±0.1% or less from the specified value. When values are expressed as approximations by use of the antecedent "about," it will be understood that the particular value forms another embodiment. Reference to a particular numerical value includes at least that particular value unless the context clearly dictates otherwise.

"Adjuvant" as used herein means any molecule added to the vaccine described herein to enhance the immunogenicity of the antigen.

"Antibody" as used herein means an antibody of classes IgG, IgM, IgA, IgD or IgE, or fragments, fragments or derivatives thereof, including Fab, F(ab') 2, Fd, and single chain antibodies, diabodies, bispecific antibodies, bifunctional antibodies and derivatives thereof. The antibody can be an antibody isolated from the serum sample of mammal, a polyclonal antibody, affinity purified antibody, or mixtures thereof which exhibits sufficient binding specificity to a desired epitope or a sequence derived therefrom.

The term "biosimilar" (of an approved reference product/biological drug, i.e., reference listed drug) refers to a biological product that is highly similar to the reference product notwithstanding minor differences in clinically inactive components with no clinically meaningful differences between the biosimilar and the reference product in terms of safety, purity and potency, based upon data derived from (a) analytical studies that demonstrate that the biological product is highly similar to the reference product notwithstanding minor differences in clinically inactive components; (b) animal studies (including the assessment of toxicity); and/or (c) a clinical study or studies (including the assessment of immunogenicity and pharmacokinetics or pharmacodynamics) that are sufficient to demonstrate safety, purity, and potency in one or more appropriate conditions of use for which the reference product is licensed and intended to be used and for which licensure is sought for the biosimilar. The biosimilar may be an interchangeable product that may be substituted for the reference product at the pharmacy without the intervention of the prescribing healthcare professional. To meet the additional standard of "interchangeability," the biosimilar is to be expected to produce the same clinical result as the reference product in any given patient and, if the biosimilar is administered more than once to an individual, the risk in terms of safety or diminished efficacy of alternating or switching between the use of the biosimilar and the reference product is not greater than the risk of using the reference product without such alternation or switch. The biosimilar utilizes the same mechanisms of action for the proposed conditions of use to the extent the mechanisms are known for the reference product. The condition or conditions of use prescribed, recommended, or suggested in the labeling proposed for the biosimilar have been previously approved for the reference product. The route of administration, the dosage form, and/or the strength of the biosimilar are the same as those of the reference product and the biosimilar is manufactured, processed, packed or held in a facility that meets standards designed to assure that the biosimilar continues to be safe, pure and potent. The biosimilar may include minor modifications in the amino acid sequence when compared to the reference product, such as N- or C-terminal truncations that are not expected to change the biosimilar performance.

"Coding sequence" or "encoding nucleic acid" as used herein means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of an individual or mammal to which the nucleic acid is administered.

"Complement" or "complementary" as used herein means Watson-Crick (e.g., A-T/U and C-G) or Hoogsteen base pairing between nucleotides or nucleotide analogs of nucleic acid molecules.

"Consensus" or "Consensus Sequence" as used herein may mean a synthetic nucleic acid sequence, or corresponding polypeptide sequence, constructed based on analysis of an alignment of multiple subtypes of a particular antigen. The sequence may be used to induce broad immunity against multiple subtypes, serotypes, or strains of a particular antigen. Synthetic antigens, such as fusion proteins, may be manipulated to generate consensus sequences (or consensus antigens).

"Electroporation," "electro-permeabilization," or "electro-kinetic enhancement" ("EP") as used interchangeably herein means the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

"Fragment" as used herein means a nucleic acid sequence or a portion thereof that encodes a polypeptide capable of eliciting an immune response in a mammal. The fragments can be DNA fragments selected from at least one of the various nucleotide sequences that encode protein fragments set forth below.

"Fragment" or "immunogenic fragment" with respect to polypeptide sequences means a polypeptide capable of eliciting an immune response in a mammal that cross reacts with a full-length wild type strain SARS-CoV-2 antigen. Fragments of consensus proteins can comprise at least 10%, at least 20%, at least 30%, at least 40%, at least 50%, at least 60%, at least 70%, at least 80%, at least 90% or at least 95% of a consensus protein. In some embodiments, fragments of consensus proteins can comprise at least 20 amino acids or more, at least 30 amino acids or more, at least 40 amino acids or more, at least 50 amino acids or more, at least 60 amino acids or more, at least 70 amino acids or more, at least 80 amino acids or more, at least 90 amino acids or more, at least 100 amino acids or more, at least 110 amino acids or more, at least 120 amino acids or more, at least 130 amino acids or more, at least 140 amino acids or more, at least 150 amino acids or more, at least 160 amino acids or more, at least 170 amino acids or more, at least 180 amino acids or more, at least 190 amino acids or more, at least 200 amino acids or more, at least 210 amino acids or more, at least 220 amino acids or more, at least 230 amino acids or more, or at least 240 amino acids or more of a consensus protein.

As used herein, the term "genetic construct" refers to the DNA or RNA molecules that comprise a nucleotide sequence which encodes a protein. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

"Identical" or "identity" as used herein in the context of two or more nucleic acids or polypeptide sequences, means that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

"Immune response" as used herein means the activation of a host's immune system, e.g., that of a mammal, in response to the introduction of antigen. The immune response can be in the form of a cellular or humoral response, or both.

"Nucleic acid" or "oligonucleotide" or "polynucleotide" or "nucleic acid molecule" as used herein means at least two nucleotides covalently linked together. The depiction of a single strand also defines the sequence of the complementary strand. Thus, a nucleic acid also encompasses the complementary strand of a depicted single strand. Many variants of a nucleic acid can be used for the same purpose as a given nucleic acid. Thus, a nucleic acid also encompasses substantially identical nucleic acids and complements thereof. A single strand provides a probe that can hybridize to a target sequence under stringent hybridization conditions. Thus, a nucleic acid also encompasses a probe that hybridizes under stringent hybridization conditions.

Nucleic acids can be single stranded or double-stranded or can contain portions of both double-stranded and single-stranded sequence. The nucleic acid can be DNA, both genomic and cDNA, RNA, or a hybrid, where the nucleic acid can contain combinations of deoxyribo- and ribo-nucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods.

"Operably linked" as used herein means that expression of a gene is under the control of a promoter with which it is spatially connected. A promoter can be positioned 5' (upstream) or 3' (downstream) of a gene under its control. The distance between the promoter and a gene can be approximately the same as the distance between that promoter and the gene it controls in the gene from which the promoter is derived. As is known in the art, variation in this distance can be accommodated without loss of promoter function.

A "peptide," "protein," or "polypeptide" as used herein can mean a linked sequence of amino acids and can be natural, synthetic, or a modification or combination of natural and synthetic.

"Promoter" as used herein means a synthetic or naturally derived molecule which is capable of conferring, activating or enhancing expression of a nucleic acid in a cell. A promoter can comprise one or more specific transcriptional regulatory sequences to further enhance expression and/or to alter the spatial expression and/or temporal expression of same. A promoter can also comprise distal enhancer or repressor elements, which can be located as much as several thousand base pairs from the start site of transcription. A promoter can be derived from sources including viral, bacterial, fungal, plants, insects, and animals. A promoter can regulate the expression of a gene component constitutively or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, and CMV IE promoter.

"Signal peptide" and "leader sequence" are used interchangeably herein and refer to an amino acid sequence that can be linked at the amino terminus of a SARS-CoV-2 protein set forth herein. Signal peptides/leader sequences typically direct localization of a protein. Signal peptides/leader sequences used herein preferably facilitate secretion of the protein from the cell in which it is produced. Signal peptides/leader sequences are often cleaved from the remainder of the protein, often referred to as the mature protein, upon secretion from the cell. Signal peptides/leader sequences are linked at the N terminus of the protein.

"Subject" as used herein can mean a mammal that wants or is in need of being immunized with a herein described immunogenic composition or vaccine. The mammal can be a human, chimpanzee, guinea pig, dog, cat, horse, cow, mouse, rabbit, or rat.

"Substantially identical" as used herein can mean that a first and second amino acid sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 or more amino acids. Substantially identical can also mean that a first nucleic acid sequence and a second nucleic acid sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 or more nucleotides.

"Treatment" or "treating," as used herein can mean protecting of an animal from a disease through means of preventing, suppressing, repressing, or completely eliminating the disease. Preventing the disease involves administering an immunogenic composition or a vaccine of the present invention to an animal prior to onset of the disease. Suppressing the disease involves administering an immunogenic composition or a vaccine of the present invention to an animal after induction of the disease but before its clinical appearance. Repressing the disease involves administering an immunogenic composition or a vaccine of the present invention to an animal after clinical appearance of the disease.

As used herein, unless otherwise noted, the term "clinically proven" (used independently or to modify the terms "safe" and/or "effective") shall mean that it has been proven by a clinical trial wherein the clinical trial has met the approval standards of U.S. Food and Drug Administration, EMA or a corresponding national regulatory agency. For example, proof may be provided by the clinical trial(s) described in the examples provided herein.

The term "clinically proven safe", as it relates to a dose, dosage regimen, treatment or method with a SARS-CoV-2 antigen (for example, a SARS-CoV-2 spike antigen administered as pGX9501 or INO-4800 or a biosimilar thereof) refers to a favorable risk:benefit ratio with an acceptable frequency and/or acceptable severity of treatment-emergent adverse events (referred to as AEs or TEAEs) compared to the standard of care or to another comparator. An adverse event is an untoward medical occurrence in a patient administered a medicinal product. One index of safety is the National Cancer Institute (NCI) incidence of adverse events (AE) graded per Common Toxicity Criteria for Adverse Events CTCAE v4.03.

The terms "clinically proven efficacy" and "clinically proven effective" as used herein in the context of a dose, dosage regimen, treatment or method refer to the effectiveness of a particular dose, dosage or treatment regimen. Efficacy can be measured based on change in the course of the disease in response to an agent of the present invention. For example, a SARS-CoV-2 antigen (for example, a SARS- CoV-2 spike antigen administered as pGX9501 or INO-4800 or a biosimilar thereof) is administered to a patient in an amount and for a time sufficient to induce an improvement, preferably a sustained improvement, in at least one indicator that reflects the severity of the disorder that is being treated. Various indicators that reflect the extent of the subject's illness, disease or condition may be assessed for determining whether the amount and time of the treatment is sufficient. Such indicators include, for example, clinically recognized indicators of disease severity, symptoms, or manifestations of the disorder in question. The degree of improvement generally is determined by a physician, who may make this determination based on signs, symptoms, biopsies, or other test results, and who may also employ questionnaires that are administered to the subject, such as quality-of-life questionnaires developed for a given disease. For example, a SARS-CoV-2 antigen (for example, a SARS-CoV-2 spike antigen administered as pGX9501 or INO-4800 or a biosimilar thereof) may be administered to achieve an improvement in a patient's condition related to SARS-CoV-2 infection. Improvement may be indicated by an improvement in an index of disease activity, by amelioration of clinical symptoms or by any other measure of disease activity.

"Variant" used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

Variant can further be defined as a peptide or polypeptide that differs in amino acid sequence by the insertion, deletion, or conservative substitution of amino acids, but retain at least one biological activity. Representative examples of "biological activity" include the ability to be bound by a specific antibody or to promote an immune response. Variant can also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., *J. Mol. Biol.* 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. Substitution of amino acids having similar hydrophilicity values can result in peptides retaining biological activity, for example immunogenicity, as is understood in the art. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant may be a nucleic acid sequence that is substantially identical over the full length of the full gene sequence or a fragment thereof. The nucleic acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant may be an amino acid sequence that is substantially identical over the full length of the amino acid sequence or fragment thereof. The amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

"Vector" as used herein means a nucleic acid sequence containing an origin of replication. A vector can be a viral vector, bacteriophage, bacterial artificial chromosome or yeast artificial chromosome. A vector can be a DNA or RNA vector. A vector can be a self-replicating extrachromosomal vector, and preferably, is a DNA plasmid.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

Nucleic Acid Molecules, Antigens, and Immunogenic Compositions

Provided herein are immunogenic compositions, such as vaccines, comprising a nucleic acid molecule encoding a SARS-CoV-2 antigen, a fragment thereof, a variant thereof, or a combination thereof. Also provided herein are immunogenic compositions, such as vaccines, comprising a SARS-CoV-2 antigen, a fragment thereof, a variant thereof, or a combination thereof. The immunogenic compositions can be used to protect against and treat any number of strains of SARS-CoV-2, thereby treating, preventing, and/or protecting against SARS-CoV-2-based pathologies. The immunogenic compositions can significantly induce an immune response of a subject administered the immunogenic compositions, thereby protecting against and treating SARS-CoV-2 infection.

The immunogenic composition can be a DNA vaccine, a peptide vaccine, or a combination DNA and peptide vaccine. The DNA vaccine can include a nucleic acid molecule encoding the SARS-CoV-2 antigen. The nucleic acid molecule can be DNA, RNA, cDNA, a variant thereof, a fragment thereof, or a combination thereof. The nucleic acid molecule can also include additional sequences that encode linker, leader, or tag sequences that are linked to the nucleic acid molecule encoding the SARS-CoV-2 antigen by a peptide bond. The peptide vaccine can include a SARS-CoV-2 antigenic peptide, a SARS-CoV-2 antigenic protein, a variant thereof, a fragment thereof, or a combination thereof. The combination DNA and peptide vaccine can include the above described nucleic acid molecule encoding the SARS-CoV-2 antigen and the SARS-CoV-2 antigenic peptide or protein, in which the SARS-CoV-2 antigenic peptide or protein and the encoded SARS-CoV-2 antigen have the same amino acid sequence.

The disclosed immunogenic compositions can elicit both humoral and cellular immune responses that target the SARS-CoV-2 antigen in the subject administered the immunogenic composition. The disclosed immunogenic compositions can elicit neutralizing antibodies and immunoglobulin G (IgG) antibodies that are reactive with the SARS-CoV-2 spike antigen. The immunogenic composition can also elicit CD8+ and CD4+ T cell responses that are reactive to the SARS-CoV-2 antigen and produce interferon-gamma (IFN-γ), tumor necrosis factor alpha (TNF-α), and interleukin-2 (IL-2).

The immunogenic composition can induce a humoral immune response in the subject administered the immunogenic composition. The induced humoral immune response can be specific for the SARS-CoV-2 antigen. The induced humoral immune response can be reactive with the SARS-CoV-2 antigen. The humoral immune response can be induced in the subject administered the vaccine by about 1.5-fold to about 16-fold, about 2-fold to about 12-fold, or about 3-fold to about 10-fold. The humoral immune response can be induced in the subject administered the vaccine by at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 15.5-fold, or at least about 16.0-fold.

The humoral immune response induced by the immunogenic composition can include an increased level of neutralizing antibodies associated with the subject administered the immunogenic composition as compared to a subject not administered the immunogenic composition. The neutralizing antibodies can be specific for the SARS-CoV-2 antigen. The neutralizing antibodies can be reactive with the SARS-CoV-2 antigen. The neutralizing antibodies can provide protection against and/or treatment of SARS-CoV-2 infection and its associated pathologies in the subject administered the immunogenic composition.

The humoral immune response induced by the immunogenic composition can include an increased level of IgG antibodies associated with the subject administered the immunogenic composition as compared to a subject not administered the immunogenic composition. These IgG antibodies can be specific for the SARS-CoV-2 antigen. These IgG antibodies can be reactive with the SARS-CoV-2 antigen. The level of IgG antibody associated with the subject administered the immunogenic composition can be increased by about 1.5-fold to about 16-fold, about 2-fold to about 12-fold, or about 3-fold to about 10-fold as compared to the subject not administered the immunogenic composition. The level of IgG antibody associated with the subject administered the immunogenic composition can be increased by at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 15.5-fold, or at least about 16.0-fold as compared to the subject not administered the immunogenic composition.

The immunogenic composition can induce a cellular immune response in the subject administered the immunogenic composition. The induced cellular immune response can be specific for the SARS-CoV-2 antigen. The induced cellular immune response can be reactive to the SARS-CoV-2 antigen. The induced cellular immune response can include eliciting a CD8+ T cell response. The elicited CD8+ T cell response can be reactive with the SARS-CoV-2 antigen. The elicited CD8+ T cell response can be polyfunctional. The induced cellular immune response can include eliciting a CD8+ T cell response, in which the CD8+ T cells produce interferon-gamma (IFN-γ), tumor necrosis factor alpha (TNF-α), interleukin-2 (IL-2), or a combination of IFN-γ and TNF-α.

The induced cellular immune response can include an increased CD8+ T cell response associated with the subject administered the immunogenic composition as compared to the subject not administered the immunogenic composition. The CD8+ T cell response associated with the subject administered the immunogenic composition can be increased by about 2-fold to about 30-fold, about 3-fold to about 25-fold, or about 4-fold to about 20-fold as compared to the subject not administered the immunogenic composition. The CD8+ T cell response associated with the subject administered the immunogenic composition can be increased by at least about 1.5-fold, at least about 2.0-fold, at least about 3.0-fold, at least about 4.0-fold, at least about 5.0-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 16.0-fold, at least about 17.0-fold, at least about 18.0-fold, at least about 19.0-fold, at least about 20.0-fold, at least about 21.0-fold, at least about 22.0-fold, at least about 23.0-fold, at least about 24.0-fold, at least about 25.0-fold, at least about 26.0-fold, at least about 27.0-fold, at least about 28.0-fold, at least about 29.0-fold, or at least about 30.0-fold as compared to the subject not administered the immunogenic composition.

The induced cellular immune response can include an increased frequency of CD3+CD8+ T cells that produce IFN-γ. The frequency of CD3+CD8+IFN-γ+ T cells associated with the subject administered the immunogenic composition can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold as compared to the subject not administered the immunogenic composition.

The induced cellular immune response can include an increased frequency of CD3+CD8+ T cells that produce TNF-α. The frequency of CD3+CD8+TNF-α+ T cells associated with the subject administered the immunogenic composition can be increased by at least about 2-fold, 3-fold, 4-fold, 5-fold, 6-fold, 7-fold, 8-fold, 9-fold, 10-fold, 11-fold, 12-fold, 13-fold, or 14-fold as compared to the subject not administered the immunogenic composition.

The induced cellular immune response can include an increased frequency of CD3+CD8+ T cells that produce IL-2. The frequency of CD3+CD8+IL-2+ T cells associated with the subject administered the immunogenic composition can be increased by at least about 0.5-fold, 1.0-fold, 1.5-fold, 2.0-fold, 2.5-fold, 3.0-fold, 3.5-fold, 4.0-fold, 4.5-fold, or 5.0-fold as compared to the subject not administered the immunogenic composition.

The induced cellular immune response can include an increased frequency of CD3+CD8+ T cells that produce both IFN-γ and TNF-α. The frequency of CD3+CD8+IFN-γ+TNF-α+ T cells associated with the subject administered the immunogenic composition can be increased by at least about 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, 100-fold, 110-fold, 120-fold, 130-fold, 140-fold, 150-fold, 160-fold, 170-fold, or 180-fold as compared to the subject not administered the immunogenic composition.

The cellular immune response induced by the immunogenic composition can include eliciting a CD4+ T cell response. The elicited CD4+ T cell response can be reactive with the SARS-CoV-2 antigen. The elicited CD4+ T cell response can be polyfunctional. The induced cellular immune response can include eliciting a CD4+ T cell response, in which the CD4+ T cells produce IFN-γ, TNF-α, IL-2, or a combination of IFN-γ and TNF-α.

The induced cellular immune response can include an increased frequency of CD3+CD4+ T cells that produce IFN-γ. The frequency of CD3+CD4+IFN-γ+ T cells associated with the subject administered the immunogenic composition can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold as compared to the subject not administered the immunogenic composition.

The induced cellular immune response can include an increased frequency of CD3+CD4+ T cells that produce TNF-α. The frequency of CD3+CD4+TNF-α+ T cells associated with the subject administered the immunogenic composition can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 21-fold, or 22-fold as compared to the subject not administered the immunogenic composition.

The induced cellular immune response can include an increased frequency of CD3+CD4+ T cells that produce IL-2. The frequency of CD3+CD4+IL-2+ T cells associated with the subject administered the immunogenic composition can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 21-fold, 22-fold, 23-fold, 24-fold, 25-fold, 26-fold, 27-fold, 28-fold, 29-fold, 30-fold, 31-fold, 32-fold, 33-fold, 34-fold, 35-fold, 36-fold, 37-fold, 38-fold, 39-fold, 40-fold, 45-fold, 50-fold, 55-fold, or 60-fold as compared to the subject not administered the immunogenic composition.

The induced cellular immune response can include an increased frequency of CD3+CD4+ T cells that produce both IFN-γ and TNF-α. The frequency of CD3+CD4+IFN-γ+TNF-α+ associated with the subject administered the immunogenic composition can be increased by at least about 2-fold, 2.5-fold, 3.0-fold, 3.5-fold, 4.0-fold, 4.5-fold, 5.0-fold, 5.5-fold, 6.0-fold, 6.5-fold, 7.0-fold, 7.5-fold, 8.0-fold, 8.5-fold, 9.0-fold, 9.5-fold, 10.0-fold, 10.5-fold, 11.0-fold, 11.5-fold, 12.0-fold, 12.5-fold, 13.0-fold, 13.5-fold, 14.0-fold, 14.5-fold, 15.0-fold, 15.5-fold, 16.0-fold, 16.5-fold, 17.0-fold, 17.5-fold, 18.0-fold, 18.5-fold, 19.0-fold, 19.5-fold, 20.0-fold, 21-fold, 22-fold, 23-fold 24-fold, 25-fold, 26-fold, 27-fold, 28-fold, 29-fold, 30-fold, 31-fold, 32-fold, 33-fold, 34-fold, or 35-fold as compared to the subject not administered the immunogenic composition.

The immunogenic composition of the present invention can have features required of effective immunogenic compositions such as being safe so the immunogenic composition itself does not cause illness or death; is protective against illness resulting from exposure to live pathogens such as viruses or bacteria; induces neutralizing antibody to prevent invention of cells; induces protective T cells against intracellular pathogens; and provides ease of administration, few side effects, biological stability, and low cost per dose.

The immunogenic composition can further induce an immune response when administered to different tissues such as the muscle or skin. The immunogenic composition can further induce an immune response when administered via electroporation, or injection, or subcutaneously, or intramuscularly.

a. SARS-CoV-2 Antigen and Nucleic Acid Molecules Encoding the Same

As described above, provided herein are immunogenic compositions comprising a nucleic acid molecule encoding a SARS-CoV-2 antigen, a fragment thereof, a variant thereof, or a combination thereof. Also provided herein are immunogenic compositions comprising a SARS-CoV-2 antigen, a fragment thereof, a variant thereof, or a combination thereof.

Upon binding cell surface proteins and membrane fusion, the coronavirus enters the cell and its singled-stranded RNA genome is released into the cytoplasm of the infected cell. The singled-stranded RNA genome is a positive strand and thus, can be translated into a RNA polymerase, which produces additional viral RNAs that are minus strands. Accordingly, the SARS-CoV-2 antigen can also be a SARS-CoV-2 RNA polymerase.

The viral minus RNA strands are transcribed into smaller, subgenomic positive RNA strands, which are used to translate other viral proteins, for example, nucleocapsid (N) protein, envelope (E) protein, and matrix (M) protein. Accordingly, the SARS-CoV-2 antigen can comprise a SARS-CoV-2 nucleocapsid protein, a SARS-CoV-2 envelope protein, a SARS-CoV-2 matrix protein, or a fragment of the S1 subunit comprising the SARS-CoV-2 Spike Receptor Binding Domain (RBD).

The viral minus RNA strands can also be used to replicate the viral genome, which is bound by nucleocapsid protein. Matrix protein, along with spike protein, is integrated into the endoplasmic reticulum of the infected cell. Together, the nucleocapsid protein bound to the viral genome and the membrane-embedded matrix and spike proteins are budded into the lumen of the endoplasmic reticulum, thereby encasing the viral genome in a membrane. The viral progeny are then transported by golgi vesicles to the cell membrane of the infected cell and released into the extracellular space by endocytosis.

Coronaviruses, including SARS-CoV-2, are encapsulated by a membrane and have a type 1 membrane glycoprotein known as spike (S) protein, which forms protruding spikes on the surface of the coronavirus. The SARS-CoV-2 S protein is a class I membrane fusion protein, which is the major envelope protein on the surface of coronaviruses. The spike protein facilitates binding of the coronavirus to proteins located on the surface of a cell, for example, the metalloprotease amino peptidase N, and mediates cell-viral membrane fusion. In particular, the spike protein contains an S1 subunit that facilitates binding of the coronavirus to cell surface proteins. Accordingly, the S1 subunit of the spike protein controls which cells are infected by the coronavirus.

The spike protein also contains a S2 subunit, which is a transmembrane subunit that facilitates viral and cellular membrane fusion. Accordingly, the SARS-CoV-2 antigen can comprise a SARS-CoV-2 spike protein, a S1 subunit of a SARS-CoV-2 spike protein, or a S2 subunit of a SARS-CoV-2 spike protein.

In some embodiments, the SARS-CoV-2 antigen can be a SARS-CoV-2 spike protein, a SARS-CoV-2 RNA polymerase, a SARS-CoV-2 nucleocapsid protein, a SARS-CoV-2 envelope protein, a SARS-CoV-2 matrix protein, a fragment thereof, a variant thereof, or a combination thereof.

The SARS-CoV-2 antigen can be a SARS-CoV-2 spike antigen, a fragment thereof, a variant thereof, or a combination thereof. The SARS-CoV-2 spike antigen is capable of eliciting an immune response in a mammal against one or more SARS-CoV-2 strains. The SARS-CoV-2 spike antigen can comprise an epitope(s) that makes it particularly effective as an immunogen against which an anti-SARS-CoV-2 immune response can be induced.

The SARS-CoV-2 antigen can be a consensus antigen derived from two or more strains of SARS-CoV-2. In some embodiments, the SARS-CoV-2 antigen is a SARS-CoV-2 consensus spike antigen. The SARS-CoV-2 consensus spike antigen can be derived from the sequences of spike antigens from strains of SARS-CoV-2, and thus, the SARS-CoV-2 consensus spike antigen is unique. In some embodiments, the SARS-CoV-2 consensus spike antigen can be an outlier spike antigen, having a greater amino acid sequence divergence from other SARS-CoV-2 spike proteins. Accordingly, the immunogenic compositions of the present invention are widely applicable to multiple strains of SARS-CoV-2 because of the unique sequences of the SARS-CoV-2 consensus spike antigen. These unique sequences allow the vaccine to be universally protective against multiple strains of SARS-CoV-2, including genetically diverse variants of SARS-CoV-2. Nucleic acid molecules encoding the SARS-CoV-2 antigen can be modified for improved expression. Modification can include codon optimization, RNA optimization, addition of a kozak sequence for increased translation initiation, and/or the addition of an immunoglobulin leader sequence to increase the immunogenicity of the SARS-CoV-2 antigen. The SARS-CoV-2 spike antigen can comprise a signal peptide such as an immunoglobulin signal peptide, for example, but not limited to, an immunoglobulin E (IgE) or immunoglobulin (IgG) signal peptide. In some embodiments, the SARS-CoV-2 spike antigen can comprise a hemagglutinin (HA) tag. The SARS-CoV-2 spike antigen can be designed to elicit stronger and broader cellular and/or humoral immune responses than a corresponding codon optimized spike antigen.

In some embodiments, the SARS-CoV-2 antigen comprises an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% identity over an entire length of residues 19 to 1279 of SEQ ID NO: 1. In some embodiments the SARS-CoV-2 antigen comprises the amino acid sequence set forth in residues 19 to 1279 of SEQ ID NO: 1. In some embodiments, the SARS-CoV-2 antigen comprises an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% identity over an entire length of SEQ ID NO: 1. In some embodiments the SARS-CoV-2 antigen comprises the amino acid sequence of SEQ ID NO: 1. In some embodiments the nucleic acid molecule encoding the SARS-CoV-2 antigen comprises the nucleotide sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% identity to the sequence set forth in nucleotides 55 to 3837 of SEQ ID NO:2, SEQ ID NO: 2, or SEQ ID NO: 3.

In some embodiments the SARS-CoV-2 antigen comprises an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% identity over an entire length of residues 19 to 1279 of SEQ ID NO: 4 or over an entire length of SEQ ID NO: 4. In some embodiments the SARS-CoV-2 antigen comprises the amino acid sequence set forth in residues 19 to 1279 of SEQ ID NO: 4. In some embodiments the SARS-CoV-2 antigen comprises the amino acid sequence of SEQ ID NO: 4. In some embodiments the nucleic acid molecule encoding the SARS-CoV-2 antigen comprises: a nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% identity over an entire length of nucleotides 55 to 3837 of SEQ ID NO: 5 or over an entire length of SEQ ID NO: 5; the nucleic acid sequence of nucleotides 55 to 3837 of SEQ ID NO: 5; the nucleic acid sequence of SEQ ID NO: 5; a nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% identity over an entire length of SEQ ID NO: 6; or the nucleic acid sequence of SEQ ID NO: 6.

In some embodiments the SARS-CoV-2 antigen is operably linked to an IgE leader sequence. In some such embodiments, the SARS-CoV-2 antigen comprises the amino acid sequence set forth in SEQ ID NO: 1. In some embodiments, the SARS-CoV-2 antigen is encoded by the nucleotide sequence set forth in SEQ ID NO:2 or SEQ ID NO: 3. In some embodiments in which the SARS-CoV-2 antigen includes an IgE leader, the SARS-CoV-2 antigen comprises the amino acid sequence set forth in SEQ ID NO: 4. In some such embodiments, the SARS-CoV-2 antigen is encoded by the nucleotide sequence set forth in SEQ ID NO:5 or SEQ ID NO: 6.

Immunogenic fragments of SEQ ID NO:1 can be provided. Immunogenic fragments can comprise at least 60%, at least 65%, at least 70%, at least 75%, at least 80%, at least 85%, at least 90%, at least 95%, at least 96%, at least 97%, at least 98% or at least 99% of SEQ ID NO:1. In some embodiments, immunogenic fragments include a leader sequence, such as for example an immunoglobulin leader, such as the IgE leader. In some embodiments, immunogenic fragments are free of a leader sequence.

Immunogenic fragments of proteins with amino acid sequences homologous to immunogenic fragments of SEQ ID NO:1 can be provided. Such immunogenic fragments can comprise at least 60%, at least 65%, at least 70%, at least 75%, at least 80%, at least 85%, at least 90%, at least 95%, at least 96%, at least 97%, at least 98% or at least 99% of proteins that are 95% homologous to SEQ ID NO:1. Some embodiments relate to immunogenic fragments that have 96% homology to the immunogenic fragments of consensus protein sequences herein. Some embodiments relate to immunogenic fragments that have 97% homology to the immunogenic fragments of consensus protein sequences herein. Some embodiments relate to immunogenic fragments that have 98% homology to the immunogenic fragments of consensus protein sequences herein. Some embodiments relate to immunogenic fragments that have 99% homology to the immunogenic fragments of consensus protein sequences herein. In some embodiments, immunogenic fragments include a leader sequence, such as for example an immunoglobulin leader, such as the IgE leader. In some embodiments, immunogenic fragments are free of a leader sequence.

Some embodiments relate to immunogenic fragments of SEQ ID NO:1. Immunogenic fragments can be at least 60%, at least 65%, at least 70%, at least 75%, at least 80%, at least 85%, at least 90%, at least 95%, at least 96%, at least 97%, at least 98% or at least 99% of SEQ ID NO:1. Immunogenic fragments can be at least 95%, at least 96%, at least 97% at least 98% or at least 99% homologous to fragments of SEQ ID NO:1. In some embodiments, immunogenic fragments include sequences that encode a leader sequence, such as for example an immunoglobulin leader, such as the IgE leader. In some embodiments, fragments are free of coding sequences that encode a leader sequence.

Immunogenic fragments of SEQ ID NO:4 can be provided. Immunogenic fragments can comprise at least 60%, at least 65%, at least 70%, at least 75%, at least 80%, at least 85%, at least 90%, at least 95%, at least 96%, at least 97%, at least 98% or at least 99% of SEQ ID NO:4. In some embodiments, immunogenic fragments include a leader sequence, such as for example an immunoglobulin leader, such as the IgE leader. In some embodiments, immunogenic fragments are free of a leader sequence.

Immunogenic fragments of proteins with amino acid sequences homologous to immunogenic fragments of SEQ ID NO:4 can be provided. Such immunogenic fragments can comprise at least 60%, at least 65%, at least 70%, at least 75%, at least 80%, at least 85%, at least 90%, at least 95%, at least 96%, at least 97%, at least 98% or at least 99% of proteins that are 95% homologous to SEQ ID NO:4. Some embodiments relate to immunogenic fragments that have 96% homology to the immunogenic fragments of consensus protein sequences herein. Some embodiments relate to immunogenic fragments that have 97% homology to the immunogenic fragments of consensus protein sequences herein. Some embodiments relate to immunogenic fragments that have 98% homology to the immunogenic fragments of consensus protein sequences herein. Some embodiments relate to immunogenic fragments that have 99% homology to the immunogenic fragments of consensus protein sequences herein. In some embodiments, immunogenic fragments include a leader sequence, such as for example an immunoglobulin leader, such as the IgE leader. In some embodiments, immunogenic fragments are free of a leader sequence.

Some embodiments relate to immunogenic fragments of SEQ ID NO:4. Immunogenic fragments can be at least 60%, at least 65%, at least 70%, at least 75%, at least 80%, at least 85%, at least 90%, at least 95%, at least 96%, at least 97%, at least 98% or at least 99% of SEQ ID NO:4. Immunogenic fragments can be at least 95%, at least 96%, at least 97% at least 98% or at least 99% homologous to fragments of SEQ ID NO:4. In some embodiments, immunogenic fragments include sequences that encode a leader sequence, such as for example an immunoglobulin leader, such as the IgE leader. In some embodiments, fragments are free of coding sequences that encode a leader sequence.

b. Vector

The immunogenic compositions can comprise one or more vectors that include a nucleic acid molecule encoding the SARS-CoV-2 antigen. The one or more vectors can be capable of expressing the antigen. The vector can have a nucleic acid sequence containing an origin of replication. The vector can be a plasmid, bacteriophage, bacterial artificial chromosome or yeast artificial chromosome. The vector can be either a self-replicating extrachromosomal vector or a vector which integrates into a host genome.

The one or more vectors can be an expression construct, which is generally a plasmid that is used to introduce a specific gene into a target cell. Once the expression vector is inside the cell, the protein that is encoded by the gene is produced by the cellular-transcription and translation machinery ribosomal complexes. The plasmid is frequently engineered to contain regulatory sequences that act as enhancer and promoter regions and lead to efficient transcription of the gene carried on the expression vector. The vectors of the present invention express large amounts of stable messenger RNA, and therefore proteins.

The vectors may have expression signals such as a strong promoter, a strong termination codon, adjustment of the distance between the promoter and the cloned gene, and the insertion of a transcription termination sequence and a PTIS (portable translation initiation sequence).

(1) Expression Vectors

The vector can be a circular plasmid or a linear nucleic acid. The circular plasmid and linear nucleic acid are capable of directing expression of a particular nucleotide sequence in an appropriate subject cell. The vector can have a promoter operably linked to the antigen-encoding nucleotide sequence, which may be operably linked to termination signals. The vector can also contain sequences required for proper translation of the nucleotide sequence. The vector comprising the nucleotide sequence of interest may be chimeric, meaning that at least one of its components is heterologous with respect to at least one of its other components. The expression of the nucleotide sequence in the expression cassette may be under the control of a constitutive promoter or of an inducible promoter, which initiates transcription only when the host cell is exposed to some particular external stimulus. In the case of a multicellular organism, the promoter can also be specific to a particular tissue or organ or stage of development.

(2) Circular and Linear Vectors

The vector may be a circular plasmid, which may transform a target cell by integration into the cellular genome or exist extrachromosomally (e.g., autonomous replicating plasmid with an origin of replication).

The vector can be pVAX, pcDNA3.0, pGX-0001, or provax, or any other expression vector capable of expressing DNA encoding the antigen and enabling a cell to translate the sequence to an antigen that is recognized by the immune system.

Also provided herein is a linear nucleic acid immunogenic composition, or linear expression cassette ("LEC"), that is capable of being efficiently delivered to a subject via electroporation and expressing one or more desired antigens. The LEC may be any linear DNA devoid of any phosphate backbone. The DNA may encode one or more antigens. The LEC may contain a promoter, an intron, a stop codon, and/or a polyadenylation signal. The expression of the antigen may be controlled by the promoter. The LEC may not contain any antibiotic resistance genes and/or a phosphate backbone. The LEC may not contain other nucleic acid sequences unrelated to the desired antigen gene expression.

The LEC may be derived from any plasmid capable of being linearized. The plasmid may be capable of expressing the antigen. The plasmid can be pNP (Puerto Rico/34) or pM2 (New Caledonia/99). The plasmid may be WLV009, pVAX, pcDNA3.0, or provax, or any other expression vector capable of expressing DNA encoding the antigen and enabling a cell to translate the sequence to an antigen that is recognized by the immune system.

The LEC can be perM2. The LEC can be perNP. perNP and perMR can be derived from pNP (Puerto Rico/34) and pM2 (New Caledonia/99), respectively.

(3) Promoter, Intron, Stop Codon, and Polyadenylation Signal

The vector may have a promoter. A promoter may be any promoter that is capable of driving gene expression and regulating expression of the isolated nucleic acid. Such a promoter is a cis-acting sequence element required for transcription via a DNA dependent RNA polymerase, which transcribes the antigen sequence described herein. Selection of the promoter used to direct expression of a heterologous nucleic acid depends on the particular application. The promoter may be positioned about the same distance from the transcription start in the vector as it is from the transcription start site in its natural setting. However, variation in this distance may be accommodated without loss of promoter function.

The promoter may be operably linked to the nucleic acid sequence encoding the antigen and signals required for efficient polyadenylation of the transcript, ribosome binding sites, and translation termination. The promoter may be a CMV promoter, SV40 early promoter, SV40 later promoter, metallothionein promoter, murine mammary tumor virus promoter, Rous sarcoma virus promoter, polyhedrin promoter, or another promoter shown effective for expression in eukaryotic cells.

The vector may include an enhancer and an intron with functional splice donor and acceptor sites. The vector may contain a transcription termination region downstream of the structural gene to provide for efficient termination. The termination region may be obtained from the same gene as the promoter sequence or may be obtained from different genes.

c. Excipients and Other Components of the Immunogenic Compositions

The immunogenic compositions may further comprise a pharmaceutically acceptable excipient. The pharmaceutically acceptable excipient can be functional molecules such as vehicles, carriers, buffers, or diluents. As used herein. "buffer" refers to a buffered solution that resists changes in pH by the action of its acid-base conjugate components. The buffer generally has a pH from about 4.0 to about 8.0, for example from about 5.0 to about 7.0. In some embodiments, the buffer is saline-sodium citrate (SSC) buffer. In some embodiments in which the immunogenic composition comprises a nucleic acid molecule encoding a SARS-CoV-2 spike antigen as described above, the immunogenic composition comprises 10 mg/ml of vector in buffer, for example but not limited to SSC buffer. In some embodiments, the immunogenic composition comprises 10 mg/mL of the DNA plasmid pGX9501 or pGX9503 in buffer. In some embodiments, the immunogenic composition is stored at about 2° C. to about 8° C. In some embodiments, the immunogenic composition is stored at room temperature. The immunogenic composition may be stored for at least a year at room temperature. In some embodiments, the immunogenic composition is stable at room temperature for at least a year, wherein stability is defined as a supercoiled plasmid percentage of at least about 80%. In some embodiments, the supercoiled plasmid percentage is at least about 85% following storage for at least a year at room temperature.

The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent may be a polyanion, polycation, including poly-L-glutamate (LGS), or lipid. The transfection facilitating agent is poly-L-glutamate, and the poly-L-glutamate may be present in the immunogenic composition at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. The DNA plasmid immunogenic compositions may also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. The transfection facilitating agent is a polyanion, polycation, including poly-L-glutamate (LGS), or lipid. Concentration of the transfection agent in the immunogenic composition is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient can be an adjuvant. The adjuvant can be other genes that are expressed in an alternative plasmid or are delivered as proteins in combination with the plasmid above in the immunogenic composition. The adjuvant may be selected from the group consisting of: α-interferon (IFN-α), β-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, MHC, CD80, CD86 including IL-15 having the signal sequence deleted and optionally including the signal peptide from IgE. The adjuvant can be IL-12, IL-15, IL-28, CTACK, TECK, platelet derived growth factor (PDGF), TNFα, TNFβ, GM-CSF, epidermal growth factor (EGF), IL-1, IL-2, IL-4, IL-5, IL-6, IL-10, IL-12, IL-18, or a combination thereof.

Other genes that can be useful as adjuvants include those encoding: MCP-1, MIP-la, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, IL-22, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

The immunogenic composition may further comprise a genetic vaccine facilitator agent as described in U.S. Ser. No. 021,579 filed Apr. 1, 1994, which is fully incorporated by reference.

The immunogenic composition can be formulated according to the mode of administration to be used. According to some embodiments, the immunogenic composition is formulated in a buffer, optionally saline-sodium citrate buffer. For example, the immunogenic composition may formulated at a concentration of 10 mg nucleic acid molecule per milliliter of a sodium salt citrate buffer. An injectable immunogenic pharmaceutical composition can be sterile, pyrogen free and particulate free. An isotonic formulation or solution can be used. Additives for isotonicity can include sodium chloride, dextrose, mannitol, sorbitol, and lactose. The immunogenic composition can comprise a vasoconstriction agent. The isotonic solutions can include phosphate buffered saline. Immunogenic compositions can further comprise stabilizers including gelatin and albumin. The stabilizers can allow the formulation to be stable at room or ambient temperature for extended periods of time, including LGS or polycations or polyanions.

Also provided herein are articles of manufacture comprising the immunogenic composition. In some embodiments, the article of manufacture is a container holding the immunogenic composition. The container may be, for example but not limited to, a syringe or a vial. The vial may have a stopper piercable by a syringe.

The immunogenic composition can be packaged in suitably sterilized containers such as ampules, bottles, or vials, either in multi-dose or in unit dosage forms. The containers are preferably hermetically sealed after being filled with a vaccine preparation. Preferably, the vaccines are packaged in a container having a label affixed thereto, which label identifies the vaccine, and bears a notice in a form prescribed by a government agency such as the United States Food and Drug Administration reflecting approval of the vaccine under appropriate laws, dosage information, and the like. The label preferably contains information about the vaccine that is useful to a health care professional administering the vaccine to a patient. The package also preferably contains printed informational materials relating to the administration of the vaccine, instructions, indications, and any necessary required warnings.

Methods of Vaccination

Also provided herein are methods of treating, protecting against, and/or preventing disease in a subject in need thereof by administering the immunogenic composition to the subject. Administration of the immunogenic composition to the subject can induce or elicit an immune response in the subject. The induced immune response can be used to treat, prevent, and/or protect against disease, for example, pathologies relating to SARS-CoV-2 infection. The induced immune response in the subject administered the immunogenic composition can provide resistance to one or more SARS-CoV-2 strains.

The induced immune response can include an induced humoral immune response and/or an induced cellular immune response. The humoral immune response can be induced by about 1.5-fold to about 16-fold, about 2-fold to about 12-fold, or about 3-fold to about 10-fold. The induced humoral immune response can include IgG antibodies and/or neutralizing antibodies that are reactive to the antigen. The induced cellular immune response can include a CD8+ T cell response, which is induced by about 2-fold to about 30-fold, about 3-fold to about 25-fold, or about 4-fold to about 20-fold.

The vaccine dose can be between 1 μg to 10 mg active component/kg body weight/time, and can be 20 μg to 10 mg component/kg body weight/time. The vaccine can be administered every 21, 22, 23, 24, 25, 26, 27, 28, 29, 30, 31, 32, 33, 34, 35, 36, 37, 38, 39, 40 or more days or every 3, 4, 5, 6, 7, 8, 9, 10, 11, 12, 13, 14, 15, 16, 17, 18, 19, 20 or more weeks. The number of vaccine doses for effective treatment can be 1, 2, 3, 4, 5, 6, 7, 8, 9, 10, or more.

In one embodiment, the total vaccine dose is 1.0 mg of nucleic acid. In one embodiment, the total vaccine dose is 2.0 mg of nucleic acid, administered as 2×1.0 mg nucleic acid.

a. Administration

The immunogenic composition can be formulated in accordance with standard techniques well known to those skilled in the pharmaceutical art. Such compositions can be administered in dosages and by techniques well known to those skilled in the medical arts taking into consideration such factors as the age, sex, weight, and condition of the particular subject, and the route of administration. The vaccine may be administered, for example, in one, two, three, four, or more injections. In some embodiments, an initial dose of about 0.5 mg to about 2.0 mg of the nucleic acid molecule is administered to the subject. The initial dose may be administered in one, two, three, or more injections. The initial dose may be followed by administration of one, two, three, four, or more subsequent doses of about 0.5 mg to about 2.0 mg of the nucleic acid molecule about one, two, three, four, five, six, seven, eight, ten, twelve or more weeks after the immediately prior dose. Each subsequent dose may be administered in one, two, three, or more injections. In some embodiments, the immunogenic composition is administered to the subject before, with, or after the additional agent. In some embodiments, the immunogenic composition is administered as a booster following administration of an agent for the treatment of SARS-CoV-2 infection or the treatment or prevention of a disease or disorder associated with SARS-CoV-2 infection. In one embodiment, the disease or disorder associated with SARS-CoV-2 infection includes, but is not limited to, Coronavirus Disease 2019 (COVID-19) and/or Multisystem inflammatory syndrome in adults (MIS-A) or Multisystem inflammatory syndrome in children (MIS-C).

The subject can be a mammal, such as a human, a horse, a nonhuman primate, a cow, a pig, a sheep, a cat, a dog, a guinea pig, a rabbit, a rat, or a mouse.

The vaccine can be administered prophylactically or therapeutically. In prophylactic administration, the vaccines can be administered in an amount sufficient to induce an immune response. In therapeutic applications, the vaccines are administered to a subject in need thereof in an amount sufficient to elicit a therapeutic effect. An amount adequate to accomplish this is defined as "therapeutically effective dose." Amounts effective for this use will depend on, e.g., the particular composition of the vaccine regimen administered, the manner of administration, the stage and severity of the disease, the general state of health of the patient, and the judgment of the prescribing physician.

The vaccine can be administered by methods well known in the art as described in Donnelly et al. (Ann. Rev. Immunol. 15:617-648 (1997)); Felgner et al. (U.S. Pat. No. 5,580,859, issued Dec. 3, 1996); Felgner (U.S. Pat. No. 5,703,055, issued Dec. 30, 1997); and Carson et al. (U.S. Pat. No. 5,679,647, issued Oct. 21, 1997), the contents of all of which are incorporated herein by reference in their entirety. The DNA of the vaccine can be complexed to particles or beads that can be administered to an individual, for example, using a vaccine gun. One skilled in the art would know that the choice of a pharmaceutically acceptable carrier, including a physiologically acceptable compound, depends, for example, on the route of administration of the expression vector.

The vaccine can be delivered via a variety of routes. Typical delivery routes include parenteral administration, e.g., intradermal, intramuscular or subcutaneous delivery, optionally followed by electroporation as described herein. Other routes include oral administration, intranasal, and intravaginal routes. For the DNA of the vaccine in particular, the vaccine can be delivered to the interstitial spaces of tissues of an individual (Felgner et al., U.S. Pat. Nos. 5,580,859 and 5,703,055, the contents of all of which are incorporated herein by reference in their entirety). The vaccine can also be administered to muscle, or can be administered via intradermal or subcutaneous injections, or transdermally, such as by iontophoresis. Epidermal administration of the vaccine can also be employed. Epidermal administration can involve mechanically or chemically irritating the outermost layer of epidermis to stimulate an immune response to the irritant (Carson et al., U.S. Pat. No. 5,679,647, the contents of which are incorporated herein by reference in its entirety).

The vaccine can also be formulated for administration via the nasal passages. Formulations suitable for nasal administration, wherein the carrier is a solid, can include a coarse powder having a particle size, for example, in the range of about 10 to about 500 microns which is administered in the manner in which snuff is taken, i.e., by rapid inhalation through the nasal passage from a container of the powder held close up to the nose. The formulation can be a nasal spray, nasal drops, or by aerosol administration by nebulizer. The formulation can include aqueous or oily solutions of the vaccine.

The vaccine can be a liquid preparation such as a suspension, syrup or elixir. The vaccine can also be a preparation for parenteral, subcutaneous, intradermal, intramuscular or intravenous administration (e.g., injectable administration), such as a sterile suspension or emulsion.

The vaccine can be incorporated into liposomes, microspheres or other polymer matrices (Felgner et al., U.S. Pat. No. 5,703,055; Gregoriadis, Liposome Technology, Vols. I to III (2nd ed. 1993), the contents of which are incorporated herein by reference in their entirety). Liposomes can consist of phospholipids or other lipids, and can be nontoxic, physiologically acceptable and metabolizable carriers that are relatively simple to make and administer.

The vaccine can be administered via electroporation, such as by a method described in U.S. Pat. No. 7,664,545, the contents of which are incorporated herein by reference. The electroporation can be by a method and/or apparatus described in U.S. Pat. Nos. 6,302,874; 5,676,646; 6,241,701; 6,233,482; 6,216,034; 6,208,893; 6,192,270; 6,181,964; 6,150,148; 6,120,493; 6,096,020; 6,068,650; and 5,702,359, the contents of which are incorporated herein by reference in their entirety. The electroporation may be carried out via a minimally invasive device.

The minimally invasive electroporation device ("MID") may be an apparatus for injecting the vaccine described above and associated fluid into body tissue. The device may comprise a hollow needle, DNA cassette, and fluid delivery means, wherein the device is adapted to actuate the fluid delivery means in use so as to concurrently (for example, automatically) inject DNA into body tissue during insertion of the needle into the said body tissue. This has the advantage that the ability to inject the DNA and associated fluid gradually while the needle is being inserted leads to a more even distribution of the fluid through the body tissue. The pain experienced during injection may be reduced due to the distribution of the DNA being injected over a larger area.

The MID may inject the vaccine into tissue without the use of a needle. The MID may inject the vaccine as a small stream or jet with such force that the vaccine pierces the surface of the tissue and enters the underlying tissue and/or muscle. The force behind the small stream or jet may be provided by expansion of a compressed gas, such as carbon dioxide through a micro-orifice within a fraction of a second. Examples of minimally invasive electroporation devices, and methods of using them, are described in published U.S. Patent Application No. 20080234655; U.S. Pat. Nos. 6,520,950; 7,171,264; 6,208,893; 6,009,347; 6,120,493; 7,245,963; 7,328,064; and 6,763,264, the contents of each of which are herein incorporated by reference.

The MID may comprise an injector that creates a high-speed jet of liquid that painlessly pierces the tissue. Such needle-free injectors are commercially available. Examples of needle-free injectors that can be utilized herein include those described in U.S. Pat. Nos. 3,805,783; 4,447,223; 5,505,697; and 4,342,310, the contents of each of which are herein incorporated by reference.

A desired vaccine in a form suitable for direct or indirect electrotransport may be introduced (e.g., injected) using a needle-free injector into the tissue to be treated, usually by contacting the tissue surface with the injector so as to actuate delivery of a jet of the agent, with sufficient force to cause penetration of the vaccine into the tissue. For example, if the tissue to be treated is mucosa, skin or muscle, the agent is projected towards the mucosal or skin surface with sufficient force to cause the agent to penetrate through the stratum corneum and into dermal layers, or into underlying tissue and muscle, respectively.

Needle-free injectors are well suited to deliver vaccines to all types of tissues, particularly to skin and mucosa. In some embodiments, a needle-free injector may be used to propel a liquid that contains the vaccine to the surface and into the subject's skin or mucosa. Representative examples of the various types of tissues that can be treated using the invention methods include pancreas, larynx, nasopharynx, hypopharynx, oropharynx, lip, throat, lung, heart, kidney, muscle, breast, colon, prostate, thymus, testis, skin, mucosal tissue, ovary, blood vessels, or any combination thereof.

The MID may have needle electrodes that electroporate the tissue. By pulsing between multiple pairs of electrodes in a multiple electrode array, for example set up in rectangular or square patterns, provides improved results over that of pulsing between a pair of electrodes. Disclosed, for example, in U.S. Pat. No. 5,702,359 entitled "Needle Electrodes for Mediated Delivery of Drugs and Genes" is an array of needles wherein a plurality of pairs of needles may be pulsed during the therapeutic treatment. In that application, which is incorporated herein by reference as though fully set forth, needles were disposed in a circular array, but have connectors and switching apparatus enabling a pulsing between opposing pairs of needle electrodes. A pair of needle electrodes for delivering recombinant expression vectors to cells may be used. Such a device and system is described in U.S. Pat. No. 6,763,264, the contents of which are herein incorporated by reference. Alternatively, a single needle device may be used that allows injection of the DNA and electroporation with a single needle resembling a normal injection needle and applies pulses of lower voltage than those delivered by presently used devices, thus reducing the electrical sensation experienced by the patient.

The MID may comprise one or more electrode arrays. The arrays may comprise two or more needles of the same diameter or different diameters. The needles may be evenly or unevenly spaced apart. The needles may be between 0.005 inches and 0.03 inches, between 0.01 inches and 0.025 inches; or between 0.015 inches and 0.020 inches. The needle may be 0.0175 inches in diameter. The needles may be 0.5 mm, 1.0 mm, 1.5 mm, 2.0 mm, 2.5 mm, 3.0 mm, 3.5 mm, 4.0 mm, or more spaced apart.

The MID may consist of a pulse generator and a two or more-needle vaccine injectors that deliver the vaccine and electroporation pulses in a single step. The pulse generator may allow for flexible programming of pulse and injection parameters via a flash card operated personal computer, as well as comprehensive recording and storage of electroporation and patient data. The pulse generator may deliver a variety of volt pulses during short periods of time. For example, the pulse generator may deliver three 15 volt pulses of 100 ms in duration. An example of such a MID is the Elgen 1000 system by Inovio Biomedical Corporation, which is described in U.S. Pat. No. 7,328,064, the contents of which are herein incorporated by reference.

The MID may be a CELLECTRA® (Inovio Pharmaceuticals, Blue Bell Pa.) device and system, which is a modular electrode system, that facilitates the introduction of a macromolecule, such as a DNA, into cells of a selected tissue in a body or plant. The modular electrode system may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The macromolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the macromolecule into the cell between the plurality of electrodes. Cell death due to overheating of cells is minimized by limiting the power dissipation in the tissue by virtue of constant-current pulses. The Cellectra® device and system is described in U.S. Pat. No. 7,245,963, the contents of which are herein incorporated by reference. The CELLECTRA® device may be the CELLECTRA 2000® device or CELLECTRA® 3PSP device.

The MID may be an Elgen 1000 system (Inovio Pharmaceuticals). The Elgen 1000 system may comprise device that provides a hollow needle; and fluid delivery means, wherein the apparatus is adapted to actuate the fluid delivery means in use so as to concurrently (for example automatically) inject fluid, the described vaccine herein, into body tissue during insertion of the needle into the said body tissue. The advantage is the ability to inject the fluid gradually while the needle is being inserted leads to a more even distribution of the fluid through the body tissue. It is also believed that the pain experienced during injection is reduced due to the distribution of the volume of fluid being injected over a larger area.

In addition, the automatic injection of fluid facilitates automatic monitoring and registration of an actual dose of fluid injected. This data can be stored by a control unit for documentation purposes if desired.

It will be appreciated that the rate of injection could be either linear or non-linear and that the injection may be carried out after the needles have been inserted through the skin of the subject to be treated and while they are inserted further into the body tissue.

Suitable tissues into which fluid may be injected by the apparatus of the present invention include tumor tissue, skin or liver tissue but may be muscle tissue.

The apparatus further comprises needle insertion means for guiding insertion of the needle into the body tissue. The rate of fluid injection is controlled by the rate of needle insertion. This has the advantage that both the needle insertion and injection of fluid can be controlled such that the rate of insertion can be matched to the rate of injection as desired. It also makes the apparatus easier for a user to operate. If desired means for automatically inserting the needle into body tissue could be provided.

A user could choose when to commence injection of fluid. Ideally however, injection is commenced when the tip of the needle has reached muscle tissue and the apparatus may include means for sensing when the needle has been inserted to a sufficient depth for injection of the fluid to commence. This means that injection of fluid can be prompted to commence automatically when the needle has reached a desired depth (which will normally be the depth at which muscle tissue begins). The depth at which muscle tissue begins could for example be taken to be a preset needle insertion depth such as a value of 4 mm which would be deemed sufficient for the needle to get through the skin layer.

The sensing means may comprise an ultrasound probe. The sensing means may comprise a means for sensing a change in impedance or resistance. In this case, the means may not as such record the depth of the needle in the body tissue but will rather be adapted to sense a change in impedance or resistance as the needle moves from a different type of body tissue into muscle. Either of these alternatives provides a relatively accurate and simple to operate means of sensing that injection may commence. The depth of insertion of the needle can further be recorded if desired and could be used to control injection of fluid such that the volume of fluid to be injected is determined as the depth of needle insertion is being recorded.

The apparatus may further comprise: a base for supporting the needle; and a housing for receiving the base therein, wherein the base is moveable relative to the housing such that the needle is retracted within the housing when the base is in a first rearward position relative to the housing and the needle extends out of the housing when the base is in a second forward position within the housing. This is advantageous for a user as the housing can be lined up on the skin of a patient, and the needles can then be inserted into the patient's skin by moving the housing relative to the base.

As stated above, it is desirable to achieve a controlled rate of fluid injection such that the fluid is evenly distributed over the length of the needle as it is inserted into the skin. The fluid delivery means may comprise piston driving means adapted to inject fluid at a controlled rate. The piston driving means could for example be activated by a servo motor. However, the piston driving means may be actuated by the base being moved in the axial direction relative to the housing. It will be appreciated that alternative means for fluid delivery could be provided. Thus, for example, a closed container which can be squeezed for fluid delivery at a controlled or non-controlled rate could be provided in the place of a syringe and piston system.

The apparatus described above could be used for any type of injection. It is however envisaged to be particularly useful in the field of electroporation and so it may further comprises means for applying a voltage to the needle. This allows the needle to be used not only for injection but also as an electrode during, electroporation. This is particularly advantageous as it means that the electric field is applied to the same area as the injected fluid. There has traditionally been a problem with electroporation in that it is very difficult to accurately align an electrode with previously injected fluid and so users have tended to inject a larger volume of fluid than is required over a larger area and to apply an electric field over a higher area to attempt to guarantee an overlap between the injected substance and the electric field. Using the present invention, both the volume of fluid injected and the size of electric field applied may be reduced while achieving a good fit between the electric field and the fluid.

Use in Combination

In some embodiments, the present invention provides a method of treating SARS-CoV-2 infection, or treating, protecting against, and/or preventing a disease or disorder associated with SARS-CoV-2 infection in a subject in need thereof by administering a combination of a nucleic acid molecule encoding a SARS-CoV-2 antigen, or fragment or variant thereof in combination with one or more additional agents for the treatment of SARS-CoV-2 infection or the treatment or prevention of disease or disorder associated with SARS-CoV-2 infection. In some embodiments, the disease or disorder associated with SARS-CoV-2 infection is Coronavirus Disease 2019 (COVID-19), Multisystem inflammatory syndrome in adults (MIS-A), or Multisystem inflammatory syndrome in children (MIS-C).

The nucleic acid molecule encoding a SARS-CoV-2 antigen and additional agent may be administered using any suitable method such that a combination of the nucleic acid molecule encoding a SARS-CoV-2 antigen and the additional agent are both present in the subject. In one embodiment, the method may comprise administration of a first composition comprising an agent for the treatment of SARS-CoV-2 infection or the treatment or prevention of disease or disorder associated with SARS-CoV-2 infection and administration of a second composition comprising a nucleic acid molecule encoding a SARS-CoV-2 antigen less than 1, less than 2, less than 3, less than 4, less than 5, less than 6, less than 7, less than 8, less than 9 or less than 10 days following administration of the first composition comprising the agent for the treatment of SARS-CoV-2 infection or the treatment or prevention of disease or disorder associated with SARS-CoV-2 infection. In one embodiment, the method may comprise administration of a first composition comprising a nucleic acid molecule encoding a SARS-CoV-2 antigen and administration of a second composition comprising an agent for the treatment of SARS-CoV-2 infection or the treatment or prevention of disease or disorder associated with SARS-CoV-2 infection less than 1, less than 2, less than 3, less than 4, less than 5, less than 6, less than 7, less than 8, less than 9 or less than 10 days following administration of the nucleic acid molecule encoding a SARS-CoV-2 antigen. In one embodiment, the method may comprise administration of a first composition comprising an agent for the treatment of SARS-CoV-2 infection or the treatment or prevention of disease or disorder associated with SARS-CoV-2 infection and a second composition comprising a nucleic acid molecule encoding a SARS-CoV-2 antigen concurrently. In one embodiment, the method may comprise administration of a single composition comprising an agent for the treatment of SARS-CoV-2 infection or the treatment or prevention of disease or disorder associated with SARS-CoV-2 infection and a nucleic acid molecule encoding a SARS-CoV-2 antigen.

In some embodiments, the agent for the treatment of SARS-CoV-2 infection or the treatment or prevention of disease or disorder associated with SARS-CoV-2 infection is a therapeutic agent. In one embodiment, the therapeutic agent is an antiviral agent. In one embodiment, the therapeutic agent is an antibiotic agent.

Non-limiting examples of antibiotics that can be used in combination with the a nucleic acid molecule encoding a SARS-CoV-2 antigen of the invention include aminoglycosides (e.g., gentamicin, amikacin, tobramycin), quinolones (e.g., ciprofloxacin, levofloxacin), cephalosporins (e.g., ceftazidime, cefepime, cefoperazone, cefpirome, ceftobiprole), antipseudomonal penicillins: carboxypenicillins (e.g., carbenicillin and ticarcillin) and ureidopenicillins (e.g., mezlocillin, azlocillin, and piperacillin), carbapenems (e.g., meropenem, imipenem, doripenem), polymyxins (e.g., polymyxin B and colistin) and monobactams (e.g., aztreonam).

Administration as a Booster

In one embodiment, the immunogenic composition is administered as a booster vaccine following administration of an initial agent or vaccine for the treatment of SARS-CoV-2 infection or the treatment or prevention of a disease or disorder associated with SARS-CoV-2 infection, including, but not limited to COVID-19, Multisystem inflammatory syndrome in adults (MIS-A), or Multisystem inflammatory syndrome in children (MIS-C). In one embodiment, the booster vaccine is administered at least once, at least twice, at least 3 times, at least 4 times, or at least 5 times following administration of an initial agent or vaccine for the treatment of SARS-CoV-2 infection or the treatment or prevention of a disease or disorder associated with SARS-CoV-2 infection, including, but not limited to COVID-19, Multisystem inflammatory syndrome in adults (MIS-A), or Multisystem inflammatory syndrome in children (MIS-C). In one embodiment, the booster vaccine is administered at least 8 hours, at least 12 hours, at least 16 hours, at least 20 hours, at least 24 hours, at least 36 hours, at least 48 hours, at least 60 hours, at least 72 hours, at least 4 days, at least 5 days, at least 6 days, at least 1 week at least 2 weeks, at least 3 weeks, at least 4 weeks, at least 1 month, at least 2 months, at least 3 months, at least 4 months, at least 5 months, at least 6 months, at least 7 months, at least 8 months, at least 9 months, at least 10 months, at least 11 months, at least 1 year or greater than 1 year following administration of an initial agent or vaccine for the treatment of SARS-CoV-2 infection or the treatment or prevention of a disease or disorder associated with SARS-CoV-2 infection, including, but not limited to COVID-19, Multisystem inflammatory syndrome in adults (MIS-A), or Multisystem inflammatory syndrome in children (MIS-C).

Use in Assays

In some embodiments, the nucleic acid molecules, or encoded antigens, of the invention can be used in assays in vivo or in vitro. In some embodiments, the nucleic acid molecules, or encoded antigens can be used in assays for detecting the presence of anti-SARS-CoV-2 spike antibodies. Exemplary assays in which the nucleic acid molecules or encoded antigens can be incorporated into include, but are not limited to, Western blot, dot blot, surface plasmon resonance methods, Flow Cytometry methods, various immunoassays, for example, immunohistochemistry assays, immunocytochemistry assays, ELISA, capture ELISA, enzyme-linked immunospot (ELISpot) assays, sandwich assays, enzyme immunoassay, radioimmunoassay, fluorescent immunoassay, and the like, all of which are known to those of skill in the art. See e.g. Harlow et al., 1988, Antibodies: A Laboratory Manual, Cold Spring Harbor, N.Y.; Harlow et al., 1999, Using Antibodies: A Laboratory Manual, Cold Spring Harbor Laboratory Press, NY.

In one embodiment, the SARS-CoV-2 spike antigen, or fragments thereof, of the invention can be used in an assay for intracellular cytokine staining combined with flow cytometry, to assess T-cell immune responses. This assay enables the simultaneous assessment of multiple phenotypic, differentiation and functional parameters pertaining to responding T-cells, most notably, the expression of multiple effector cytokines. These attributes make the technique particularly suitable for the assessment of T-cell immune responses induced by the vaccine of the invention.

In one embodiment, the SARS-CoV-2 spike antigen, or fragments thereof, of the invention can be used in an ELIspot assay. The ELISpot assay is a highly sensitive immunoassay that measures the frequency of cytokine-secreting cells at the single-cell level. In this assay, cells are cultured on a surface coated with a specific capture antibody in the presence or absence of stimuli. In one embodiment, the SARS-CoV-2 spike antigen, or fragments thereof, of the invention can be used as the stimulus in the ELISpot assay.

Diagnostic Methods

In some embodiments, the invention relates to methods of diagnosing a subject as having SARS-CoV-2 infection or having SARS-CoV-2 antibodies. In some embodiments, the methods include contacting a sample from a subject with a SARS-CoV-2 antigen of the invention, or a cell comprising a nucleic acid molecule for expression of the SARS-CoV-2 antigen, and detecting binding of an anti-SARS-CoV-2 spike antibody to the SARS-CoV-2 antigen of the invention. In such an embodiment, binding of an anti-SARS-CoV-2 spike antibody present in the sample of the subject to the antigen, or fragment thereof, of the invention would indicate that the subject is currently infected or was previously infected with SARS-CoV-2.

Kits and Articles of Manufacture

Provided herein is a kit, which can be used for treating a subject using the method of vaccination described above. The kit can comprise the immunogenic composition described herein.

The kit can also comprise instructions for carrying out the vaccination method described above and/or how to use the kit. Instructions included in the kit can be affixed to packaging material or can be included as a package insert. While instructions are typically written or printed materials, they are not limited to such. Any medium capable of storing instructions and communicating them to an end user is contemplated by this disclosure. Such media include, but are not limited to, electronic storage media (e.g., magnetic discs, tapes, cartridges), optical media (e.g., CD ROM), and the like. As used herein, the term "instructions" can include the address of an internet site which provides instructions.

Further provided herein are articles of manufacture containing the immunogenic composition described herein. In some embodiments, the article of manufacture is a container, such as a vial, optionally a single-use vial. In one embodiment, the article of manufacture is a single-use glass vial equipped with a stopper, which contains the immunogenic composition described herein to be administered. In some embodiments, the vial comprises a stopper, pierceable by a syringe, and a seal. In some embodiments, the article of manufacture is a syringe.

The present invention has multiple aspects, illustrated by the following non-limiting examples.

EXAMPLES

Example 1

Materials & Methods:

Cell lines. Human embryonic kidney (HEK)-293T (ATCC® CRL-3216™) and African green monkey kidney COS-7 (ATCC® CRL-1651™) cell lines were obtained from ATCC (Old Town Manassas, Va.). All cell lines were maintained in DMEM supplemented with 10% fetal bovine serum (FBS) and penicillin-streptomycin.

In vitro protein expression (Western blot). Human embryonic kidney cells, 293T were cultured and transfected as described previously (Yan, et al. Enhanced cellular immune responses elicited by an engineered HIV-1 subtype B consensus-based envelope DNA vaccine. *Mol Ther.* 2007; 15(2): 411-421). 293T cells were transfected with pDNA using TurboFectin8.0 (OriGene) transfection reagent following the manufacturer's protocol. Forty-eight hours later, cell lysates were harvested using modified RIPA cell lysis buffer. Proteins were separated on a 4-12% BIS-TRIS gel (ThermoFisher Scientific). Following transfer, blots were incubated with an anti-SARS-CoV spike protein polyclonal antibody (Novus Biologicals), and then visualized with horseradish peroxidase (HRP)-conjugated anti-mouse IgG (GE Amersham).

Immunofluorescence of transfected 293T cells. For in vitro staining of Spike protein expression, 293T cells were cultured on 4-well glass slides (Lab-Tek) and transfected with 3 μg/well of pDNA using TurboFectin8.0 (OriGene) transfection reagent following the manufacturer's protocol. Cells were fixed 48 hrs after transfection with 10% Neutral-buffered Formalin (BBC Biochemical, Washington State) for 10 min at room temperature (RT) and then washed with PBS. Before staining, chamber slides were blocked with 0.3% (v/v) Triton-X (Sigma), 2% (v/v) donkey serum in PBS for 1 hr at RT. Cells were stained with a rabbit anti-SARS-CoV spike protein polyclonal antibody (Novus Biologicals) diluted in 1% (w/v) BSA (Sigma), 2% (v/v) donkey serum, 0.3% (v/v) Triton-X (Sigma) and 0.025% (v/v) 1 g/ml Sodium Azide (Sigma) in PBS for 2 hrs at RT. Slides were washed three times for 5 min in PBS and then stained with donkey anti-rabbit IgG AF488 (Life Technologies, A21206) for 1 hr at RT. Slides were washed again and mounted and covered with DAPI-Fluoromount (SouthernBiotech).

In vitro RNA expression (qRT-PCR). In vitro mRNA expression of the plasmid was demonstrated by transfection of COS-7 with serially diluted plasmids followed by analysis of the total RNA extracted from the cells using reverse transcription and PCR. Transfections of four concentrations of the plasmid were performed using FuGENE® 6 transfection reagent (Promega) which resulted in final masses ranging between 80 and 10 ng/well. The transfections were performed in duplicate. Following 18 to 26 hours of incubation, the cells were lysed with RLT Buffer (Qiagen). Total RNA was isolated from each well using the Qiagen RNeasy kit following the kit instructions. The resulting RNA concentration was determined by $OD_{260/280}$, and samples of the RNA were diluted to 10 ng/4. One hundred nanograms of RNA was then converted to cDNA using the High Capacity cDNA Reverse Transcription (RT) kit (Applied Biosystems) following the kit instructions. RT reactions containing RNA but no reverse transcriptase (minus RT) were included as controls for plasmid DNA or cellular genomic DNA sample contamination. Eight μL of sample cDNA were then subjected to PCR using primers and probes that are specific to the target sequence (pGX9501 Forward—CAGGACAAGAACACACAGGAA (SEQ ID NO: 7); pGX9501 Reverse—CAGGCAGGATTTGGGAGAAA (SEQ ID NO: 8); pGX9501 Probe—ACCCAT-CAAGGACTTTGGAGG (SEQ ID NO: 9); and pGX9503 Forward—AGGACAAGAACACACAGGAAG (SEQ ID NO: 10); pGX9503 Reverse—CAGGATCTGG-GAGAAGTTGAAG (SEQ ID NO: 11); pGX9503 Probe—ACACCACCCATCAAGGACTTTGGA (SEQ ID NO: 12)). In a separate reaction, the same quantity of sample cDNA was subjected to PCR using primers and a probe designed for COS-7 cell line β-actin sequences (β-actin Forward—GTGACGTGGACATCCGTAAA (SEQ ID NO: 13); β-actin Reverse—CAGGGCAGTAATCTCCTTCTG (SEQ ID NO: 14); β-actin Probe—TACCCTGGCATTGCTGACAG-GATG (SEQ ID NO: 15)). The primers and probes were synthesized by Integrated DNA Technologies, Inc. and the probes were labeled with 56-FAM and Black Hole Quencher 1. The reaction used ABI Fast Advance 2× (Cat. No. 4444557), with final forward and reverse primer concentrations of 1 μM and probe concentrations of 0.3 μM. Using a QuantStudio™ 7 Flex Real Time PCR Studio System (Applied Biosystems), samples were first subjected to a hold of 1 minute at 95° C. and then 40 cycles of PCR with each cycle consisting of 1 second at 95° C. and 20 seconds at 60° C. Following PCR, the amplifications results were analyzed as follows. The negative transfection controls (NTCs), the minus RT controls, and the NTC were scrutinized for each of their respective indications. The threshold cycle ($C_T$) of each transfection concentration for the INO-4800 SARS-CoV-2 target mRNA and for the β-actin mRNA was generated from the QuantStudio™ software using an automatic threshold setting. The plasmid was considered to be active for mRNA expression if the expression in any of the plasmid-transfected wells compared to the negative transfection controls were greater than 5 $C_T$. Animals. Female, 6 week old C57/BL6 and BALB/c mice were purchased from Charles River Laboratories (Malvern, Pa.) and The Jackson Laboratory (Bar Harbor, Me.). Female, 8 week old Hartley guinea pigs were purchased from Elm Hill Labs (Chelmsford, Mass.). All animals were housed in the animal facility at The Wistar Institute Animal Facility or Acculab Life Sciences (San Diego, Calif.). All animal testing and research complied with all relevant ethical regulations and studies received ethical approval by the Wistar Institute or Acculab Institutional Animal Care and Use Committees (IACUC). For mouse studies, on day 0, doses of 2.5, 10 or 25 μg pDNA were administered to the tibialis anterior (TA) muscle by needle injection followed by CELLECTRA® in vivo electroporation (EP). The CELLECTRA® EP delivery consists of two sets of pulses with 0.2 Amp constant current. Second pulse sets is delayed 3 seconds. Within each set there are two 52 ms pulses with a 198 ms delay between the pulses. On days 0 and 14, blood was collected. Parallel groups of mice were serially sacrificed on days 4, 7, and 10 post-immunization for analysis of cellular immune responses. For guinea pig studies, on day 0, 100 μg pDNA was administered to the skin by Mantoux injection followed by CELLECTRA® in vivo EP.

Antigen binding ELISA. ELISAs were performed to determine sera antibody binding titers. Nunc ELISA plates were coated with 1 μg/ml recombinant protein antigens in Dulbecco's phosphate-buffered saline (DPBS) overnight at 4° C. Plates were washed three times, then blocked with 3% bovine serum albumin (BSA) in DPBS with 0.05% Tween 20 for 2 hours at 37° C. Plates were then washed and incubated with serial dilutions of mouse or guinea pig sera and incubated for 2 hours at 37° C. Plates were again washed and then incubated with 1:10,000 dilution of horse radish peroxidase (HRP)-conjugated anti-guinea pig IgG secondary antibody (Sigma-Aldrich, cat. A7289) or HRP-conjugated anti-mouse IgG secondary antibody (Sigma-Aldrich) and incubated for 1 hour at RT. After final wash, plates were developed using SureBlue™ TMB 1-Component Peroxidase Substrate (KPL, cat. 52-00-03), and the reaction stopped with TMB Stop Solution (KPL, cat. 50-85-06). Plates were read at 450 nm wavelength within 30 minutes using a Synergy™ HTX plate reader (BioTek Instruments, Highland Park, Vt.). Binding antibody endpoint titers (EPTs) were calculated as previously described (Bagarazzi M L, Yan J, Morrow M P, et al. Immunotherapy against HPV16/18 generates potent TH1 and cytotoxic cellular immune responses. Sci Transl Med. 2012; 4(155):155ra138). Binding antigens tested included, SARS-CoV-2 antigens: S1 spike protein (Sino Biological 40591-V08H), S1+S2 ECD spike protein (Sino Biological 40589-V08B1), RBD (University of Texas, at Austin (McLellan Lab)); SARS-COV antigens: Spike S1 protein (Sino Biological 40150-V08B1), S (1-1190) (Immune Tech IT-002-001P) and Spike C-terminal (Meridian Life Science R18572).

ACE2 Competition ELISA. For mouse studies, ELISAs were performed to determine sera IgG antibody competition against human ACE2 with a human Fc tag. Nunc ELISA plates were coated with 1 μg/mL rabbit anti-His6× in 1×PBS for 4-6 hours at room temperature (RT) and washed 4 times with washing buffer (1×PBS and 0.05% Tween® 20). Plates were blocked overnight at 4° C. with blocking buffer (1×PBS, 0.05% Tween® 20, 5% evaporated milk and 1% FBS). Plates were washed four times with washing buffer then incubated with full length (S1+S2) spike protein containing a C-terminal His tag (Sino Biologics, cat. 40589-V08B1) at 10 μg mL-1 for 1 hour at RT. Plates were washed and then serial dilutions of purified mouse IgG mixed with 0.1 μg mL-1 recombinant human ACE2 with a human Fc tag (ACE2-IgHu) were incubated for 1-2 hours at RT. Plates were again washed and then incubated with 1:10,000 dilution of horse radish peroxidase (HRP) conjugated anti-human IgG secondary antibody (Bethyl, cat. A80-304P) and incubated for 1 hour at RT. After final wash plates were developed using 1-Step Ultra TMB-ELISA Substrate (Thermo, cat. 34029) and the reaction stopped with 1 M Sulfuric Acid. Plates were read at 450 nm wavelength within 30 minutes using a SpectraMax Plus 384 Microplate Reader (Molecular Devices, Sunnyvale, Calif.). Competition curves were plotted and the area under the curve (AUC) was calculated using Prism 8 analysis software with multiple t-tests to determine statistical significance.

For guinea pig studies, 96 well half area assay plates (Costar) were coated with 25 μl per well of 5 μg/mL of SARS-CoV-2 spike S1+S2 protein (Sino Biological) diluted in 1×DPBS (Thermofisher) overnight at 4° C. Plates were washed with 1×PBS buffer with 0.05% TWEEN® 20 (Sigma). 100 μl per well of 3% (w/v) BSA (Sigma) in 1×PBS with 0.05% TWEEN® 20 were added and incubated for 1 hr at 37° C. Serum samples were diluted 1:20 in 1% (w/v) BSA in 1×PBS with 0.05% TWEEN. After washing the assay plate, 25 μl/well of diluted serum was added and incubated 1 hr at 37° C. Human recombinant ACE2-Fc-tag (Sinobiological) was added directly to the diluted serum, followed by 1 hr of incubation at 37° C. Plates were washed and 25 μl per well of 1:10,000 diluted goat anti-hu Fc fragment antibody HRP (Bethyl, A80-304P) was added to the assay plate. Plates were incubated 1 hr at RT. For development the SureBlue/TMB Stop Solution (KPL, MD) was used and O.D. was recorded at 450 nm.

SARS-CoV-2 Pseudovirus neutralization assay. SARS-CoV-2 pseudotyped viruses were produced using HEK293T cells transfected with GeneJammer (Agilent) using IgE-SARS-CoV-2 S plasmid (Genscript) and pNL4-3.Luc.R-E-plasmid (NIH AIDS reagent) at a 1:1 ratio. Forty-eight hours post transfection, transfection supernatant was collected, enriched with FBS to 12% final volume, steri-filtered (Millipore Sigma), and aliquoted for storage at −80° C. SARS-CoV-2 pseudotyped viruses were titered and yielded greater than 50 times the relative luminescence units (RLU) to cells alone after 72 h of infection. Mouse sera from INO-4800 vaccinated and naive groups were heat inactivated for 15 minutes at 56° C. and serially diluted three fold starting at a 1:10 dilution for assay. Sera were incubated with a fixed amount of SARS-CoV-2 pseudotyped virus for 90 minutes. HEK293T cells stably expressing ACE2 were added after 90 minutes and allowed to incubate in standard incubator (37% humidity, 5% $CO_2$) for 72 hours. Post infection, cells were lysed using Britelite™ plus luminescence reporter gene assay system (Perkin Elmer Catalog no. 6066769) and relative luminescence units (RLU) were measured using the Biotek plate reader. Neutralization titers ($ID_{50}$) were calculated as the serum dilution at which RLU were reduced by 50% compared to RLU in virus control wells after subtraction of background RLU in cell control wells.

SARS-CoV-2 wildtype virus neutralization assays. SARS-CoV-2/Australia/VIC01/2020 isolate neutralization assays were performed at Public Health England (Porton Down, UK). Neutralizing virus titers were measured in serum samples that had been heat-inactivated at 56° C. for 30 minutes. SARS-CoV-2 (Australia/VIC01/2020 isolate) (Caly et al., Isolation and rapid sharing of the 2019 novel coronavirus (SARS-CoV-2) from the first patient diagnosed with COVID-19 in Australia. *Med. J. Aust.* (2020) doi: 10.5694/mja2.50569; Published online: 13 Apr. 2020) was diluted to a concentration of 933 pfu/ml and mixed 50:50 in 1% FCS/MEM containing 25 mM HEPES buffer with doubling serum dilutions from 1:10 to 1:320 in a 96-well V-bottomed plate. The plate was incubated at 37° C. in a humidified box for 1 hour before the virus was transferred into the wells of a twice DPBS-washed 24-well plate that had been seeded the previous day at $1.5 \times 10^5$ Vero E6 cells per well in 10% FCS/MEM. Virus was allowed to adsorb at 37° C. for a further hour and overlaid with plaque assay overlay media (1×MEM/1.5% CMC/4% FCS final). After 5 days incubation at 37° C. in a humidified box, the plates were fixed, stained and plaques counted. Median neutralizing titers (ND50) were determined using the Spearman-Karber formula relative to virus only control wells.

SARS-CoV-2/WH-09/human/2020 isolate neutralization assays were performed at the Institute of Laboratory Animal Science, Chinese Academy of Medical Sciences (CAMS) approved by the National Health Commission of the People's Republic of China. Seed SARS-CoV-2 (SARS-CoV-2/WH-09/human/2020) stocks and virus isolation studies were performed in Vero E6 cells, which are maintained in Dulbecco's modified Eagle's medium (DMEM, Invitrogen, Carlsbad, USA) supplemented with 10% fetal bovine serum (FBS), 100 IU/ml penicillin, and 100 μg/ml streptomycin, and incubated at 36.5° C., 5% $CO_2$. Virus titer were determined using a standard 50% tissue culture infection dose (TCID50) assay. Serum samples collected from immunized animals were inactivated at 56° C. for 30 minutes and serially diluted with cell culture medium in two-fold steps. The diluted samples were mixed with a virus suspension of 100 TCID50 in 96-well plates at a ratio of 1:1, followed by 2 hours incubation at 36.5° C. in a 5% $CO_2$ incubator. $1-2 \times 10^4$ Vero cells were then added to the serum-virus mixture, and the plates were incubated for 3-5 days at 36.5° C. in a 5% $CO_2$ incubator. Cytopathic effect (CPE) of each well was recorded under microscopes, and the neutralizing titer was calculated by the dilution number of 50% protective condition.

Bronchoalveolar lavage collection. Bronchoalveolar lavage (BAL) fluid was collected by washing the lungs of euthanized and exsanguinated mice with 700-1000 ul of ice-cold PBS containing 100 μm EDTA, 0.05% sodium azide, 0.05% Tween® 20, and 1× protease inhibitor (Pierce) (mucosal prep solutions (MPS)) with a blunt-ended needle. Guinea pig lungs were washed with 20 ml of MPS via 16G catheter inserted into the trachea. Collected BAL fluid was stored at −20° C. until the time of assay.

IFN-γ ELISpot. Mice: Spleens from mice were collected individually in RPMI1640 media supplemented with 10% FBS (R10) and penicillin/streptomycin and processed into single cell suspensions. Cell pellets were re-suspended in 5 mL of ACK lysis buffer (Life Technologies, Carlsbad, Calif.) for 5 min at room temperature, and PBS was then added to stop the reaction. The samples were again centrifuged at 1,500 g for 10 min, cell pellets re-suspended in R10, and then passed through a 45 μm nylon filter before use in ELISpot assay. ELISpot assays were performed using the Mouse IFN-γ ELISpot$^{PLUS}$ plates (MABTECH). 96-well ELISpot plates pre-coated with capture antibody were blocked with R10 medium overnight at 4° C. 200,000 mouse splenocytes were plated into each well and stimulated for 20 hours with pools of 15-mer peptides overlapping by 9 amino acid from the SARS-CoV-2, SARS-CoV, or MERS-CoV Spike proteins (5 peptide pools per protein). Additionally, matrix mapping was performed using peptide pools in a matrix designed to identify immunodominant responses. Cells were stimulated with a final concentration of 5 μL of each peptide/well in RPMI+10% FBS (R10). The spots were developed based on manufacturer's instructions. R10 and cell stimulation cocktails (Invitrogen) were used for negative and positive controls, respectively. Spots were scanned and quantified by ImmunoSpot™ CTL reader. Spot-forming unit (SFU) per million cells was calculated by subtracting the negative control wells.

Flow cytometry. Intracellular cytokine staining was performed on splenocytes harvested from BALB/c and C57BL/6 mice stimulated with the overlapping peptides spanning the SARS-CoV-2 S protein for 6 hours at 37° C., 5% $CO_2$. Cells were stained with the following antibodies from BD Biosciences, unless stated, with the dilutions stated in parentheses: FITC anti-mouse CD107a (1:100), PerCP-Cy5.5 anti-mouse CD4 (1:100), APC anti-mouse CD8a (1:100), ViViD Dye (1-40) (LIVE/DEAD® Fixable Violet Dead Cell Stain kit; Invitrogen, L34955), APC-Cy7 anti-mouse CD3e (1:100), and BV605 anti-mouse IFN-γ (1:75) (eBiosciences). Phorbol Myristate Acetate (PMA) were used as a positive control, and complete medium only as the negative control. Cells were washed, fixed and, cell events were acquired using an FACS CANTO (BD Biosciences), followed by FlowJo software (FlowJo LLC, Ashland, Oreg.) analysis.

Statistics. All statistical analyses were performed using GraphPad Prism 7 or 8 software (La Jolla, Calif.). These data were considered significant if $p<0.05$. The lines in all graphs represent the mean value and error bars represent the standard deviation. No samples or animals were excluded from the analysis. Randomization was not performed for the animal studies. Samples and animals were not blinded before performing each experiment.

Results

Design and Synthesis of SARS-CoV-2 DNA Vaccine Constructs

Four spike protein sequences were retrieved from the first four available SARS-CoV-2 full genome sequences published on GISAID (Global Initiative on Sharing All Influenza Data). Three Spike sequences were 100% matched and one was considered an outlier (98.6% sequence identity with the other sequences). After performing a sequence alignment, the SARS-CoV-2 spike glycoprotein sequence ("Covid-19 spike antigen"; SEQ ID NO: 1) was generated and an N-terminal IgE leader sequence was added. The highly optimized DNA sequence encoding SARS-CoV-2 IgE-spike was created as described elsewhere herein to enhance expression and immunogenicity. SARS-CoV-2 spike outlier glycoprotein sequence ("Covid-19 spike-OL antigen"; SEQ ID NO: 4) was generated and an N-terminal IgE leader sequence was added. The optimized DNA sequence was synthesized, digested with BamHI and XhoI, and cloned into the expression vector pGX0001 under the control of the human cytomegalovirus immediate-early promoter and a bovine growth hormone polyadenylation signal. The resulting plasmids were designated as pGX9501 and pGX9503, designed to encode the SARS-CoV-2 S protein from the 3 matched sequences and the outlier sequence, respectively (FIG. 1A).

In Vitro Characterization of Synthetic DNA Vaccine Constructs

Figure 1B:
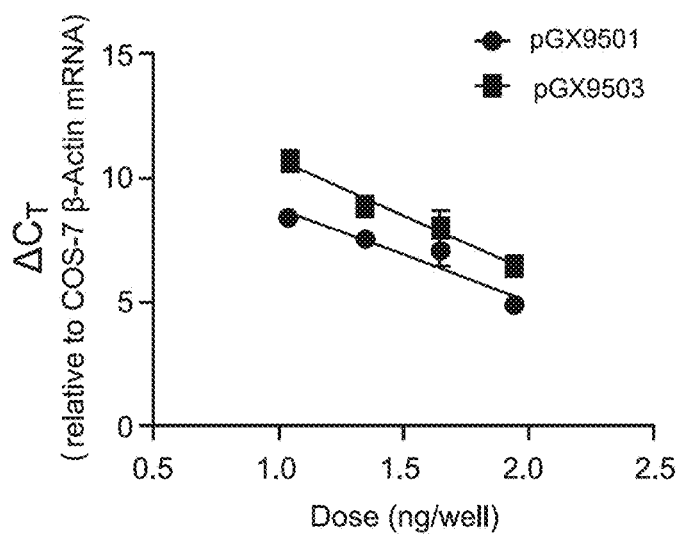
Figure 1C:
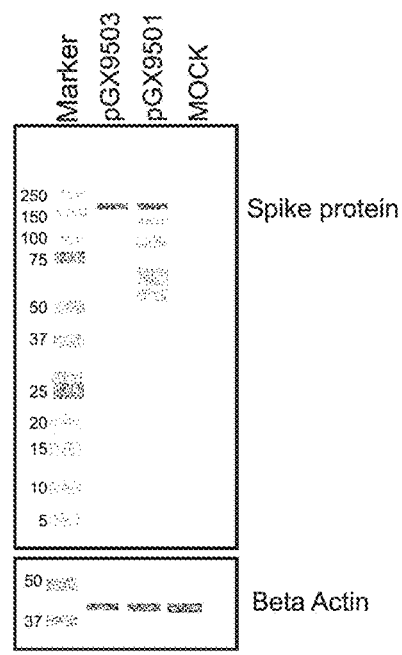
Figure 1D:
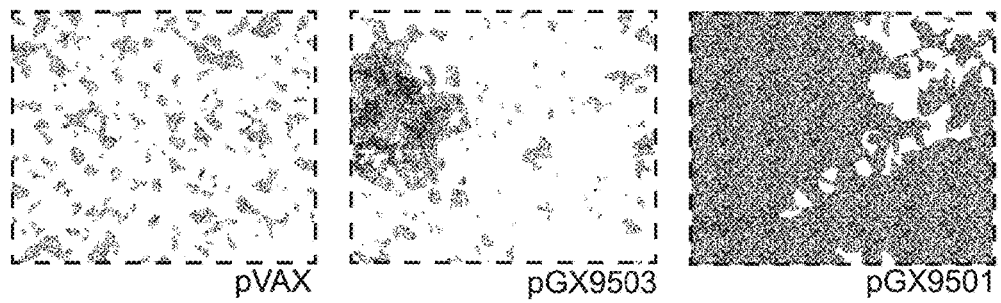

Expression of the encoded SARS-CoV-2 spike transgene at the RNA level in COS-7 cells transfected with pGX9501 and pGX9503 was measured. Using the total RNA extracted from the transfected COS-7 cells, expression of the spike transgene was confirmed by RT-PCR (FIG. 1B). In vitro spike protein expression in 293T cells was measured by Western blot analysis using a cross-reactive antibody against SARS-CoV S protein on cell lysates. Western blots of the lysates of HEK-293T cells transfected with pGX9501 or pGX9503 constructs revealed bands approximate to the predicted S protein molecular weight, 140-142 kDa, with slight shifts likely due to the 22 potential N-linked glycans in the S protein (FIG. 1C). In immunofluorescent studies, the S protein was detected in 293T cells transfected with pGX9501 or pGX9503 (FIG. 1D). In summary, in vitro studies revealed the expression of the Spike protein at both the RNA and protein level after transfection of cell lines with the candidate vaccine constructs.

Figure 2:
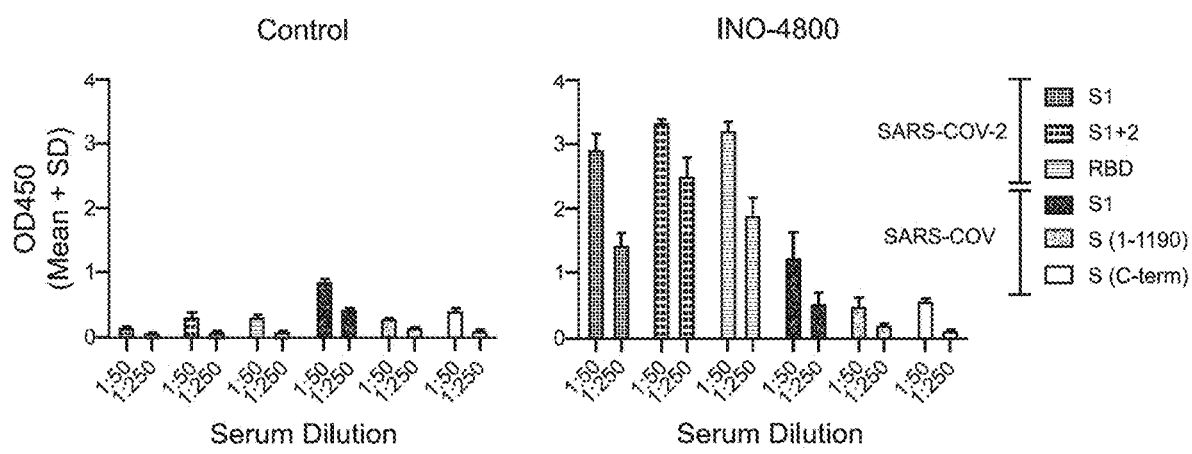
FIG. 2 illustrates an IgG binding screen of a panel of SARS-CoV-2 and SARS-CoV antigens using sera from INO-4800-treated mice. BALB/c mice were immunized on Day 0 with 25 µg INO-4800 or pVAX-empty vector (Control) as described in the methods. Protein antigen binding of IgG at 1:50 and 1:250 serum dilutions from mice at day 14. Data shown represent mean OD450 nm values (mean+SD) for each group of 4 mice.
Figure 3A:
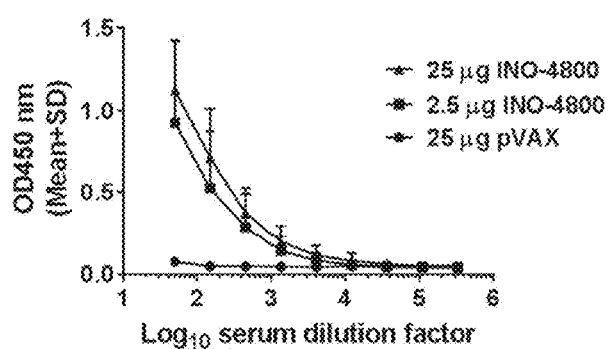
FIGS. 3A, 3B, 3C, and 3D demonstrate humoral responses to SARS-CoV-2 S 1+2 and S receptor binding domain (RBD) protein antigen in BALB/c mice after a single dose of INO-4800. BALB/c mice were immunized on Day 0 with indicated doses of INO-4800 or pVAX-empty vector as described in Example 1. SARS-CoV-2 S1+2 (FIG. 3A) or SARS-CoV-2 RBD (FIG. 3B) protein antigen binding of IgG in serial serum dilutions from mice at day 14 are shown. Data shown represent mean OD450 nm values (mean+SD) for each group of 8 mice (FIGS. 3A and 3B) and 5 mice (FIGS. 3C and 3D). Serum IgG binding endpoint titers to SARS-CoV-2 S1+2 (FIG. 3B) and SARS-CoV-2 RBD (FIG. 3D) protein. Data representative of 2 independent experiments.
Figure 3B:
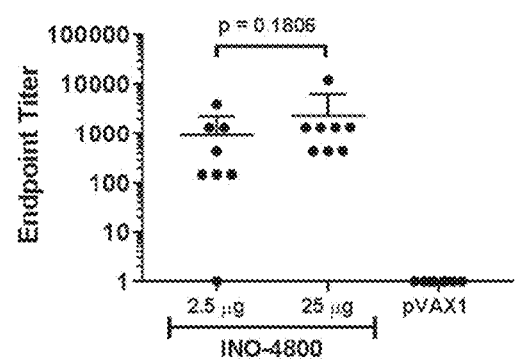
Figure 3C:
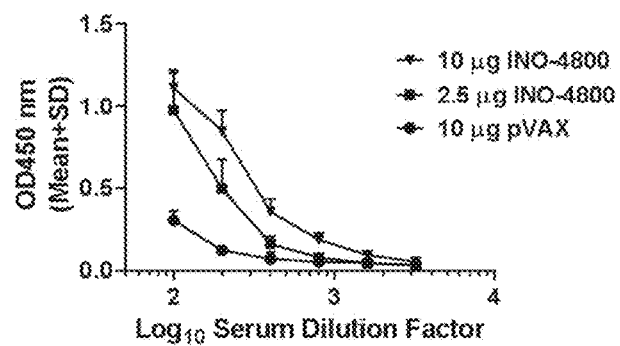
Figure 3D:
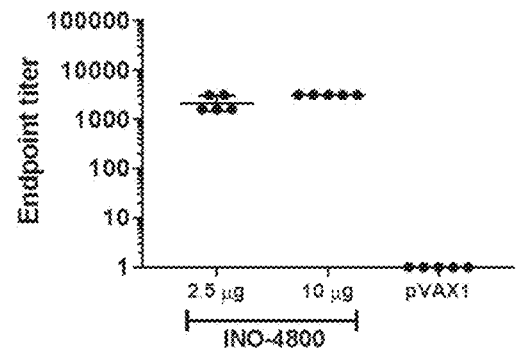

Humoral immune responses in mice. pGX9501 was selected as the vaccine construct to advance to immunogenicity studies, due to the broader coverage it would likely provide compared to the outlier, pGX9503. pGX9501 was subsequently termed INO-4800. The immunogenicity of INO-4800 was evaluated in BALB/c mice, post-administration to the tibialis anterior muscle using the CELLECTRA® delivery device. (Sardesai & Weiner, Curr. Opin. Immunol., 23, 421-429 (2011). The reactivity of the sera from a group of mice immunized with INO-4800 was measured against a panel of SARS-CoV-2 and SARS-CoV antigens (FIG. 2). Analysis revealed IgG binding against SARS-CoV-2 S protein antigens, with limited cross-reactivity to SARS-CoV S protein antigens in the sera of INO-4800-immunized mice. The serum IgG binding endpoint titers in mice immunized with pDNA against recombinant SARS-CoV-2 spike protein S1+S2 regions (FIGS. 3A and 3B) and recombinant SARS-CoV-2 spike protein receptor binding domain (RBD) (FIGS. 3C and 3D) were measured. Endpoint titers were observed in the sera of mice at day 14 after immunization with a single dose of INO-4800 (FIGS. 3B, 3C, 3D).

Figure 4A:
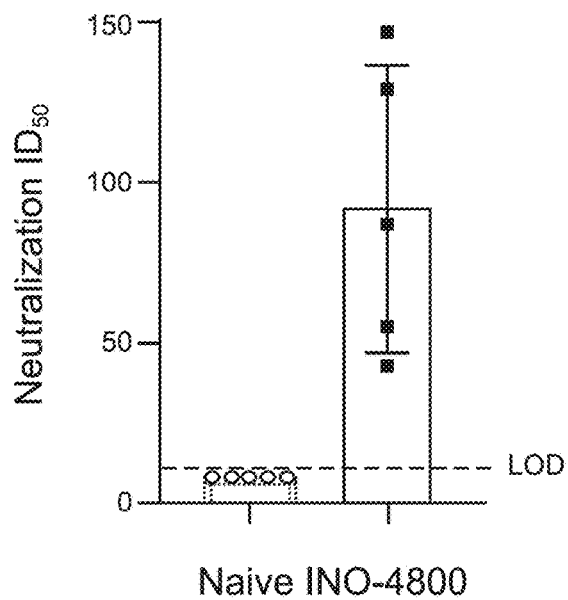
FIGS. 4A and 4B illustrate neutralizing antibody responses after immunization with INO-4800. BALB/c mice (n of 5 per group) were immunized twice on days 0 and 14 with 10 µg of INO-4800. Sera was collected on day 7 post-2nd immunization and serial dilutions were incubated with a pseudovirus displaying the SARS-CoV-2 Spike and co-incubated with ACE2-293T cells.
Figure 4B:
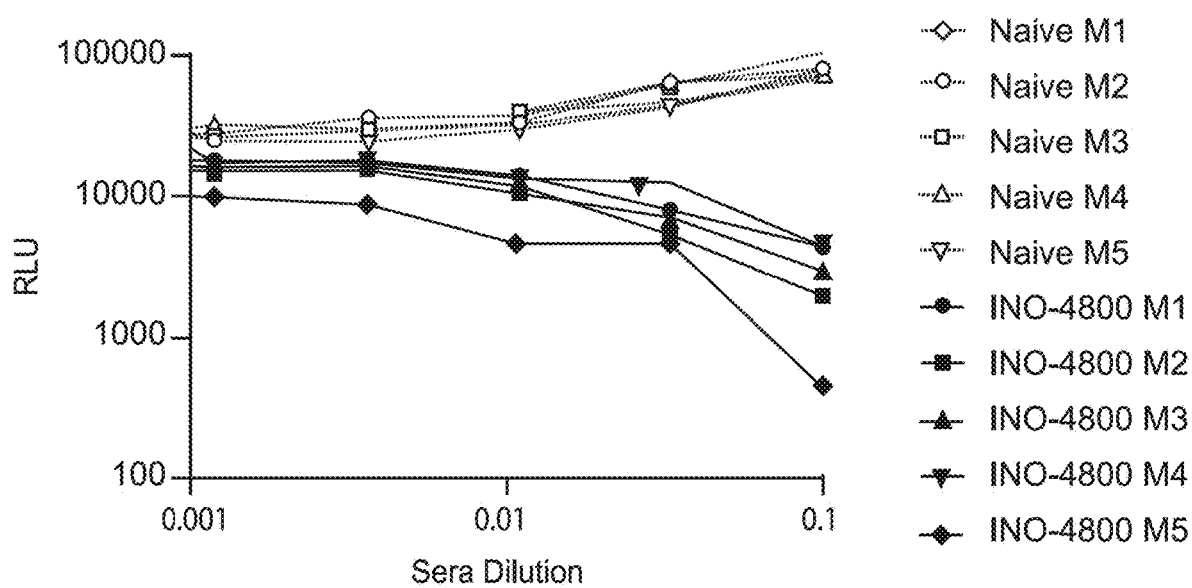

Neutralization assay. A neutralization assay with a pNL4-3.Luc.R-E-based pseudovirus displaying the SARS-CoV-2 Spike protein was developed. Neutralization titers were detected by a reduction in relative luciferase units (RLU) compared to controls which had no decrease in RLU signal. BALB/c mice were immunized twice with INO-4800, on days 0 and 14, and sera was collected on day 7 post-$2^{nd}$ immunization. The pseudovirus was incubated with serial dilutions of mouse sera and the sera-virus mixture was added to 293T cells stably expressing the human ACE2 receptor (ACE2-293T) for 72 hours. Neutralization ID50 average titers of 92.2 were observed in INO-4800 immunized mice (FIGS. 4A and 4B). No reduction in RLU was observed for the control animals. Neutralizing titers were additionally measured against two wildtype SARS-CoV-2 virus strains by plaque reduction neutralization test (PRNT) assay. Sera from INO-4800 immunized BALB/c mice neutralized both SARS-CoV-2/WH-09/human/2020 and SARS-CoV-2/Australia/VIC01/2020 virus strains with average ND50 titers of 97.5 and 128.1, respectively (Table 1). Live virus neutralizing titers were also evaluated in C57BL/6 mice following the same INO-4800 immunization regimen. Sera from INO-4800 immunized C57BL/6 mice neutralized wildtype SARS-CoV-2 virus with average ND50 titer of 340 (Table 1).

TABLE 1

Sera neutralizing activity after INO-4800 administration to mice and guinea pigs.

| Model | Vaccine | N | Immunization Regimen | Sample Time point | Neutralization Assay | Serum ND50 (Reciprocal Dilution) |
|---|---|---|---|---|---|---|
| BALB/c Mouse | pVAX | 4 | 25 µg Days 0, 14 | Day 21 | SARS-CoV-2 (WH-09/human/2020) | <20, <20, <20, <20 |
| | INO-4800 | 4 | 25 µg Days 0, 14 | Day 21 | SARS-CoV-2 (WH-09/human/2020) | 30, 40, 80, 240 |
| | pVAX | 8 | 25 µg Days 0, 14 | Day 21 | SARS-CoV-2 (Australia/VIC01/2020) | <10, 12, 13, 15, 16, 17, 19, 24 |
| | INO-4800 | 8 | 25 µg Days 0, 14 | Day 21 | SARS-CoV-2 (Australia/VIC01/2020) | 27, 46, 91, 108, 130, 161, 221, 241 |
| | pVAX | 5 | 10 µg Days 0, 14 | Day 21 | SARS-CoV-2 Pseudovirus | 8, 8, 8, 8, 8 |
| | INO-4800 | 5 | 10 µg Days 0, 14 | Day 21 | SARS-CoV-2 Pseudovirus | 43, 55, 87, 129, 147 |

TABLE 1-continued

Sera neutralizing activity after INO-4800 administration to mice and guinea pigs.

| Model | Vaccine | N | Immunization Regimen | Sample Time point | Neutralization Assay | Serum ND50 (Reciprocal Dilution) |
|---|---|---|---|---|---|---|
| C57BL/6 Mouse | pVAX | 4 | 25 µg Days 0, 14 | Day 21 | SARS-CoV-2 (WH-09/human/2020) | <20, <20, <20, <20 |
|  | INO-4800 | 4 | 25 µg Days 0, 14 | Day 21 | SARS-CoV-2 (WH-09/human/2020) | 240, 240, 240, 640 |
| Guinea Pig | pVAX | 5 | 100 µg Days 0, 14, 28 | Day 42 | SARS-CoV-2 (Australia/VIC01/2020) | <10, 14, 20, 21,25 |
|  | INO-4800 | 5 | 100 µg Days 0, 14, 28 | Day 42 | SARS-CoV-2 (Australia/VIC01/2020) | >320, >320, >320, >320, >320 |
|  | pVAX | 5 | 100 µg Days 0, 14, 28 | Day 35 | SARS-CoV-2 Pseudovirus | <20, <20, <20, <20, <20 |
|  | INO-4800 | 5 | 100 µg Days 0, 14, 28 | Day 35 | SARS-CoV-2 Pseudovirus | 527, 532, 579, 614, 616 |
| New Zealand White Rabbit | SSC | 5 | Days 0, 28 | Day 42 | SARS-CoV-2 Pseudovirus | <10, <10, <10, <10, <10 |
|  | INO-4800 | 5 | 1 mg, Days 0, 28 | Day 42 | SARS-CoV-2 Pseudovirus | 12, 23, 32, 148, 178 |
|  | INO-4800 | 5 | 2 mg, Days 0. 28 | Day 42 | SARS-CoV-2 Pseudovirus | 202, 237, 252, 455, 995 |
| Non-human primates | INO-4800 | 5 | 1 mg, Days 0, 28 | Day 42 | SARS-CoV-2 Pseudovirus | 15, 27, 55, 61, 1489 |
|  | INO-4800 | 5 | 2 mg, Days 0. 28 | Day 42 | SARS-CoV-2 Pseudovirus | 78, 23, 13, 48, <10 |

Figure 5A:
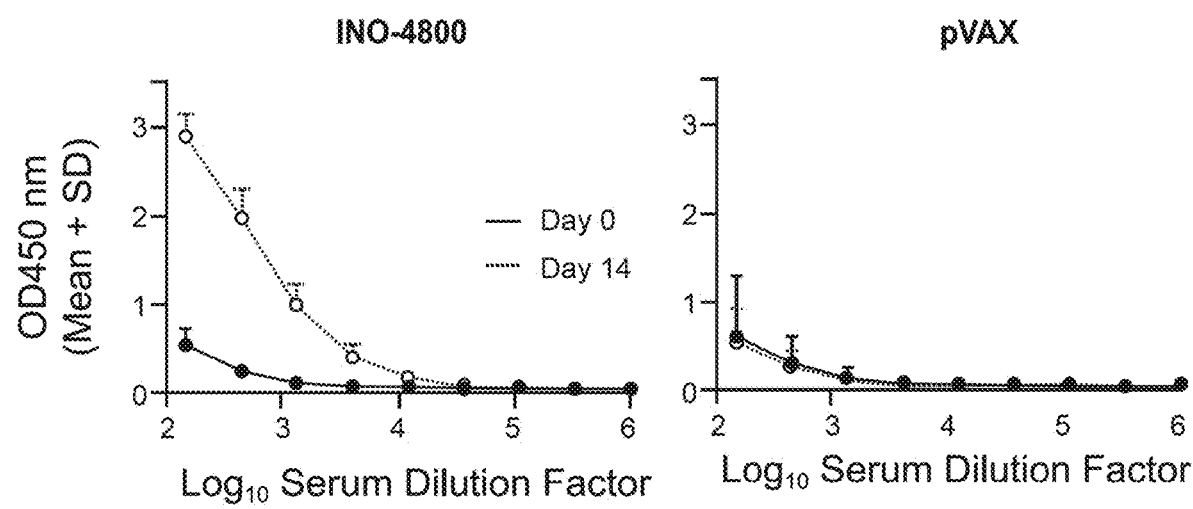
FIGS. 5A and 5B show humoral responses to SARS-CoV-2 in Hartley guinea pigs after a single dose of INO-4800. Hartley guinea pigs mice were immunized on Day 0 with 100 µg INO-4800 or pVAX-empty vector as described in Example 1.
Figure 5B:
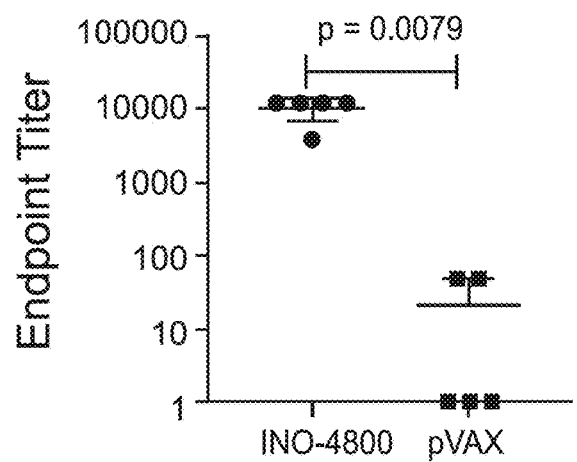
Figure 6A:
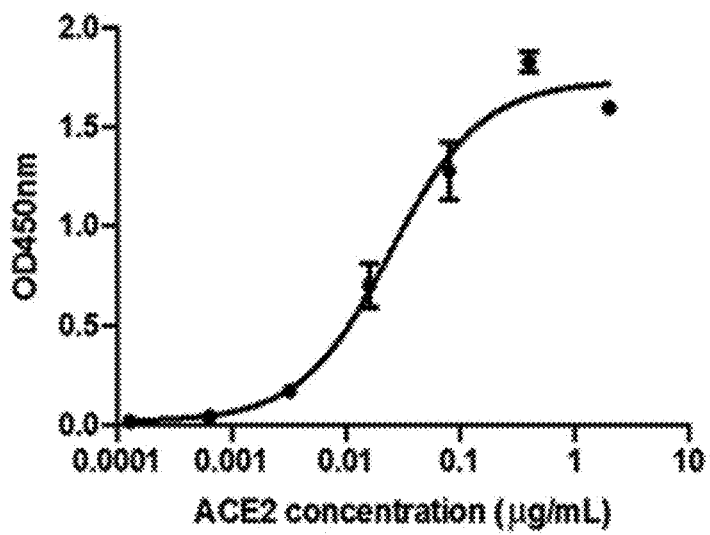
FIGS. 6A-6F demonstrate that INO-4800 immunized mouse and guinea pig sera compete with ACE2 receptor for SARS-CoV-2 Spike protein binding.
Figure 6B:
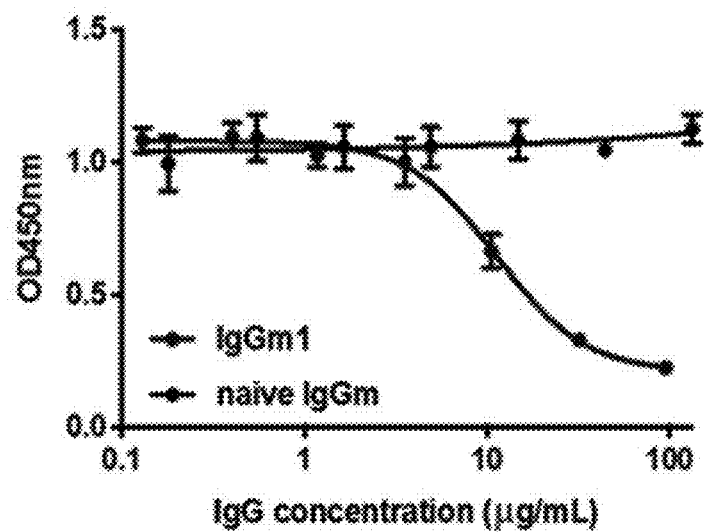
Figure 6C:
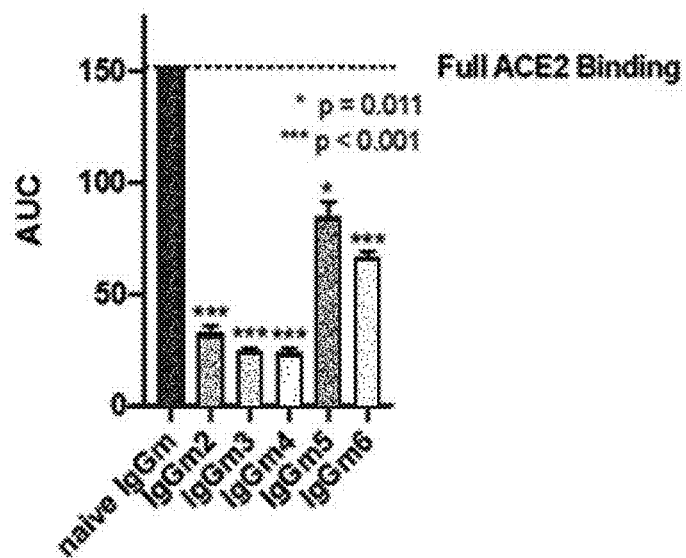
Figure 6D:
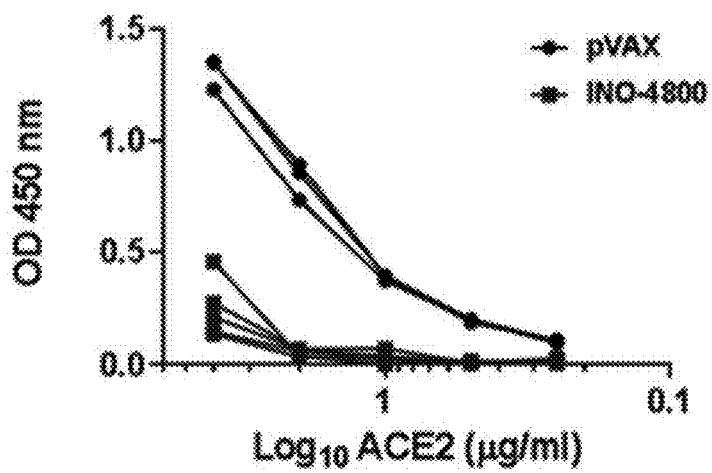
Figure 6E:
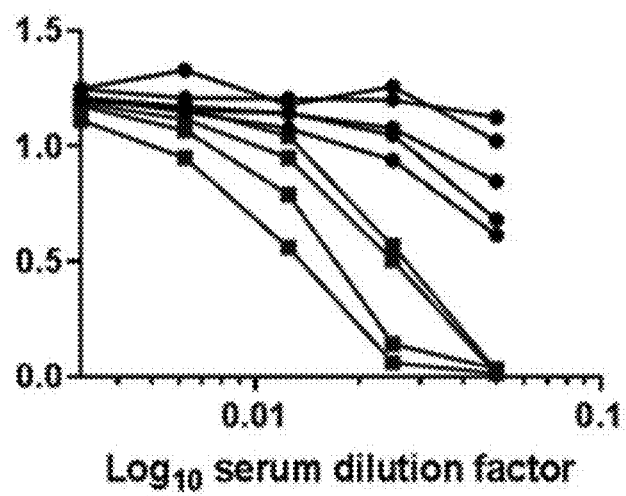
Figure 6F:
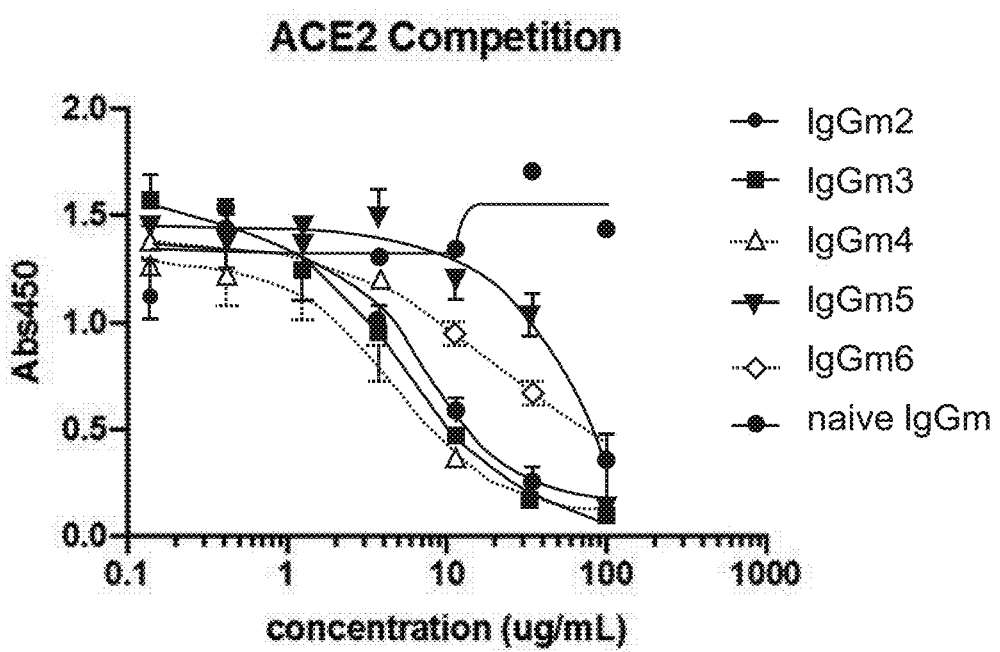
Figure 7A:
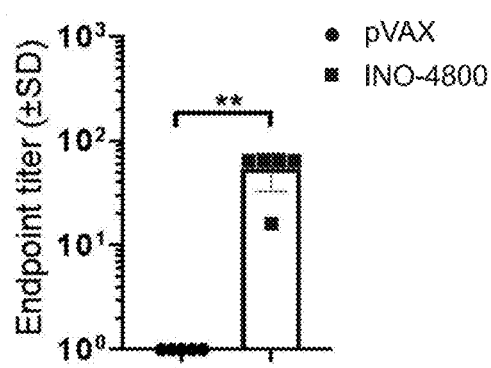
FIGS. 7A-7D illustrate detection of SARS-CoV-2 S protein-reactive antibodies in the BAL of INO-4800 immunized animals. BALB/c mice (n of 5 per group) were immunized on days 0 and 14 with INO-4800 or pVAX and BAL collected at day 21 (FIGS. 7A and 7B). Hartley guinea pigs (n of 5 per group) were immunized on days 0, 14 and 21 with INO-4800 or pVAX and BAL collected at day 42 (FIGS. 7C and 7D). Bronchoalveolar lavage fluid was assayed in duplicate for SARS-CoV-2 Spike protein-specific IgG antibodies by ELISA. Data are presented as endpoint titers (FIGS. 7A and 7C), and BAL dilution curves with raw OD 450 nm values (FIGS. 7B and 7D).
Figure 7B:
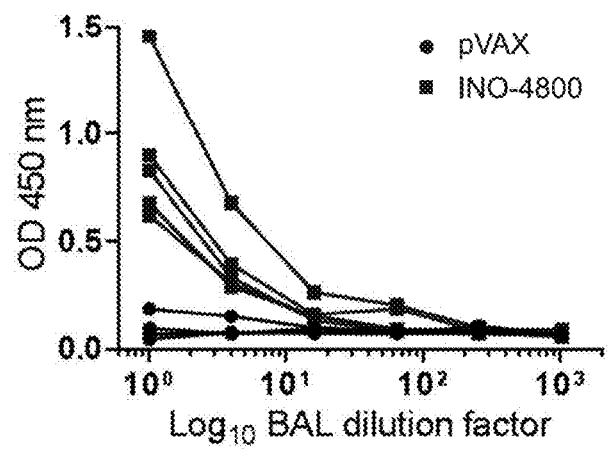
Figure 7C:
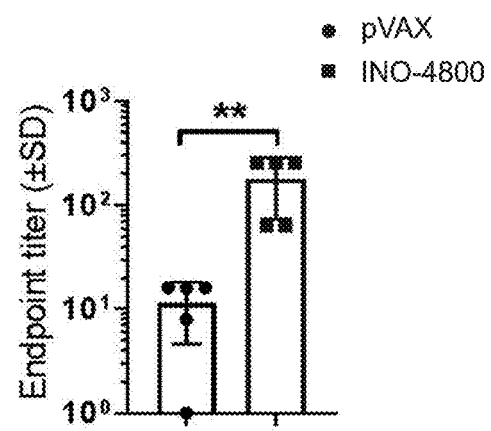
Figure 7D:
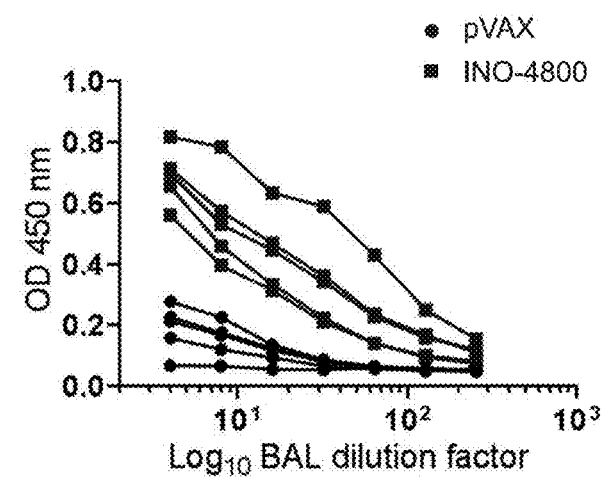

The immunogenicity of INO-4800 in the Hartley guinea pig model, an established model for intradermal vaccine delivery (Carter, et al. The adjuvant GLA-AF enhances human intradermal vaccine responses. Sci Adv. 2018; 4(9): eaas9930; Schultheis, et al. Characterization of guinea pig T cell responses elicited after EP-assisted delivery of DNA vaccines to the skin. Vaccine. 2017; 35(1):61-70), was assessed. 100 µg of pDNA was administered by Mantoux injection to the skin and followed by CELLECTRA® device on day as described in the methods section above. On day 14, anti-spike protein binding of serum antibodies was measured by ELISA. Immunization with INO-4800 revealed an immune response in respect to SARS-CoV-2 S1+2 protein binding IgG levels in the sera (FIGS. 5A and 5B). The endpoint SARS-CoV-2 S protein binding titer at day 14 was 10,530 and 21 in guinea pigs treated with 100 µg INO-4800 or pVAX (control), respectively (FIG. 5B). Antibody neutralizing activity following intradermal INO-4800 immunization in the guinea pig model was evaluated. Guinea pigs were treated on days 0, 14, and 28 with pVAX or INO-4800, and sera samples were collected on days 35 or 42 to measure sera neutralizing activity against pseudovirus or wildtype virus, respectively. SARS-CoV-2 pseudovirus neutralizing activity with average ND50 titers of 573.5 was observed for the INO-4800 immunized guinea pigs (Table 1). Wildtype SARS-CoV-2 virus activity was also observed for the INO-4800 immunized guinea pigs with ND50 titers >320 by PRNT assay observed in all animals (Table 1). The functionality of the serum antibodies was further measured by assessing their ability to inhibit ACE2 binding to SARS-CoV-2 spike protein. Serum (1:20 dilution) collected from INO-4800 immunized guinea pigs after 2nd immunization inhibited binding of SARS-CoV-2 Spike protein over range of concentrations of ACE-2 (0.25 µg/ml through 4 µg/ml) (FIG. 6E). Furthermore, serum dilution curves revealed serum collected from INO-4800 immunized guinea pigs blocked binding of ACE-2 to SARS-CoV-2 in a dilution-dependent manner (FIG. 6F). Serum collected from pVAX-treated animals displayed negligible activity in the inhibition of ACE-2 binding to the virus protein, the decrease in OD signal at the highest concentration of serum is considered a matrix effect in the assay.

Inhibition of SARS-CoV-2 S protein binding to ACE2 receptor. The receptor inhibiting functionality of INO-4800-induced antibody responses was examined. An ELISA-based ACE2 inhibition assay was developed as a surrogate for neutralization. As a control in the assay, ACE2 is shown to bind to SARS-CoV-2 Spike protein with an EC50 of 0.025 µg/ml (FIG. 6A). BALB/c mice were immunized on Days 0 and Day 14 with 10 µg of INO-4800, and serum IgG was purified on Day 21 post-immunization to ensure inhibition is antibody-mediated. Inhibition of the Spike-ACE2 interaction using serum IgG from a naïve mouse and from an INO-4800 vaccinated mouse were compared (FIG. 6B). The receptor inhibition assay was repeated with a group of five immunized mice, demonstrating that INO-4800-induced antibodies competed with ACE2 binding to the SARS-CoV-2 Spike protein (FIGS. 6C and 6F). ACE2 binding inhibition was further evaluated in the guinea pig model. Sera collected from INO-4800 immunized guinea pigs inhibited binding of SARS-CoV-2 Spike protein over range of concentrations of ACE2 (0.25 µg/ml through 4 µg/ml) (FIG. 6D). Furthermore, serum dilution curves revealed sera collected from INO-4800 immunized guinea pigs blocked binding of ACE2 to SARS-CoV-2 in a dilution-dependent manner (FIG. 6E). Sera collected from pVAX-treated animals displayed negligible activity in the inhibition of ACE2 binding to the virus protein, the decrease in OD signal at the highest concentration of serum is considered a matrix effect in the assay. FIG. 6F depicts IgGs purified from n=5 mice day 14 post second immunization with INO-4800 show competition against ACE2 receptor binding to SARS-CoV-2 Spike protein compared to pooled naïve mice IgGs.

In summary, immunogenicity testing in both mice and guinea pigs revealed the SARS-CoV-2 vaccine candidate, INO-4800, was capable of eliciting antibody responses to SARS-CoV-2 spike protein. ACE2 is considered to be the primary receptor for SARS-CoV-2 cellular entry, blocking this interaction suggests INO-4800-induced antibodies may prevent host infection.

Biodistribution of SARS-CoV-2 reactive IgG to the lung. Lower respiratory disease (LRD) is associated with severe cases of COVID-19. The presence of antibodies at the lung mucosa targeting SARS-CoV-2 could potentially mediate protection against LRD. The presence of SARS-CoV-2 specific antibody in the lungs of immunized mice and guinea pigs was evaluated. BALB/c mice and Hartley guinea pigs were immunized, on days 0 and 14 or 0, 14 and 28, respectively, with INO-4800 or pVAX control pDNA. Bronchoalveolar lavage (BAL) fluid was collected following sacrifice, and SARS-CoV-2 S protein ELISAs were performed. In both BALB/c and Hartley guinea pigs which received INO-4800, a statistically significant increase in SARS-CoV-2 S protein binding IgG in BAL fluid compared to animals receiving pVAX control was measured (FIGS. 7A-7D). Taken together, these data demonstrate the presence of anti-SARS-CoV-2 specific antibody in the lungs following immunization with INO-4800.

Figure 8A:
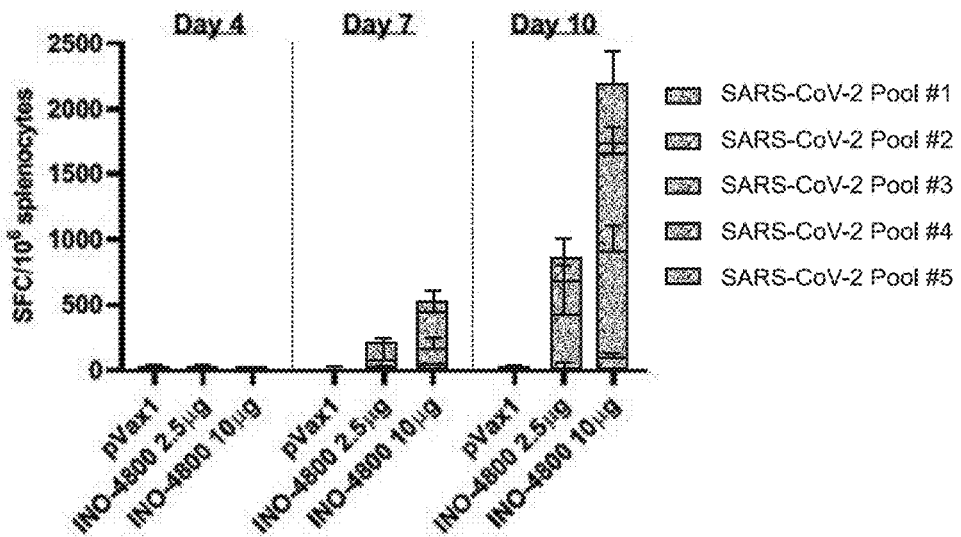
FIG. 8A-8C show induction of T cell responses in BALB/c mice post-administration of INO-4800. BALB/c mice (n=5/group) were immunized with 2.5 or 10 µg INO-4800. T cell responses were analyzed in the animals on days 4, 7, 10 (FIGS. 8A and 8B), and day 14 (FIG. 8C). T cell responses were measured by IFN-γ ELISpot in splenocytes stimulated for 20 hours with overlapping peptide pools spanning the SARS-CoV-2 (FIG. 8A), SARS-CoV (FIG. 8B), or MERS-CoV (FIG. 8C) Spike proteins. Bars represent the mean+SD.
Figure 8B:
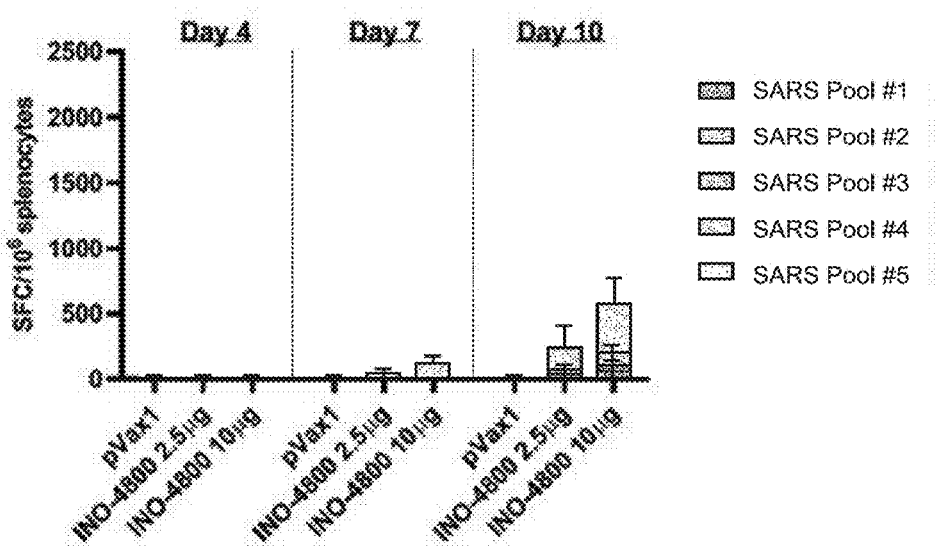
Figure 8C:
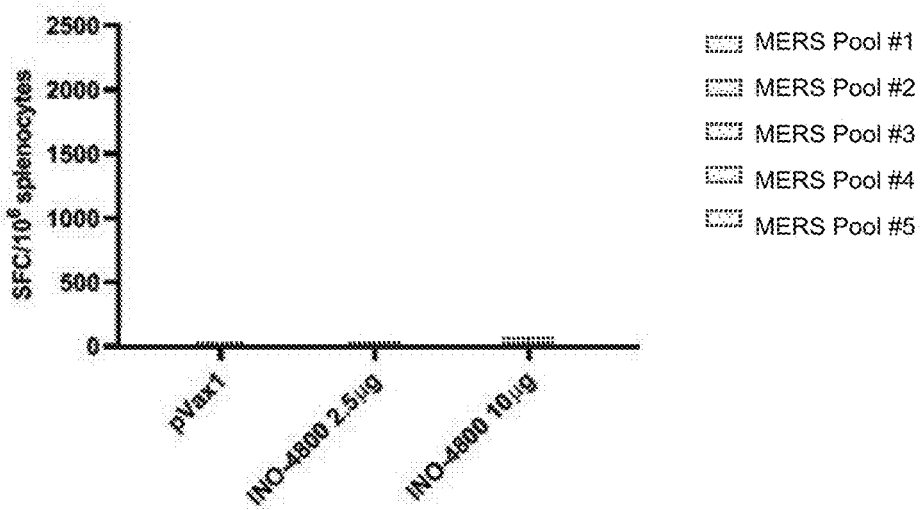
Figure 32A:
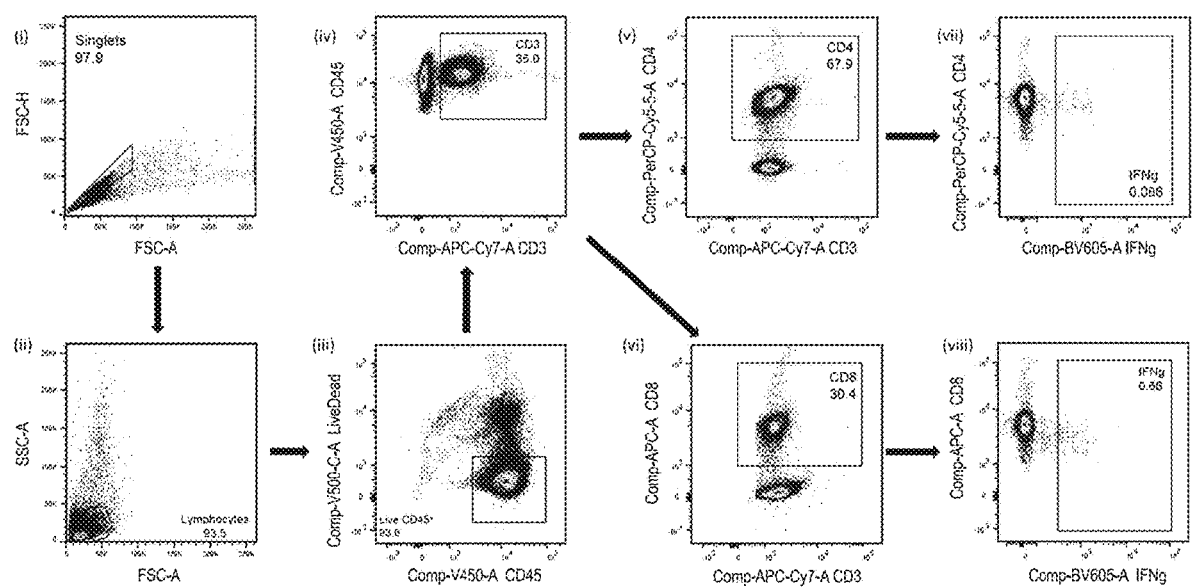
FIG. 32A and FIG. 32B depict flow cytometric analysis of T cell populations producing IFN-γ upon SARS-CoV-2 S protein stimulation. Splenocytes harvested from BALB/c and C57BL/6 mice 14 days after pVAX or INO-4800 treatment were made into single cell suspensions. The cells were stimulated for 6 hours with SARS-CoV-2 overlapping peptide pools.
Figure 32B:
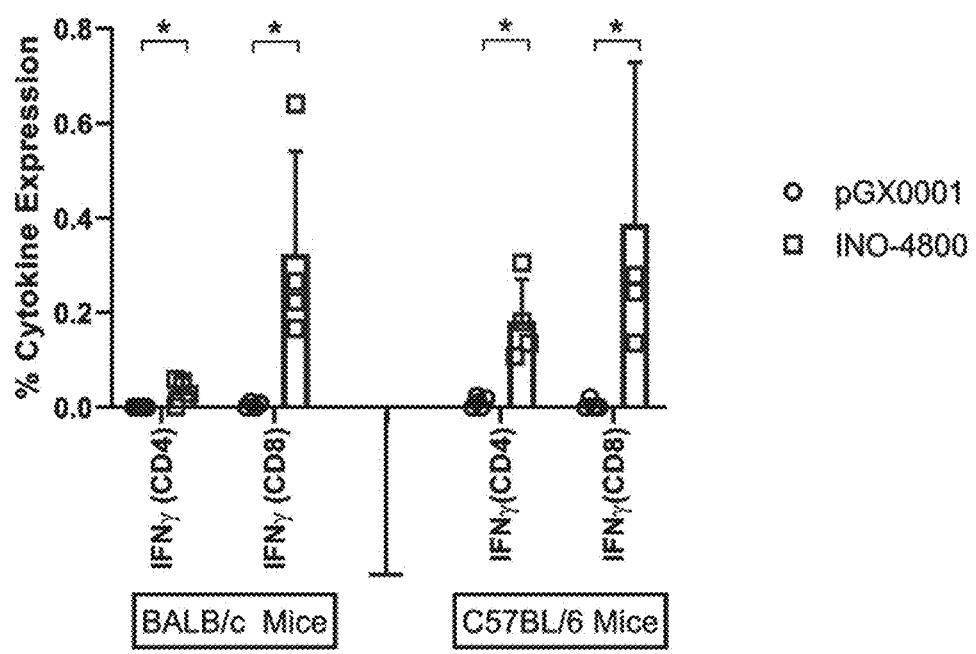

Coronavirus cross-reactive cellular immune responses in mice. T cell responses against SARS-CoV-2, SARS-CoV, and MERS-CoV S antigens were assayed by IFN-γ ELISpot. Groups of BALB/c mice were sacrificed at days 4, 7, or 10 post-INO-4800 administration (2.5 or 10 µg of pDNA), splenocytes were harvested, and a single-cell suspension was stimulated for 20 hours with pools of 15-mer overlapping peptides spanning the SARS-CoV-2, SARS-CoV, and MERS-CoV spike protein. Day 7 post-INO-4800 administration, T cell responses of 205 and 552 SFU per $10^6$ splenocytes against SARS-CoV-2 were measured for the 2.5 and 10 µg doses, respectively (FIG. 8A). Higher magnitude responses of 852 and 2,193 SFU per $10^6$ splenocytes against SARS-CoV-2 were observed on Day 10 post-INO-4800 administration. Additionally, the cross-reactivity of the cellular response elicited by INO-4800 against SARS-CoV was assayed, showing detectable, albeit lower, T cell responses on both Day 7 (74 [2.5 µg dose] and 140 [10 µg dose] SFU per $10^6$ 104409.000605 splenocytes) and Day 10 post-administration (242 [2.5 µg dose] and 588 [10 µg dose] SFU per $10^6$ splenocytes) (FIG. 8B). Interestingly, no cross-reactive T cell responses were observed against MERS-CoV peptides (FIG. 8C). Representative images of the IFN-γ ELISpot plates are provided in FIG. 31. The T cell populations which were producing IFN-γ were identified. Flow cytometric analysis on splenocytes harvested from BALB/c mice on Day 14 after a single INO-4800 immunization revealed the T cell compartment to contain 0.04% CD4+ and 0.32% CD8+ IFN-γ+ T cells after stimulation with SARS-CoV-2 antigens (FIG. 32).

Figure 14A:
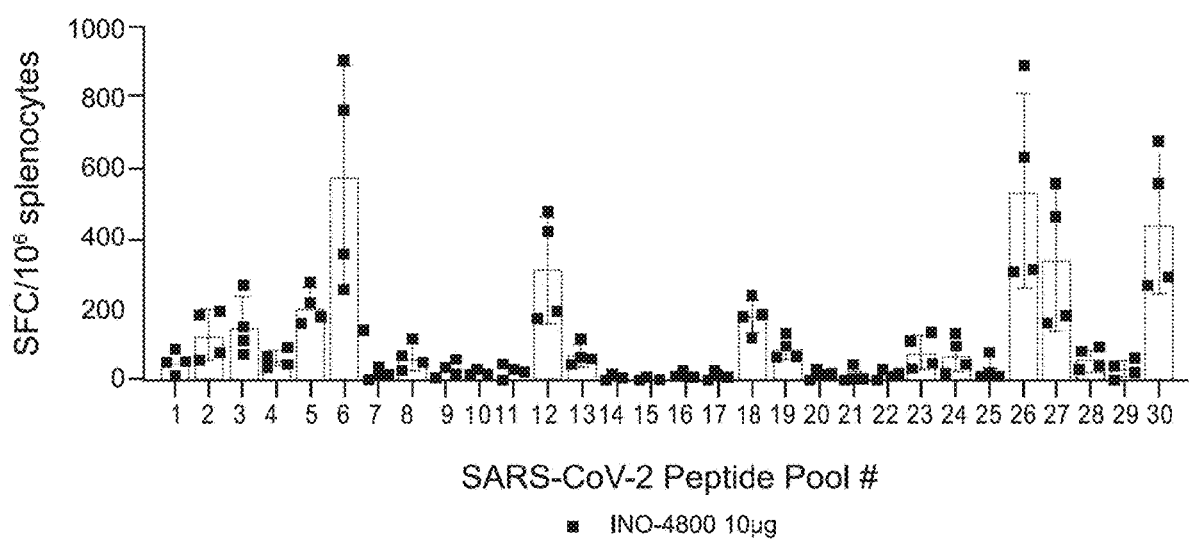
FIGS. 14A and 14B show T cell epitope mapping after INO-4800 administration to BALB/c mice. Splenocytes were stimulated for 20 hours with SARS-CoV-2 peptide matrix mapping pools.
Figure 14B:
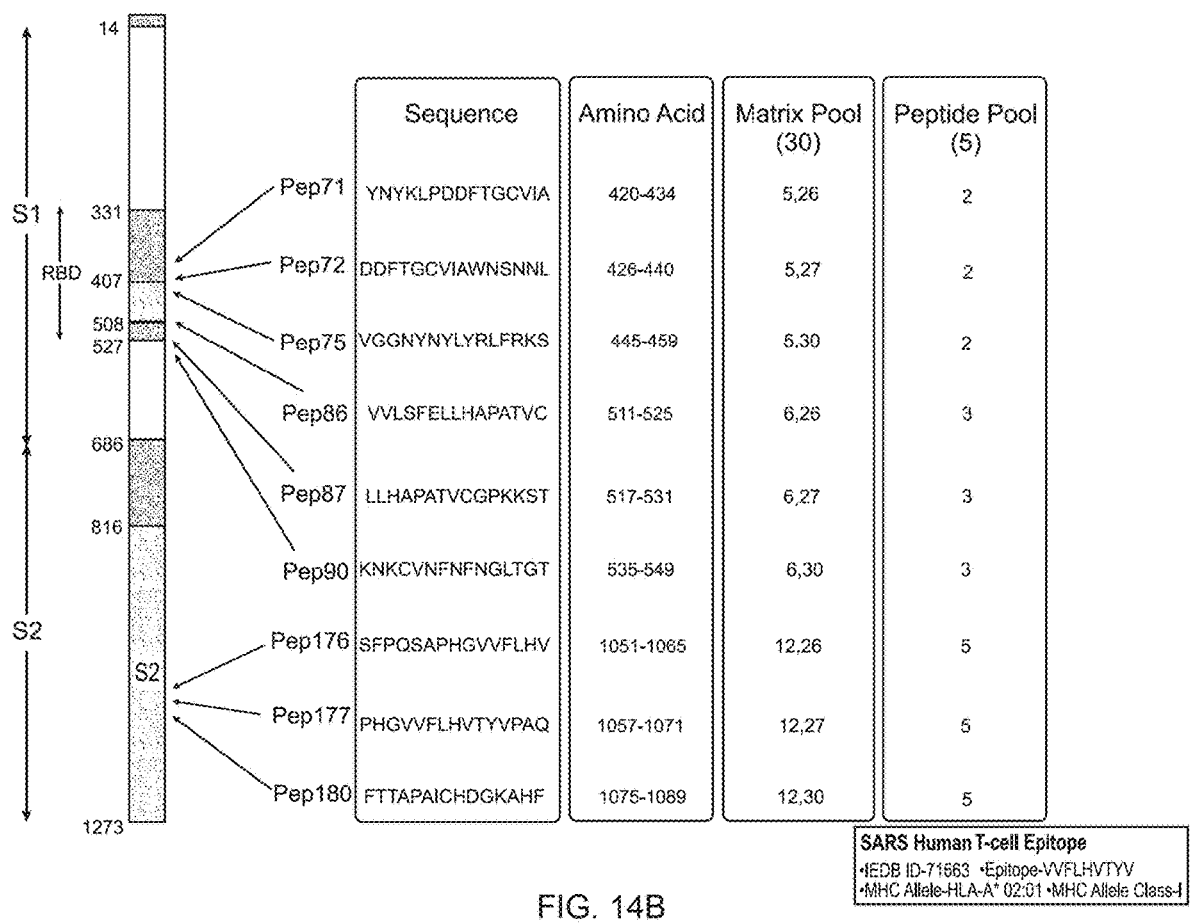
Figure 15A:
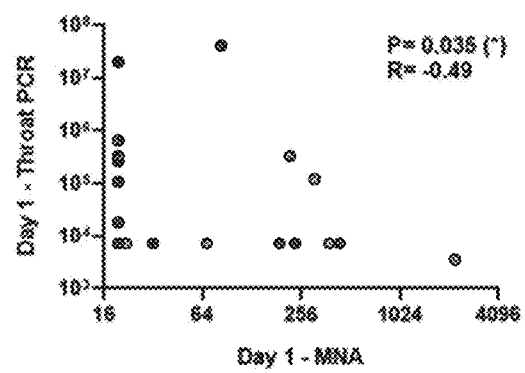
FIGS. 15A-15H depict humoral correlates of protection in throat and nasal compartments.
Figure 15B:
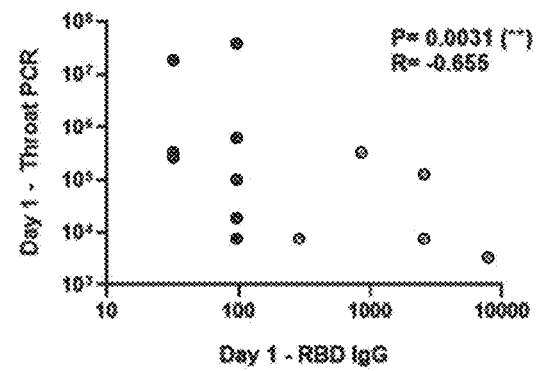
Figure 15C:
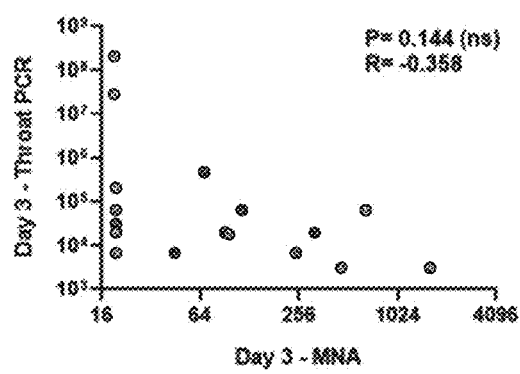
Figure 15D:
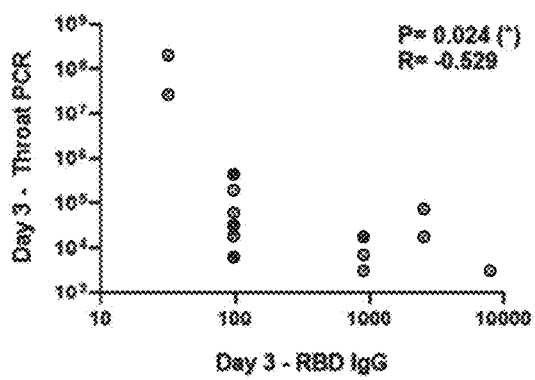
Figure 15E:
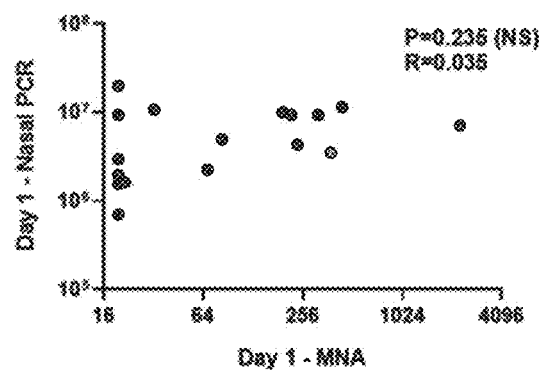
Figure 15F:
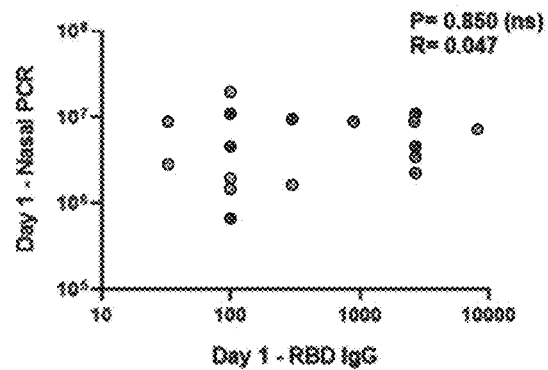
Figure 15G:
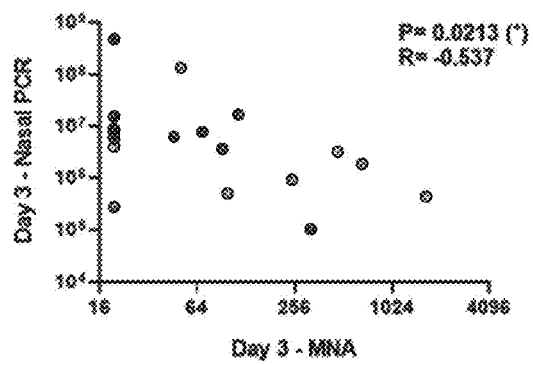
Figure 15H:
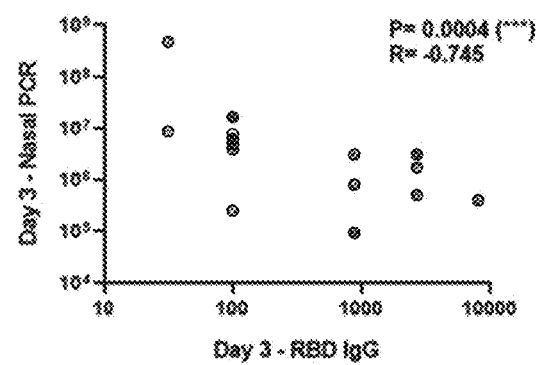

BALB/c SARS-CoV-2 epitope mapping. Epitope mapping was performed on the splenocytes from BALB/c mice receiving the 10 µg INO-4800 dose. Thirty matrix mapping pools were used to stimulate splenocytes for 20 hours and immunodominant responses were detected in multiple peptide pools (FIG. 14A). The responses were deconvoluted to identify several epitopes (H2-Kd) clustering in the receptor binding domain and in the S2 domain (FIG. 14B). Interestingly, one SARS-CoV-2 H2-Kd epitope, PHGVVFLHV (SEQ ID NO: 16), was observed to be overlapping and adjacent to the SARS-CoV human HLA-A2 restricted epitope VVFLHVTVYV (SEQ ID NO: 17).

In summary, T cell responses against SARS-CoV-2 S protein epitopes were detected in mice immunized with INO-4800.

Figure 9:
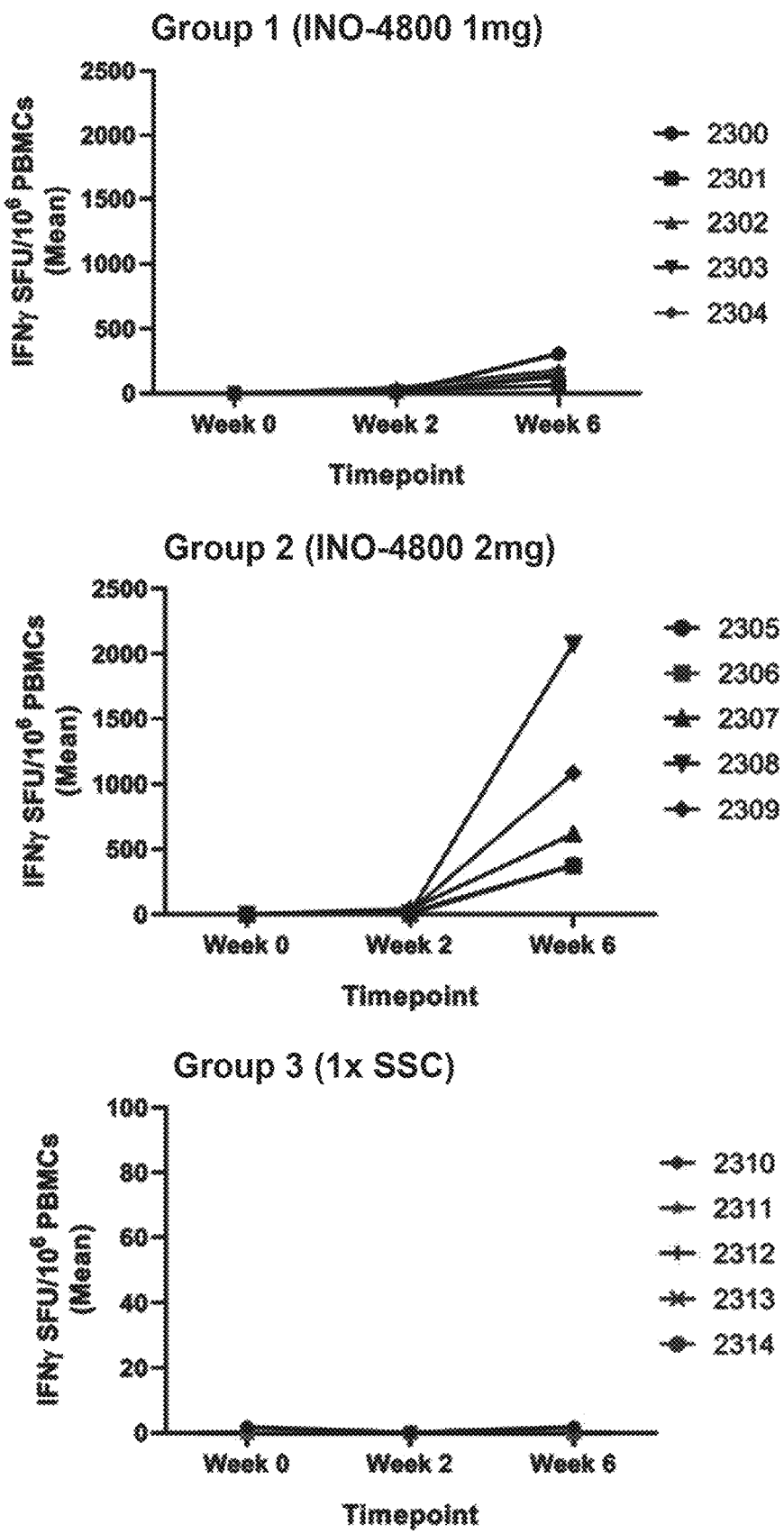
FIGS. 9 and 10 illustrate cellular and humoral immune responses measured in INO-4800-treated New Zealand White (NZW) rabbits. Day 0 and 28 intradermal delivery of pDNA. PBMC IFN-γ ELISpot (FIG. 9); Serum IgG binding ELISA (FIG. 10).
Figure 10:
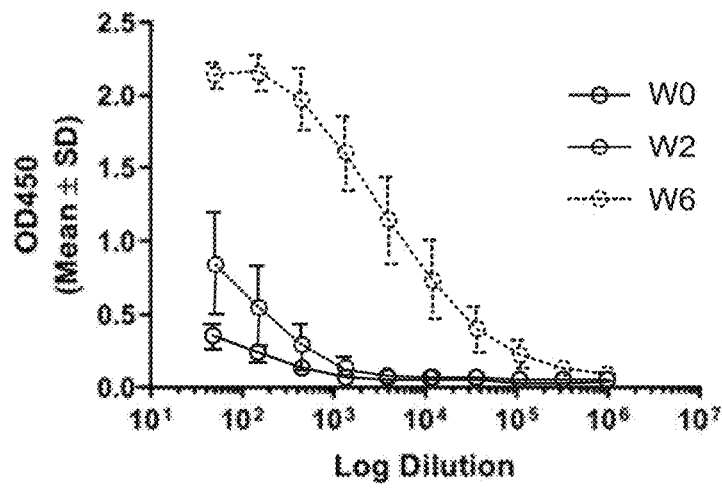
Figure 10:
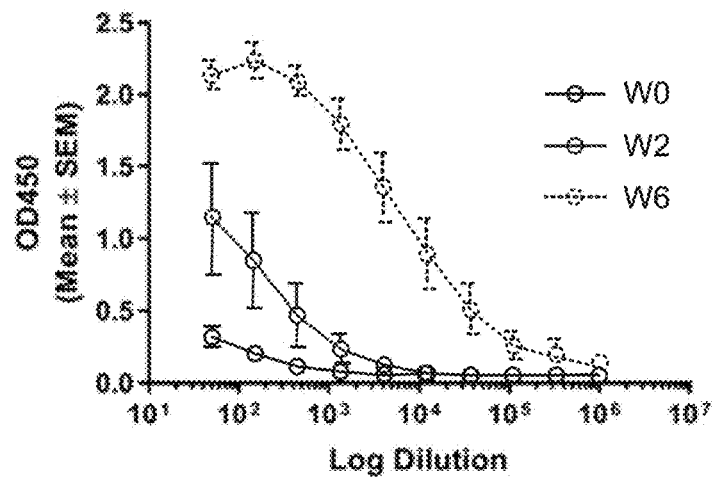
Figure 10:
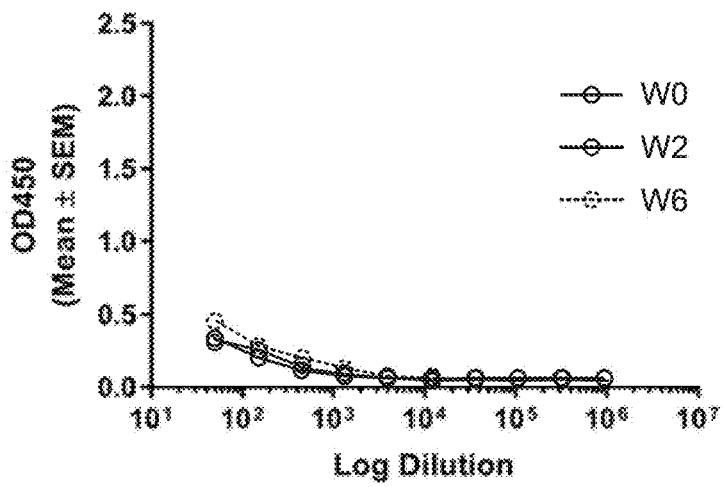
Figure 11A:
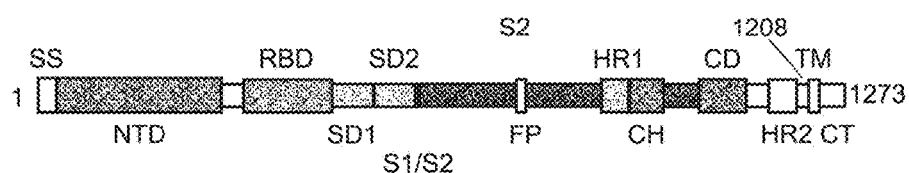
FIGS. 11A-11E illustrate humoral immune responses to SARS-CoV-2 spike protein measured in INO-4800 treated in rhesus monkeys. Day 0 and 28 intradermal delivery of pDNA. Serum IgG binding ELISA.
Figure 11B:
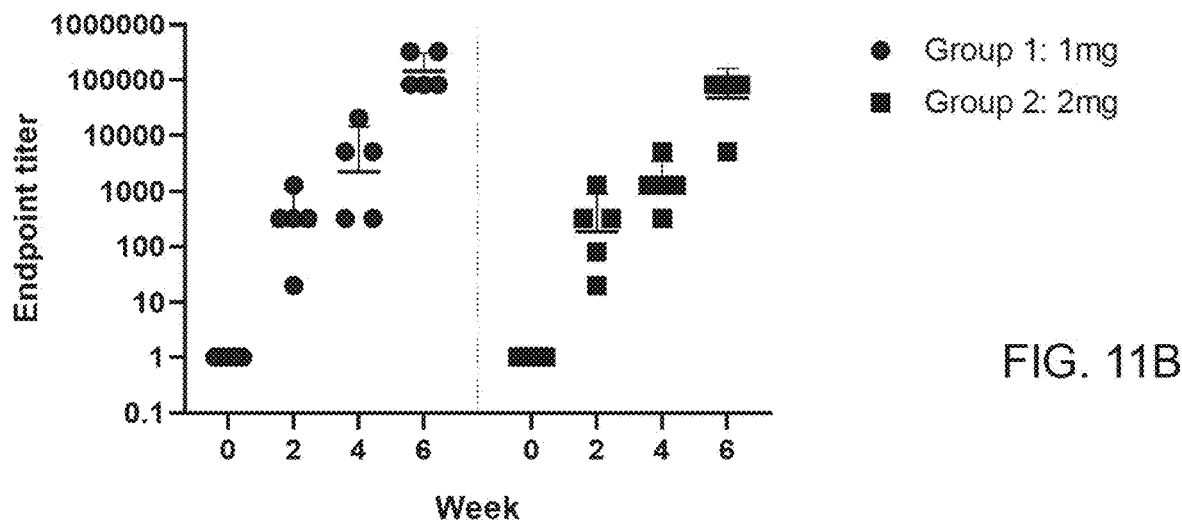
Figure 11C:
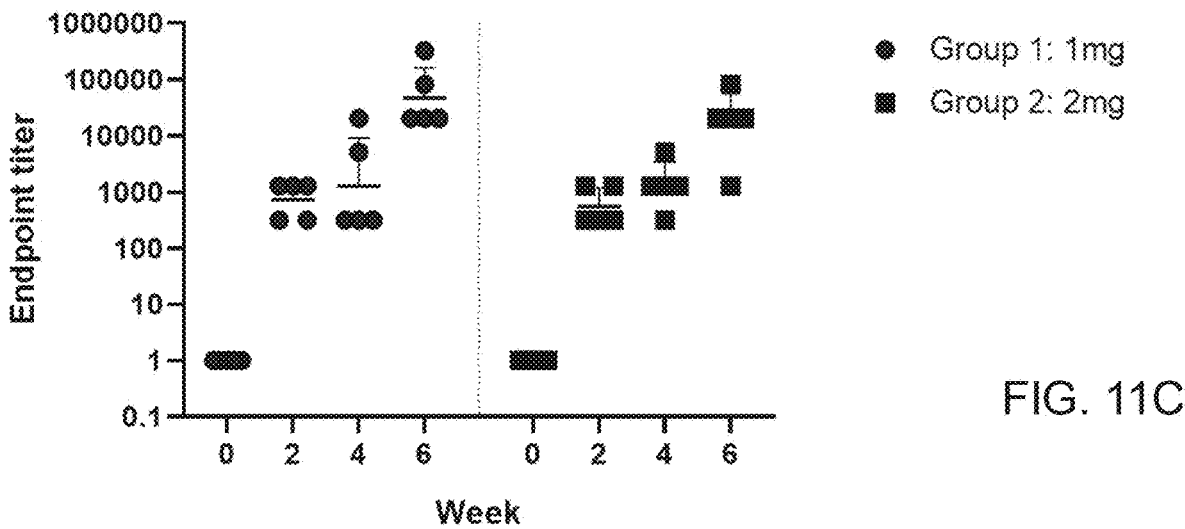
Figure 11D:
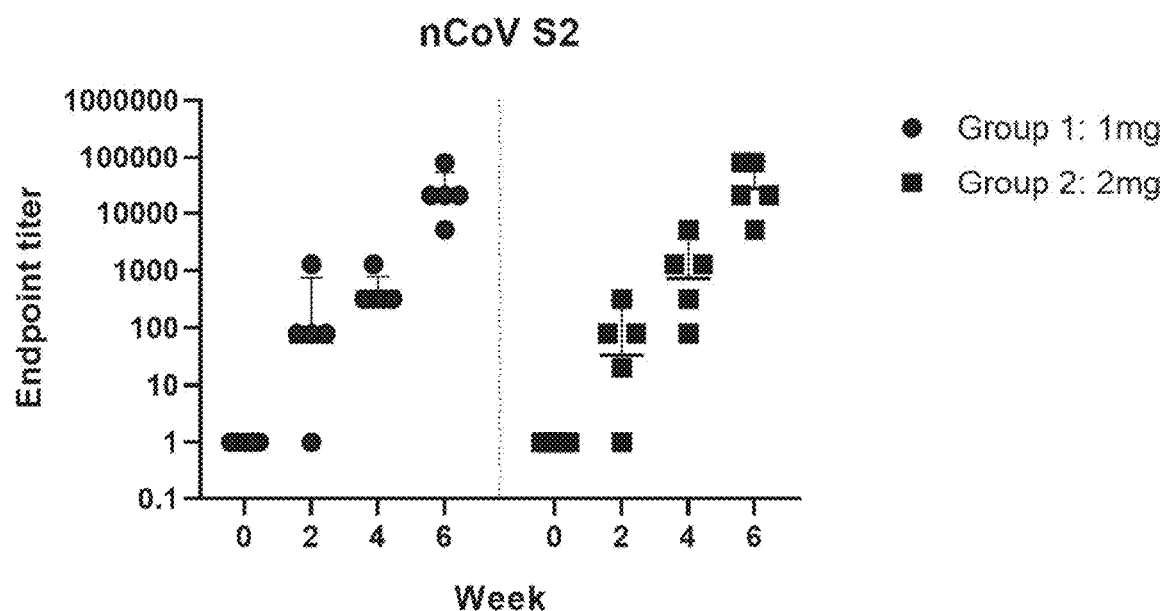
Figure 11E:
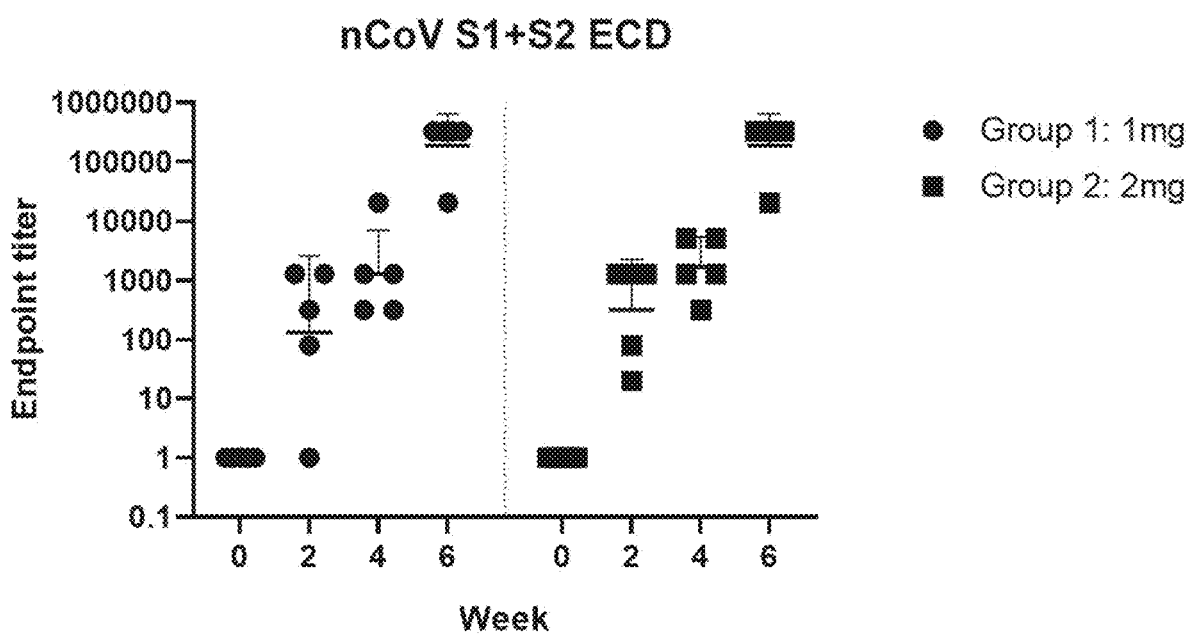
Figure 12A:
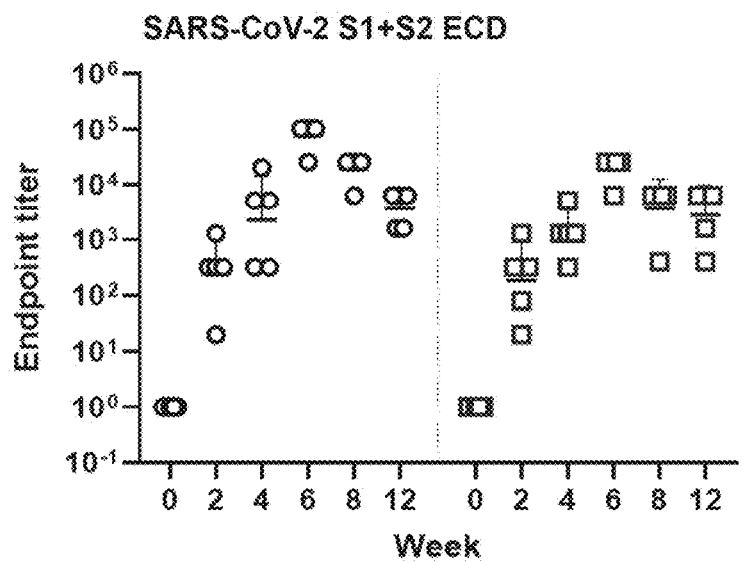
FIGS. 12A-12G illustrate humoral immune responses to SARS and MERS spike protein measured in INO-4800 treated rhesus monkeys. Day 0 and 28 intradermal delivery of pDNA. Serum IgG binding ELISA.
Figure 12B:
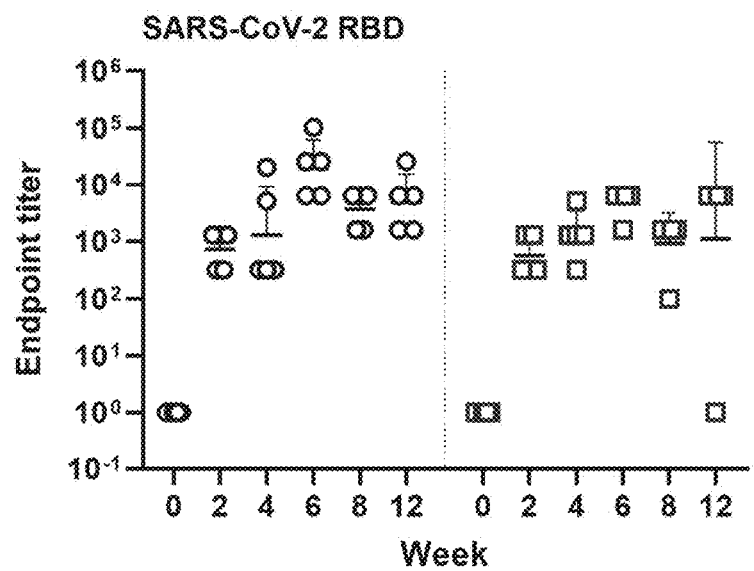
Figure 12C:
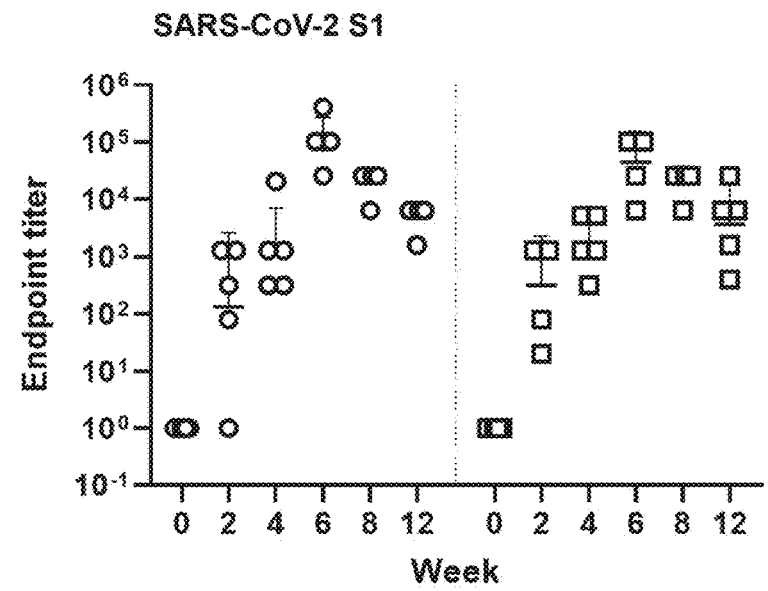
Figure 12D:
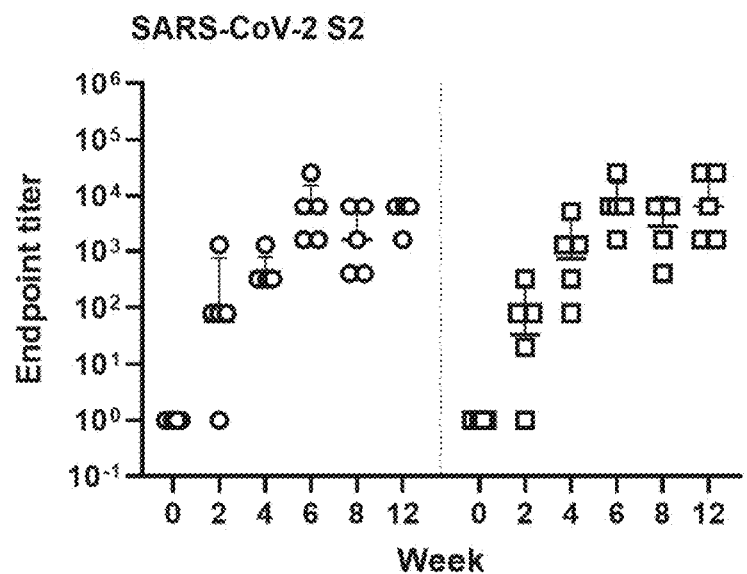
Figure 12E:
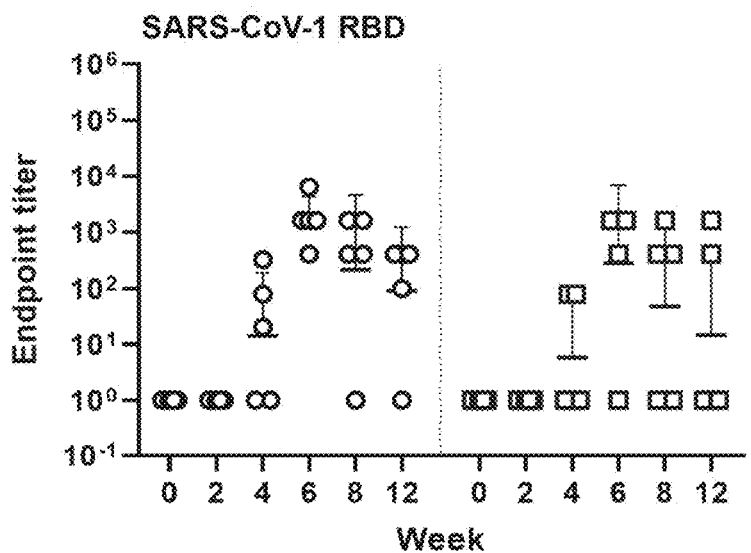
Figure 12F:
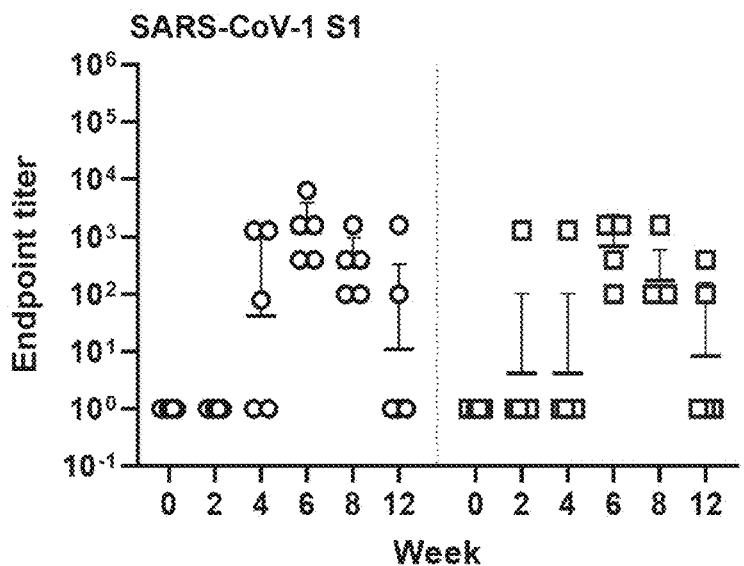
Figure 12G:
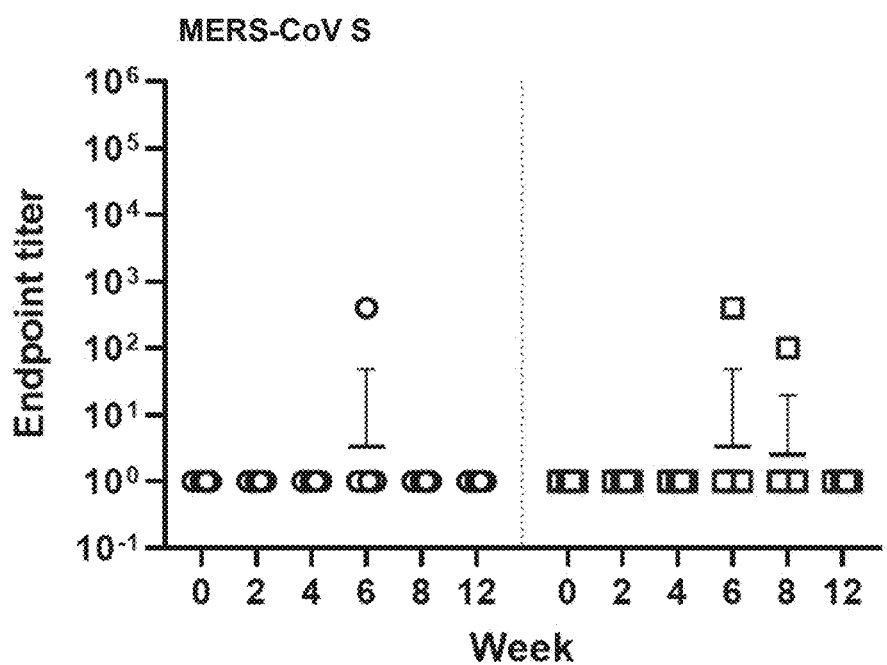

Example 2—Cellular and Humoral Immune Responses Measured in INO-4800-Treated New Zealand White (NZW) Rabbits Day 0 and 28 intradermal delivery of pDNA. PBMC IFN-γ ELISpot (FIG. 9); Serum IgG binding ELISA (FIG. 10).

Example 3

Humoral Immune Responses to SARS-CoV-2 Spike Protein Measured in INO-4800 Treated in Rhesus Monkeys.

Day 0 and 28 intradermal delivery of pDNA. Serum IgG binding ELISA. (FIGS. 11A-11E.)

Humoral immune responses to SARS and MERS spike protein measured in INO-4800 treated rhesus monkeys. Day 0 and 28 intradermal delivery of pDNA. Serum IgG binding ELISA. (FIGS. 12A-12G; left panel, 1 mg INO-4800; right panel, 2 mg INO-4800).

Figure 13A:
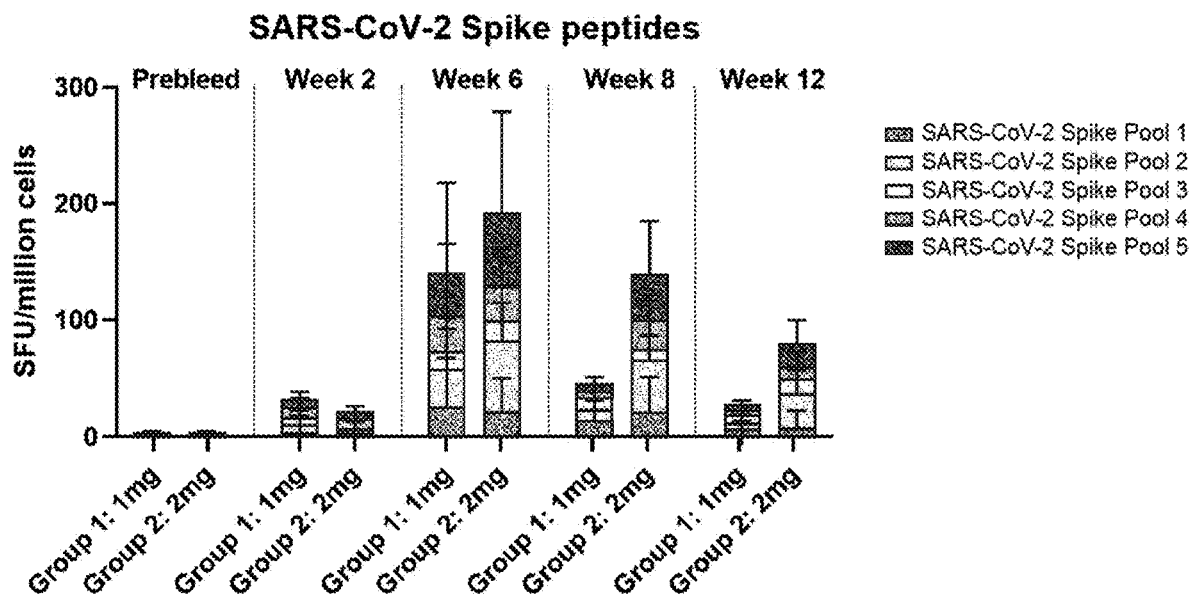
FIGS. 13A-13C illustrate cellular immune responses measured by PBMC IFN-γ ELISpot in INO-4800-treated in rhesus monkeys following intradermal delivery of pDNA on days 0 and 28 intradermal. Results are shown in FIG. 13A (SARS CoV-2 Spike peptides); 13B (SARS CoV Spike peptides); and 13C (MERS CoV Spike peptides).
Figure 13B:
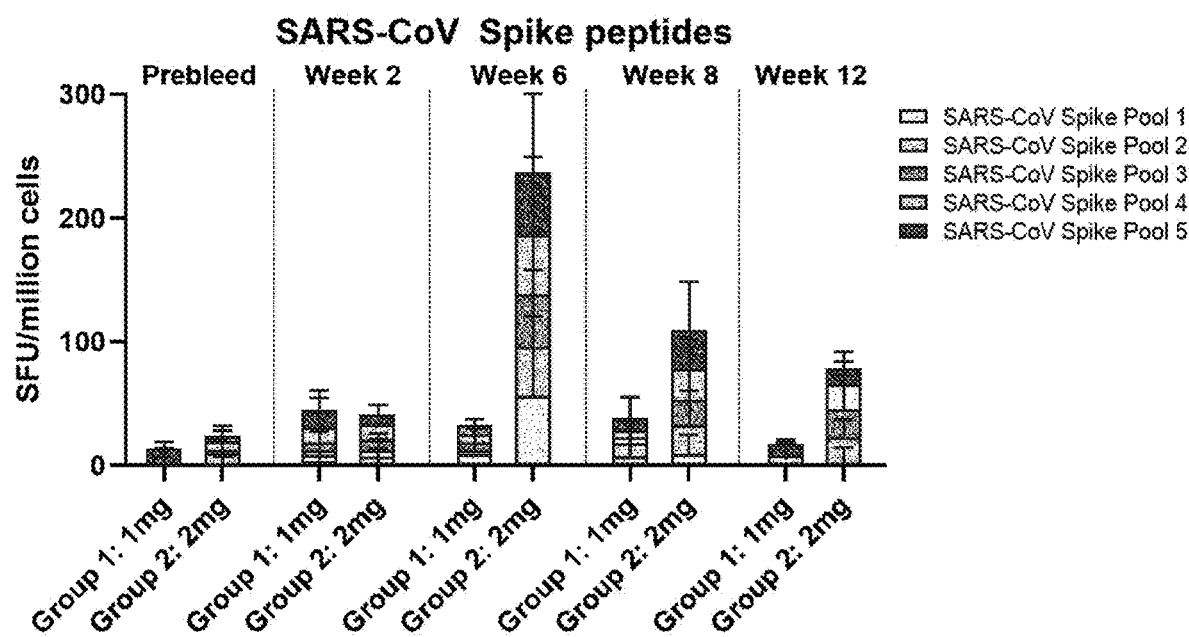
Figure 13C:
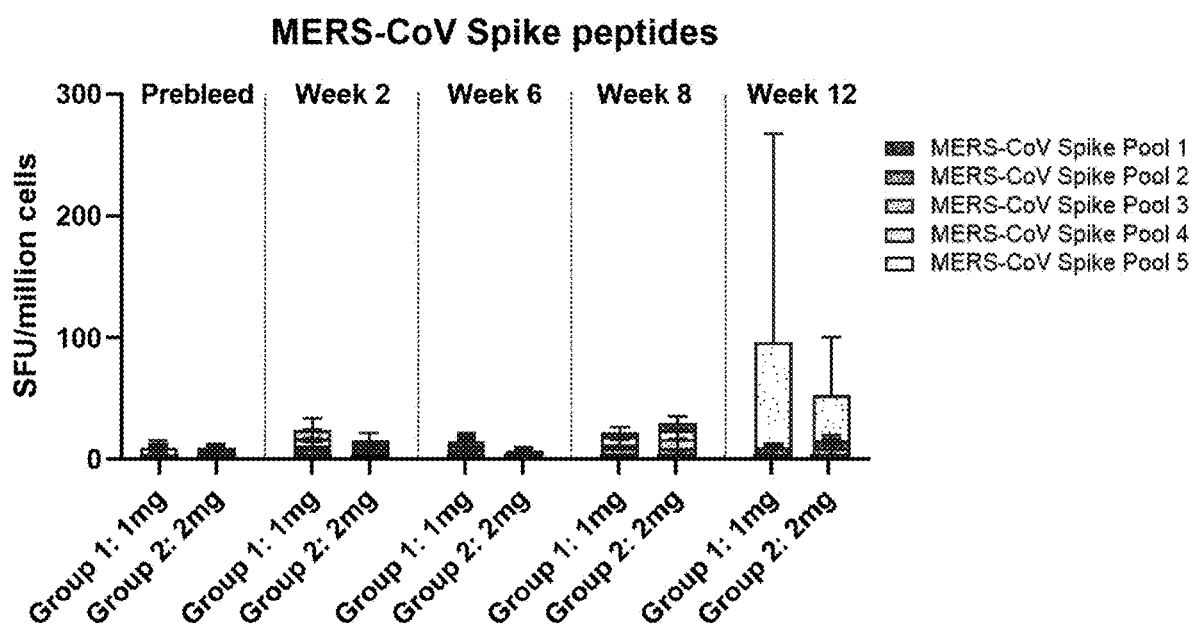

Cellular immune responses measured by PBMC IFN-γ ELISpot in INO-4800-treated in rhesus monkeys following intradermal delivery of pDNA on days 0 and 28. Results are shown in FIG. 13A (SARS CoV-2 Spike peptides); 13B (SARS CoV Spike peptides); and 13C (MERS CoV Spike peptides).

Example 4 INO-4800 SARS-CoV-2 Spike ELISA Assay

The SARS-CoV-2 spike protein is coated onto wells of a 96-well microplate by incubating over night or for up to three days. Blocking buffer is then added to block remaining free binding sites. Human serum samples containing antibodies to SARS-COV-2 spike protein and assay controls are added to the blocked plate and incubated for 1 hour. During the incubation, anti-spike protein antibodies present in the samples and positive controls bind to spike protein immobilized onto the plate. Plates are then washed to remove unbound serum components. Next, a horseradish peroxidase (HRP) labeled anti-human IgG antibody is added to allow for detection of antibody bound to the spike protein. After a one hour incubation, plates are washed to remove unbound HRP detection antibody, and TMB substrate is added to plates. In the presence of horseradish peroxidase, the TMB substrate turns deep blue, proportional to the amount of HRP present in the well. After allowing the reaction to proceed for approximately 10 minutes, an acid-based stop solution is added, which halts the enzymatic reaction and turns the TMB yellow. The yellow color is proportional to the amount of bound anti-spike protein antibodies in each well and is read at 450 nm. The magnitude of the assay response is expressed as titers. Titer values are defined as the greatest serial dilution at which the assay signal is greater than a cutoff value based on the assay background levels for a panel of serum from normal human donors.

ELISA Assay Method Qualification

The INO-4800 SARS-CoV-2 Spike ELISA assay has been qualified and has been found suitable for the its intended use to measure the humoral response in subjects participating in clinical trials involving INO-4800. The formal qualification consisted of 18 plates and was conducted by two operators over the course of four days. The qualification determined the assay sensitivity, specificity, selectivity, and precision. At the time the assay was developed convalescent sera was not available. A monoclonal antibody was therefore used in development. The monoclonal antibody diluted in normal human sera was used to test all parameters in this assay. The overall assay sensitivity was found to be 16.1 ng/mL for 1/20-diluted serum, which is 322 ng/mL for undiluted serum. Specificity was assessed by pre-incubating anti-spike protein antibody with recombinant spike protein prior to assay. Preincubation with the recombinant spike protein resulted in greater than 60% signal reduction, indicating that the antibody was binding specifically to the spike protein coated to the plate and not to a different assay component. Selectivity was investigated by spiking individual human serum samples with positive control anti-spike antibody at a concentration near the limit of detection. Seven out of 10 individuals had signal above the cutoff, and eight out of the ten individuals had assay signal within 20% of the mean signal for the ten individuals, demonstrating that matrix effects are expected to be minor for most human serum samples when diluted 1/20. Assay precision was assessed by assaying a high, low, and medium anti-spike protein antibody positive control six times on each of six plates. Results indicated low intra-assay raw signal variation but high raw signal inter-assay variation. Since each individual plate cutoff is based on the signal of negative controls on each plate, inter-assay variation in raw signal is not expected to influence the precision of final titer calculations. To test this, the precision of plate cutoffs was evaluated in this qualification by titering the HPC (high positive control) six times on each of six plates for a total of thirty-six titer evaluations. Thirty-five out of the thirty-six values were identical (titer of 180), while one of the titer determinations was one step lower than the rest (60 instead of 180). This resulted in an inter-assay CV of 4.6%.

Example 5 INO-4800 SARS-CoV-2 Spike ELISPOT Assay

The enzyme-linked immunospot (ELISPOT) assay is a highly sensitive immunoassay that measures the frequency of cytokine-secreting cells at the single-cell level. In this assay, cells are cultured on a surface coated with a specific capture antibody in the presence or absence of stimuli. After an appropriate incubation time, cells are removed and the secreted molecule is detected using a detection antibody in a similar procedure to that employed by the ELISA. The detection antibody is biotinylated and followed by a streptavidin-enzyme conjugate. By using a substrate with a precipitating rather than a soluble product, the end result is visible spots on the surface. Each spot corresponds to an individual cytokine-secreting cell. The IFN-γ ELISPOT assay qualification was successfully completed with an assessment of assay specificity, reproducibility and precision (intra-assay precision and inter-assay precision), dynamic range, linearity, relative accuracy, limit of detection and quantitation and assay robustness. The assay has been tested and qualified under GLP/GCLP laboratory guidelines.

ELISPOT Assay Method Qualification. Specificity readings gave a mean value of <10 spot-forming units (SFU) for the assay negative control (medium with DMSO), a mean of 565 SFU for the positive control peptide pool CEF and a mean of 593 SFU in response to stimulation with mitogen (Phorbol Myristate Acetate+Ionomycin). The highest reported % CV for intra-assay variation was 7.37%. The highest reported % CV for inter-assay variation was 17.23%. The highest observed % CV for inter-operator variability was 8.11%. These values fall below the FDA-recommended standard acceptance criteria of 20%.

Linearity of the dilution curve was demonstrated with a slope of 0.15 and an R2 value of 0.99. Assay accuracy was >90% over the listed dynamic range (156-5000 cells/well), falling within the acceptance criteria of 80-120%. Limit of detection was determined to be 11 SFU/1×$10^6$ PBMCs, limit of quantitation was observed at 20 SFU/1×$10^6$ PBMCs. Robustness of the assay was evaluated by varying (i) peptide concentration; (ii) secondary antibody concentration; (iii) incubation times, and (iv) drying-out of plate membranes.

Based on the results of this qualification, the IFN-γ ELISPOT is considered qualified and ready for use in clinical trials.

Example 6 Phase 1 Open-Label Study to Evaluate the Safety, Tolerability and Immunogenicity of INO-4800, a Prophylactic Vaccine Against SARS-CoV-2, Administered Intradermally Followed by Electroporation in Healthy Volunteers This is a Phase 1, open-label, multi-center trial (clinicaltrials_gov identifier NCT04336410) to evaluate the safety, tolerability and immunological profile of INO-4800 (pGX9501) administered by intradermal (ID) injection followed by electroporation (EP) using CELLECTRA® 2000 device in healthy adult volunteers. Approximately 40 healthy volunteers will be evaluated across two (2) dose levels: Study Group 1 and Study Group 2 as shown in Table 2. A total of 20 subjects will be enrolled into each Study Group.

TABLE 2

COVID 19-001 Base Study Dose Groups

| Study Group | Number of Subjects | Dosing Weeks | Number of Injections + EP per Dosing Visit | INO-4800 (mg) per injection | IN0-4800 (mg) per Dosing Visit | Total Dose of INO-4800 (mg) |
| --- | --- | --- | --- | --- | --- | --- |
| 1 | 20 | 0, 4 | 1 | 1.0 | 1.0 | 2.0 |
| 2 | 20 | 0, 4 | $2^a$ | 1.0 | 2.0 | 4.0 |
| Total | 40 | | | | | |

$^a$INO-4800 will be injected ID followed by EP in an acceptable location on two different limbs at each dosing visit All subjects are followed for 24 weeks following the last dose. Week 28 is the End of Study (EOS) visit.

Primary Objectives:

Evaluate the tolerability and safety of INO-4800 administered by ID injection followed by EP in healthy adult volunteers Evaluate the cellular and humoral immune response to INO-4800 administered by ID injection followed by EP Primary Safety Endpoints:

Incidence of adverse events by system organ class (SOC), preferred term (PT), severity and relationship to investigational product Administration (i.e., injection) site reactions (described by frequency and severity)
Incidence of adverse events of special interest Primary Immunogenicity Endpoints:
SARS-CoV-2 Spike glycoprotein antigen-specific antibodies by binding assays Antigen-specific cellular immune response by IFN-γ, ELISpot and/or flow cytometry assays Exploratory Objective:
Evaluate the expanded immunological profile by assessing both T and B cell immune response Exploratory Endpoint:
Expanded immunological profile which may include (but not limited to) additional assessment of T and B cell numbers, neutralization response and T and B cell molecular changes by measuring immunologic proteins and mRNA levels of genes of interest at all weeks as determined by sample availability Safety Assessment:
Subjects are followed for safety for the duration of the trial through the end of study (EOS) or the subject's last visit. Adverse events are collected at every visit (and a Day 1 phone call). Laboratory blood and urine samples are drawn at Screening, Day 0 (pregnancy test only), Week 1, Week 4 (pregnancy test only), Week 6, Week 8, Week 12 and Week 28, according to the Schedule of Events (Table 3). All adverse events, regardless of relationship, are collected from the time of consent until EOS. All serious adverse events, adverse events of special interest and treatment-related adverse events are followed to resolution or stabilization.

TABLE 3

Clinical Trial Schedule of Events

| Tests and assessments | Screen[a] | Day 0 Pre | Day 0 Post | Day 1 (+1 d) | Week 1 (±3 d) | Week 4 (±5 d) Pre | Week 4 (±5 d) Post | Week 6 (±5 d) | Week 8 (±5 d) | Week 12 (±5 d) | Week 28 (±5 d) |
|---|---|---|---|---|---|---|---|---|---|---|---|
| Informed Consent | X | | | | | | | | | | |
| Inclusion/Exclusion Criteria | X | | | | | | | | | | |
| Medical History | X | X | | | | | | | | | |
| Demographics | X | | | | | | | | | | |
| Concomitant Medications | X | X | | | X | X | | X | X | X | X |
| Physical Exam[b] | X | X | | | X | X | | X | X | X | X |
| Vital Signs | X | X | | | X | X | | X | X | X | X |
| Height and Weight | X | | | | | | | | | | |
| CBC with Differential | X | | | | X | | | X | X | X | X |
| Chemistry[c] | X | | | | X | | | X | X | X | X |
| Serology[d] | X | | | | | | | | | | |
| 12-lead ECG | X | | | | | | | | | | |
| Urinalysis Routine[e] | X | | | | X | | | X | X | X | X |
| Pregnancy Test[f] | X | X | | | | X | | | | | |
| INO-4800 + EP[g] | | X[h] | | | | X[h] | | | | | |
| Download EP Data[i] | | | X | | | | X | | | | |
| Adverse Events[j] | X | X | X | X[k] | X | X | X | X | X | X | X |
| Immunology (Whole blood)[l] | X | X | | | | X | | X | X | X | X |
| Immunology (Serum)[m] | X | X | | | | X | | X | X | X | X |

[a]Screening assessment occurs from −30 days to −1 day prior to Day 0.
[b]Full physical examination at screening and Week 28 (or any other study discontinuation visit) only. Targeted physical exam at all other visits.
[c]Includes Na, K, Cl, HCO3, Ca, PO4, glucose, BUN, and Cr.
[d]HIV antibody or rapid test, HBsAg, HCV antibody.
[e]Dipstick for glucose, protein, and hematuria. Microscopic examination should be performed if dipstick is abnormal.
[f]Serum pregnancy test at screening. Urine pregnancy test at other visits.
[g]All doses delivered via intradermal injection followed by EP.
[h]For Study Group 1, one injection in skin preferably over deltoid muscle at Day 0 and Week 4. For Study Group 2, two injections in skin with each injection over a different deltoid or lateral quadriceps; preferably over the deltoid muscles, at Day 0 and Week 4.
[i]Following administration of INO-4800, EP data will be downloaded from the CELLECTRA ® 2000 device and provided to Inovio.
[j]Includes AEs from the time of consent and all injection site reactions that qualify as an AE.
[k]Follow-up phone call to collect AEs.
[l]4 × 8.5 mL (34 mL) whole blood in 10 mL Acid Citrate Dextrose (ACD, Yellow top) tubes per time point.
Note:
Collect a total of 68 mL whole blood prior to 1st dose (screening and prior to Day 0 dosing).
[m]1 × 8 mL blood in 10 mL red top serum collection tube per time point.
Note:
Collect four aliquots of 1 mL each (total 4 mL) serum at each time point prior to 1st dose (Screening and prior to Day 0 dosing).

Immunogenicity Assessment:
Immunology blood samples are collected at Screening, Day 0 (prior to dose), Week 4 (prior to dose), Week 6, Week 8, Week 12 and Week 28. Determination of analysis of collected samples for immunological endpoints are determined on an ongoing basis throughout the study.

Clinical Trial Population:
Healthy adult volunteers between the ages of 18-50 years, inclusive.

Inclusion Criteria:
a. Adults aged 18 to 50 years, inclusive;
b. Judged to be healthy by the Investigator on the basis of medical history, physical examination and vital signs performed at Screening;
c. Able and willing to comply with all study procedures;
d. Screening laboratory results within normal limits or deemed not clinically significant by the Investigator;
e. Negative serological tests for Hepatitis B surface antigen (HBsAg), Hepatitis C antibody and Human Immunodeficiency Virus (HIV) antibody screening;

f. Screening electrocardiogram (ECG) deemed by the Investigator as having no clinically significant findings (e.g. Wolff-Parkinson-White syndrome);
g. Use of medically effective contraception with a failure rate of <1% per year when used consistently and correctly from screening until 3 months following last dose, be post-menopausal, be surgically sterile or have a partner who is sterile.

Exclusion Criteria:
a. Pregnant or breastfeeding, or intending to become pregnant or father children within the projected duration of the trial starting with the screening visit until 3 months following last dose;
b. Is currently participating in or has participated in a study with an investigational product within 30 days preceding Day 0;
c. Previous exposure to SARS-CoV-2 (laboratory testing at the Investigator's discretion) or receipt of an investigational vaccine product for prevention of COVID-19, MERS or SARS;
d. Current or history of the following medical conditions:
Respiratory diseases (e.g., asthma, chronic obstructive pulmonary disease);
Hypertension, sitting systolic blood pressure >150 mm Hg or a diastolic blood pressure >95 mm Hg;
Malignancy within 5 years of screening;
Cardiovascular diseases (e.g., myocardial infarction, congestive heart failure, cardiomyopathy or clinically significant arrhythmias);
e. Immunosuppression as a result of underlying illness or treatment including:
Primary immunodeficiencies;
Long term use (≥7 days) of oral or parenteral glucocorticoids;
Current or anticipated use of disease modifying doses of anti-rheumatic drugs and biologic disease modifying drugs;
History of solid organ or bone marrow transplantation;
Prior history of other clinically significant immunosuppressive or clinically diagnosed autoimmune disease.
f. Fewer than two acceptable sites available for ID injection and EP considering the deltoid and anterolateral quadriceps muscles;
g. Any physical examination findings and/or history of any illness that, in the opinion of the study investigator, might confound the results of the study or pose an additional risk to the patient by their participation in the study.

Clinical Trial Treatment:

The INO-4800 drug product contains 10 mg/mL of the DNA plasmid pGX9501 in 1×SSC buffer (150 mM sodium chloride and 15 mM sodium citrate). A volume of 0.4 mL is filled into 2-mL glass vials that are fitted with rubber stoppers and sealed aluminum caps. INO-4800 is stored at 2-8° C.

Study Group 1 is administered one 1.0 milligram (mg) intradermal (ID) injection of INO-4800 followed by electroporation (EP) using the CELLECTRA® 2000 device per dosing visit at Day 0 and Week 4. Study Group 2 is administered two 1.0 mg ID injections (total 2.0 mg per dosing visit) (in an acceptable location on two different limbs) of INO-4800 followed by EP using the CELLECTRA® 2000 device at Day 0 and Week 4.

Peripheral Blood Immunogenicity Assessments

Whole blood and serum samples are obtained. Immunology blood and serum samples are collected at Screening and at visits specified in the Schedule of Events (Table 2). Both Screening and Day 0 immunology samples are required to enable all immunology testing. The T and B cell immune responses to INO-4800 are measured using assays that may include but are not limited to ELISA, neutralization, assessment of immunological gene expression, assessment of immunological protein expression, flow cytometry and ELISPOT. The ELISA binding assay is a standard plate-based ELISA using 96-well ELISA plates. Plates are coated with SARS-CoV-2 spike protein and blocked. Following blocking, sera from vaccinated subjects are serially diluted and incubated on the plate. A secondary antibody that is able to bind human IgG is used to assess the level of vaccine specific antibodies in the sera. T-cell response is assessed by an IFN-gamma ELISPOT assay. PBMCs isolated from study volunteers are incubated with peptide fragments of the SARS-CoV-2 spike protein. The cells and peptides are placed in a MabTech plates coated with an antibody that captures IFN-gamma. Following 24 hours of stimulation, cells are washed out and a secondary antibody that binds IFN-gamma is added. Each vaccine specific cell creates a spot that can be counted to determine the level of cellular responses induced. In addition, humoral responses to SARS-CoV-2 Nucleocapsid Protein (NP) may also be assessed to rule out potential infection by wild-type SARS-CoV-2 post INO-4800 treatment during the study. Determination of analysis of collected samples for immunological endpoints is determined on an ongoing basis throughout the study.

Primary Outcome Measure:
1. Percentage of Participants with Adverse Events (AEs) [Time Frame: Baseline up to Week 28]
2. Percentage of Patients with Administration (Injection) Site Reactions [Time Frame: Day 0 up to Week 28]
3. Incidence of Adverse Events of Special Interest (AESIs) [Time Frame: Baseline up to Week 28]
4. Change from Baseline in Antigen-Specific Binding Antibody Titers [Time Frame: Baseline up to Week 28] A subject is considered to have a positive antibody response if the optical density post vaccine is 2.0 SD higher than the optical density at day 0 and above the ELISA specific cut off
5. Change from Baseline in Antigen-Specific Interferon-Gamma (IFN-γ) Cellular Immune Response [Time Frame: Baseline up to Week 28] A subject is considered to have a positive cellular response if the number of IFN-gamma producing cells (spots) post vaccine is 2.0 SD higher than the number of spots at day 0 and above the assay LOD.

The safety of INO-4800 is measured and graded in accordance with the "Toxicity Grading Scale for Healthy Adult and Adolescent Volunteers Enrolled in Preventive Vaccine Clinical Trials", issued September 2007 (Appendix A). An adverse event of special interest (AESI) (serious or non-serious) is one of scientific and medical concern specific to the product or program. AESIs include those listed in Table 4.

TABLE 4

| Body System | AESI |
| --- | --- |
| Respiratory | Acute respiratory distress syndrome (ARDS) |
|  | Pneumonitis/Pneumonia |
| Neurologic | Generalized convulsion |
|  | Aseptic meningitis |
|  | Guillain-Barré Syndrome (GBS) |
|  | Encephalitis/Myelitis |

TABLE 4-continued

| Body System | AESI |
|---|---|
| | Acute disseminated encephalomyelitis (ADEM) |
| | CNS vasculopathy (stroke) |
| Hematologic | Thrombocytopenia |
| | Disseminated intravascular coagulation (DIC) |
| Immunologic | Anaphylaxis |
| | Vasculitides |
| | Enhanced disease following immunization |
| Other | Local/systemic SAEs |
| | Acute cardiac injury |
| | Acute kidney injury |
| | Septic shock-like syndrome |

Dose Limiting Toxicity (DLT)

For the purpose of this clinical trial, the following are dose limiting toxicities:

Grade 3 or greater local injection site erythema, swelling and/or induration observed ≥1 day after INO-4800 administration (see Table 5);

Pain or tenderness at the injection site that requires hospitalization despite proper use of non-narcotic analgesics;

Grade 4 or greater non-injection site adverse event assessed by the PI as related to INO-4800 administration;

Grade 4 or greater clinically significant laboratory abnormalities assessed by the PI as related to INO-4800 administration.

TABLE 5

Grading Scale for Injection Site Reactions

| Local Reaction to Injectable Product (Grade) | Mild (1) | Moderate (2) | Severe (3) | Potentially Life Threatening (4) |
|---|---|---|---|---|
| Pain | Does not interfere with activity | Repeated use of non-narcotic pain reliever >24 hours or interferes with activity | Any use of narcotic pain reliever or prevents daily activity | Emergency room visit or hospitalization |
| Tenderness | Mild discomfort to touch | Discomfort with movement | Significant discomfort at rest | ER visit or hospitalization |
| Erythema/Redness[a] | 2.5-5 cm | 5.1-10 cm | >10 cm | Necrosis or exfoliative dermatitis |
| Induration/Swelling[b] | 2.5-5 cm and no interference w/ activity | 5.1-10 cm or interferes with activity | >10 cm or prevents daily activity | Necrosis |

September 2007 "FDA Guidance for Industry-Toxicity Grading Scale for Healthy Adult and Adolescent Volunteers Enrolled in Preventive Vaccine Clinical Trials"
[a]In addition to grading the measured local reaction at the greatest single diameter, the measurement should be recorded as a continuous variable
[b]Should be evaluated and graded using the functional scale as well as the actual measurement.

Analytical Populations

Analysis populations are:

The modified intention to treat (mITT) population includes all subjects who receive at least one dose of the INO-4800. Subjects in this sample are analyzed by their assigned dose group of INO-4800. The mITT population is used to analyze co-primary and exploratory immunological endpoints.

The per-protocol (PP) population is comprised of mITT subjects who receive all their planned administrations and who have no Medical Monitor-assessed important protocol violations. Analyses on the PP population is considered supportive of the corresponding mITT analyses.

The safety analysis population includes all subjects who receive at least one dose of INO 4800 administered by ID injection. Subjects for this population are grouped in accordance with the dose of INO-4800 that they received. This population is used for all safety analyses in the study.

Primary Safety Analyses

The primary analyses for this trial are safety analyses of treatment emergent adverse events (TEAEs), administration site reactions and clinically significant changes in safety laboratory parameters from baseline.

TEAEs are defined for this trial as any adverse events, adverse events of special interest, or serious adverse events that occur on or after Day 0 following IP administration. All TEAEs are summarized by frequency, percentage and associated 95% Clopper-Pearson confidence interval. The frequencies are presented separately by dose number and are depicted by system order class and preferred term. Additional frequencies are presented with respect to maximum severity and relationship to IP. Multiple occurrences of the same AE in a single subject are counted only once following a worst-case approach with respect to severity and relationship to IP. All serious TEAEs are summarized as above. AE duration is calculated as AE stop date–AE start date+1 day. AEs and SAEs that are not TEAEs or serious TEAEs are presented in listings.

All of these primary safety analyses are conducted on the subjects in the safety population.

Primary Immunogenicity Analyses

SARS-CoV-2 Spike glycoprotein antigen specific binding antibody titers, and specific cellular immune responses are analyzed by Study Group within age strata. Binding antibody titer is analyzed for each Study Group using the geometric mean and associated 95% confidence intervals. Antigen specific cellular immune response increases are analyzed for each Study Group using medians, inter-quartile range and 95% confidence intervals. Change from baseline for both binding antibody titer and antigen specific cellular response increases are analyzed using Geometric Mean Fold Rise and 95% confidence intervals. Binding antibody titers are analyzed between each Study Group pair within age strata using the geometric mean ratio and associated 95% confidence intervals. Antigen specific cellular immune responses are analyzed between each Study Group pair within age strata using median differences and associated 95% confidence intervals. All of these primary immunogenicity analyses are conducted on the subjects in the mITT and PP populations.

Exploratory Analyses

T and B post baseline cell number will be analyzed descriptively by Study Group with means/medians and associated 95% confidence intervals. Percent neutralizing antibodies will be analyzed for each Study Group using medians, inter-quartile range and 95% confidence intervals.

The safety and immunogenicity of the optional booster dose of INO-4800 following a prior two-dose regimen will be analyzed as described below. Live neutralization reciprocal antibody titer and pseudoneutralization reciprocal antibody titer will be analyzed for each Study Group within age strata using the geometric mean and associated 95% confidence intervals. Fold rise from baseline will tabulated for each immunogenic biomarker. If there is sufficient data for analysis, exploratory between group immunogenic comparisons between subjects who opt for just 2 administrations and subjects who opt for 2 administrations plus the booster administration will be undertaken.

Further exploration of the effect of age and other potential confounders on the relationship between immune biomarkers and INO-4800 dose may involve the use of ANCOVA and/or Logistic regression models.

Preliminary Base Study Results

All 8 adverse events reported were Grade 1; 5 due to local injection site reactions. No serious adverse events, adverse events of special interest, or dose limiting toxicities were reported.

Preliminary Binding ELISA Analysis demonstrated 7/9 (78%) subjects had positive antibody responses. Responders had a four-fold increase in titer.

At week six, multiple immunology assays, including those for humoral and cellular immune response, were conducted for both 1.0 mg and 2.0 mg dose cohorts after two doses. Analyses at that point showed that 94% (34 out of 36 total trial participants) demonstrated overall immunological response rates based on preliminary data assessing humoral (binding and neutralizing) and T cell immune responses. One participant in the 1 mg dose cohort and two participants in the 2 mg dose cohort were excluded from the immune analyses as they tested positive for COVID-19 immune responses at study entry, indicating prior infection. One participant in the 2 mg dose cohort discontinued the study for reasons unrelated to safety or tolerability.

Through week eight, INO-4800 was generally safe and well-tolerated in all participants in both cohorts. All ten reported adverse events (AEs) were grade 1 in severity, with most being injection site redness. There were no reported serious adverse events (SAEs).

Initial Phase I Results

Study Population Demographics

Figure 16:
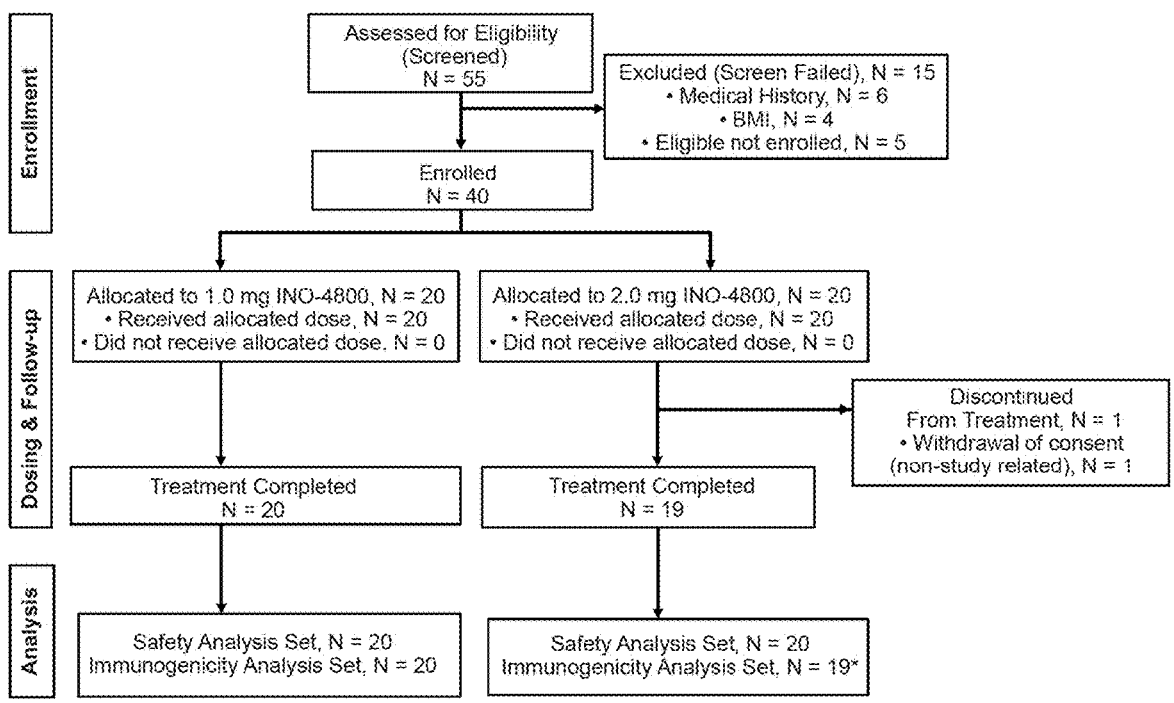
FIG. 16 illustrates the Phase I study flow diagram.

A total of 55 participants were screened and 40 participants were enrolled into the initial two groups (FIG. 16). The median age was 34.5 years (range 18 to 50 years). Participants were 55% male (Table 6). Most participants were white (82.5%).

TABLE 6

| Variable | Statistic | Group 1, 1 mg (N = 20) | Group 2, 2 mg (N-20) | Overall (N = 40) |
|---|---|---|---|---|
| Gender | | | | |
| Male | n (%) | 11 (55.0) | 11 (55.0) | 22 (55.0) |
| Female | n (%) | 9 (45.0) | 9 (45.0) | 18 (45.0) |
| Race | | | | |
| White | n (%) | 18 (90.0) | 15 (75.0) | 33 (82.5) |
| Black or African American | n (%) | 1 (5.0) | 1 (5.0) | 2 (5.0) |
| Asian | n (%) | 1 (5.0) | 4 (20.0) | 5 (12.5) |
| Ethnicity | | | | |
| Hispanic or Latino | n (%) | 0 | 0 | 0 |
| Not Hispanic or Latino | n (%) | 20 (100.0) | 20 (100.0) | 40 (100.0) |
| Age (years) | n | 20 | 20 | 40 |
| | Mean (SD) | 35.0 (10.69) | 35.6 (9.18) | 35.3 (9.84) |
| | Median | 33.0 | 38.0 | 34.5 |
| | Min, Max | 18, 50 | 19, 50 | 18, 50 |
| Baseline Height (cm) | n | 20 | 19 | 39 |
| | Mean (SD) | 172.59 (10.853) | 172.16 (8.631) | 172.38 (9.707) |
| | Median | 169.75 | 170.10 | 170.10 |
| | Min, Max | 155.9, 195.6 | 158.0, 188.0 | 155.9, 195.6 |
| Baseline Weight (kg) | n | 20 | 19 | 39 |
| | Mean (SD) | 74.13 (14.701) | 71.35 (12.611) | 72.77 (13.615) |
| | Median | 70.45 | 69.00 | 69.60 |
| | Min, Max | 58.5, 110.0 | 55.0, 92.5 | 55.0, 110.0 |

The vaccine was administered in 0.1 ml intradermal injections followed by EP at the site of vaccination. EP was performed using CELLECTRA® 2000 with four 52-msec pulses at 0.2 A (40 to 200 V, depending on tissue resistance) per season. The first two pulses were spaced 0.2 seconds apart followed by a 3-second pause before the final two pulses that were also spaced by 0.2 seconds. The dose groups were enrolled sequentially with a safety run-in for each. Participants were and will be evaluated clinically and for safety on Day 1 and at Weeks 1, 4 (Dose 2), 6, 8, 12, 28, 40 and 52. Safety laboratory testing (complete blood count, comprehensive metabolic panel and urinalysis) were and will be conducted on all follow-up visits except for Day 0, Day 1 and Week 4. Immunology specimens were obtained at all time points post-dose 1 except Day 1 and Week 1. Local and systemic AEs, regardless of relationship to the vaccine, were recorded and graded by the investigator. AEs were graded according to the Toxicity Grading Scale for Healthy Adult and Adolescent Volunteers Enrolled in Preventive Vaccine Clinical Trials guidelines that were issued by the Food and Drug Administration in September 2007.

Vaccine Safety and Tolerability 39 (97.5%) completed both doses and 1 subject in the 2.0 mg group discontinued trial participation prior to receiving the second dose due to lack of transportation to the clinical sites, unrelated to the study or the dosing. All 39 remaining subjects completed the visit 8 weeks post-dose 1. There were a total of 11 local and systemic AEs reported by 8 weeks post-dose 1, six of these were deemed related to vaccine. All AEs were mild or Grade 1 in severity. The most frequent AEs were injection site reactions including injection site pain (3) and erythema (2). One systemic AE related to the vaccine was nausea. There were no febrile reactions. No subjects discontinued the trial due to an AE. No serious adverse events (SAEs) nor AESIs were reported. There were no abnormal laboratory values of clinical concern throughout the initial 8-week follow-up period. There was no increase in the number of participants who experienced AEs related to the vaccine in the 2.0 mg group (10% of subjects), compared to that in the 1.0 mg group (15% of subjects). In addition, there was no increase in frequencies of AEs with the second dose over the first dose in both dose level groups. The INO-4800 Phase 1 safety data thus suggests that the vaccine is likely a safe booster as there was no increase frequency of side effects after the second vaccine administration compared to the first dose.

Immunogenicity: Thirty-eight subjects were included in the immunogenicity analysis. In addition to one subject in the 2.0 mg group who discontinued prior to completing dosing, one subject in the 1.0 mg group was deemed seropositive at baseline and was excluded.

Humoral Immune Responses: Serum samples were used to measure neutralizing antibody titers against SARS-CoV-2/Australia/VIC01/2020 isolate and binding antibodies to RBD and whole spike S1+S2 protein.

Figure 17A:
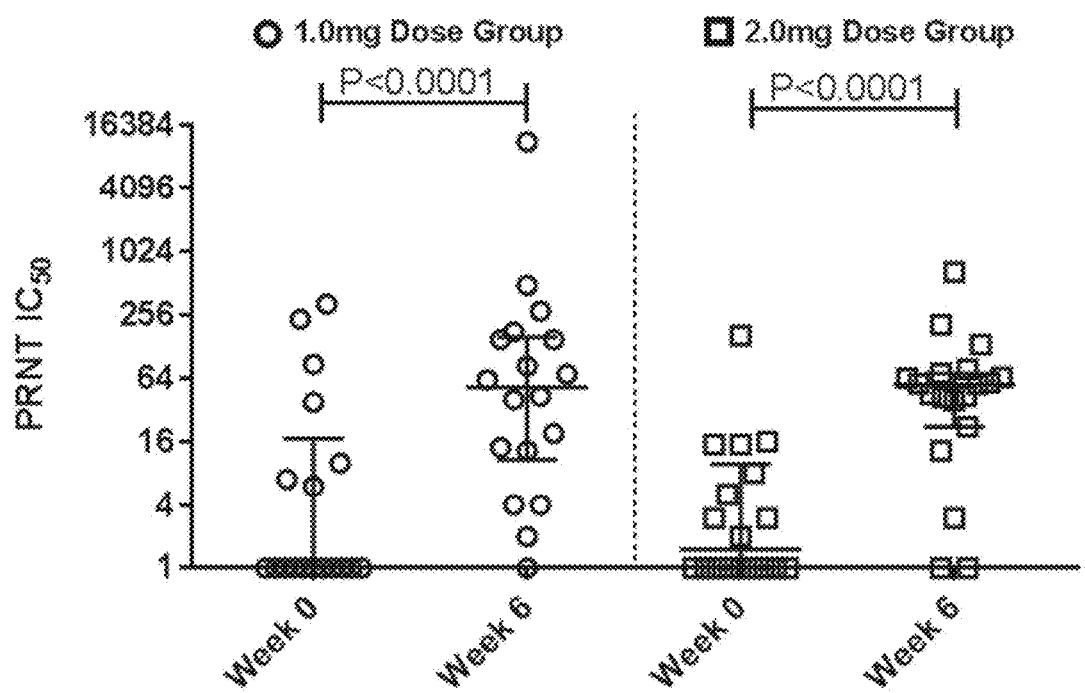
FIGS. 17A, 17B, 17C, and 17D illustrate the humoral antibody response of the phase I clinical study. The humoral response in the 1.0 mg dose group and 2.0 mg dose group was assessed for the ability to neutralize of live virus (n=18, 1.0 mg; n=19, 2.0 mg) (FIG. 17A); binding to the RBD regions (FIG. 17B); and binding to whole spike protein (S1 and S2) (FIG. 17C). End point titers were calculated as the titer that exhibited an OD 3.0 SD above baseline, titers at baseline were set at 1.
Figure 17B:
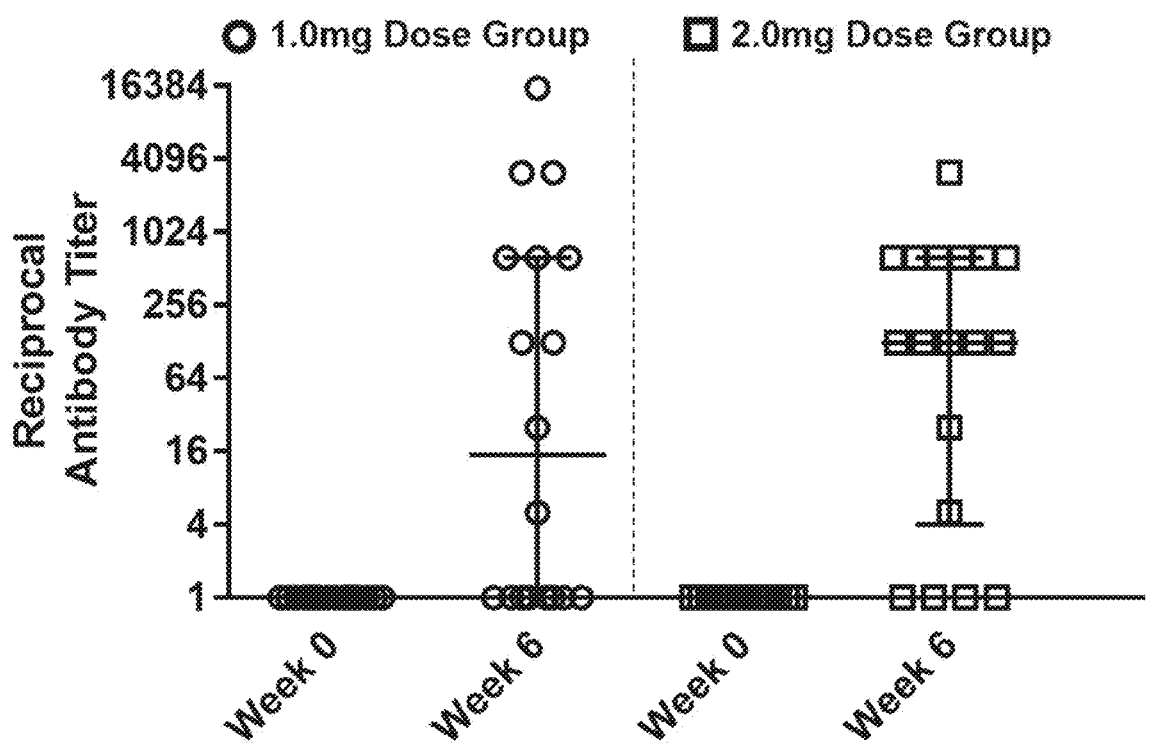
Figure 17C:
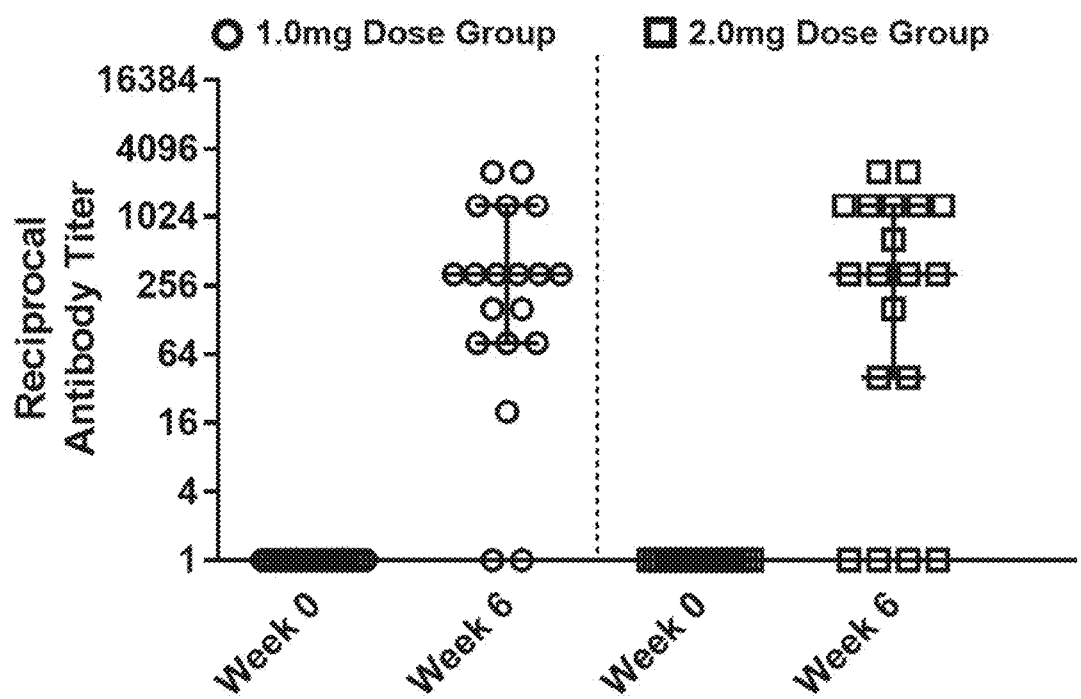
Figure 17D:
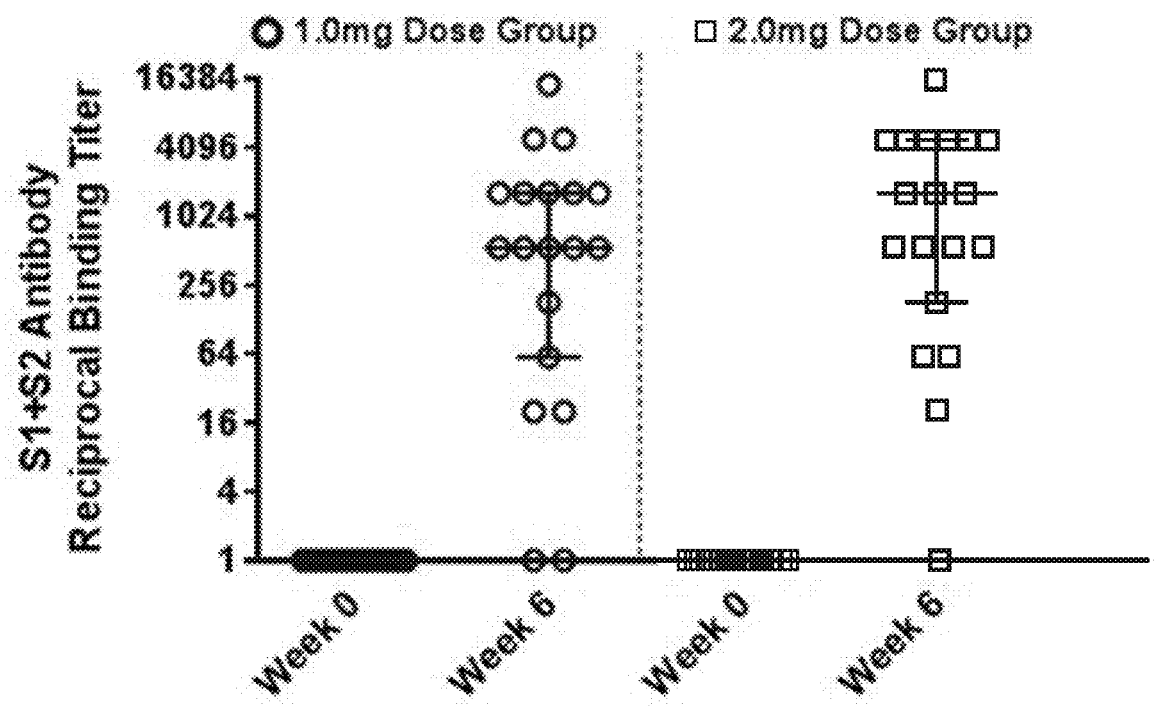

S1+S2 Enzyme-Linked Immunosorbent Assay (ELISA): A standard binding ELISA was used to detect serum binding anti-SARS-CoV-2 spike antibodies. ELISA plates were coated with recombinant S1+S2 SARS-CoV-2 spike protein (Sino Biological) and incubated overnight and blocked. Samples were serially diluted and incubated on the blocked assay plates for one hour. The magnitude of the assay response was expressed as titers which were defined as the greatest serial dilution at which the optical density 3 SD above background Day 0. 68% of participants in the 1.0 mg group and 70% of participants in the 2.0 mg group had at least an increase in serum IgG binding titers to S1+S2 spike protein when compared to their pre-vaccination time point (Day 0), with the responder GMT of 320.0 (95% CI: 160.5, 638.1) and 508.0 (95% CI: 243.6, 1059.4) in the 1.0 mg and 2.0 mg groups, respectively (FIG. 17C). In FIG. 17D, the humoral response in the 1.0 mg dose group and 2.0 mg dose group was assessed for the ability to bind whole spike protein (S1 and S2) (n=19, 1.0 mg; n=19, 2.0 mg). End point titers were calculated as the titer that exhibited an OD 3.0 SD above baseline, titers at baseline were set at 1. A response to live virus neutralization was a PRNT IC50≥10. In all graphs horizontal lines represent the Median and bars represent the Interquartile Range.

Sera was also tested for the ability to neutralize live virus in SARS-CoV-2 wildtype virus neutralization assays. SARS-CoV-2/Australia/VIC01/2020 isolate neutralization assays were performed at Public Health England (Porton Down, UK). Neutralizing virus titers were measured in serum samples that had been heat-inactivated at 56° C. for 30 min. SARS-CoV-2 (Australia/VIC01/2020 isolate44) was diluted to a concentration of 933 pfu ml-1 and mixed 50:50 in 1% FCS/MEM containing 25 mM HEPES buffer with doubling serum dilutions. After 5 days incubation at 37° C. in a humidified box, the plates were fixed, stained and plaques counted. Virus titer were determined using a standard 50% tissue culture infection dose (TCID50) assay. After the second vaccination at week 6, the responder geometric mean titer (GMT) by live virus PRNT IC50 neutralization assay were 82.4 and 63.5 in the 1.0 mg and 2.0 mg groups, respectively. The percentage of responders (post vaccination PRNT IC50≥10) were 83% and 84% in the 1.0 mg and 2.0 mg groups, respectively (FIG. 17A and Table 7).

TABLE 7

| Live SARS-CoV-2 Neutralization | | |
|---|---|---|
| | 1.0 mg<br>N = 18* | 2.0 mg<br>N = 19 |
| Overall | | |
| Week 6 GMT Reciprocal Titer (95% CI) | 44.4 (14.6, 134.8) | 34.9 (15.8, 77.2) |
| Range | 1, 11647 | 1, 652 |
| Responders** | | |
| n (%) | 15 (83%) | 16 (84%) |
| Week 6 GMT Reciprocal Titer (95% CI) | 82.4 (29.1, 233.3) | 63.5 (39.6, 101.8) |
| Range | 4, 11647 | 13, 652 |

*Excludes one subject with baseline positive NP ELISA
**Week 6 PRNT IC$_{50}$ ≥10, or ≥4 if binding ELISA activity is seen RBD Enzyme-Linked Immunosorbent Assay (ELISA): MaxiSorp 96-well plates (ThermoFisher, 439454) were coated with 50 ul/well of 1 ug/ml of SARS-CoV-2 RBD (SinoBiological, 40592-V08H), protein diluted in PBS and incubated at 4° C. overnight. Plates were washed 4 times with PBST (PBS with 0.05% Tween-20) and blocked with 200 ul/well of blocking buffer (PBS with 5% non-fat dry milk and 0.1% Tween-20) at room temperature for 2 hr. After washing with PBST, 50 ul/well of sera sample serially diluted in blocking buffer was added to the plate in duplicate and incubated at room temperature for 2 hr. After washing with PBST, 50 ul/well of anti-human-IgG-HRP detection antibody (BD Pharmingen, 555788) diluted 500-fold in blocking buffer was added and incubated at room temperature for 1 hr. After washing with PBST, 50 ul/well of 1-Step Ultra TMB (Thermo, 34028) was added and incubated at room temperature for 5 min. 50 ul/well of 2M sulfuric acid was added to stop the color change reaction and optical absorbance was measured at 450 and 570 nm on a Synergy 2 microplate reader (Biotek). Endpoint titers were defined as the greatest serial dilution at which the OD450-570 values were 3 standard deviations above the matched Day 0 signal. At week 6, the responder GMT were 385.6 (95% CI: 69.0, 2154.9) and 222.1 (95% CI: 87.0, 566.8) in the 1.0 mg and 2.0 mg groups, respectively (FIG. 17B).

Overall seroconversion (defined as those participants who respond with neutralization or binding antibodies to S protein or RBD) after 2 vaccine doses in 1.0 mg and 2.0 mg dose group were 89% and 95%, respectively.

Cellular Responses: Peripheral Blood Mononuclear Cells (PBMCs) were isolated from blood samples, frozen and stored in liquid nitrogen for subsequent analyses.

INO-4800 SARS-CoV-2 Spike ELISPOT. Peripheral mononuclear cells (PBMCs) were isolated pre- and post-vaccination. Cells were stimulated in vitro with a pool of 15-mer peptides (overlapping by 9 residues) spanning the full-length consensus spike protein sequence. Cells were incubated overnight (18-22 h, 37 C, 5% CO2) with peptide pools (225 μg/ml), DMSO alone (0.5%, negative control) or PMA and Ionomycin (positive controls). The next day, cells were washed off, and the plates were developed: The detection antibody is biotinylated and followed by a streptavidin-enzyme conjugate. By using a substrate with a precipitating rather than a soluble product, resulting in visible spots. Each spot corresponds to an individual cytokine-secreting cell. After plates were developed, spots were scanned and quantified using the CTL S6 Micro Analyzer (CTL) with ImmunoCapture™ and ImmunoSpot™ software. Values are shown as background-subtracted average of measured triplicates.

Figure 18A:
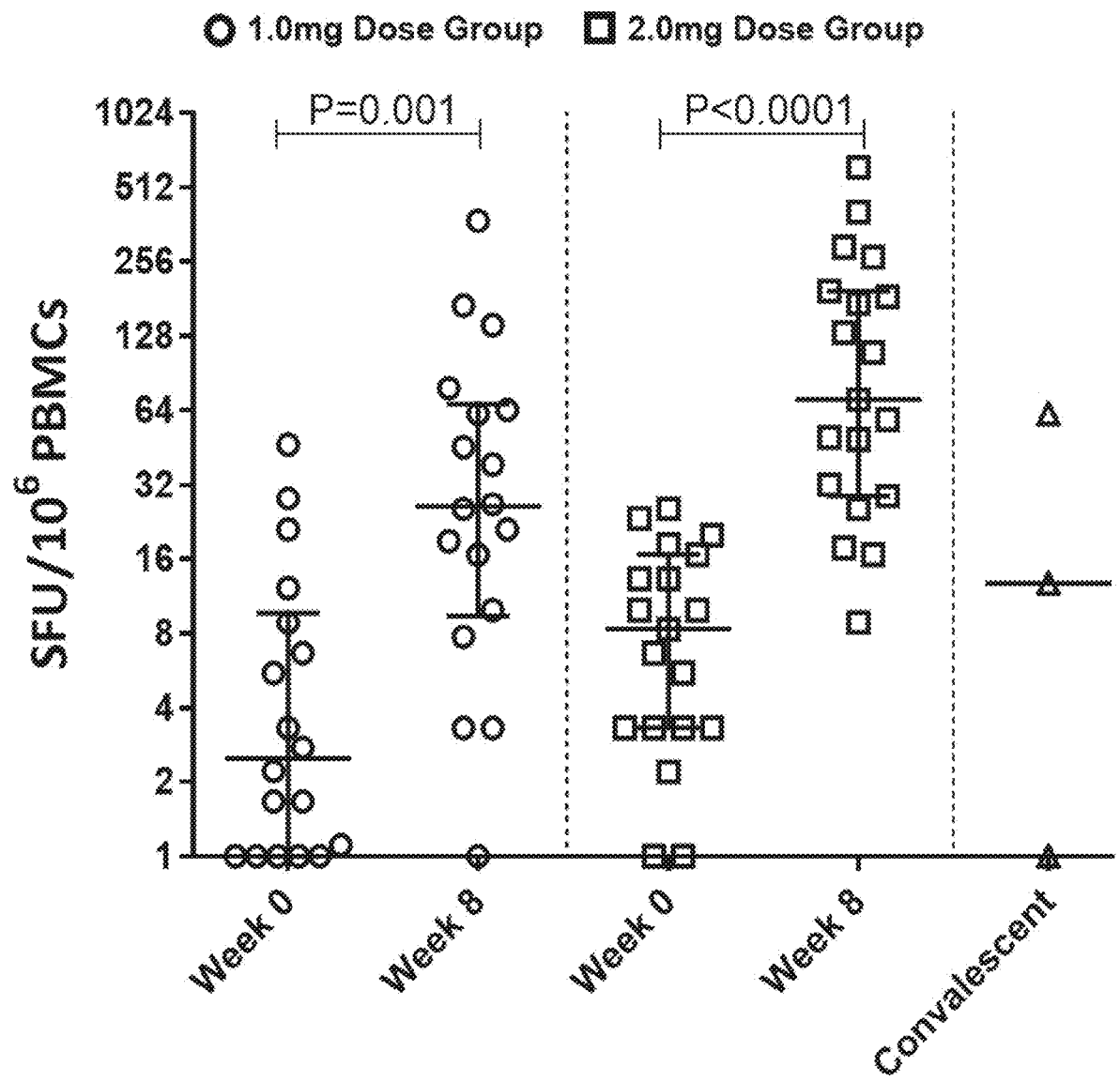
FIGS. 18A-18G illustrate Phase I clinical study cellular immune response analytical results. PBMCs isolated from vaccinated individuals were stimulated in vitro with SARS-CoV-2 spike antigen. The number of cells capable of secreting IFN-gamma were measured in a standard ELISpot assay for the 1.0 mg dose group and 2.0 mg dose group (FIG. 18A). Horizontal lines represent Medians and bars represent Interquartile Ranges.
Figure 18B:
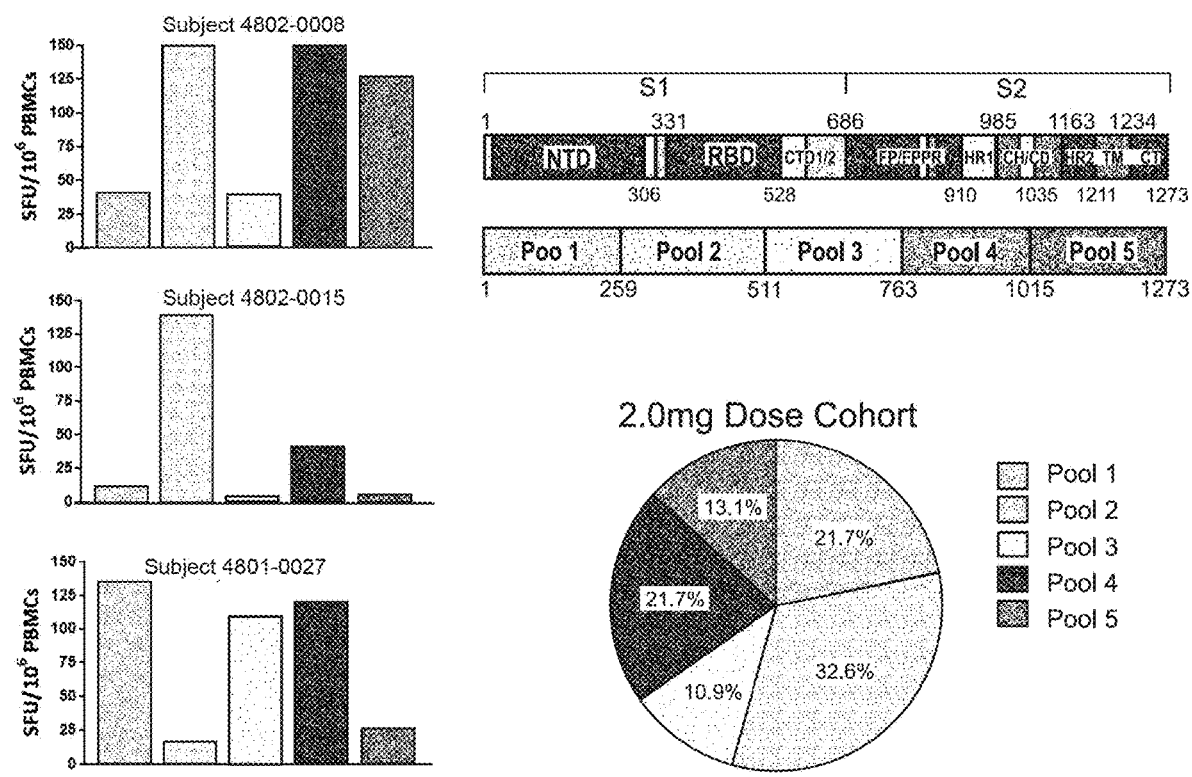

The percentage of responders at week 8 was 74% in the 1.0 mg dose group, and 100% in the 2.0 mg dose group (Table 8). The Median SFU per $10^6$ PBMC was 46 and 71 for the responders in 1.0 mg and 2.0 mg dose groups, respectively. In each group, there were statistically significant increases in the numbers of interferon-γ-secreting cells (SFU) obtained per million PBMCs over baseline (P=0.001 and P<0.0001, respectively, Wilcoxon matched-pairs signed rank test, post-hoc analysis), FIG. 18A. Interestingly, 5 non-responders in 1.0 mg group by T cell ELISPot assay showed strong reactivity by live virus neutralization assay. It is also interesting to note that 3 convalescent samples tested by the ELISpot assay showed lower T cell responses, with a median of 33, than the 2.0 mg dose group at Week 8. INO-4800 generated strong T cell responses that were more frequent and a higher responder median response (45.6 vs 71.1) in the 2.0 mg dose group. The 2.0 mg group's T cell responses were mapped to 5 epitope pools as shown in FIG. 18B. Interestingly T cell responses in the all regions of the Spike protein were observed.

immune response against INO-4800 was assessed by intracellular cytokine staining (ICS). PBMCs were also used for Intracellular Cytokine Staining (ICS) analysis using flow cytometry. One million PMBCs in 200 uL complete RPMI media were stimulated for six hours (37° C., 5% $CO_2$) with DMSO (negative control), PMA and Ionomycin (positive control, 100 ng/mL and 2 μg/mL, respectively), or with the indicated peptide pools (225 μg/mL). After one hour of stimulation, Brefeldin A and Monensin (BD GolgiStop and GolgiPlug, 0.001% and 0.0015%, respectively) were added to block secretion of expressed cytokines. After stimulation the cells were moved to 4° C. overnight. Next, cells were washed in PBS for live/dead staining (Life Technologies Live/Dead aqua fixable viability dye, as previously described), and then resuspended in FACS buffer (0.5% BSA, 2 mM EDTA, 20 mM HEPES). Next, cells were stained for extracellular markers, fixed and permeabilized, and then stained for the indicated cytokines (Table 9) for antibodies used for flow cytometry.

TABLE 9

Flow Cytometry Panel

| Tube | Channel | Marker/Cytokine |
|---|---|---|
| 1 | Unstained | NA |
| 2 | BV510 | Live/Dead Fix Aqua |
| 3 | BUV737 | CD8 |
| 4 | APC-Cy7 | IL-2 |
| 5 | BV650 | CD45RA |
| 6 | APC | CD3 |
| 7 | BV786 | CD14/CD16/CD19 |
| 8 | BV711 | IFN-gamma |
| 9 | BV421 | CCR7 |
| 10 | PE-Cy7 | IL-17 |
| 11 | FITC | FITC |
| 12 | PE Dazzle (PE-CF594) | IL-4 |
| 13 | PE | CD107a |
| 14 | PerCP-eFluor710 (PerCP-Cy5.5) | CD4 |

TABLE 8

Immune Responses

| | 1.0 mg Cohort | | 2.0 mg Cohort | |
|---|---|---|---|---|
| Immune Assay | Output Value | Responders‡ n (%) | Output Value | Responders‡ n (%) |
| Neutralization Week 6 GMT Reciprocal Titer [95% CI] (Range) | 44.4 [14.6, 134.8] (1, 11647) | 15/18 (83%) | 34.9 [15.8, 77.2] (1, 652) | 16/19 (84%) |
| RBD Binding Antibody Week 6 GMT Reciprocal Titer [95% CI] (Range) | 27.3 [4.8, 156.8] (1, 15625) | 10/18 (56%) | 66.8 [17.4, 257.5] (1, 3125) | 14/18 (78%) |
| S1 + S2 Binding Antibody Week 6 GMT Reciprocal Titer [95% CI] (Range) | 174.4 [59.9, 507.3] (1, 2560) | 17/19 (89%) | 136.8 [34.5, 543.1] (1, 2560) | 15/19 (79%) |
| IFN-gamma ELISpot Week 8 Median SFU per [95% CI] (Range) | 26.2 SFU [10-64] (1, 374.4) | 14/19 (74%) µ | 71 SFU [32-194] (8.9, 615.6) | 19/19 (100%) µ |

1.0 mg Cohort excludes one subject with baseline ELISA titer of 1280
‡Response criteria: Neutralization -Week 6 PRNT $IC_{50}$ ≥10, or ≥4 if binding ELISA activity is seen RBD Binding -Week 6 value >1 ELISpot - Value ≥12 SFU over Week 0
µ Responders generated using Week 6 and Week 8 data INO-4800 SARS-CoV-2 Spike Flow Cytometry Assay: The contribution of CD4+ and CD8+ T cells to the cellular CD8+ T cells producing IFN-γ, TNF-α and/or IL-2 (any response) were statistically significantly increased post vaccination in the 2.0 mg dose group (FIG. 18C, P=0.0181, Wilcoxon matched-pairs signed rank test, post-hoc analysis). CD4+ T cells producing TNF-α were also statistically significantly increased in the 2.0 mg dose group (FIG. 18C, P=0.0020, Wilcoxon matched-pairs signed rank test, post-hoc analysis).

Figure 18C:
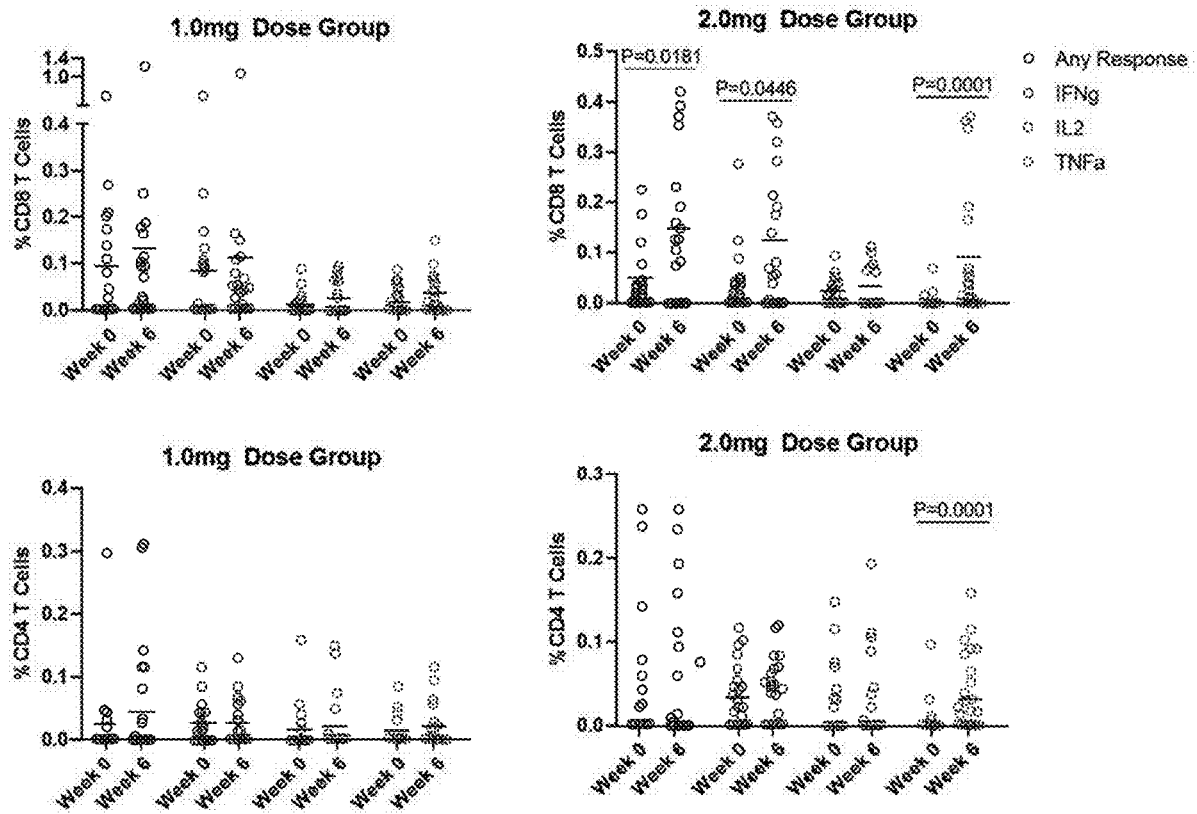

CD4+ and CD8+ T cells were explored following vaccination. Nearly half (47%) of the CD8+ T cells in the 2.0 mg dose group were dual producing IFN-γ and TNF-α (FIG. 18E). CD8+ T cells producing cytokine in the 1.0 mg dose group were primarily monofunctional IFN-γ producing cells. The CD4+ T cell compartment was highly polyfunctional with 6% and 9% (in the 1.0 mg and 2.0 mg dose groups, respectively) producing all 3 cytokines, IFN-γ, TNF-α, and IL-2.

Figure 18D:
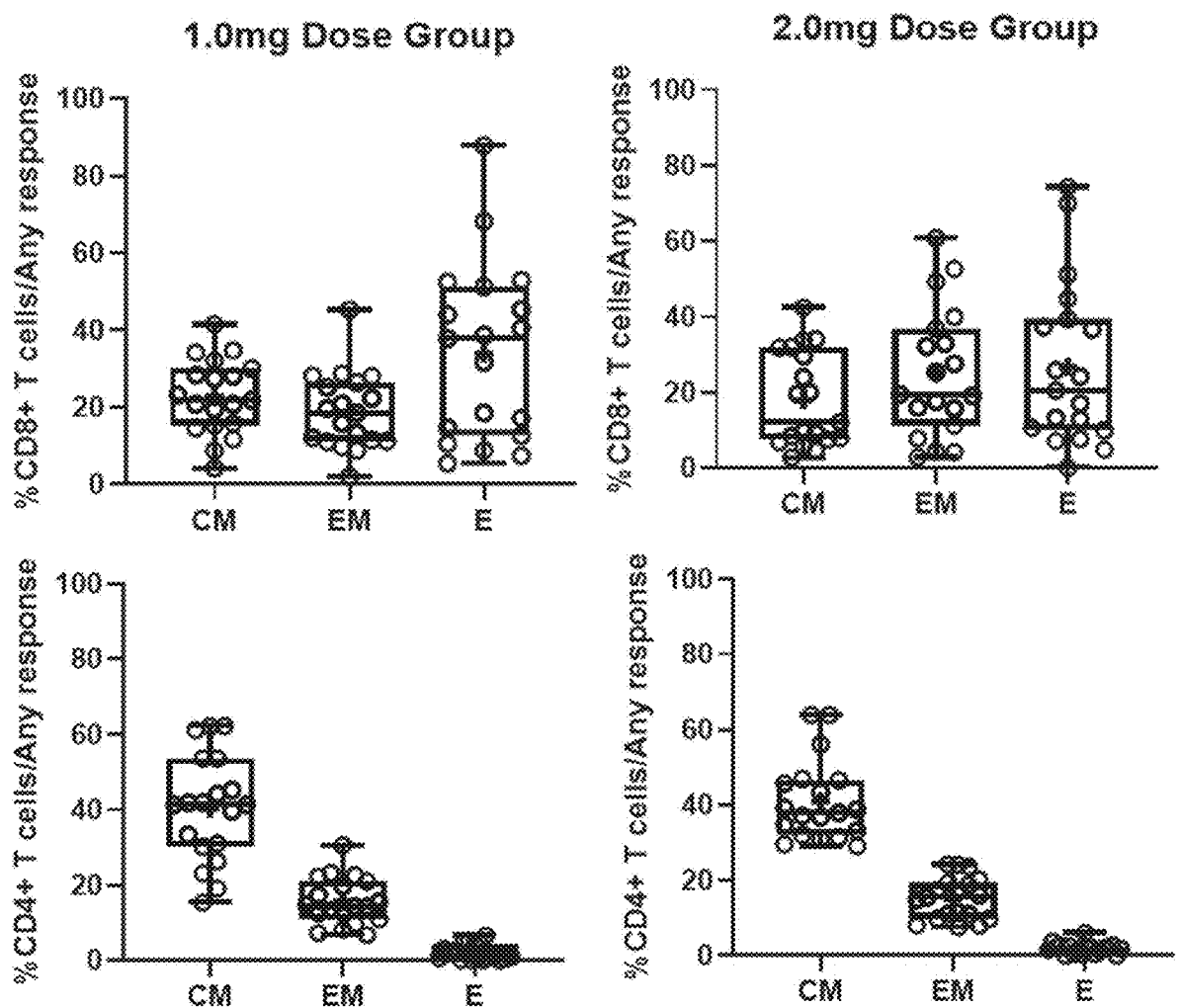
Figure 18E:
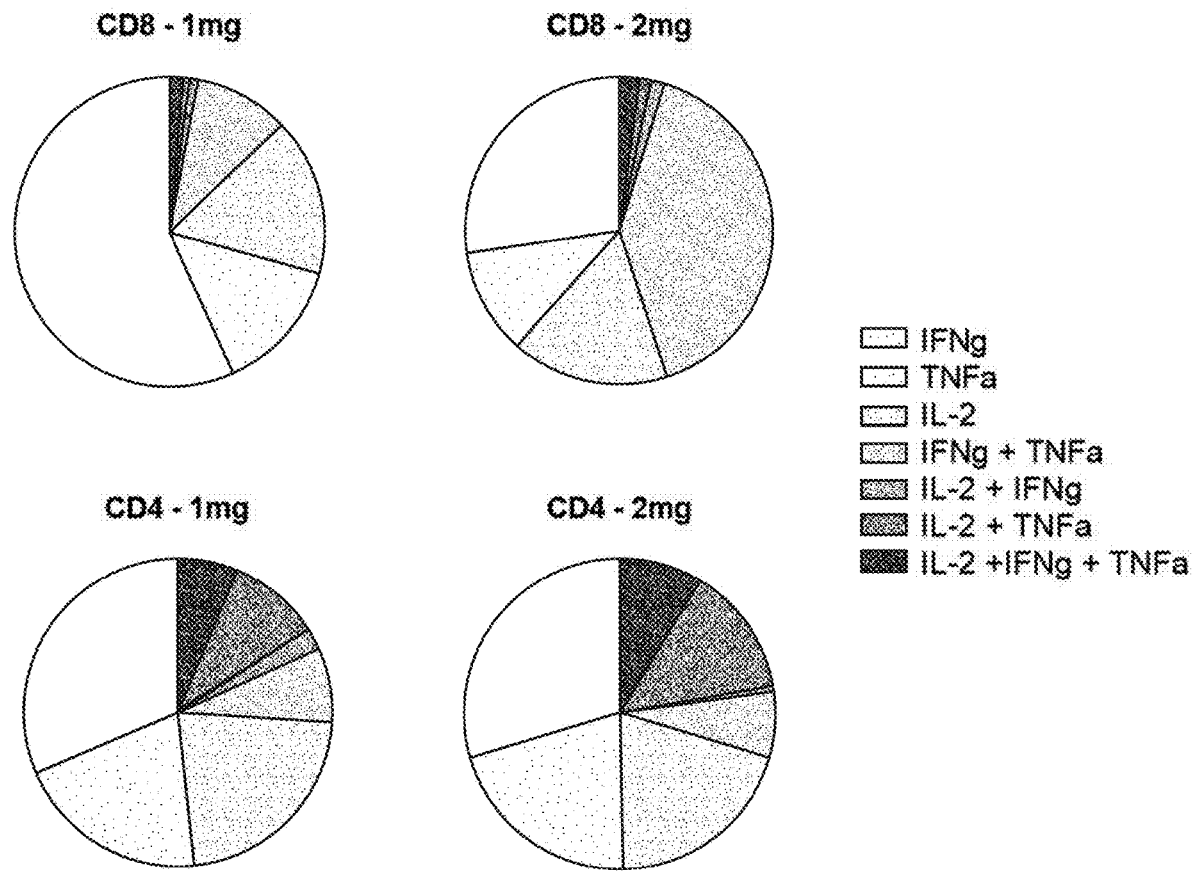

The composition of CD4+ or CD8+ T cells producing any cytokine (any response, IFN-γ or TNF-α or IL-2 following vaccination) was also assessed for surface markers CCR7 and CD45RA to characterize effector (CCR7-CD45RA+), effector memory (CCR7-CD45RA-), and central memory (CCR7+CD45RA-) cells (FIG. 18D). In both dose groups, CD8+ T cells making cytokine in response to stimulation with spike peptides were balanced across the three populations, whereas CD4+ T cells were predominantly of the central memory phenotype (FIG. 18D).

Figure 18F:
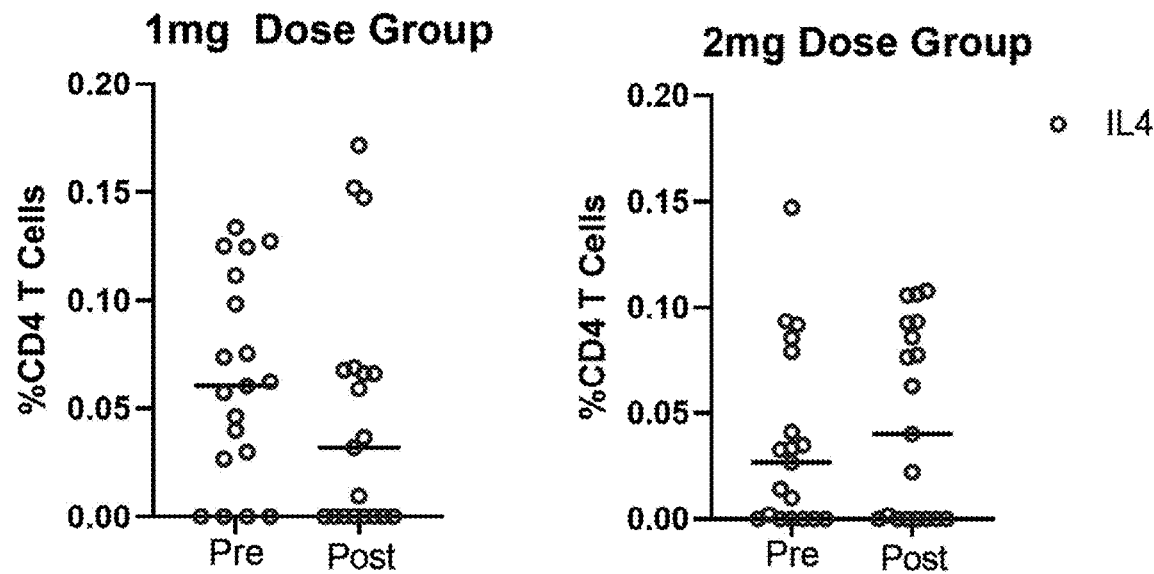
Figure 18F:
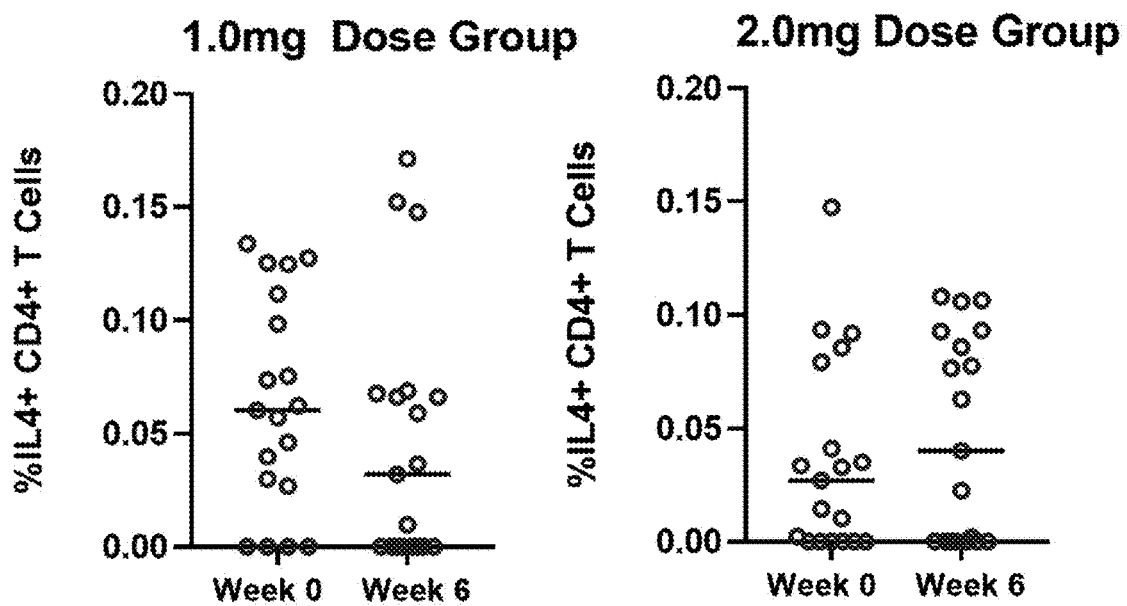

Th2 responses were also measured by assessing IL-4 production, and no statistically significant increases (Wilcoxon matched-pairs signed rank test, post-hoc analysis) were observed in either group post vaccination (FIG. 18F).

In this Phase 1 trial, INO-4800 vaccination led to potent T cell responses with increased Th1 phenotype, demonstrated by both IFN-γ ELISpot as well as multiparametric flow cytometry, as evidenced by increased expression of Th1-type cytokines IFN-γ, TNF-α. and IL-2 (FIG. 18C). Assessment of polyfunctionality of T cells induced by INO-4800 suggested the presence of SARS-CoV-2 specific CD4+ and CD8+ T cells exhibiting hallmarks of memory status suggest that a persistent cellular response has been established (FIG. 18D). Importantly, this was accomplished while minimizing induction of IL-4, a prototypical Th2 cytokine (FIG. 18F).

Phase 1 Update

This was designed as a Phase 1, open-label, multicenter trial (NCT04336410) to evaluate the safety, tolerability and immunogenicity of INO-4800 administered intradermally (ID) followed by electroporation using the CELLECTRA 2000 device. Healthy participants 18 to 50 years of age without a known history of COVID-19 illness received either a 1.0 mg or 2.0 mg dose of INO-4800 in a 2-dose regimen (Weeks 0 and 4).

DNA vaccine INO-4800. The vaccine was produced according to current Good Manufacturing Practices. INO-4800 contains plasmid pGX9501 expressing a synthetic, optimized sequence of the SARS-CoV-2 full length spike glycoprotein which was optimized as previously described at a concentration of 10 mg/ml in a saline sodium citrate buffer.

Endpoints. Safety endpoints included systemic and local administration site reactions up to 8 weeks post-dose 1. Immunology endpoints include antigen-specific binding antibody titers, neutralization titers and antigen-specific interferon-gamma (IFN-1-) cellular immune responses after 2 doses of vaccine. For Live Virus Neutralization, a responder is defined as Week 6 PRNT IC50>10, or >4 if a subject is a responder in ELISA. For S1+S2 ELISA, a responder is defined as a Week 6 value>1. For the ELISpot assay, a responder is defined as a Week 6 or Week 8 value that is >12 spot forming units per $10^6$ PBMCs above Week 0.

Study Procedures.

Forty participants were enrolled into two groups; 20 participants in each of 1.0 mg and 2.0 mg dose groups that received their doses on Weeks 0 and 4. The vaccine was administered in 0.1 ml intradermal injections in the arm followed by EP at the site of vaccination. Subjects in the 1.0 mg dose group received one injection on each dosing visit. The second dose of the vaccine could be injected in the same arm or a different arm relative to the first dose. Subjects in the 2.0 mg dose group received one injection in each arm at each dosing visit. EP was performed using CELLECTRA® 2000 as previously described. The device delivers total four electrical pulses, each 52 ms in duration at strengths of 0.2 A current and voltage of 40-200 V per pulse. The dose groups were enrolled sequentially with a safety run-in for each. The 1.0 mg dose group enrolled a single participant per day for 3 days. An independent Data Safety Monitoring Board (DSMB) reviewed the Week 1 safety data and based on a favorable safety assessment, made a recommendation to complete enrollment of the additional 17 participants into that dose group. In a similar fashion, the 2.0 mg dose group was subsequently enrolled. Participants were assessed for safety and concomitant medications at all time points, including screening, Week 0 (Dose 1), post dose next day phone call, Week 1, 4 (dose 2), 6, 8, 12, 28, 40 and 52 post-dose 1. Local and systemic AEs, regardless of relationship to the vaccine, were recorded and graded by the investigator. Safety laboratory testing (complete blood count, comprehensive metabolic panel and urinalysis) were and will continue to be conducted at screening, Week 1, 6, 8, 12,28 and 52 post-dose 1. Immunology specimens were obtained at all time points post-dose 1 except at Day 1 and Week 1. AEs were graded according to the Toxicity Grading Scale for Healthy Adult and Adolescent Volunteers Enrolled in Preventive Vaccine Clinical Trials guidelines that were issued by the Food and Drug Administration in September 2007. The DSMB reviewed laboratory and AE data for the participants up to 8 weeks included in this report. There were protocol-specified safety stopping rules and adverse events of special interest (AESIs). For the purpose of this report, clinical and laboratory safety assessments up to 8 weeks post the first dose are presented.

Protocol eligibility. Eligible participants must have met the following criteria: healthy adults aged between 18 and 50 years; able and willing to comply with all study procedures; Body Mass Index of 18-30 kg/m² at screening; negative serological tests for Hepatitis B surface antigen, Hepatitis C antibody and Human Immunodeficiency Virus antibody; screening electrocardiogram (ECG) deemed by the Investigator as having no clinically significant findings; use of medically effective contraception with a failure rate of <1% per year when used consistently be post-menopausal, or surgically sterile or have a partner who is sterile. Key exclusion criteria included the following: individuals in a current occupation with high risk of exposure to SARS-CoV-2; previous known exposure to SARS-CoV-2 or receipt of an investigational product for the prevention or treatment of COVID-19; autoimmune or immunosuppression as a result of underlying illness or treatment; hypersensitivity or severe allergic reactions to vaccines or drugs; medical conditions that increased risk for severe COVID-19; reported smoking, vaping, or active drug, alcohol or substance abuse or dependence; and fewer than two acceptable sites available for intradermal injection and electroporation.

Clinical Trial Population:
Healthy adult volunteers between the ages of 18-50 years, inclusive.

Inclusion Criteria:
a. Adults aged 18 to 50 years, inclusive;
b. Judged to be healthy by the Investigator on the basis of medical history, physical examination and vital signs performed at Screening;
c. Able and willing to comply with all study procedures;
d. Screening laboratory results within normal limits or deemed not clinically significant by the Investigator;
e. Negative serological tests for Hepatitis B surface antigen (HBsAg), Hepatitis C antibody and Human Immunodeficiency Virus (HIV) antibody screening;
f. Screening electrocardiogram (ECG) deemed by the Investigator as having no clinically significant findings (e.g. Wolff-Parkinson-White syndrome);
g. Use of medically effective contraception with a failure rate of <1% per year when used consistently and correctly from screening until 3 months following last dose, be post-menopausal, be surgically sterile or have a partner who is sterile.

Exclusion Criteria:
a. Pregnant or breastfeeding, or intending to become pregnant or father children within the projected duration of the trial starting with the screening visit until 3 months following last dose;
b. Is currently participating in or has participated in a study with an investigational product within 30 days preceding Day 0;
c. Previous exposure to SARS-CoV-2 (laboratory testing at the Investigator's discretion) or receipt of an investigational vaccine product for prevention of COVID-19, MERS or SARS;
d. Current or history of the following medical conditions:
  Respiratory diseases (e.g., asthma, chronic obstructive pulmonary disease);
  Hypertension, sitting systolic blood pressure >150 mm Hg or a diastolic blood pressure >95 mm Hg;
  Malignancy within 5 years of screening;
  Cardiovascular diseases (e.g., myocardial infarction, congestive heart failure, cardiomyopathy or clinically significant arrhythmias);
e. Immunosuppression as a result of underlying illness or treatment including:
  Primary immunodeficiencies;
  Long term use (≥7 days) of oral or parenteral glucocorticoids;
  Current or anticipated use of disease modifying doses of anti-rheumatic drugs and biologic disease modifying drugs;
  History of solid organ or bone marrow transplantation;
  Prior history of other clinically significant immunosuppressive or clinically diagnosed autoimmune disease.
f. Fewer than two acceptable sites available for ID injection and EP considering the deltoid and anterolateral quadriceps muscles;
g. Any physical examination findings and/or history of any illness that, in the opinion of the study investigator, might confound the results of the study or pose an additional risk to the patient by their participation in the study.

Immunogenicity Assessment Methods
Samples collected at screening, Week 0 (prior to dose) and at Weeks 6 and 8 were analyzed. Peripheral Blood Mononuclear Cells (PBMCs) were isolated from blood samples by a standard overlay on ficoll hypaque followed by centrifugation. Isolated cells were frozen in 10% DMSO and 90% fetal calf serum. The frozen PBMCs were stored in liquid nitrogen for subsequent analyses. Serum samples were stored at −80° C. until used to measure binding and neutralizing antibody titers.

SARS-CoV-2 Wildtype Virus Neutralization Assays
SARS-CoV-2/Australia/VIC01/2020 isolate neutralization assays were performed at Public Health England (Porton Down, UK). Neutralizing virus titers were measured in serum samples that had been heat-inactivated at 56° C. for 30 min. SARS-CoV-2 (Australia/VIC01/2020 isolate44) was diluted to a concentration of 933 pfu/m l and mixed 50:50 in 1% FCS/MEM containing 25 mM HEPES buffer with doubling serum dilutions. After a 1 h incubation at 37° C., the virus-antibody mixture was transferred to confluent monolayers of Vero E6 cells (ECACC 85020206; PHE, UK). Virus was allowed to adsorb onto cells at 37° C. for a further hour in an incubator, and the cell monolayer was overlaid with MEM/4% FBS/1.5% CMC. After 5 days incubation at 37° C., the plates were fixed, stained, with 0.2% crystal violet solution (Sigma) in 25% methanol (v/v). Plaques were counted.

S1+S2 Enzyme-Linked Immunosorbent Assay (ELISA)
ELISA plates were coated with 2.0 mg/mL recombinant SARS-CoV-2 S1+S2 spike protein (Acro Biosystems; SPN-052H8) and incubated overnight at 2-8° C. The S1+S2 contains amino acids residues Val 16-Pro 1213 of the full length spike protein, GenBank #QHD43416.1. It contains two mutations to stabilize the protein to the trimeric prefusion state (R683A, R685A) and also contains a C-terminal 10×His tag (SEQ ID NO: 24). The plates were then washed with PBS with 0.05% Tween-20 (Sigma; P3563) and blocked (Starting Block, Thermo Scientific; 37,538) for 1-3 h at room temperature. Samples were serially diluted using blocking buffer and were added in duplicate, along with prepared controls, to the washed and blocked assay plates. The samples were incubated on the blocked assay plates for one hour at room temperature. Following sample and control incubation, the plates were washed and a 1/1000 preparation of anti-human IgG HRP conjugate (BD Pharmingen; 555,788) in blocking buffer was then added to each well and allowed to incubate for 1 h at room temperature. The plates were washed and TMB substrate (KPL; 5120-0077) was then added and allowed to incubate at room temperature for approximately 10 min. TMB Stop Solution (KPL; 5150-0021) was next added and the plates read at 450 nm and 650 nm on a Synergy HTX Micro-plate Reader (BioTek). The magnitude of the assay response was expressed as titers which were defined as the greatest reciprocal dilution factor of the greatest dilution serial dilution at which the plate corrected optical density is 3 SD above background a subject's corresponding Week 0.

SARS-CoV-2 Spike ELISpot Assay
Peripheral mononuclear cells (PBMCs) pre- and post-vaccination were stimulated in vitro with 15-mer peptides (overlapping by 9 residues) spanning the full-length consensus spike protein sequence. Cells were incubated overnight in an incubator with peptide pools at a concentration of 5 mg per ml in a precoated ELISpot plate, (Mab-Tech, Human IFN-g ELISpot Plus). The next day, cells were washed off, and the plates were developed via a biotinylated anti-IFN-g detection antibody followed by a streptavidin-enzyme conjugate resulting in visible spots. Each spot corresponds to an individual cytokine-secreting cell. After plates were developed, spots were scanned and quantified using the CTL S6 Micro Analyzer (CTL) with Immuno-Capture and ImmunoSpot software. Values are shown as the background-subtracted average of measured triplicates. The ELISpot assay qualification determined that 12 spot forming units was the lower limit of detection. Thus, anything above this cutoff is considered to be a signal of an antigen specific cellular response.

INO-4800 SARS-CoV-2 Spike Flow Cytometry Assay

Figure 22A:
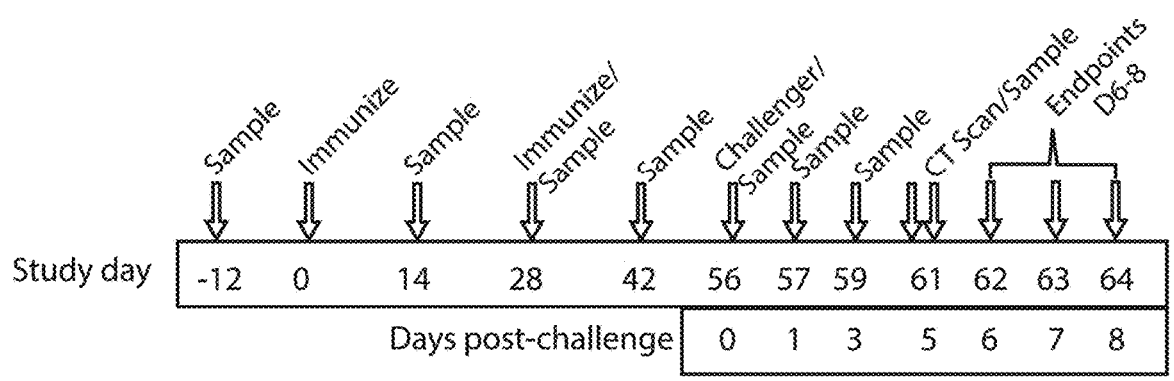
FIGS. 22A-22F depict humoral and cellular responses in rhesus macaques vaccinated with INO-4800. Study outline (FIG. 22A). Spike-specific IgG (FIG. 22B), RBD (FIG. 22C) and live virus-neutralising antibodies (FIG. 22D) measured in serum from rhesus macaques that received 1 or 2 doses of INO-4800 or were unvaccinated (Control). Lines represent the geometric means. Cellular immune responses in rhesus macaques vaccinated with INO-4800. SARS-CoV-2 Spike-specific interferon gamma (IFNγ) secretion from PBMCs was measured in rhesus macaques that received 1 or 2 doses of INO-4800 or were unvaccinated (Control) pre- (FIG. 22E) and post-challenge (FIG. 22F). PBMCs were stimulated with 5 separate peptide pools spanning the spike protein and SFU frequencies measured in response to each pool summed. Lines represent the means.
Figure 22B:
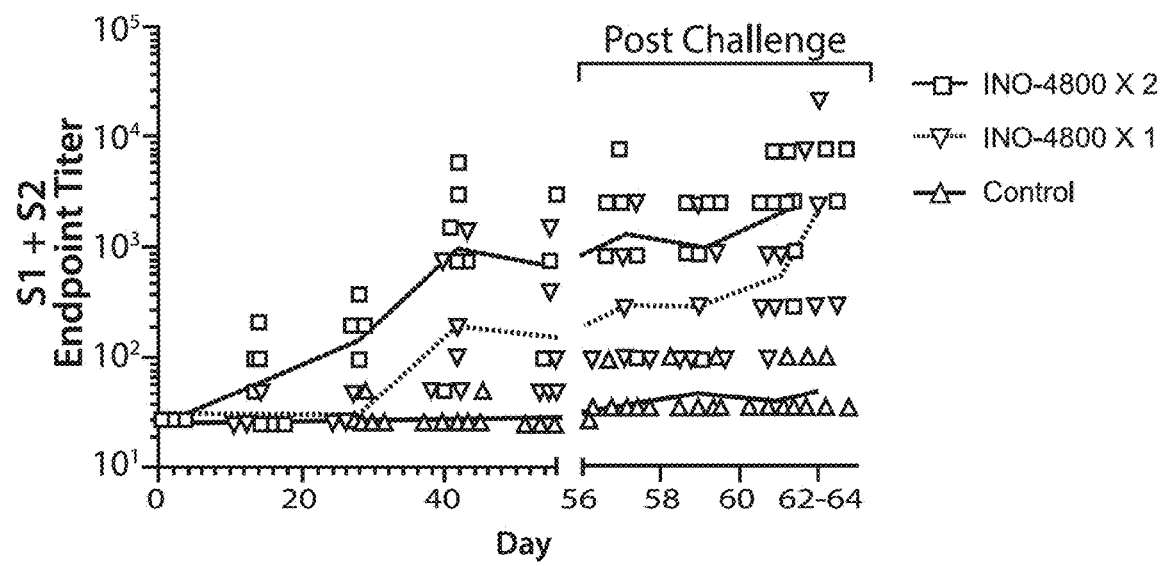

PBMCs were also used for Intracellular Cytokine Staining (ICS) analysis using flow cytometry. One million PMBCs in 200 mL complete RPMI media were stimulated for six hours (37° C., 5% $CO_2$) with DMSO (negative control), PMA and Ionomycin (positive control, 100 ng/mL and 2 mg/mL, respectively), or with the indicated peptide pools (225 μg/mL). After one hour of stimulation, Brefeldin A and Monensin (BD GolgiStop and GolgiPlug, 0.001% and 0.0015%, respectively) were added to block secretion of expressed cytokines. After stimulation the cells were moved to 4° C. overnight. Next, cells were washed in PBS for live/dead staining (Life Technologies Live/Dead aqua fixable viability dye), and then resuspended in FACS buffer (0.5% BSA, 2 mM EDTA, 20 mM HEPES). Next, extracellular markers were stained, the cells were fixed and permeabilized (eBioscience™ Foxp3Kit) and then stained for the indicated cytokines (Table 9) using fluorescently conjugated antibodies. FIGS. 22A and 22B show representative gating strategies for CD4+ and CD8+ T cells as well as examples of positive expression of IFNγ, TNFα, IL-2 and IL-4.

Statistical Analysis

No formal power analysis was applicable to this trial. Descriptive statistics were used to summarize the safety end-points: proportions with AEs, administration site reactions, and AESIs through 8 weeks. Descriptive statistics were also used to summarize the immunogenicity endpoints: median responses (with 95% confidence intervals) and percentage of responders for cellular results, and geometric mean titers (with 95% confidence intervals) and percentage of responders for humoral results. Post-hoc analyses of post-vaccination minus pre-vaccination paired differences in SARS-CoV-2 neutralization responses (on the natural log-scale, with a paired t-test), ELISpot responses (with Wilcoxon signed-rank tests), and Intracellular Flow Assay responses (with Wilcoxon signed-rank tests) were performed.

Results

Study Population Demographics

A total of 55 participants were screened and 40 participants were enrolled into the initial two groups (FIG. 16). The median age was 34.5 years (range 18 to 50 years). Participants were 55% (22/40) male (Table 6). Most participants were white (82.5%, 33/40).

Vaccine Safety and Tolerability

A total of 39 of 40 (97.5%) participants completed both doses; one participant in the 2.0 mg group discontinued trial participation prior to receiving the second dose due to lack of transportation to the clinical sites, and discontinuation was unrelated to the study or the dosing (FIG. 16). All 39 remaining subjects completed the visit 8 weeks post-dose 1. There was a total of 11 local and systemic adverse events (AEs) reported by 8 weeks post-dose 1; six of these were deemed related to vaccine (Table 10). All AEs were Grade 1 (mild) in severity. Five of the six related AEs were injection site reactions including injection site pain (3) and erythema (2). One Grade 1 systemic AE related to the vaccine was nausea. All related AEs occurred on the dosing day when the subjects received the first or second vaccination. There were no febrile reactions and no antipyretic medicine was used post vaccination. No subject discontinued the trial due to an AE. No serious adverse events (SAEs) nor adverse events of special interest (AESIs) were reported.

Figure 19A:
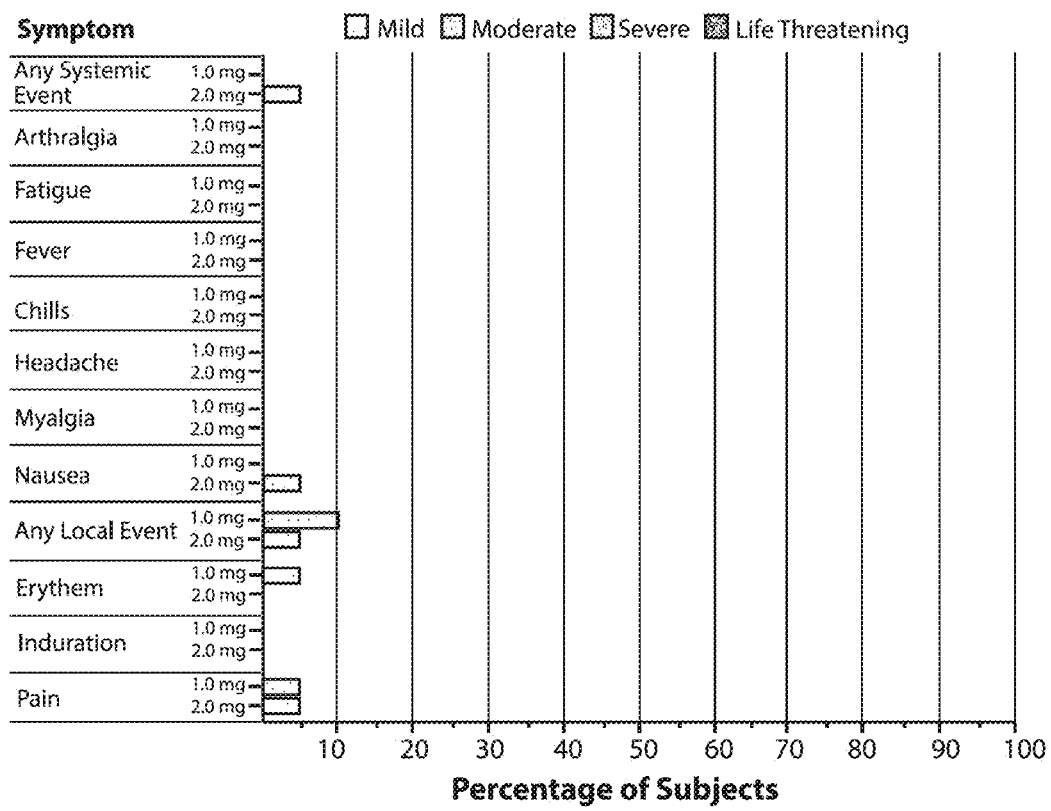
FIGS. 19A (post first-dose) and 19B (post second-dose) illustrate the Phase I Related Systemic and Local Adverse Events in severity of mild (Grade 1), moderate (Grade 2), severe (Grade 3) and life-threatening (Grade 4).
Figure 19B:
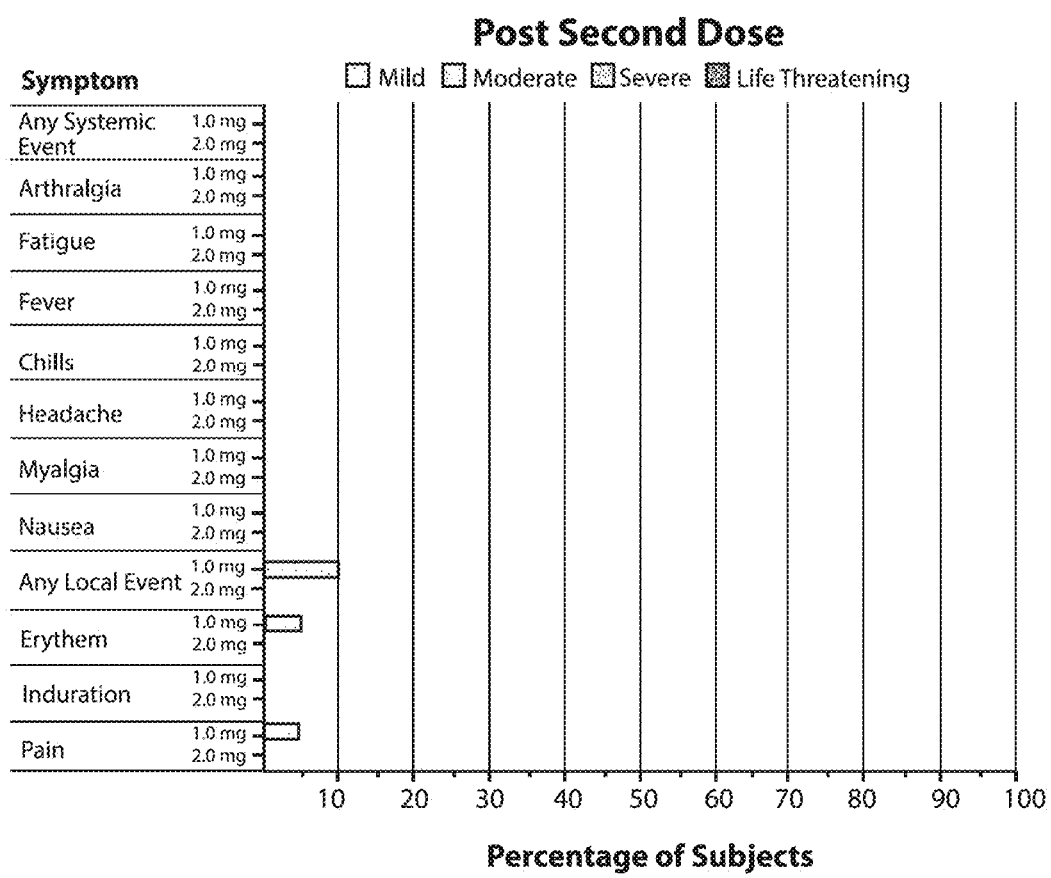

There were no abnormal laboratory values that were deemed clinically significant by the Investigators throughout the initial 8-week follow-up period. There was no increase in the number of participants who experienced AEs related to the vaccine in the 2.0 mg group (10%, 2/20), compared to that in the 1.0 mg group (15%, 3/20) (FIGS. 19A and 19B). In addition, there was no increase in frequencies of AEs with the second dose over the first dose in both dose groups.

TABLE 10

Number of Adverse Events classified by MedDRA ® System Organ Class, severity, and investigator assigned relationship to study vaccination

| MedDRA ® System Organ Class | Severity | Not related to vaccination | Related to vaccination | Total number |
|---|---|---|---|---|
| Any system Organ Class | Mild | 5 | 6 | 11 |
| | Moderate | — | — | — |
| | Severe | — | — | — |
| Gastrointestinal Disorders | Mild | 1 | 1 | 2 |
| | Moderate | — | — | — |
| | Severe | — | — | — |
| General Disorders and Administration Site Conditions | Mild | — | 5 | 5 |
| | Moderate | — | — | — |
| | Severe | — | — | — |
| Injury, Poisoning, and Procedural Complications | Mild | 2 | — | 2 |
| | Moderate | — | — | — |
| | Severe | — | — | — |
| Neoplasm Benign, Malignant and Unspecified | Mild | 1 | — | 1 |
| | Moderate | — | — | — |
| | Severe | — | — | — |
| Nervous System Disorders | Mild | 1 | — | 1 |
| | Moderate | — | — | — |
| | Severe | — | — | — |

Immunogenicity

Thirty-eight subjects were included in the immunogenicity analyses. In addition to one subject in the 2.0 mg group who discontinued prior to completing dosing, one subject in the 1.0 mg group was deemed seropositive at baseline and was excluded. Data for this subject can be found in Table 11.

TABLE 11

Immune Responses for subject who was Sero-positive at enrollment, INO-4800 1.0 mg Dose Group

| Immune Assay | Output at Week 0 | Output at Week 6 |
|---|---|---|
| Neutralization Week 6 Reciprocal Titer | 785 | 1089 |
| RBD Binding Antibody Week 6 Reciprocal Titer | 1 | 1 |
| S1 + S2 Binding Antibody Week 6 Reciprocal Titer | 1 | 14580 |
| IFN-gamma ELISpot Week 6 SFU/10^6 PBMC | 55.6 | 27.8 |

Humoral Immune Responses

Figure 20:
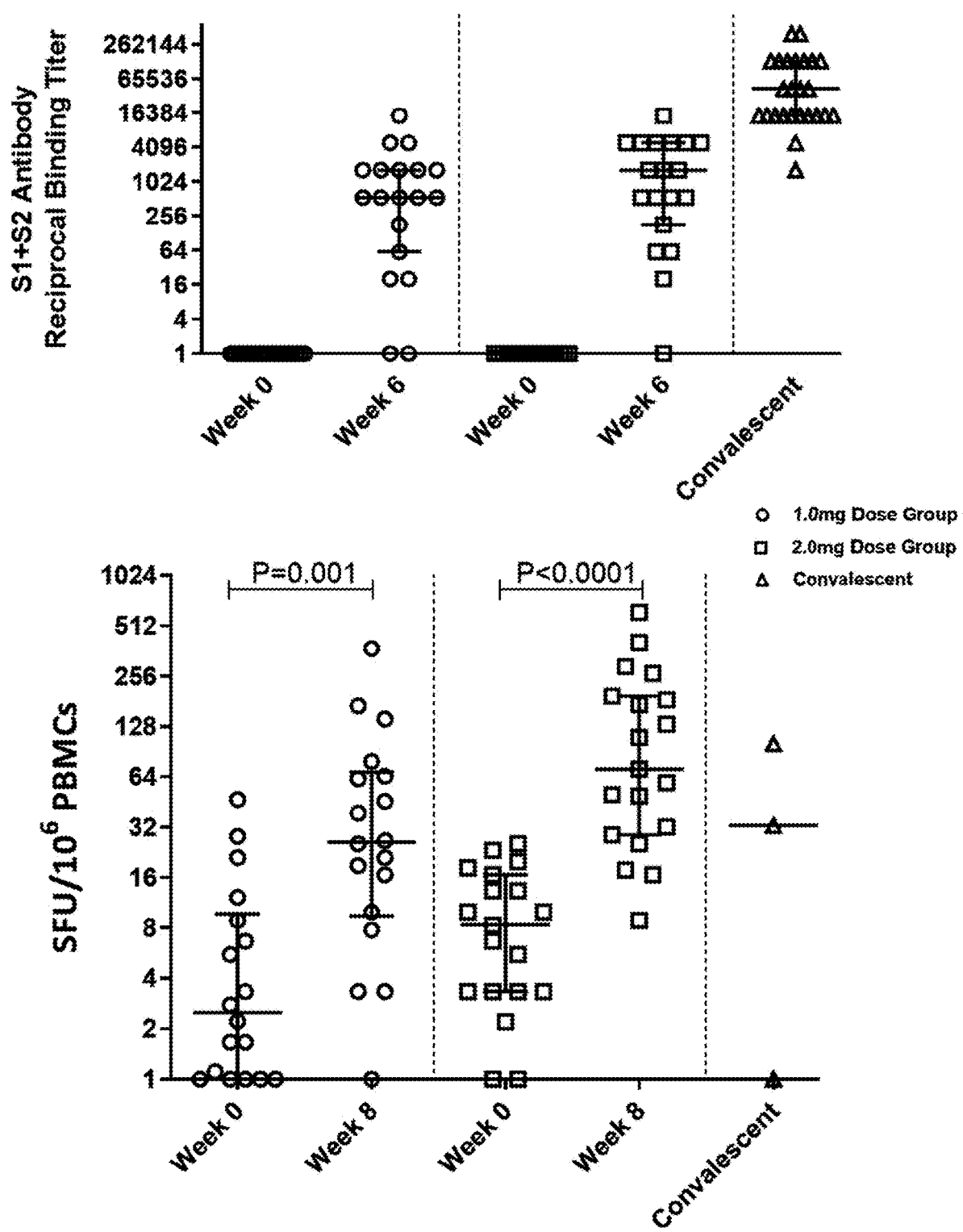
FIG. 20 provides supplementary data for humoral immune response. Three convalescent samples (all 3 with symptoms but non-hospitalized), tested by the ELISpot assay showed lower T cell responses, with a median of 33, than the 2.0 mg dose group at Week 8.

Sera was tested for the ability to bind S1+S2 spike protein. 89%(17/19) of participants in the 1.0 mg group and 95% (18/19) of participants in the 2.0 mg group had an increase in serum IgG binding titers to S1+S2 spike protein when compared to their pre-vaccination timepoint (Week 0), with the responder GMT of 655.5 (95% CI:255.6,1681.0) and 994.2 (95% CI: 395.3, 2500.3) in the 1.0 mg and 2.0 mg groups, respectively (FIG. 17B, FIG. 20 and Table 13). Sera was also tested for the ability to neutralize live virus by live virus PRNTIC50 neutralization assay. The geometric mean fold-rise at Week 6 relative to baseline was 10.8 with a 95% CI of (4.4, 27.0) and 11.5 with a 95% CI of (5.3, 24.9) in the 1.0 mg and 2.0 mg groups, respectively. In each group, there was a statistically significant increase at Week 6 over baseline (P<0.0001 paired t-test, post-hoc analysis), FIG. 17A. At Week 6, the percentage of responders were 78% (14/18) and 84% (16/19) in the 1.0 mg and 2.0 mg groups, respectively (FIG. 17A and Table 13), and the responder geometric mean titer (GMT) were 102.3 (95% CI: 37.4, 280.3) and 63.5 (95% CI: 39.6, 101.8) in the 1.0 mg and 2.0 mg groups, respectively. Overall seroconversion (defined as those participants who respond with neutralization and/or binding anti-bodies to S protein) at Week 6 in 1.0 mg and 2.0 mg dose group were 95% (18/19) for each group (Table 13).

Enzyme-Linked Immunospot (ELISpot)

Figure 18G:
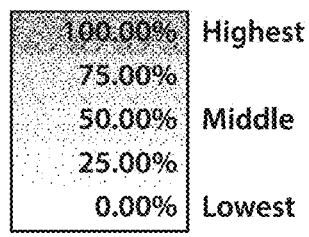
Figure 21:
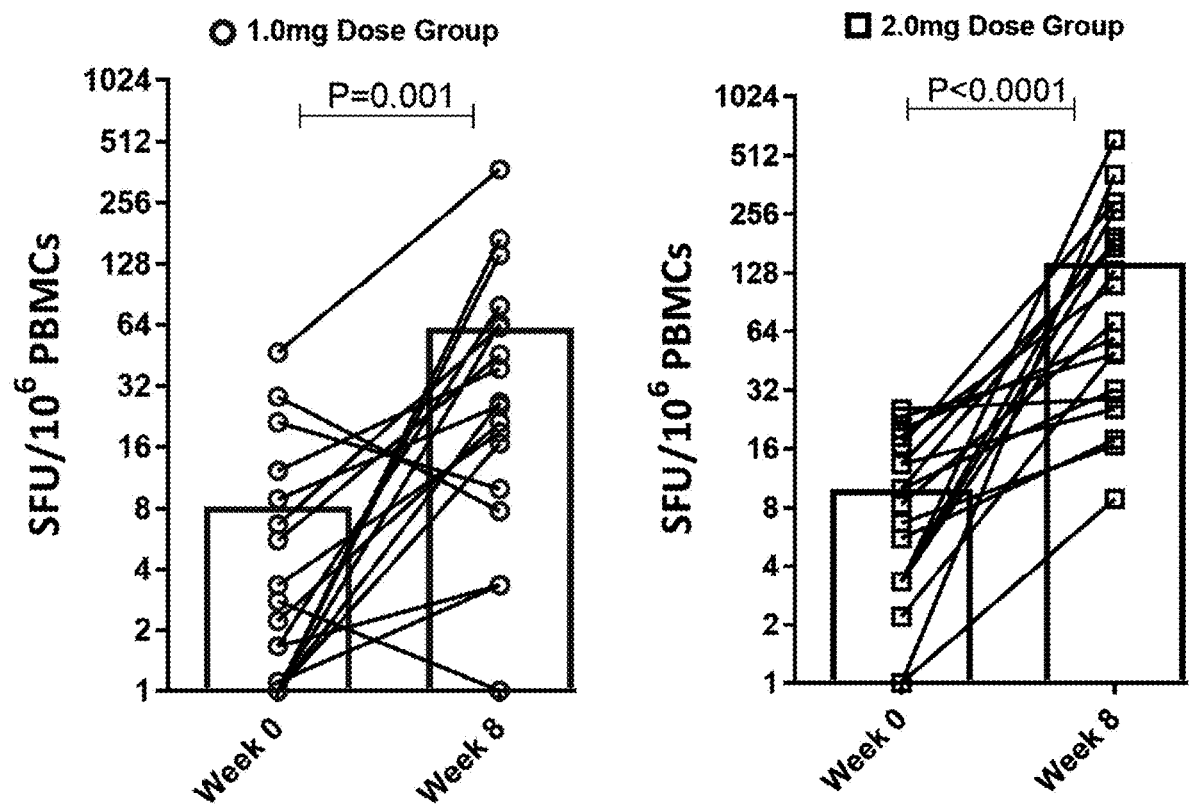
FIG. 21 provides supplementary Enzyme-linked immunospot (ELISpot) data.

The percentage of responders at week 8 was 74% (14/19) in the 1.0 mg dose group, and 100% (19/19) in the 2.0 mg dose group. These data taken with the seroconversion data result in a 100% (19/19) overall immune response in each group (Table 13, FIGS. 18A and 21). The Median SFU per $10^6$ PBMC was 46 (95% CI: 21.1, 142.2) and 71 (95% CI: 32.2-194.4) for the responders in 1.0 mg and 2.0 mg dose groups, respectively. The median change at week 8 relative to base-line was 22.3 (95% CI: 2.2, 63.4) and 62.8 (95% CI: 22.2, 191.1) in the respective groups, and in each group, there were statistically significant increases over baseline (P=0.001 and P<0.0001, respectively, Wilcoxon matched-pairs signed rank test, post-hoc analysis), FIG. 18A. It is also interesting to note that 3 convalescent samples (all 3 with symptoms but non-hospitalized), tested by the ELISpot assay showed lower T cell responses, with a median of 33, than the 2.0 mg dose group at Week 8 (FIG. 20). As shown in FIGS. 18B and 18G, the 2.0 mg group's T cell responses were mapped to 5 epitope pools. Encouragingly, T cell responses were seen in all regions of the spike protein, with the dominant pool encompassing the Receptor Binding Domain region, followed by pools covering the N Terminal Domain, as well as the Fusion Peptide, Heptad Repeat 1 and the Central Helix.

Intracellular Flow Assay

The contribution of CD4+ and CD8+ T cells to the cellular immune response against INO-4800 was assessed by intracellular cytokine staining (ICS). In the 2.0 mg dose group, the median change from baseline to Week 6 in CD8+ T cells producing IFN-γ, TNF-α and/or IL-2 (Any Response) was 0.11 with a 95% CI of (−0.02, 0.23); the change was significantly increased (P=0.0181, Wilcoxon matched-pairs signed rank test, post-hoc analysis). owing chiefly to significant increases in IFN-γ as well as TNF-α production (FIG. 18C). Also in the 2.0 mg dose group, the median change from baseline to Week 6 in CD4+ T cells producing TNF-α was 0.02 with a 95% CI of (0.01 to 0.09); the change was also significantly increased (P=0.0020, Wilcoxon matched-pairs signed rank test, post-hoc analysis, FIG. 18C). The composition of CD4+ or CD8+ T cells producing any cytokine (IFN-γ or TNF-α or IL-2 following vaccination) was also assessed for surface markers CCR7 and CD45RA to characterize effector (CCR7-CD45RA+), effector memory (CCR7-CD45RA−), and central memory (CCR7+CD45RA−) cells (FIG. 18D). In both dose groups, CD8+ T cells producing cytokine in response to stimulation with SARS-CoV-2spike peptides were generally balanced across the three populations, whereas CD4+ T cells were predominantly of the central memory phenotype (FIG. 18D). CD4+ and CD8+ T cells following vaccination were further explored for their ability to produce more than one cytokine at a time and were encouraged to note that nearly half (41%) of the CD8+ T cells in the 2.0 mg dose group were dual producing IFN-γ and TNF-α (FIG. 18E). CD8+ T cells producing cytokine in the 1.0 mg dose group were primarily monofunctional IFN-γ producing cells (57%). The CD4+ T cell compartment was also polyfunctional in nature with 6% and 9%, in the 1.0 mg and 2.0 mg dose groups, respectively, producing all 3 cytokines, IFN-γ, TNF-α, and IL-2 (Table 12). Th2 responses were also measured by assessing IL-4 production, and no statistically significant increases (Wilcoxon matched-pairs signed rank test, post-hoc analysis) were observed in either group post vaccination (FIG. 18F).

INO-4800 was well tolerated with a frequency of product-related Grade 1 AEs of 15% (3/20 subjects) and 10% (2/20 subjects) of the participants in 1.0 mg and 2.0 mg dose group, respectively. Only Grade 1 AEs were noted in the study, which compares favorably with existing licensed vaccines. The safety profile of a successful COVID-19 vaccine is important and supports broad development of INO-4800 in at-risk populations who are at more serious risk of complications from SARS-CoV-2 infection, including the elderly and those with comorbidities. INO-4800 also generated balanced humoral and cellular immune responses with all 38 evaluable participants displaying either or both antibody or T cell responses following two doses of INO-4800. Humoral responses measured by binding or neutralizing antibodies were observed in 95% (18/19) of the participants in each dose group. The neutralizing antibodies, measured by live virus neutralization assay, were seen in 78% (14/18) and 84% (16/19) of participants, and the corresponding GMTs were 102.3 [95% CI (37.4, 280.3)] and 63.5[95% CI (39.6, 101.8)] for the 1.0 mg and 2.0 mg dose groups, respectively. The range overlaps that of the PRNT IC50 titers reported from convalescent patients as well as the PRNT IC50 titers in NHPs which were protected in a SARS-CoV-2 challenge. Furthermore, there was a statistically significant increase in titers. It is important to note that all but one vaccine recipient that did not develop neutralizing antibody titers responded positively in the T cell ELISpot assay, suggesting that the immune responses generated by the vaccine are registering differentially in these assays. Cellular immune responses were observed in 74% (14/19) and 100% (19/19) of 1.0 mg and 2.0 mg dose groups, respectively. Importantly, INO-4800 generated T cell responses that were more frequent and with higher responder median responses (46 [95% CI (21.1, 142.2)] vs. 71 [95% CI (32.2,194.4)] SFU $10^6$ PBMC) in the 1.0 mg and 2.0 mg dose groups respectively. These T cell responses in the 2.0 mg dose group were higher in magnitude than convalescent samples tested (FIG. 18A). Furthermore, there was a statistically significant increase in SFU. In the flow cytometric assays, both the 1.0 mg and 2.0 mg Dose Groups showed increases in cytokine production from both the CD4+ and CD8+ T cell compartments, especially in the 2.0 mg group. The 2.0 mg group exhibited a number of statistically significant cytokine outputs, including IFN-γ and TNF-α and "any cytokine" from the CD8+ T cell compartment and TNF-α from the CD4+ T cell compartment (FIG. 18C). Of considerable importance is that CD8+ T cell responses in the 2.0 mg dose group were dominated by cells expressing both IFN-γ and TNF-α with or without IL-2 (FIG. 18E and Table 12). In total, these cells amounted to nearly half of the total CD8+ T cell response (42.7%, Table 12).

In this Phase 1 trial, INO-4800 vaccination led to substantial T cell responses with increased Th1 phenotype, measured by both IFN-γ ELISpot as well as multiparametric flow cytometry, as evidenced by increased expression of Th1-type cytokines IFN-γ, TNF-α, and IL-2 (FIG. 18C). Assessment of cellular responses induced by INO-4800 displayed the presence of SARS-CoV-2 specific CD4+ and CD8+ T cells exhibiting hallmarks of differentiation into both central and effector memory cells, suggesting that a persistent cellular response has been established (FIG. 18D). Importantly, this was accomplished while minimizing induction of IL-4, a prototypical Th2 cytokine (FIG. 18F), supporting that this vaccine has an immune phenotype, along with induction of protection in preclinical models, which makes it unlikely to be a risk for induction of enhanced disease.

Expanded Phase I Study

Approximately 120 healthy volunteers will be evaluated across three (3) dose levels (Study Groups). A total of 40 subjects will be enrolled into each Study Group. Enrollment into each Study Group will be stratified by age; n=20 for 18-50 years, n=10 for 51-64 years, and n=10≥65 years (Table 14).

Subjects will be adults aged at least 18 years; judged to be healthy by the Investigator on the basis of medical history, physical examination and vital signs performed at Screening; able and willing to comply with all study procedures; screening laboratory results within normal limits for testing laboratory or deemed not clinically significant by the Investigator; Body Mass Index of 18-30 kg/m², inclusive, at

TABLE 12

Flow Cytometry Polyfunctionality

| Parameter Output | 1.0 mg Cohort | | 2.0 mg Cohort | |
|---|---|---|---|---|
| | CD4 Cytokine Frequency (%) | CD8 Cytokine Frequency (%) | CD4 Cytokine Frequency (%) | CD8 Cytokine Frequency (%) |
| IFN-gamma only | 31.2 | 56.7 | 29.5 | 27.1 |
| TNF-alpha only | 20.4 | 14 | 20.9 | 11.2 |
| IL-2 only | 22.3 | 16.5 | 20.1 | 16.5 |
| IFN-gamma and TNF-alpha only | 8.0 | 9.7 | 6.7 | 40.6 |
| IFN-gamma and IL-2 only | 2.1 | 0.9 | 0.6 | 1.3 |
| IL-2 and TNF-alpha only | 9.6 | 0.7 | 13.5 | 1.2 |
| IFN-gamma and IL-2 and TNF-alpha | 6.4 | 1.5 | 8.7 | 2.1 |

Percents listed are the contributions of each output to the total cytokine response

TABLE 13

| Immune Assay | 1.0 mg Cohort | | | 2.0 mg Cohort | | |
|---|---|---|---|---|---|---|
| | Overall Value | Responder Value | Responders[‡] n (%) | Overall Value | Responder Value | Responders[‡] n(%) |
| Neutralization Week 6 GMT Reciprocal Titer [95% CI] (Range) | 44.4 [14.6, 134.8] (1, 11647) | 102.3 [37.4, 280.3] (13, 11647) | 14/18 (78%) | 34.9 [15.8, 77.2] (1, 652) | 63.5 [39.6, 101.8] (13652) | 16/19 (84%) |
| S1 + S2 Binding Antibody Week 6 GMT Reciprocal Titer [95% CI] (Range) | 331.2 [91.2, 1203.2] (1, 14580) | 655.5 [255.6, 168.1] (20, 14580) | 17/19 (89%) | 691.4 [217.5, 2197.2] (1, 14580) | 994.2 [395.3, 2500.3] (20, 14580) | 18/19 (95%) |
| Total Seroconversion (Response in S1 + S2 or Neutralization) | N/A | N/A | 18/19 (95%) | N/A | N/A | 18/19 (95%) |
| IFN-gamma ELISpot Week 8 Median SFU per [95% CI] (Range) | 26.2 SFU [10.0-64.4] (1, 374.4) | 45.6 [21.1, 142.2] (16.7, 374.4) | 14/19 (74%) [µ] | 71 SFU [32.2-194.4] (8.9, 615.6) | 71 SFU [32.2-194.4] (8.9, 615.6) | 19/19 (100%) [µ] |
| Overall Immune Response Rate (Seroconversion or ELISpot) | N/A | N/A | 19/19 (100%) | N/A | N/A | 19/19 (100%) |

1.0 mg Cohort excludes one subject with baseline positive NP ELISA
[‡]Response criteria: Live Neutralization -Week 6 PRNT IC$_{50}$ ≥10, or ≥4 if binding ELISA activity is seen; S1 + S2 Binding - Week 6 Value >1; RBD Binding -Week 6 value >1; ELISpot - Value ≥12 SFU over Week 0
[µ] Responders generated using Week 6 or Week 8 data Screening; negative serological tests for Hepatitis B surface antigen (HBsAg), Hepatitis C antibody and Human Immunodeficiency Virus (HIV) antibody at screening; screening ECG deemed by the Investigator as having no clinically significant findings (e.g. Wolff-Parkinson-White syndrome); and must meet one of the following criteria with respect to reproductive capacity: women who are post-menopausal as defined by spontaneous amenorrhea for ≥12 months; surgically sterile or have a partner who is sterile; use of medically effective contraception. Exclusion criteria are as follows: pregnant or breastfeeding, or intending to become pregnant or father children within the projected duration of the trial starting with the screening visit until 3 months following last dose; positive serum pregnancy test during screening or positive urine pregnancy test prior to dosing; currently participating in or has participated in a study with an investigational product within 30 days preceding Day 0; previous exposure to severe acute respiratory syndrome coronavirus 2 (SARS-CoV-2) or receipt of an investigational product for the prevention or treatment of COVID-19, middle east respiratory syndrome (MERS), or severe acute respiratory syndrome (SARS); in a current occupation with high risk of exposure to SARS-CoV-2 (e.g., health care workers or emergency response personnel having direct interactions with or providing direct care to patients); current or history of respiratory disease, hypersensitivity or severe allergic reactions to vaccines or drugs, diagnosis of diabetes mellitus, hypertension, malignancy within 5 years of screening, or cardiovascular disease; immunosuppression as a result of underlying illness or treatment, including primary immunodeficiencies, long term use (≥7 days) of oral or parenteral glucocorticoids, current or anticipated use of disease-modifying doses of anti-rheumatic drugs and biologic disease-modifying drugs, history of solid organ or bone marrow transplantation, and prior history of other clinically significant immunosuppressive or clinically diagnosed autoimmune disease; fewer than two acceptable sites available for ID injection and EP considering the deltoid and anterolateral quadriceps muscles; or reported smoking, vaping, or active drug, alcohol or substance abuse or dependence; or any physical examination findings and/or history of any illness that, in the opinion of the study investigator, might confound the results of the study or pose an additional risk to the patient by their participation in the study.

All subjects will receive dosing on Day 0 and Week 4 (Table 15). Subjects who consent to receive the booster dose (Table 16) will receive the booster dose no earlier than Week 12 in their dosing schedule with the same dose previously received for their two-dose regimen (Day 0 and Week 4). Safety and immunogenicity will be evaluated at 2 weeks following the booster dose.

TABLE 14

| Study Group | Number Total Subjects | Number Subjects by Age | Age (years) | Dosing Weeks | INO-4800 Dose per injection | No. Injections/EP per Dosing Visit | INO-4800 Dose per Dosing Visit | Total INO-4800 Dose |
|---|---|---|---|---|---|---|---|---|
| 1 | 40 | 20* | 18-50 | 0, 4 (±5 days), Optional Booster[b] | 1.0 mg | 1 | 1.0 mg | 3.0 mg |
|  |  | 10 | 51-64 |  |  |  |  |  |
|  |  | 10 | ≥65 |  |  |  |  |  |
| 2 | 40 | 20* | 18-50 | 0, 4 (±5 days), Optional Booster[b] | 1.0 mg | 2[a] | 2.0 mg | 6.0 mg |
|  |  | 10 | 51-64 |  |  |  |  |  |
|  |  | 10 | ≥65 |  |  |  |  |  |
| 3 | 40 | 20 | 18-50 | 0, 4 (±5 days), Optional Booster[b] | 0.5 mg | 1 | 0.5 mg | 1.5 mg |
|  |  | 10 | 51-64 |  |  |  |  |  |
|  |  | 10 | ≥65 |  |  |  |  |  |
| Total | 120 |  |  | * Base Study (Others in expanded study) |  |  |  |  |

[a]INO-4800 will be injected ID followed by EP in an acceptable location on two different limbs at each dosing visit
[b]Optional booster dose delivered no earlier than Week 12 in their dosing schedule with the same dose previously received for their two-dose regimen.

Subjects not receiving an optional booster dose will be followed to the End of Study (EOS) visit at Week 52 will be the End of Study (EOS) visit (Table 15). For subjects receiving an optional booster dose, the 48 Week Post-Booster Dose Visit will be the EOS visit (Table 16).

Primary Objectives:

Evaluate the tolerability and safety of INO-4800 administered by ID injection followed by EP in healthy adult volunteers Evaluate the cellular and humoral immune response to INO-4800 administered by ID injection followed by EP Primary Safety Endpoints:

Incidence of adverse events by system organ class (SOC), preferred term (PT), severity and relationship to investigational product. Percentage of Participants with Adverse Events (AEs) [Time Frame: Baseline up to Week 52 (if not receiving an optional booster dose) or the 48 Week Post-Booster Dose Visit (if receiving an optional booster dose)].

Administration (i.e., injection) site reactions (described by frequency and severity). Percentage of Participants with Administration (Injection) Site Reactions [Time Frame: Day 0 up to Week 52 (if not receiving an optional booster dose) or the 48 Week Post-Booster Dose Visit (if receiving an optional booster dose)].

Incidence of adverse events of special interest. Percentage of Participants with Adverse Events of Special Interest (AESIs). [Time Frame: Baseline up to Week 52 (if not receiving an optional booster dose) or the 48 Week Post-Booster Dose Visit (if receiving an optional booster dose)].

Primary Immunogenicity Endpoints:

SARS-CoV-2 Spike glycoprotein antigen-specific antibodies by binding assays. Change from Baseline in SARS-CoV-2 Spike Glycoprotein Antigen-Specific Binding Antibody Titers [Time Frame: Baseline up to Week 52 (if not receiving an optional booster dose) or the 48 Week Post-Booster Dose Visit (if receiving an optional booster dose)].

Antigen-specific cellular immune response by IFN-gamma ELISpot and/or flow cytometry assays. Change from Baseline in Antigen-Specific Cellular Immune Response [Time Frame: Baseline up to Week 52 (if not receiving an optional booster dose) or the 48 Week Post-Booster Dose Visit (if receiving an optional booster dose)].

Exploratory Objectives:

Evaluate the expanded immunological profile by assessing both T and B cell immune response Evaluate the safety and immunogenicity of an optional booster dose of INO-4800 administered by ID injection followed by EP subsequent to a two-dose regimen Exploratory Endpoints:

Expanded immunological profile which may include (but not limited to) additional assessment of T and B cell numbers, neutralization response and T and B cell molecular changes by measuring immunologic proteins and mRNA levels of genes of interest at all weeks as determined by sample availability Incidence of all adverse events subsequent to an optional booster dose of INO-4800 administered by ID injection followed by EP SARS-CoV-2 Spike glycoprotein antigen-specific neutralizing and binding antibodies subsequent to an optional booster dose of INO-4800 administered by ID injection followed by EP Antigen-specific cellular immune response by IFN-γ ELISpot and/or flow cytometry subsequent to an optional booster dose of INO-4800 administered by ID injection followed by EP Safety Assessment:

Subjects will be followed for safety for the duration of the trial through EOS or the subject's last visit. Adverse events will be collected at every visit (including the Day 1 and 36 Week Post-Booster Dose phone calls). Laboratory blood and urine samples will be drawn according to the Schedule of Events (Table 15 and Table 16).

TABLE 15

NON-BOOSTER CLINICAL TRIAL SCHEDULE OF EVENTS

| Tests and assessments | Screen[a] | Day 0 Pre | Day 0 Post | Day 1 (+1 d) | Week 1 (±3 d) | Week 4 (±5 d) Pre | Week 4 (±5 d) Post | Week 6 (±5 d) |
|---|---|---|---|---|---|---|---|---|
| Informed Consent | X | | | | | | | |
| Inclusion/Exclusion Criteria | X | | | | | | | |
| Medical History | X | X | | | | | | |
| Demographics | X | | | | | | | |
| Concomitant Medications | X | X | | | X | X | | X |
| Physical Exam[b] | X | X | | | X | X | | X |
| Vital Signs | X | X | | | X | X | | X |
| Height and Weight | X | | | | | | | |
| CBC with Differential | X | | | | X | | | X |
| Chemistry[c] | X | | | | X | | | X |
| HIV, HBV, HCV Serology[d] | X | | | | | | | |
| SARS-CoV-2 Serology | X | | | | | | | |
| 12-lead ECG | X | | | | | | | |
| Urinalysis Routine[e] | X | | | | X | | | X |
| Pregnancy Test[f] | X | X | | | | X | | |
| INO-4800 + EP[g] | | X[h] | | | | X[h] | | |
| Download EP Data[i] | | | X | | | | X | |
| Adverse Events[j] | X | X | X | X[k] | X | X | X | X |
| Immunology (Whole blood)[l] | X | X | | | | X | | X |
| Immunology (Serum)[m] | X | X | | | | X | | X |

| Tests and assessments | Week 8 (±5 d) | Week 12 (±5 d) | Week 28 (±5 d) | Week 40 (+5 d) | Week 52 (±5 d) |
|---|---|---|---|---|---|
| Informed Consent | | | | | |
| Inclusion/Exclusion Criteria | | | | | |
| Medical History | | | | | |
| Demographics | | | | | |
| Concomitant Medications | X | X | X | X | X |
| Physical Exam[b] | X | X | X | X | X |
| Vital Signs | X | X | X | X | X |
| Height and Weight | | | | | |
| CBC with Differential | X | X | X | X | X |
| Chemistry[c] | X | X | X | X | X |
| HIV, HBV, HCV Serology[d] | | | | | |
| SARS-CoV-2 Serology | | | | | |
| 12-lead ECG | | | | | |
| Urinalysis Routine[e] | X | X | X | X | X |
| Pregnancy Test[f] | | | | | |
| INO-4800 + EP[g] | | | | | |
| Download EP Data[i] | | | | | |

TABLE 15-continued

NON-BOOSTER CLINICAL TRIAL SCHEDULE OF EVENTS

| | | | | | |
|---|---|---|---|---|---|
| Adverse Events[j] | X | X | X | X | X |
| Immunology (Whole blood)[l] | X | X | X | X | X |
| Immunology (Serum)[m] | X | X | X | X | X |

[a]Screening assessment occurs from −30 days to −1 day prior to Day 0.
[b]Full physical examination at screening and Week 52 (or any other study discontinuation visit) only. Targeted physical exam at all other visits.
[c]Includes Na, K, Cl, HCO3, Ca, PO4, glucose, BUN, Cr, AST, ALT and TBili.
[d]HIV antibody or rapid test, HBsAg, HCV antibody.
[e]Dipstick for glucose, protein, and hematuria. Microscopic examination should be performed if dipstick is abnormal.
[f]Serum pregnancy test at screening. Urine pregnancy test at other visits.
[g]All doses delivered via intradermal injection followed by EP.
[h]For Study Groups Groups 1 and 3, one injection in skin preferably over deltiod muscle at Day 0 and Week 4. For Study Group 2, two injections in skin with each injection over a different deltoid or lateral quadriceps; preferably over the deltoid muscles, at Day 0 and Week 4.
[i]Following administration of INO-4800 + EP, EP data will be downloaded from the CELLECTRA ® 2000 device and provided to Inovio.
[j]Includes AEs from the time of consent and all injection site reactions that qualify as an AE.
[k]Follow-up phone call to collect AEs.
[l]4 × 8.5 mL (34 mL) whole blood in 10 mL Acid Citrate Dextrose (ACD, Yellow top) tubes per time point.
Note:
Collect a total of 68 mL whole blood prior to 1st dose (screening and prior to Day 0 dosing).
[m]1 × 8 mL blood in 10 mL red top serum collection tube per time point.
Note:
Collect four aliquots of 1 mL each (total 4 mL) serum at each time point prior to 1st dose (Screening and prior to Day 0 dosing).

TABLE 16

Booster Clinical Trial Schedule of Events

| Tests and assessments | Booster Dose Visit | | 2 Week Post-Booster Dose Visit (±5 d) | 12 Week Post-Booster Dose Visit (±5 d) | 24 Week Post-Booster Dose Visit (±5 d) | 36 Week Post-Booster Dose Phone Call (+5 d) | 48 Week Post-Booster Dose Visit (±5 d) |
|---|---|---|---|---|---|---|---|
| | Pre | Post | | | | | |
| Concomitant Medications | X | | X | X | X | | X |
| Physical Exam[a] | X | | X | X | X | | X |
| Vital Signs | X | | X | X | X | | X |
| CBC with Differential | X | | X | X | X | | X |
| Chemistry[b] | X | | X | X | X | | X |
| Urinalysis Routine[c] | X | | X | X | X | | X |
| Pregnancy Test[d] | X | | | | | | |
| INO-4800 + EP[e] | X[f] | X | | | | | |
| Download EP Data[g] | | X | | | | | |
| Adverse Events[h] | X | X | X | X | X | X[i] | X |
| Immunology (Whole blood)[j] | X | | X | X | X | | X |
| Immunology (Serum)[k] | X | | X | X | X | | X |

[a]Full physical examination at the 48 Week Post-Booster Dose Visit (or any other study discontinuation visit) only. Targeted physical exam at all other visits.
[b]Includes Na, K, Cl, HCO3, Ca, PO4, glucose, BUN, Cr, AST, ALT and TBili.
[c]Dipstick for glucose, protein, and hematuria. Microscopic examination should be performed if dipstick is abnormal,
[d]Urine pregnancy test must be negative prior to receiving booster dose.
[e]All doses delivered via intradermal injection followed by EP.
[f]For Study Groups 1 and 3, one injection in skin preferably over deltoid muscle (or alternatively, lateral quadriceps) at the Booster Dose Visit. For Study Group 2, two injections in skin with each injection over a different deltoid or lateral quadriceps; preferably over the deltoid muscles, at the Booster Dose Visit.
[g]Following administration of INO-4800 + EP, EP data will be downloaded from the CELLECTRA ® 2000 device and provided to Inovio.
[h]Includes AEs from the time of consent and all injection site reactions that qualify as an AE.
[i]Follow-up phone call to collect AEs.
[j]4 × 8.5 mL (34 mL) whole blood in 10 mL Acid Citrate Dextrose (ACD, Yellow top) tubes per time point.
[k]1 × 8 mL blood in 10 mL red top serum collection tube per time point.

Immunogenicity Assessment:

Immunology blood samples will be collected according to the Schedule of Events (Table 15 and Table 16). Determination of analysis of collected samples for immunological endpoints will be determined on an ongoing basis throughout the study.

INO-4800 delivered ID followed by EP using CELLECTRA® 2000 in healthy volunteers is expected to be well tolerated, exhibit an acceptable safety profile, and result in generation of immune responses to SARS-CoV-2 Spike glycoprotein.

Example 7 Phase 2/3 Randomized, Blinded, Placebo-Controlled Trial to Evaluate the Safety, Immunogenicity, and Efficacy of INO-4800, a Prophylactic Vaccine Against COVID-19 Disease, Administered Intradermally Followed by Electroporation (EP) in Healthy Seronegative Adults at High Risk of SARS-CoV-2 Exposure This is a Phase 2/3, randomized, placebo-controlled, multi-center trial to evaluate the safety, immunogenicity and efficacy of INO-4800 administered by intradermal (ID) injection followed by electroporation (EP) using CELLECTRA® 2000 device to prevent COVID-19 disease in participants at high risk of exposure to SARS-CoV-2. The Phase 2 segment will evaluate immunogenicity and safety in approximately 400 participants at two dose levels across three age groups. Safety and immunogenicity information from the Phase 2 segment will be used to determine the dose level for the Phase 3 efficacy segment of the study involving approximately 6178 participants.

TABLE 17

| Arm | Intervention/treatment |
|---|---|
| Experimental Phase 2: INO-4800 Dose Group 1 Participants will receive one intradermal (ID) injection of 1.0 milligram (mg) of INO-4800 followed by electroporation (EP) using the CELLECTRA ® 2000 device on Day 0 and Day 28. | Drug: INO-4800 INO-4800 will be administered ID on Day 0 and Day 28. Device: CELLECTRA ® 2000 EP using the CELLECTRA ® 2000 device will be administered following ID delivery of INO-4800 on Day 0 and Day 28. |
| Experimental: Phase 2: INO-4800 Dose Group 2 Participants will receive two ID injections of 1.0 mg (total 2.0 mg per dosing visit) of INO-4800 followed by EP using the CELLECTRA ® 2000 device on Day 0 and Day 28. | Drug: INO-4800 INO-4800 will be administered ID on Day 0 and Day 28. Device: CELLECTRA ® 2000 EP using the CELLECTRA ® 2000 device will be administered following ID delivery of INO-4800 on Day 0 and Day 28. |
| Placebo Comparator: Phase 2: Placebo Dose Group 1 Participants will receive one ID injection of placebo followed by EP using the CELLECTRA ® 2000 device on Day 0 and Day 28. | Drug: Placebo Sterile saline sodium citrate (SSC) buffer (SSC-0001) will be administered ID on Day 0 and Day 28. Other Names: SSC-0001 Device: CELLECTRA ® 2000 EP using the CELLECTRA ® 2000 device will be administered following ID delivery of sterile saline sodium citrate (SSC) buffer (SSC-0001) on Day 0 and Day 28. |
| Placebo Comparator: Phase 2: Placebo Dose Group 2 Participants will receive two ID injections of placebo followed by EP using the CELLECTRA ® 2000 device on Day 0 and Day 28. | Drug: Placebo Sterile saline sodium citrate (SSC) buffer (SSC-0001) will be administered ID on Day 0 and Day 28. Other Names: SSC-0001 Device: CELLECTRA ® 2000 EP using the CELLECTRA ® 2000 device will be administered following ID delivery of sterile saline sodium citrate (SSC) buffer (SSC-0001) on Day 0 and Day 28. |
| Experimental: Phase 3: INO-4800 Optimum Dose Participants will receive either one or two 1.0 mg ID injections of INO-4800 based on results from Phase 2 segment, followed by EP using the CELLECTRA ® 2000 device on Day 0 and Day 28. | Drug: INO-4800 INO-4800 will be administered ID on Day 0 and Day 28. Device: CELLECTRA ® 2000 EP using the CELLECTRA ® 2000 device will be administered following ID delivery of INO-4800 on Day 0 and Day 28. |
| Placebo Comparator: Phase 3: Placebo Optimum Dose Participants will receive either one or two ID injections of placebo based on results from Phase 2 segment, followed by EP using the CELLECTRA ® 2000 device on Day 0 and Day 28. | Drug: Placebo Sterile saline sodium citrate (SSC) buffer (SSC-0001) will be administered ID on Day 0 and Day 28. Other Names: SSC-0001 Device: CELLECTRA ® 2000 EP using the CELLECTRA ® 2000 device will be administered following ID delivery of sterile saline sodium citrate (SSC) buffer (SSC-0001) on Day 0 and Day 28. |

Primary Outcome Measure:

1. Phase 2: Change From Baseline in Antigen-specific Cellular Immune Response Measured by Interferon-gamma (IFN-γ) Enzyme-linked Immunospot (ELISpot) Assay [Time Frame: Baseline up to Day 393]
2. Phase 2: Change From Baseline in Neutralizing Antibody Response Measured by a Pseudovirus-based Neutralization Assay [Time Frame: Baseline up to Day 393]
3. Percentage of Participants With Virologically Confirmed COVID-19 Disease [Time Frame: From 14 days after completion of the 2-dose regimen up to 12 months post-dose 2 (i.e. Day 42 up to Day 393)]

Secondary Outcome Measures:

1. Phase 2 and 3: Percentage of Participants with Unsolicited and Solicited Injection Site Reactions [Time Frame: From time of consent up to 28 days post-dose 2 (up to Day 56)]
2. Phase 2 and 3: Percentage of Participants with Solicited and Unsolicited Systemic Adverse Events (AEs) [Time Frame: From time of consent up to 28 days post-dose 2 (up to Day 56)]
3. Phase 2 and 3: Percentage of Participants with Serious Adverse Events (SAEs) [Time Frame: Baseline up to Day 393]
4. Phase 2 and 3: Percentage of Participants with Adverse Events of Special Interest (AESIs) [Time Frame: Baseline up to Day 393]
5. Phase 3: Percentage of Participants With Death from All Causes [Time Frame: Baseline up to Day 393]
6. Phase 3: Percentage of Participants With Non-Severe COVID-19 Disease [Time Frame: From 14 days after completion of the 2-dose regimen up to 12 months post-dose 2 (i.e. Day 42 up to Day 393)]
7. Phase 3: Percentage of Participants With Severe COVID-19 Disease [Time Frame: From 14 days after completion of the 2-dose regimen up to 12 months post-dose 2 (i.e. Day 42 up to Day 393)]
8. Phase 3: Percentage of Participant With Death from COVID-19 Disease [Time Frame: From 14 days after completion of the 2-dose regimen up to 12 months post-dose 2 (i.e. Day 42 up to Day 393)]
9. Phase 3: Percentage of Participants With Virologically-Confirmed SARS-CoV-2 Infections [Time Frame: From 14 days after completion of the 2-dose regimen up to 12 months post-dose 2 (i.e. Day 42 up to Day 393)]
10. Phase 3: Days to Symptom Resolution in Participants With COVID-19 Disease [Time Frame: From 14 days after completion of the 2-dose regimen up to 12 months post-dose 2 (i.e. Day 42 up to Day 393)]
11. Phase 3: Change From Baseline in Antigen-specific Cellular Immune Response Measured by IFN-gamma ELISpot Assay [Time Frame: Baseline up to Day 393]
12. Phase 3: Change From Baseline in Neutralizing Antibody Response Measured by a Pseudovirus-based Neutralization Assay [Time Frame: Baseline up to Day 393]

Eligibility Criteria

Ages Eligible for Study: 18 Years and older
Sexes Eligible for Study: All
Gender Based: No
Accepts Healthy Volunteers: Yes
Key Inclusion Criteria:

Working or residing in an environment with high risk of exposure to SARS-CoV-2 for whom exposure may be relatively prolonged or for whom personal protective equipment (PPE) may be inconsistently used, especially in confined settings Screening laboratory results within normal limits for testing laboratory or are deemed not clinically significant by the Investigator.

Be post-menopausal or be surgically sterile or have a partner who is sterile or use medically effective contraception with a failure rate of <1% per year when used consistently and correctly from screening until 3 months following last dose.

Key Exclusion Criteria:

Acute febrile illness with temperature >100.4° F. (38.0° C.) or acute onset of upper or lower respiratory tract symptoms (e.g., cough, shortness of breath, sore throat).

Positive serologic or molecular (Reverse transcription polymerase chain reaction [RT-PCR]) test for SARS-CoV-2 at Screening Pregnant or breastfeeding or intending to become pregnant or intending to father children within the projected duration of the trial starting from the screening visit until 3 months following the last dose.

Known history of uncontrolled HIV based on a CD4 count less than 200 cells per cubic millimeter (/mm^3) or a detectable viral load within the past 3 months.

Is currently participating or has participated in a study with an investigational product within 30 days preceding Day 0.

Previous receipt of an investigational vaccine for prevention or treatment of COVID-19, middle east respiratory syndrome (MERS), or severe acute respiratory syndrome (SARS) (documented receipt of placebo in previous trial would be permissible for trial eligibility).

Respiratory diseases (e.g., asthma, chronic obstructive pulmonary disease) requiring significant changes in therapy or hospitalization for worsening disease during the 6 weeks prior to enrollment.

Immunosuppression as a result of underlying illness or treatment

Lack of acceptable sites available for ID injection and EP

Blood donation or transfusion within 1 month prior to Day 0.

Reported alcohol or substance abuse or dependence, or illicit drug use (excluding marijuana use).

Any illness or condition that in the opinion of the investigator may affect the safety of the participant or the evaluation of any study endpoint.

Example 8 One or Two Dose Regimen of the SARS-CoV-2 DNA Vaccine INO-4800 Protects Against Respiratory Tract Disease Burden in Nonhuman Primate (NHP) Challenge Model The safety, immunogenicity and efficacy of the intradermal delivery of INO-4800, a synthetic DNA vaccine candidate encoding a SARS-CoV-2 spike antigen, was evaluated in the rhesus macaque model. Single and two dose vaccination regimens were evaluated. Vaccination induced both binding and neutralizing antibodies, along with IFN-γ-producing T cells against SARS-CoV-2. A high dose of SARS-CoV-2 Victoria01 strain (5×10^6 pfu) was used to specifically assess the impact of INO-4800 vaccination on lung disease burden to provide both vaccine safety and efficacy data. A broad range of lower respiratory tract disease parameters were measured by applying histopathology, lung disease scoring metric system, in situ hybridization, viral RNA RT-PCR and computed tomography (CT) scans to provide an understanding of the impact of vaccine induced immunity on protective efficacy and potential vaccine enhanced disease (VED).

This example describes the immunogenicity, efficacy and safety assessment of the SARS-CoV-2 DNA vaccine INO-4800 in a stringent high dose nonhuman primate challenge model. Intradermal delivery of 1 mg of INO-4800 to rhesus macaques induces humoral and T cell responses against the SARS-CoV-2 spike antigen in both a 2-dose regimen and a suboptimal 1 dose regimen. Throughout the study no overt clinical events were recorded in the animals. After a high dose SARS-CoV-2 challenge, a reduction in viral loads was observed and lung disease burden in both the 1 and 2 dose vaccine groups supporting the efficacy of INO-4800. Importantly, vaccine enhanced disease (VED) was not observed, even with the 1 dose group.

Methods

Vaccine. The optimized DNA sequence encoding SARS-CoV-2 IgELS-spike was created using Inovio's proprietary in silico Gene Optimization Algorithm to enhance expression and immunogenicity. The optimized DNA sequence was synthesized, digested with BamHI and XhoI, and cloned into the expression vector pGX0001 under the control of the human cytomegalovirus immediate-early promoter and a bovine growth hormone polyadenylation signal.

Animals. Eighteen rhesus macaques of Indian origin (*Macaca mulatta*) were used in this study. Study groups comprised three males and three females of each species and all were adults aged between 2.5 and 3.5 years of age and weighing >4 Kg at time of challenge. Prior to the start of the experiment, socially compatible animals were randomly assigned to challenge groups, to minimize bias. Animals were housed in compatible social groups, in cages in accordance with the UK Home Office Code of Practice for the Housing and Care of Animals Bred, Supplied or Used for Scientific Procedures (2014) and National Committee for Refinement, Reduction and Replacement (NC3Rs) Guidelines on Primate Accommodation, Care and Use, August 2006. Housing prior and for the duration of challenge is described in [Salguero, F. J., et al., Comparison of Rhesus and Cynomolgus macaques as an authentic model for COVID-19. bioRxiv, 2020: p. 2020.09.17.301093]. All experimental work was conducted under the authority of a UK Home Office approved project license (PDC57C033) that had been subject to local ethical review at PHE Porton Down by the Animal Welfare and Ethical Review Body (AWERB) and approved as required by the Home Office Animals (Scientific Procedures) Act 1986. Animals were sedated by intramuscular (IM) injection with ketamine hydrochloride (Ketaset, 100 mg/ml, Fort Dodge Animal Health Ltd, Southampton, UK; 10 mg/kg) for procedures requiring removal from their housing. None of the animals had been used previously for experimental procedures.

Vaccine administration. Animals received 1 mg of SARS-CoV-2 DNA vaccine, INO-4800, by intradermal injection at day 28 only (1 dose group) or 0 and 28 (2 dose group) followed by an EP treatment using the CELLECTRA 2000® Adaptive Constant Current Electroporation Device with a 3P array (Inovio Pharmaceuticals).

Serum and heparinised whole blood were collected whilst animals were sedated at bi-weekly intervals during the vaccination phase. Nasal and throat swabs were also collected on the day of challenge on D56. After challenge, nasal swabs, throat swabs and serum were collected at 1, 3, 5 dpc and at cull (6, 7 or 8 dpc—staggered due to the high level of labor involved in procedures), with heparinised whole blood collected at 3 dpc and at cull. Nasal and throat swabs were obtained as described [Salguero, F. J., et al., Comparison of Rhesus and Cynomolgus macaques as an authentic model for COVID-19. bioRxiv, 2020: p. 2020.09.17.301093].

Clinical observations. Animals were monitored multiple times per day for behavioral and clinical changes. Behavior was evaluated for contra-indicators including depression, withdrawal from the group, aggression, changes in feeding patterns, breathing pattern, respiration rate and cough. Animals were observed and scored as follows for activity and health throughout the study. Key: Activity Level: A0=Active & Alert; A1=Only active when stimulated by operator; A2=Inactive even when stimulated/Immobile; H=Healthy; S=Sneeze, C=Cough, Nd=Nasal Discharge, Od=Ocular Discharge, Rn=Respiratory Noises, Lb=Laboured breathing, L=Lethargy, Di=Diarrhoea, Ax=Loss of Appetite, Dx=Dehydration, RD=Respiratory Distress. Animal body weight, temperature and haemoglobin levels were measured and recorded throughout the study.

Viruses and Cells

SARS-CoV-2 Victoria/01/2020 [Caly, L., et al., Isolation and rapid sharing of the 2019 novel coronavirus (SARS-CoV-2) from the first patient diagnosed with COVID-19 in Australia. Med J Aust, 2020. 212(10): p. 459-462] was generously provided by The Doherty Institute, Melbourne, Australia at P1 after primary growth in Vero/hSLAM cells and subsequently passaged twice at PHE Porton Down in Vero/hSLAM cells [ECACC 04091501]. Infection of cells was with ~0.0005 MOI of virus and harvested at day 4 by dissociation of the remaining attached cells by gentle rocking with sterile 5 mm borosilicate beads followed by clarification by centrifugation at 1,000×g for 10 mins. Whole genome sequencing was performed, on the P3 challenge stock, using both Nanopore and Illumina as described in Lewandowski, K., et al., Metagenomic Nanopore Sequencing of Influenza Virus Direct from Clinical Respiratory Samples. J Clin Microbiol, 2019. 58(1). Virus titer of the challenge stocks was determined by plaque assay on Vero/E6 cells [ECACC 85020206]. Cell lines were obtained from the European Collection of Authenticated Cell Cultures (ECACC) PHE, Porton Down, UK. Cell cultures were maintained at 37° C. in Minimum essential medium (MEM) (Life Technologies, California, USA) supplemented with 10% fetal bovine serum (FBS) (Sigma, Dorset, UK) and 25 mM HEPES (Life Technologies, California, USA). In addition, Vero/hSLAM cultures were supplemented with 0.4 mg/ml of geneticin (Invitrogen) to maintain the expression plasmid. Challenge substance dilutions were conducted in phosphate buffer saline (PBS). Inoculum ($5\times10^6$ PFU) was delivered by intratracheal route (2 ml) and intranasal instillation (1.0 ml total, 0.5 ml per nostril).

Clinical Signs and In-Life Imaging by Computerized Tomography

CT scans were performed two weeks before and five days after challenge with SARS-CoV2. CT imaging was performed on sedated animals using a 16 slice Lightspeed CT scanner (General Electric Healthcare, Milwaukee, Wis., USA) in both the prone and supine position and scans evaluated by a medical radiologist expert in respiratory diseases (as described previously [Salguero, F. J., et al., Comparison of Rhesus and Cynomolgus macaques as an authentic model for COVID-19. 2020: p. 2020.09.17.301093.]). To provide the power to discriminate differences between individual NHP's with low disease volume (i.e. <25% lung involvement), a refined score system was designed in which scores were attributed for possession of abnormal features characteristic of COVID in human patients (COVID pattern score) and for the distribution of features through the lung (Zone score). The COVID pattern score was calculated as sum of scores assigned for the number of nodules identified, and the possession and extent of GGO and consolidation according to the following system: Nodule(s): Score 1 for 1, 2 for 2 or 3, 3 for 4 or more; GGO: each affected area was attributed with a score according to the following: Score 1 if area measured <1 cm, 2 if 1 to 2 cm, 3 if 2-3 cm, 4 if >3 cm and scores for each area of GGO were summed to provide a total GGO score; Consolidation: each affected area was attributed with a score according to the following: 1 if area measured <1 cm, 2 if 1 to 2 cm, 3 if 2-3 cm, 4 if >3 cm. Scores for each area of consolidation are summed to provide a total consolidation score. To account for estimated additional disease impact on the host of consolidation compared to GGO, the score system was weighted by doubling the score assigned for consolidation. To determine the zone score, the lung was divided into 12 zones and each side of the lung divided (from top to bottom) into three zones: the upper zone (above the carina), the middle zone (from the carina to the inferior pulmonary vein), and the lower zone (below the inferior pulmonary vein). Each zone was further divided into two areas: the anterior area (the area before the vertical line of the midpoint of the diaphragm in the sagittal position) and the posterior area (the area after the vertical line of the mid-point of the diaphragm in the sagittal position). This results in 12 zones in total where a score of one is attributed to each zone containing structural changes. The COVID pattern score and the zone are summed to provide the Total CT score.

Post-mortem examination and histopathology. Animals were euthanized at 3 different time-points, in groups of six (including one animal from each species and sex) at 6, 7 and 8 dpc. The bronchial alveolar lavage fluid (BAL) was collected at necropsy from the right lung. The left lung was dissected prior to BAL collection and used for subsequent histopathology and virology procedures. At necropsy nasal and throat swabs, heparinised whole blood and serum were taken alongside tissue samples for histopathology. Samples from the left cranial and left caudal lung lobe together with spleen, kidney, liver, mediastinal and axillary lymph nodes, small intestine (duodenum), large intestine (colon), trachea, larynx inoculation site and draining lymph node, were fixed by immersion in 10% neutral-buffered formalin and processed routinely into paraffin wax. Four µm sections were cut and stained with hematoxylin and eosin (H&E) and examined microscopically. A lung histopathology scoring system [Salguero, F. J., et al., Comparison of Rhesus and Cynomolgus macaques as an authentic model for COVID-19. bioRxiv, 2020: p. 2020.09.17.301093] was used to evaluate lesions affecting the airways and the parenchyma. Three tissue sections from each left lung lobe were used to evaluate the lung histopathology. In addition, samples were stained using the RNAscope technique to identify the SARS-CoV-2 virus RNA in lung tissue sections. Briefly, tissues were pre-treated with hydrogen peroxide for 10 mins (RT), target retrieval for 15 mins (98-102° C.) and protease plus for 30 mins (40° C.) (Advanced Cell Diagnostics). A V-nCoV2019-S probe (SARS-CoV-2 Spike gene specific) was incubated on the tissues for two hours at 40° C. In addition, samples were stained using the RNAscope technique to identify the SARS-CoV-2 virus RNA. Amplification of the signal was carried out following the RNAscope protocol using the RNAscope 2.5 HD Detection kit—Red (Advanced Cell Diagnostics, Biotechne). All H&E and ISH stained slides were digitally scanned using a Panoramic 3D-Histech scanner and viewed using CaseViewer v2.4 software. The presence of viral RNA by ISH was evaluated using the whole lung tissue section slides. Digital image analysis was performed in RNAscope labelled slides to ascertain the percentage of stained cells within the lesions, by using the Nikon-NIS-Ar software package.

Viral load quantification by RT-qPCR. RNA was isolated from nasal swabs and throat swabs. Samples were inactivated in AVL (Qiagen) and ethanol. Downstream extraction was then performed using the BioSprint™96 One-For-All vet kit (Indical) and Kingfisher Flex platform as per manufacturer's instructions. Tissues were homogenized in Buffer RLT+ betamercaptoethanol (Qiagen). Tissue homogenate was then centrifuged through a QIAshredder homogenizer (Qiagen) and supplemented with ethanol as per manufacturer's instructions. Downstream extraction from tissue samples was then performed using the BioSprint™96 One-For-All vet kit (Indical) and Kingfisher Flex platform as per manufacturer's instructions.

Reverse transcription-quantitative polymerase chain reaction (RT-qPCR) targeting a region of the SARS-CoV-2 nucleocapsid (N) gene was used to determine viral loads and was performed using TaqPath™ 1-Step RT-qPCR Master Mix, CG (Applied Biosystems™) 2019-nCoV CDC RUO Kit (Integrated DNA Technologies) and QuantStudio™ 7 Flex Real-Time PCR System. Sequences of the N1 primers and probe were: 2019-nCoV_N1-forward, 5' GACCC-CAAAATCAGCGAAAT 3' (SEQ ID NO: 18); 2019-nCoV_N1-reverse, 5' TCTGGTTACTGCCAGTT-GAATCTG 3'(SEQ ID NO: 19); 2019-nCoV_N1-probe, 5' FAM-ACCCCGCATTACGTTTGGTGGACC-BHQ1 3'(SEQ ID NO: 20). The cycling conditions were: 25° C. for 2 minutes, 50° C. for 15 minutes, 95° C. for 2 minutes, followed by 45 cycles of 95° C. for 3 seconds, 55° C. for 30 seconds. The quantification standard was in vitro transcribed RNA of the SARS-CoV-2 N ORF (accession number NC_045512.2) with quantification between 1 and 6 log copies/μl. Positive swab and fluid samples detected below the limit of quantification (LoQ) of 4.11 log copies/ml, were assigned the value of 5 copies/μl, this equates to 3.81 log copies/ml, whilst undetected samples were assigned the value of <2.3 copies/μl, equivalent to the assay's lower limit of detection (LoD) which equates to 3.47 log copies/ml. Positive tissue samples detected below the limit of quantification (LoQ) of 4.76 log copies/ml were assigned the value of 5 copies/μl, this equates to 4.46 log copies/g, whilst undetected samples were assigned the value of <2.3 copies/μl, equivalent to the assay's lower limit of detection (LoD) which equates to 4.76 log copies/g.

Subgenomic RT-qPCR was performed on the QuantStudio™ 7 Flex Real-Time PCR System using TaqMan™ Fast Virus 1-Step Master Mix (Thermo Fisher Scientific) and oligonucleotides as specified by Wölfel, et al. Virological assessment of hospitalized patients with COVID-2019. Nature 581, 465-469 (2020), with forward primer, probe and reverse primer at a final concentration of 250 nM, 125 nM and 500 nM respectively. Sequences of the sgE primers and probe were:

```
2019-nCoV_sgE-forward,
                                         (SEQ ID NO: 21)
  5' CGATCTCTTGTAGATCTGTTCTC 3';

2019-nCoV_sgE-reverse,
                                         (SEQ ID NO: 22)
  5' ATATTGCAGCAGTACGCACACA 3';

2019-nCoV_sgE-probe,
                                         (SEQ ID NO: 23)
  5' FAM- ACACTAGCCATCCTTACTGCGCTTCG-BHQ1 3'.
```

Cycling conditions were 50° C. for 10 minutes, 95° C. for 2 minutes, followed by 45 cycles of 95° C. for 10 seconds and 60° C. for 30 seconds. RT-qPCR amplicons were quantified against an in vitro transcribed RNA standard of the full length SARS-CoV-2 E ORF (accession number NC_045512.2) preceded by the UTR leader sequence and putative E gene transcription regulatory sequence described by Wolfel et al [Wölfel, R., Corman, V. M., Guggemos, W. et al. Virological assessment of hospitalized patients with COVID-2019. Nature 581, 465-469 (2020).]. Positive samples detected below the lower limit of quantification (LLOQ) were assigned the value of 5 copies/μl, whilst undetected samples were assigned the value of ≤0.9 copies/μl, equivalent to the assays lower limit of detection (LLOD). For nasal swab, throat swab and BAL samples extracted samples this equates to an LLOQ of 4.11 log copies/mL and LLOD of 3.06 log copies/mL. For tissue samples this equates to an LLOQ of 4.76 log copies/g and LLOD of 3.71 log copies/g.

Plaque reduction neutralization test. Neutralizing virus titers were measured in heat-inactivated (56° C. for 30 minutes) serum samples. SARS-CoV-2 was diluted to a concentration of $1.4 \times 10^3$ pfu/ml (70 pfu/50 μl) and mixed 50:50 in 1% FCS/MEM with doubling serum dilutions from 1:10 to 1:320 in a 96-well V-bottomed plate. The plate was incubated at 37° C. in a humidified box for one hour to allow the antibody in the serum samples to neutralize the virus. The neutralized virus was transferred into the wells of a washed plaque assay 24-well plate (see plaque assay method), allowed to adsorb at 37° C. for a further hour, and overlaid with plaque assay overlay media. After five days incubation at 37° C. in a humified box, the plates were fixed, stained and plaques counted.

Antigen Binding ELISA. Recombinant SARS-CoV-2 Spike- and RBD-specific IgG responses were determined by ELISA. A full-length trimeric and stabilized version of the SARS-CoV-2 Spike protein was supplied by Lake Pharma (#46328). Recombinant SARS-CoV-2 Receptor-Binding-Domain (319-541) Myc-His was developed and kindly provided by MassBiologics. High-binding 96-well plates (Nunc Maxisorp, 442404) were coated with 50 μl per well of 2 μg/ml Spike trimer (S1+S2) or RBD in 1×PBS (Gibco) and incubated overnight at 4° C. The ELISA plates were washed and blocked with 5% Fetal Bovine Serum (FBS, Sigma, F9665) in 1×PBS/0.1% Tween 20 for 1 hour at room temperature. Serum collected from animals after vaccination had a starting dilution of 1/50 followed by 8 two-fold serial dilutions. Post-challenge samples were inactivated in 0.5% triton and had a starting dilution of 1/100 followed by 8 three-fold serial dilutions. Serial dilutions were performed in 10% FBS in 1×PBS/0.1% Tween 20. After washing the plates, 50 μl/well of each serum dilution was added to the antigen-coated plate in duplicate and incubated for 2 hours at room temperature. Following washing, anti-monkey IgG conjugated to HRP (Invitrogen, PA1-84631) was diluted (1:10,000) in 10% FBS in 1×PBS/0.1% Tween 20 and 100 μl/well was added to the plate. Plates were then incubated for 1 hour at room temperature. After washing, 1 mg/ml 0-Phenylenediamine dihydrochloride solution (Sigma P9187) was prepared and 100 μl per well were added. The development was stopped with 50 μl per well 1M Hydrochloric acid (Fisher Chemical, J/4320/15) and the absorbance at 490 nm was read on a Molecular Devices versamax plate reader using Softmax (version 7.0). Titers were determined using the endpoint titer determination method. For each sample, an endpoint titer is defined as the reciprocal of the highest sample dilution that gives a reading (OD) above the cut-off. The cut-off was determined for each experimental group as the mean OD+3SD of naïve samples.

Peripheral blood mononuclear cell isolation and resuscitation. PBMCs were isolated from whole blood anticoagulated with heparin (132 Units per 8 720 ml blood) (BD Biosciences, Oxford, UK) using standard methods. PBMCs isolated from tissues were stored at −180° C. For resuscitation PBMCs were thawed, washed in R10 medium (consisting of RPMI 1640 supplemented with 2 mM L-glutamine, 50 U/ml penicillin-50 µg/ml streptomycin, and 10% heat-inactivated FBS) with 1 U/ml of DNase (Sigma), and resuspended in R10 medium and incubated at 37° C. 5% $CO_2$ overnight.

ELISpot. An IFNγ ELISpot assay was used to estimate the frequency and IFNγ production capacity of SARS-CoV-2-specific T cells in PBMCs using a human/simian IFNγ kit (MabTech, Nacka. Sweden), as described previously [Sibley, L. S., et al., ELISPOT Refinement Using Spot Morphology for Assessing Host Responses to Tuberculosis. Cells, 2012. 1(1): p. 5-14]. The cells were assayed at $2 \times 10^5$ cells per well. Cells were stimulated overnight with SARS-CoV-2 peptide pools spanning the ECD spike protein. Five peptide pools were 748 used, comprising of 15mer peptides, overlapping by 9 amino acids. Phorbol 12-myristate (Sigma) (100 ng/ml) and ionomycin (CN Biosciences, 753 Nottingham, UK) (1 mg/ml) were used as a positive control. Results were calculated and reported as spot forming units (SFU) per million cells. All SARS-CoV-2 peptides were assayed in duplicate and media only wells subtracted to give the antigen-specific SFU. ELISPOT plates were analyzed using a CTL scanner and software (CTL, Germany) and further analysis carried out using GraphPad Prism (GraphPad Software, USA).

Statistics. All statistical analyses were performed using GraphPad Prism 7 or 8 software (La Jolla, Calif.). These data were considered significant if p<0.05. The type of statistical analysis performed is detailed in the figure legend. No samples or animals were excluded from the analysis.

Figure 22C:
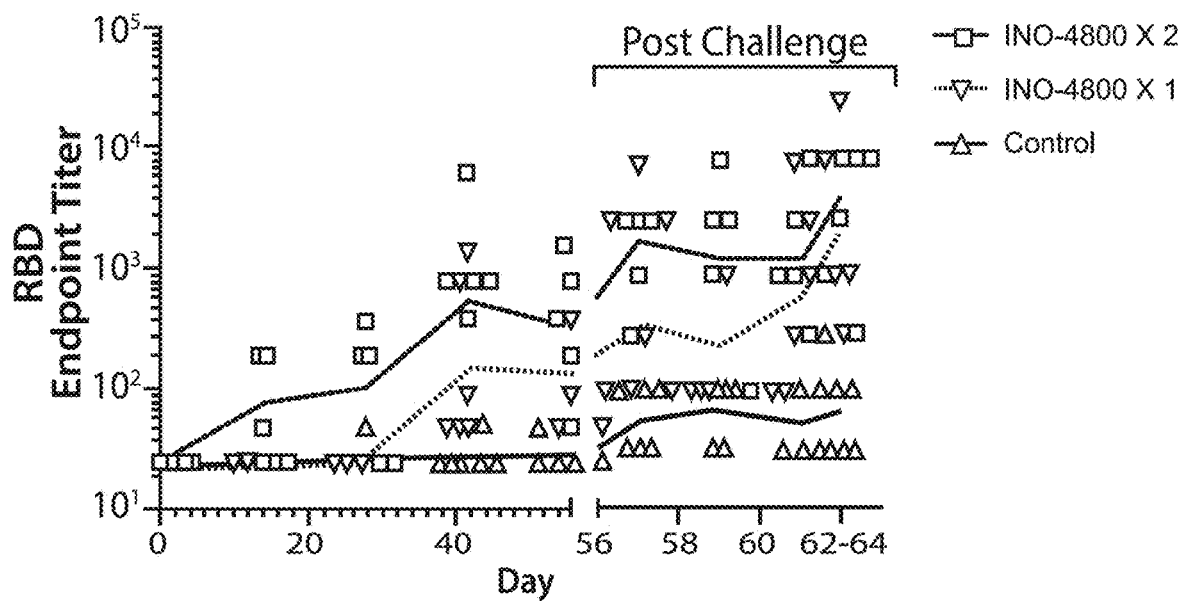
Figure 22D:
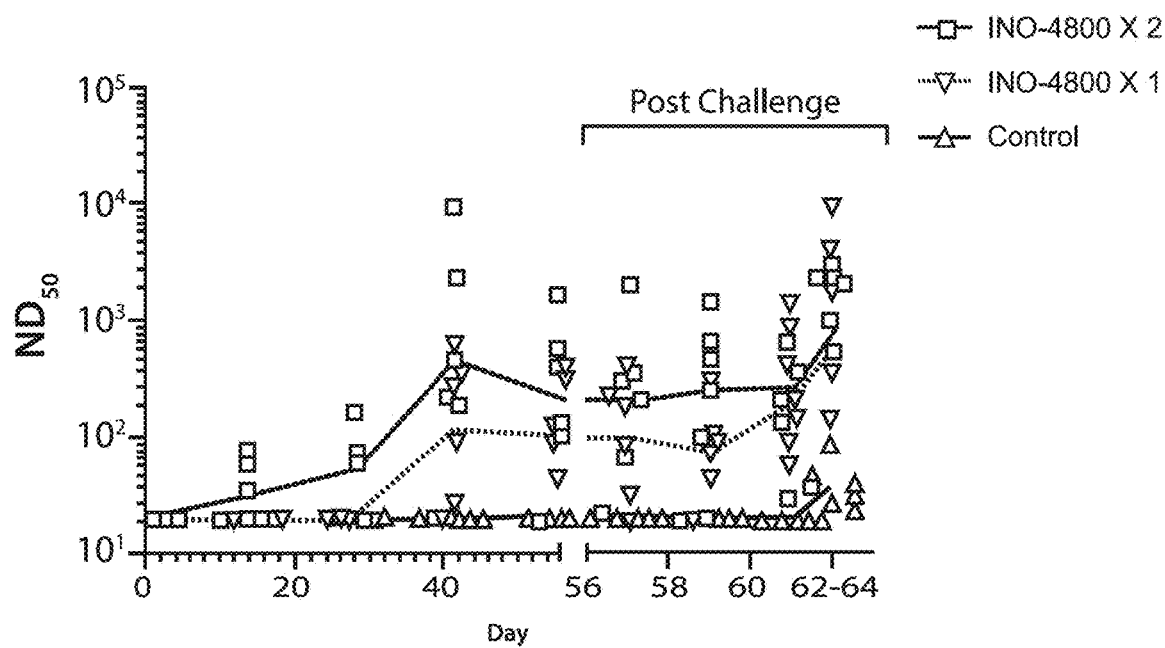
Figure 22E:
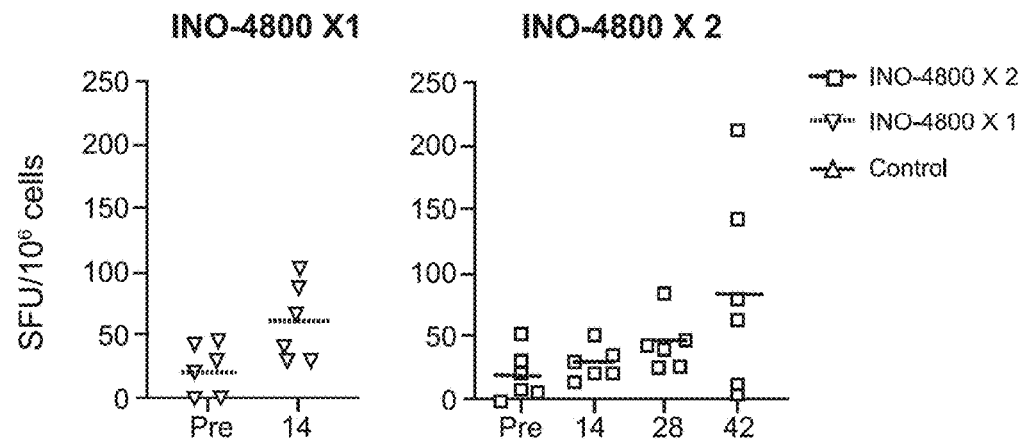
Figure 22F:
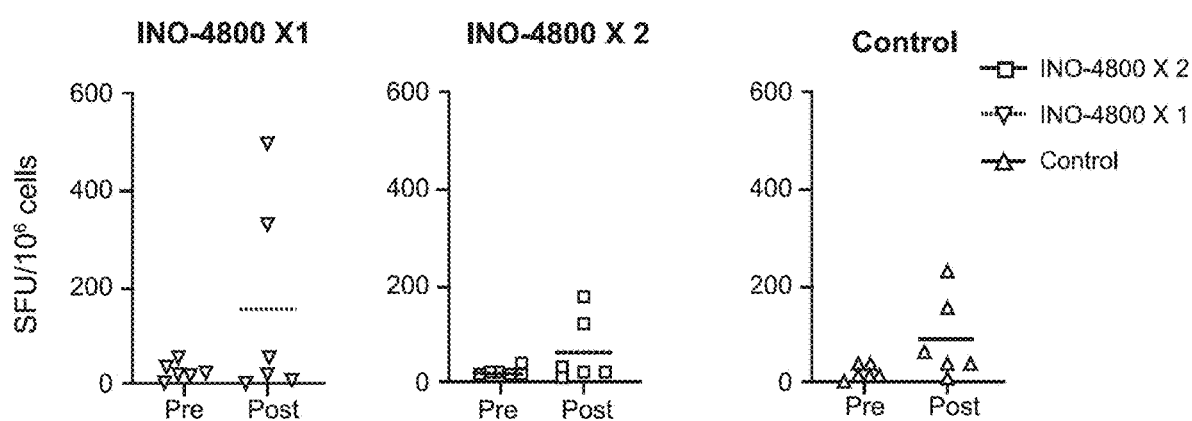

Results:

Immunogenicity of one and two dose regimens of INO-4800. Twelve (6 male and 6 female) rhesus macaques were vaccinated with 1 dose (6 animals) or 2 doses (6 animals) of INO-4800 on day 28 or 0 and 28, respectively (FIG. 22A). For each treatment 1 mg INO-4800 was administered intradermally followed by CELLECTRA-ID EP. A further six age- and sex-matched animals were not vaccinated and provided the control group. Animals were observed and scored as alert and healthy for the duration of the study, and no adverse events or clinical anomalies were recorded in the animals (FIG. 23). The serum titers of SARS-CoV-2 spike antigen reactive IgG antibodies in all animals were measured biweekly between days 0 and 56. In the single dose group (INO-4800 X1) a mean endpoint titer of 467 against the SARS-CoV-2 spike antigen trimeric S1+S2 ECD form and 442 against the RBD antigen, and a live virus (Victoria/01/2020 matched to the challenge strain) neutralization titer of 239 14 days after vaccination (FIGS. 22B, 22C, 22D). In the 2 dose group (INO-4800 X2) a mean endpoint titer of 2,142 against the S1+S2 ECD and 1,538 against the RBD antigen, and a live virus neutralization titer of 2,199 was measured 14 days after the 2nd vaccination (FIGS. 22B, 22C, 22D). Vaccination with INO-4800 induced SARS-CoV-2 spike antigen-specific Th1 T cell responses in the PBMC population as measured by an IFN-γ ELISpot (FIG. 22E). In summary, intradermal delivery of INO-4800 induced a functional humoral and T cell response against SARS-CoV-2 spike protein which was boosted after a second dose. At the day of viral challenge (Day 56) the level of SARS-CoV-2 neutralizing antibodies in the serum was significantly higher in the vaccinated groups compared to the control group (p=0.015). Following viral challenge there was a slight increase in SARS-CoV-2 spike binding and neutralizing antibody titers in all the groups between days 56 and 62-64 (FIGS. 22B, 22C, 22D). In the control group there was an increase in the cellular immune response to peptides spanning the SARS-CoV-2 spike antigen after viral challenge, but little change in the vaccinated groups, likely due to control of viral infection by the humoral arm of the host immune system (FIG. 22F).

Figure 23A:
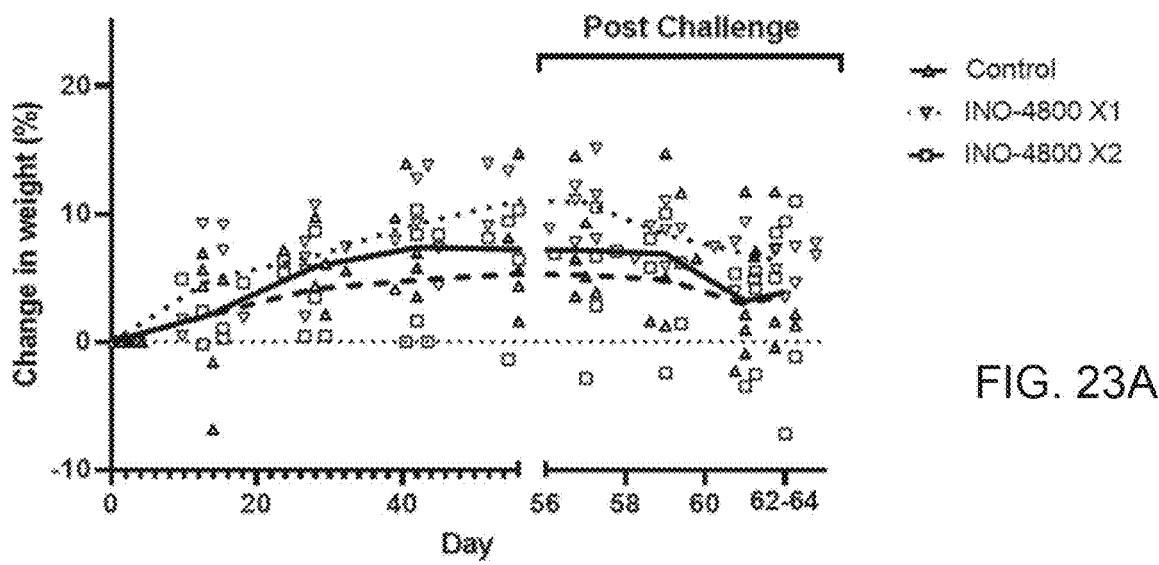
FIGS. 23A-23C illustrate change in weight, temperature and hemoglobin in the animals through the duration of the study. Animals received one (INO-4800X1) or two (INO-4800X2) doses of INO-4800 or were unvaccinated (control). Percentage change in body weights (FIG. 23A), temperature (FIG. 23B) and hemoglobin counts (FIG. 23C) of individual animals were recorded and plotted at the indicated time points pre- and post-challenge. Lines represent mean (FIG. 23A) and geometric mean (FIG. 23B & FIG. 23C) value for each group.
Figure 23B:
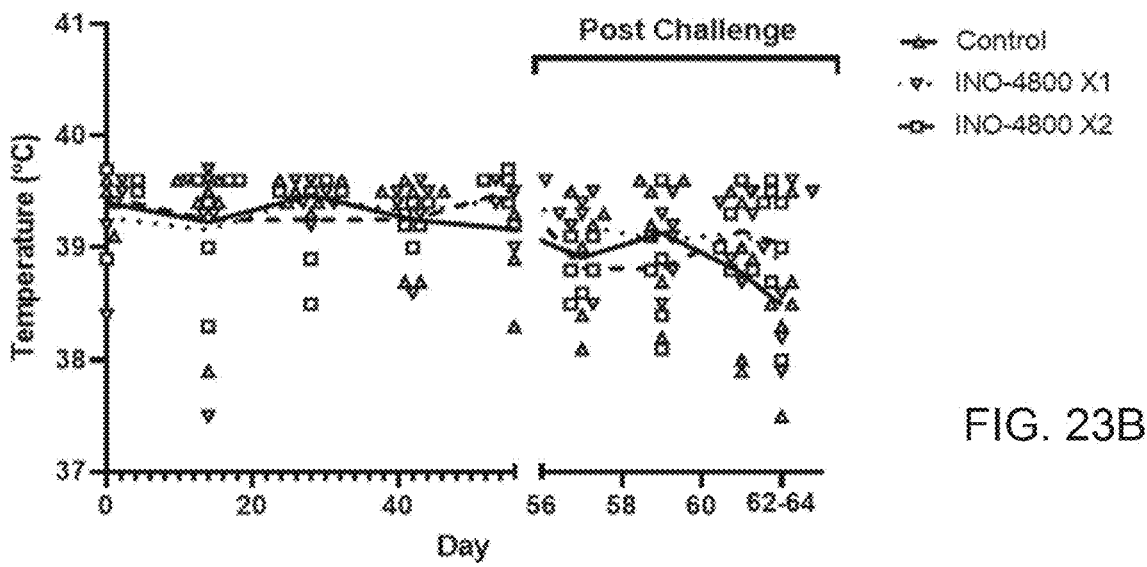
Figure 23C:
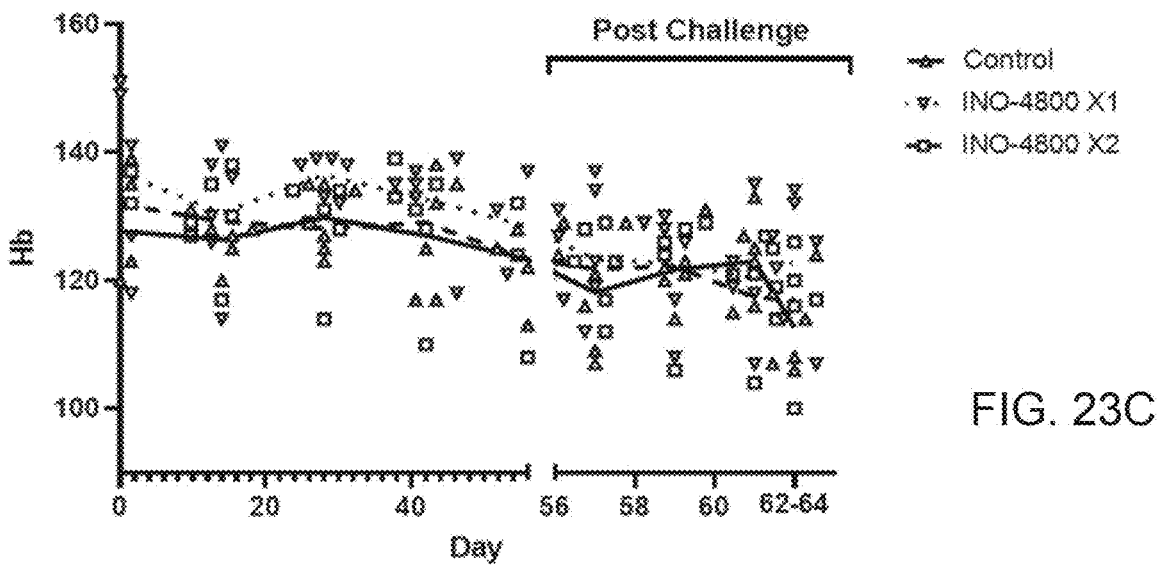
Figure 24A:
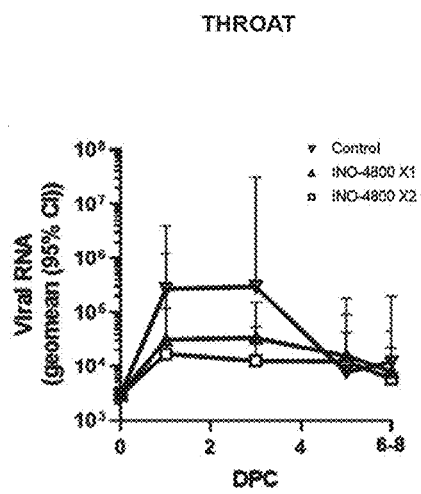
FIGS. 24A-24F illustrate the upper respiratory tract viral loads detected by RT-qPCR following challenge with SARS-CoV-2. Animals received one (INO-4800X1) or two (INO-4800X2) doses of INO-4800 or were unvaccinated (control). Viral load plotted as Log 10 cDNA copies/ml for each animal in throat swabs (FIGS. 24A-24C) and nasal swabs (FIGS. 24D-24F).
Figure 24B:
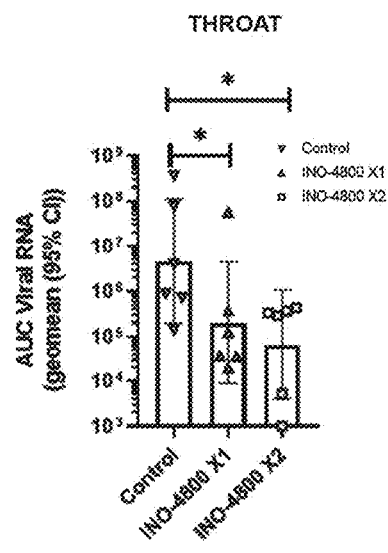
Figure 24C:
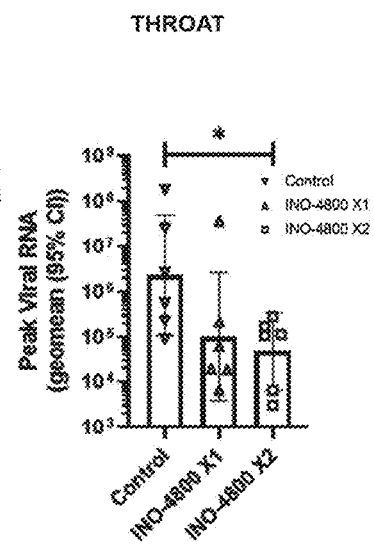
Figure 24D:
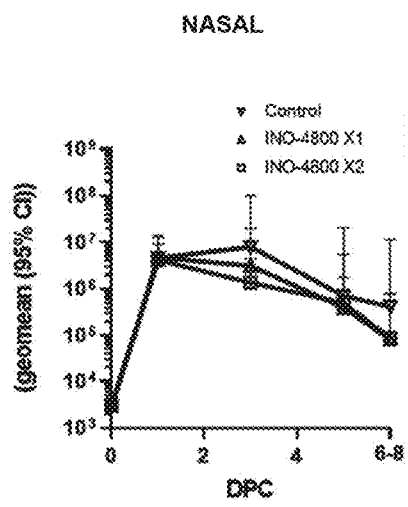
Figure 24E:
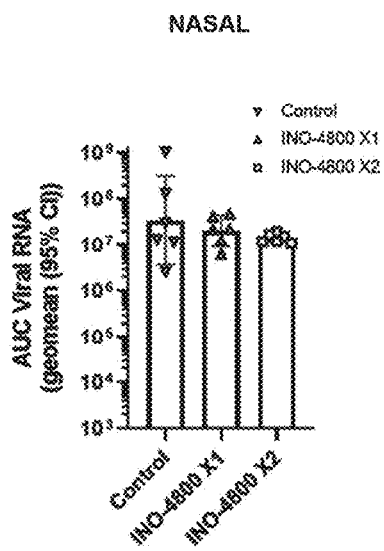
Figure 24F:
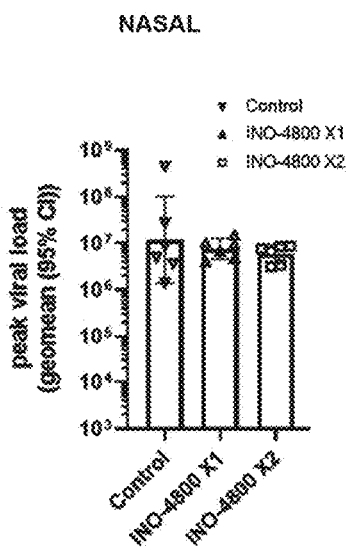
Figure 25A:
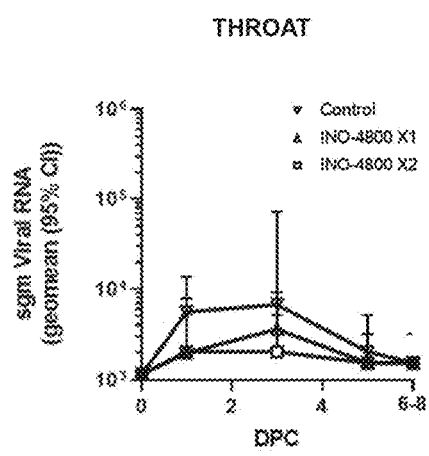
FIGS. 25A-25F illustrate the upper respiratory tract subgenomic viral loads detected by RT-qPCR following challenge with SARS-CoV-2. Animals received one (INO-4800X1) or two (INO-4800X2) doses of INO-4800 or were unvaccinated (control). Viral load plotted as Log 10 cDNA copies/ml for each animal in throat swabs (FIGS. 25A-25C) and nasal swabs (FIGS. 25D-25F).
Figure 25B:
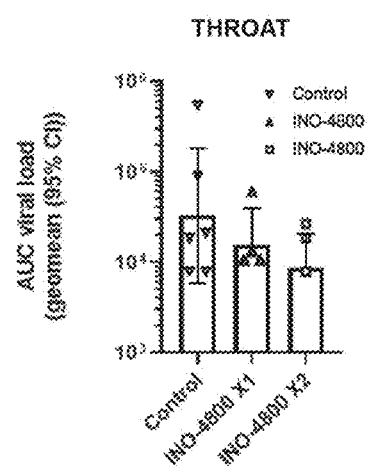
Figure 25C:
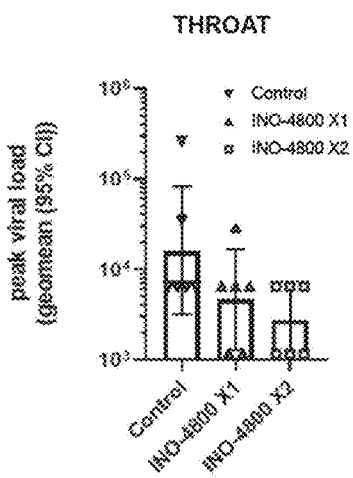
Figure 25D:
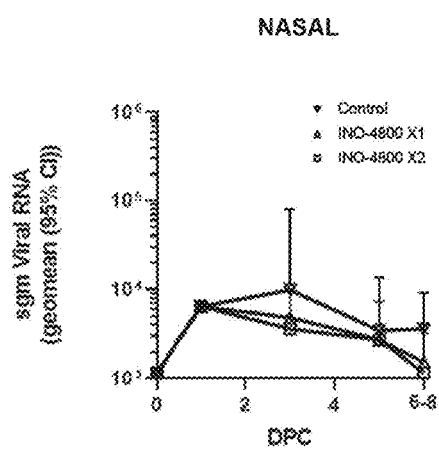
Figure 25E:
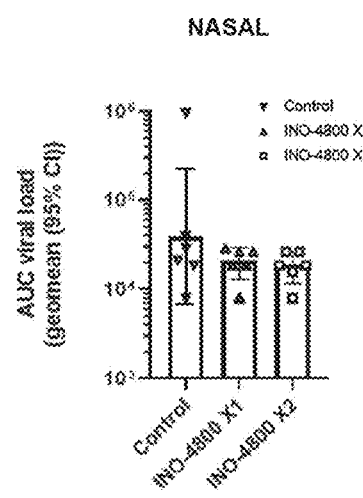
Figure 25F:
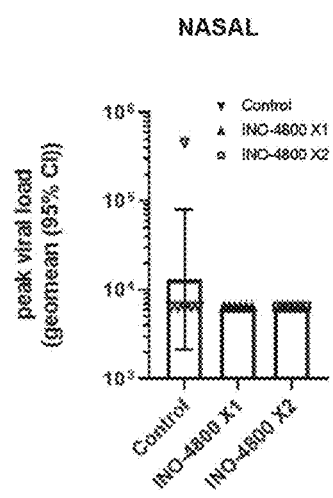

Viral Loads in the Upper and Lower Respiratory Tracts after SARS-CoV-2 Challenge On day 56 all animals were challenged with a total of $5 \times 10^6$ pfu SARS-CoV-2 delivered to both the upper and lower respiratory tract. No overt clinical symptoms were observed throughout the duration (6-8 days) of the challenge in any of the animals (FIGS. 23A-23C). At indicated timepoints nasal and throat swabs were collected from the animals. SARS-CoV-2 viral genomic (viral RNA) and sub-genomic (sgmRNA), which represents replicating virus were measured by RT-qPCR (FIGS. 24A and 25A). Analysis of viral RNA area under the curve (AUC) levels in the throat revealed significantly reduced levels in the vaccinated groups (FIG. 24B). Additionally, the peak viral load level measured in the INO-4800 X2 group was significantly reduced compared to the control group (FIG. 24C). Analysis revealed a significant negative correlation between throat viral loads and neutralizing and anti-RBD IgG titers (FIGS. 15A-15D). SARS-CoV-2 sgmRNA data revealed a similar trend to reduction of viral load in the vaccinated groups compared to controls (FIGS. 25A-25C). Analysis in the nasal compartment revealed a trend for reduction and accelerated clearance of viral RNA and sgmRNA in the vaccinated groups compared to control, but did not reach a level of significance (FIGS. 24D-F and 25D-F). Analysis revealed a significant negative correlation between nasal viral loads and neutralizing and anti-RBD IgG titers on day 3, but not day 1 (FIGS. 15E-15H).

Figure 26A:
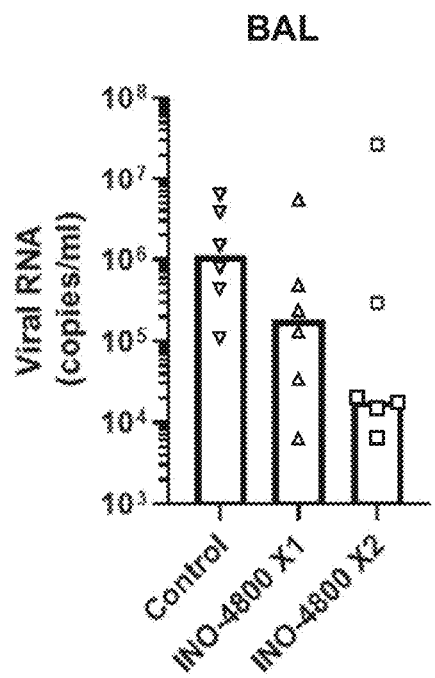
FIGS. 26A-26D illustrate lower respiratory tract viral loads detected by RT-qPCR following challenge with SARS-CoV-2. Animals received one (INO-4800X1) or two (INO-4800X1) doses of INO-4800 or were unvaccinated (control). SARS-CoV-2 genomic and subgenomic viral loads were measured for individual animals in bronchoalveolar lavage (BAL (FIGS. 26A and 26B)) and lung tissue (FIGS. 26C and 26D) samples collected at necropsy (6-8 days post challenge). Bars represent group medians. Assay LLOQ's and LLOD's are provided in the methods section.
Figure 26B:
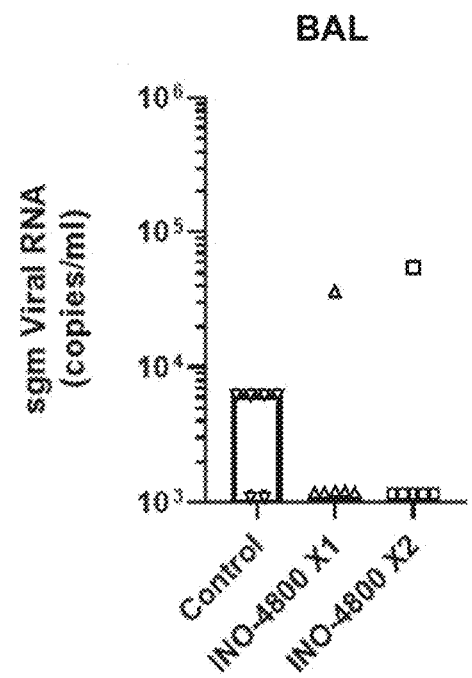
Figure 26C:
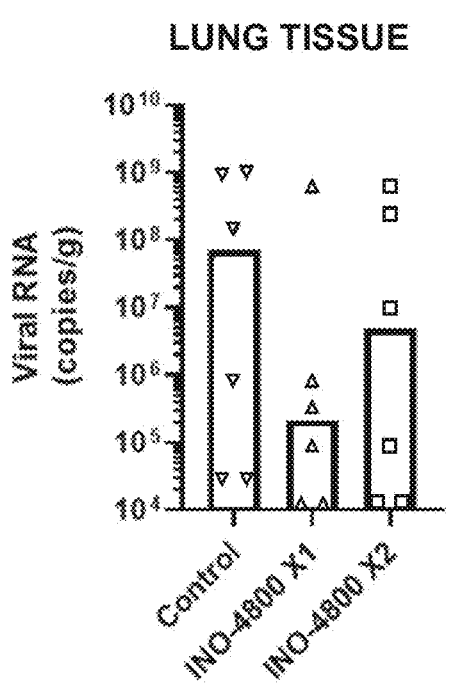
Figure 26D:
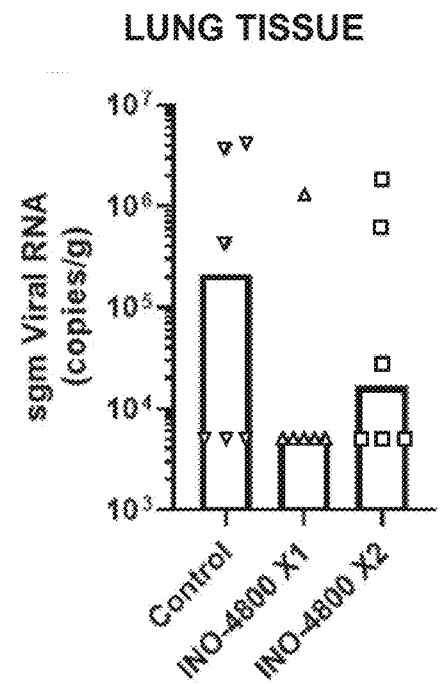
Figure 27:
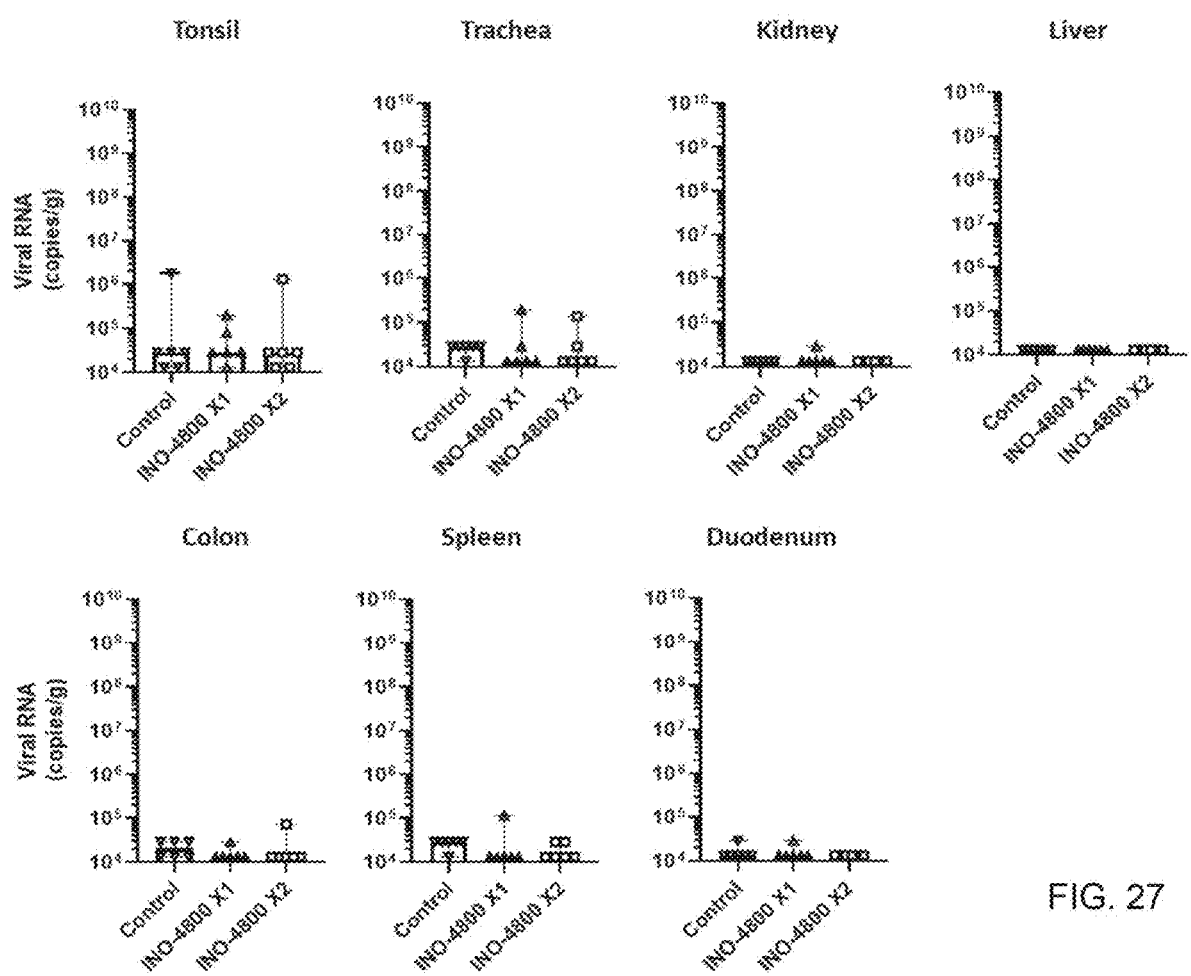
FIG. 27 illustrates viral RNA in animal tissue post challenge. Animals received one (INO-4800X1) or two (INO-4800X2) doses of INO-4800 or were unvaccinated (control). SARS-CoV-2 viral loads were measured for individual animals in tissue samples collected at necropsy (6-8 DPC). Bars represent group median with 95% CI. Positive tissue samples detected below the limit of quantification (LoQ) of 4.76 log copies/ml were assigned the value of 5 copies/µl, this equates to 4.46 log copies/g, whilst undetected samples were assigned the value of <2.3 copies/µl, equivalent to the assay's lower limit of detection (LoD) which equates to 4.76 log copies/g.

At the time of necropsy (6-8 days post challenge), BAL fluid was collected from each animal. Measurement of the levels of SARS-CoV-2 viral RNA and sgmRNA revealed a reduction of the average virus in vaccinated groups, even though the levels were variable within each group dependent on the day of necropsy (FIGS. 26A, 26B). RT-qPCR was also performed on tissues collected at necropsy. At these timepoints post challenge the SARS-CoV-2 viral RNA levels detected were below limit of quantification in most tissues except the lungs (FIG. 27). Measurements of the level of SARS-CoV-2 viral mRNA and sgmRNA detected in the lung tissue samples indicated reduced average viral load in the vaccinated animals (FIGS. 26C and 26D).

In summary data showed a significant reduction of viral load in the throat, and a trend for a reduction of viral loads in the lungs of the vaccinated groups. The collection of BAL and lung tissue samples at different timepoints (days 6, 7 or 8) after challenge likely added to the intragroup variability observed impacting statistical analysis. RT-qPCR viral load data indicate INO-4800 vaccination has a positive effect in reducing viral loads in rhesus macaques challenged with high dose SARS-CoV-2, in general, lower viral levels were measured in the 2 dose vaccine group compared to one dose vaccine group.

Disease Burden in the Lungs after SARS-CoV-2 Challenge.

Figure 28:
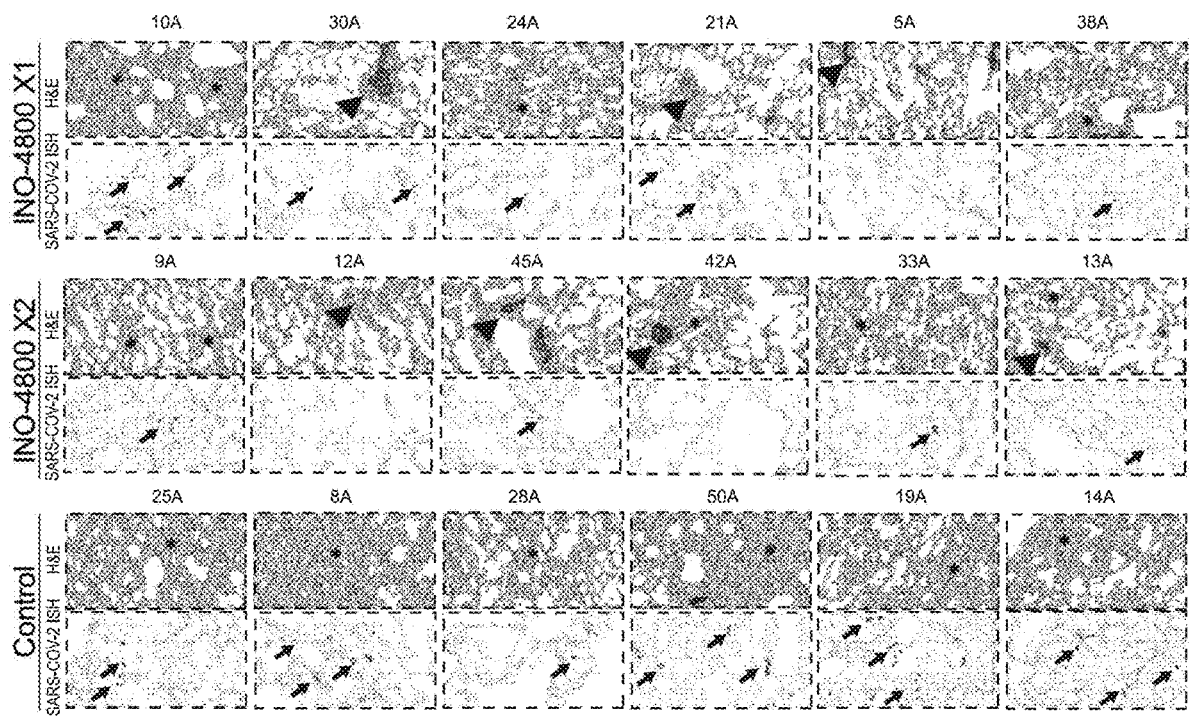
FIG. 28 shows representative histopathology (H&E stain) and presence of SARS-CoV-2 viral RNA (ISH RNAScope stain) in animals vaccinated with 1 dose (top), 2 doses (middle) or unvaccinated (bottom). Animals vaccinated with 1 dose showed multifocal minimal to mild alveolar and interstitial pneumonia (*), with higher severity in animal 10A. The remaining animals from group 1 show minimal/mild inflammatory infiltrates (*). Mild perivascular cuffing was also observed (arrowheads) and viral RNA was shown by ISH within the lesions (arrows), abundantly in animal 10A, and in small amounts in animals 30A, 24A, 21A and 38A (arrows). Animals vaccinated with 2 doses showed multifocal minimal to mild alveolar and interstitial pneumonia (*) together with minimal perivascular cuffing (arrowheads). Small quantities of viral RNA were observed by ISH within the lesions from animals 9A, 45A, 33A and 13A (arrows). Unvaccinated animals showed moderate multifocal alveolar and interstitial pneumonia (*), with presence of abundant viral RNA within the lesions from all animals (arrows).

The pulmonary disease burden was assessed on harvested lung tissues collected at necropsy 6 to 8 days after challenge. Analysis was performed on all animals in the study in a double blinded manner. Histopathological analysis of lung tissue was performed on multiple organ tissues, but only the lungs showed remarkable lesions, compatible with SARS-CoV-2 infection. Pulmonary lesions consistent with infection with SARS-CoV-2 were observed in the lungs of animals from the unvaccinated control and at a reduced level in vaccinated groups. Representative histopathology images are provided in FIG. 28. Briefly, the lung parenchyma was comprised of multifocal to coalescing areas of pneumonia surrounded by unaffected parenchyma. Alveolar damage, with necrosis of pneumocytes was a prominent feature in the affected areas. Alveolar spaces and interalveolar septa contained mixed inflammatory cells (including macrophages, lymphocytes, viable and degenerated neutrophils, and occasional eosinophils), and edema. Type II pneumocyte hyperplasia was also observed in distal bronchioles and bronchiolo-alveolar junctions. In the larger airways occasional, focal, epithelial degeneration and sloughing was observed in the respiratory epithelium. Low numbers of mixed inflammatory cells, comprising neutrophils, lymphoid cells, and occasional eosinophils, infiltrated bronchial and bronchiolar walls. In the lumen of some airways, mucus admixed with degenerative cells, mainly neutrophils and epithelial cells, was seen. Within the parenchyma, perivascular and peribronchiolar cuffing was also observed, being mostly lymphoid cells comprising the infiltrates.

Figure 29A:
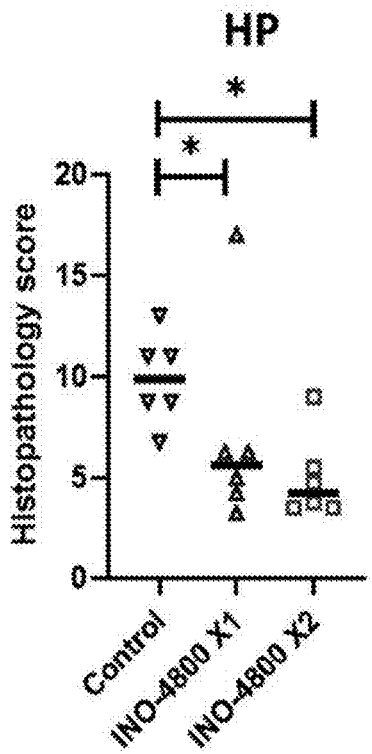
FIGS. 29A-29G illustrate lung disease burden measured by histopathology and CT scan following challenge with SARS-CoV-2. Total histopathology score (FIG. 29A), and image analysis of area positively stained area in ISH RNA-Scope labelled sections for viral RNA (FIG. 29B).
Figure 29B:
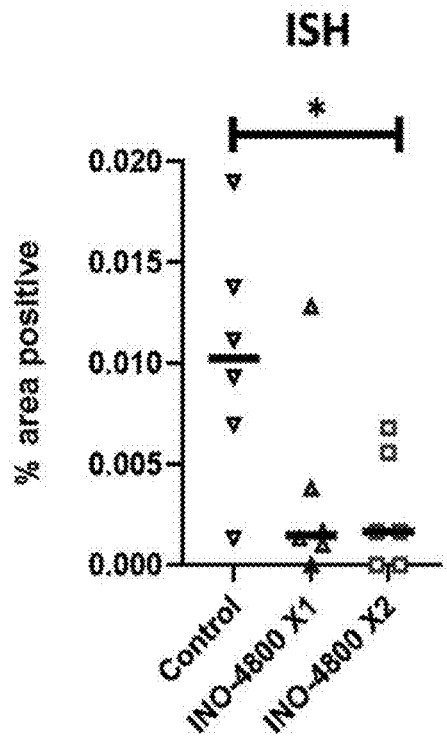
Figure 29C:
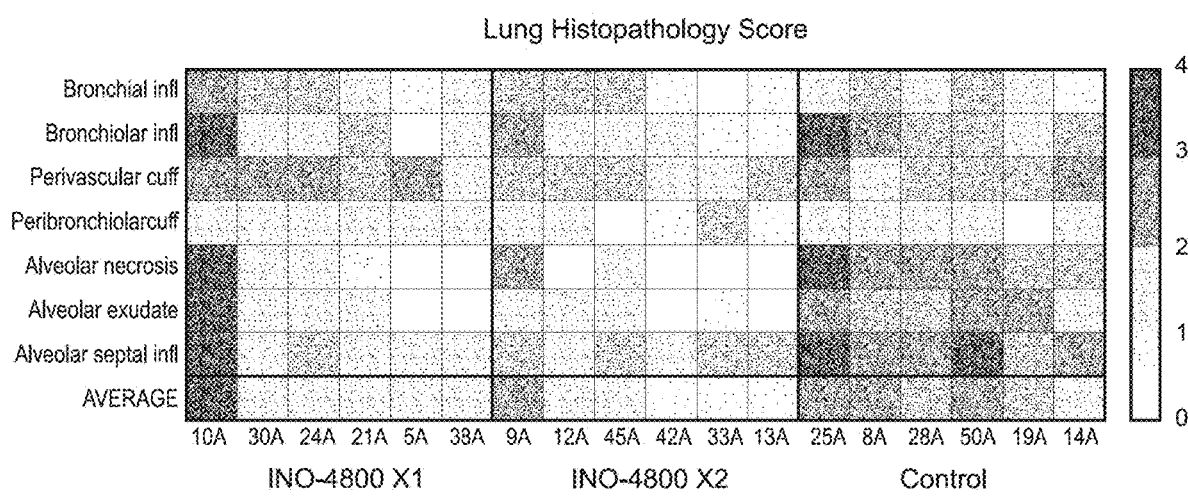

The histopathology score and percent tissue area of SARS-CoV-2 RNA positivity were applied to quantify the disease burden. The unvaccinated group showed the highest histopathological scores in the lung when compared with the vaccinated groups (FIGS. 29A and 29C). Animals from vaccinated groups showed reduced pathology when compared with unvaccinated animals, except for animal #10A from INO-4800X1 group, which showed histopathological scores similar to the unvaccinated animals. To detect the presence of SARS-CoV-2 RNA in the lung tissue, in situ hybridization (ISH) was performed. Viral RNA was observed in pneumocytes and inflammatory cells within the histopathological lesions with reduced frequency in the vaccinated animals (FIG. 29B).

Figure 29D:
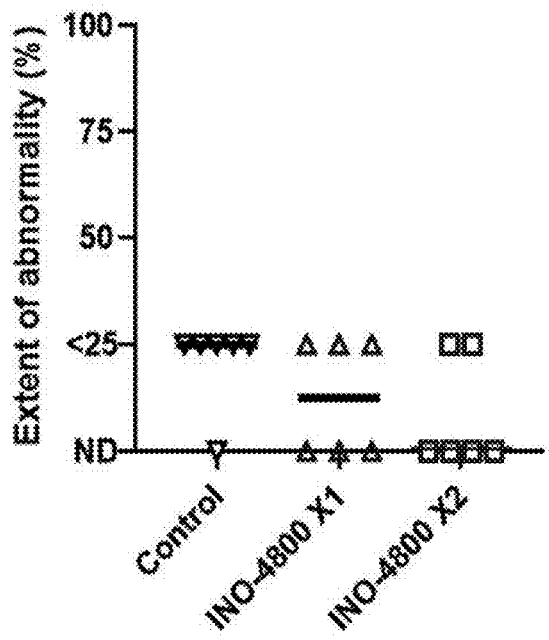
Figure 29E:
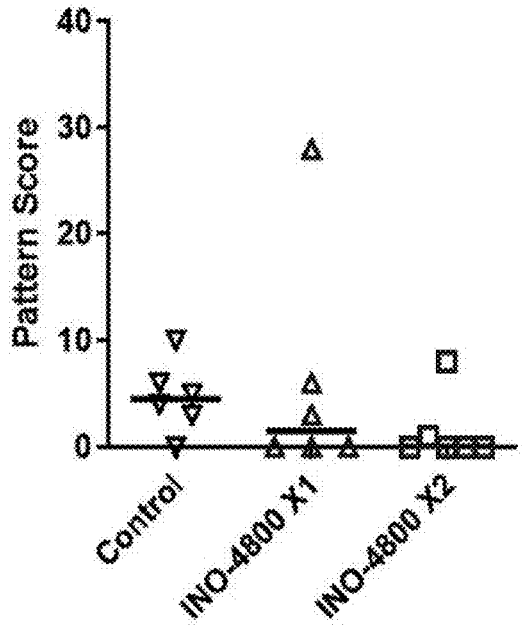
Figure 29F:
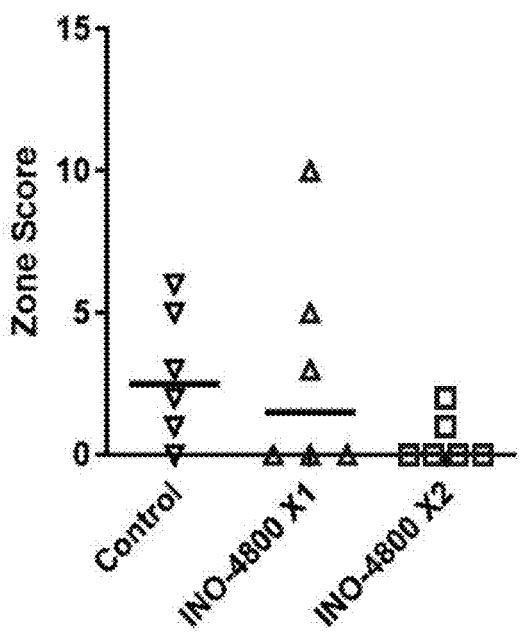
Figure 29G:
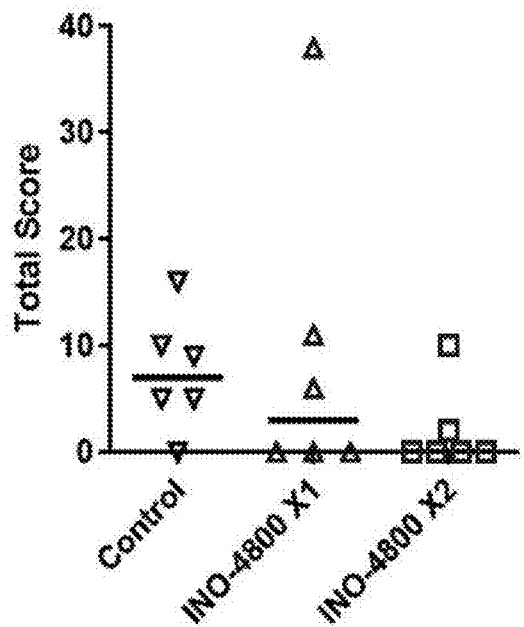
Figure 30:
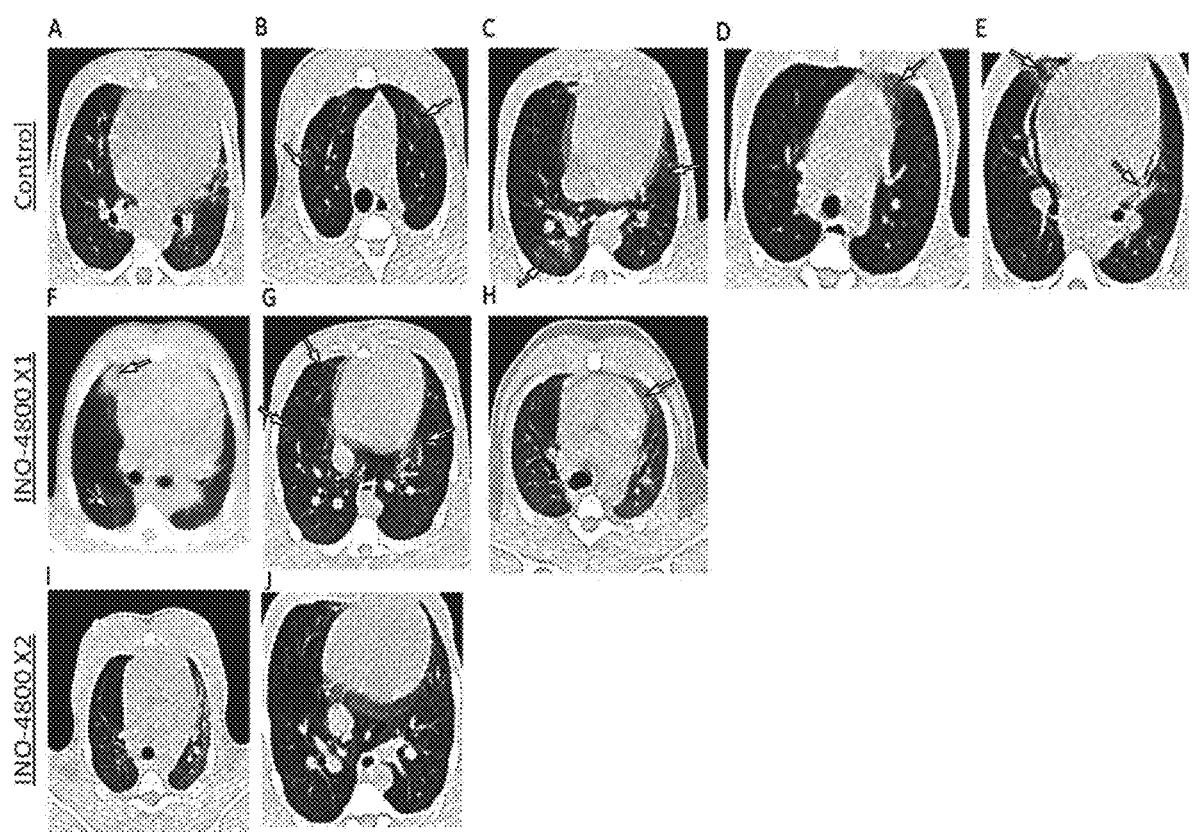
FIG. 30 illustrates representative example of pulmonary abnormalities identified on images constructed from CT scans. Images represent animals that did not receive a vaccination (control): 8A [A], 25A [B], 28A [C], 14A [D], 50A [E]; animals that received a single dose of INO-4800 vaccine: 10A [F], 21A [G], 38A [H]; animals that received two doses of INO-4800 vaccine: 21A [I], 33A [J]. Arrows indicate areas of ground glass opacification and areas of consolidation. Images from macaques that did not have abnormal features are not shown.
Figure 31A:
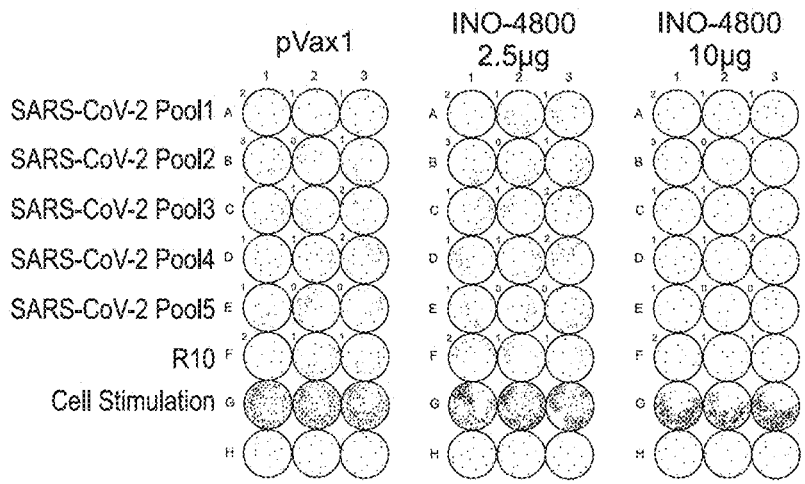
FIG. 31A through FIG. 31F depict ELISpot images of IFN-γ+ mouse splenocytes after stimulation with SARS-CoV-2 and SARS antigens. Mice were immunized on day 0 and splenocytes harvested at the indicated time points. IFNγ-secreting cells in the spleens of immunized animals were enumerated via ELISpot assay. Representative images show SARS-CoV-2 specific (FIG. 31A through FIG. 31C) and SARS-CoV-specific (FIG. 31D through FIG. 31F) IFNγ spot forming units in the splenocyte population at days 4, 7, and 10 post-immunization. Images were captured by ImmunoSpot CTL reader.
Figure 31B:
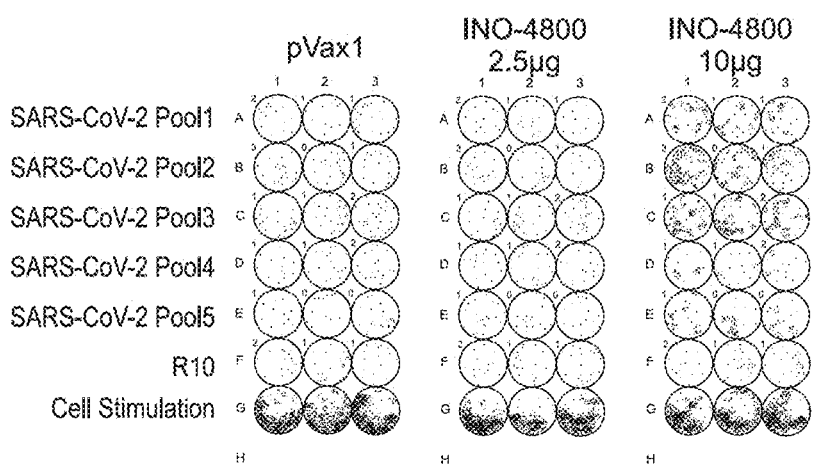
Figure 31C:
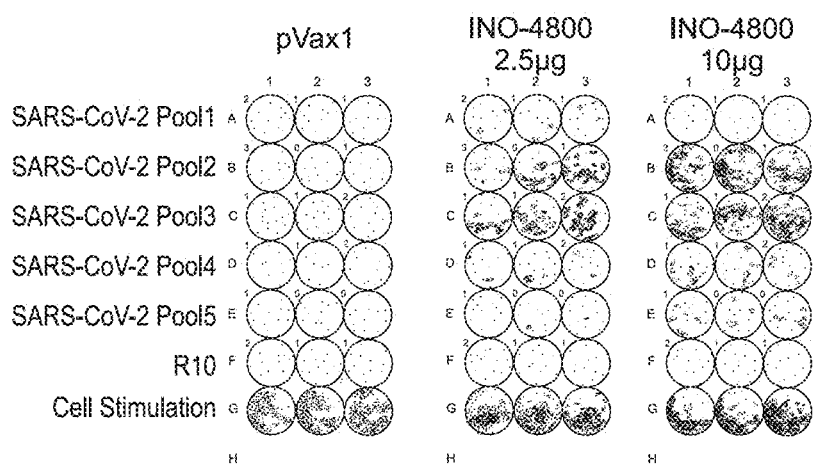
Figure 31D:
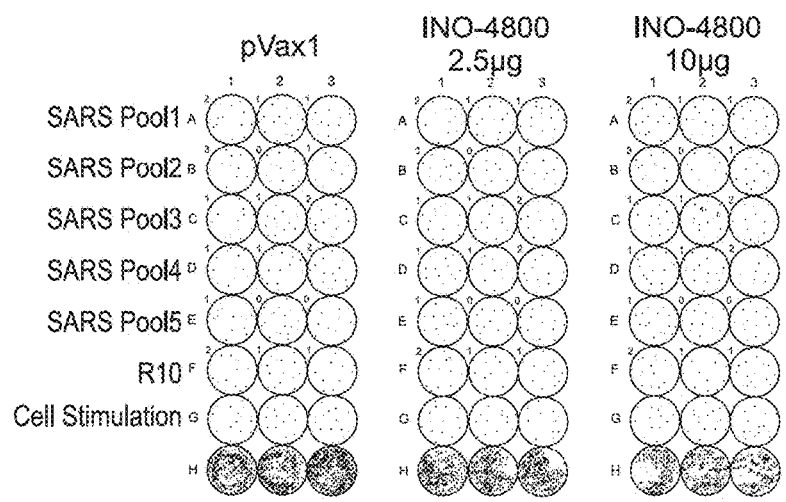
Figure 31E:
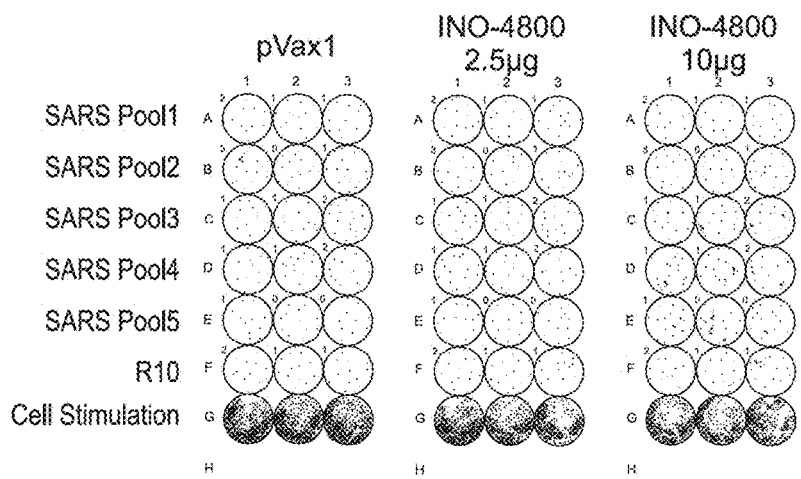
Figure 31F:
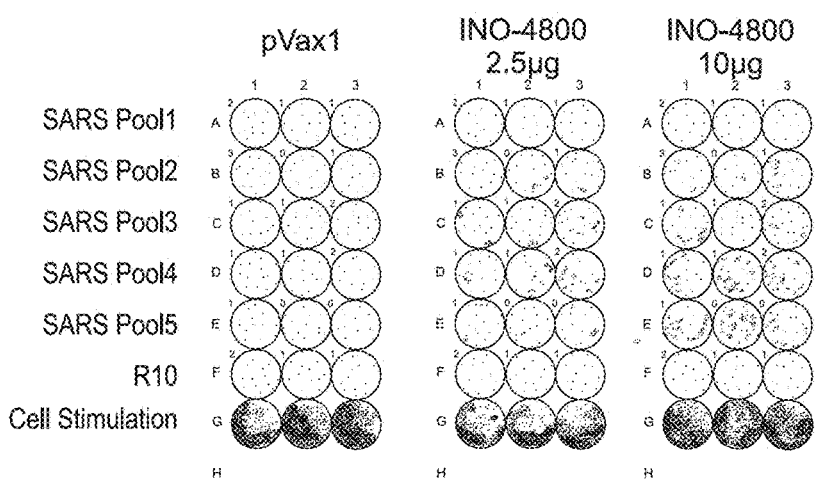

CT scans were performed to provide an in-life, unbiased, and quantifiable metric of lung disease. Results from lung CT imaging performed 5 days after challenge with SARS-CoV-2 were evaluated for the presence of COVID-19 disease features: ground glass opacity (GGO), consolidation, crazy paving, nodules, pen-lobular consolidation; distribution—upper, middle, lower, central 2/3, peripheral, bronchocentric, and for pulmonary embolus. The medical radiologist was blinded to the animal's treatment and clinical status. The extent of lung involvement was evaluated and quantified using a scoring system developed for COVID disease. The score system parameters are provided in materials and methods section. Pulmonary abnormalities characteristic of COVID-19 disease where observed in 3 out of 6 and 2 out of 6 animals in the INO-4800 one dose or two dose groups, respectively, and in 5 out of 6 unvaccinated animals in the control group (representative CT scan images are provided in FIG. 30). The extent of lung involvement in the animals with disease involvement was less than 25% and considered low level disease (FIG. 29D). There was a trend for disease scores to be highest in the unvaccinated control group with a reduction in the INO-4800 one and two dose groups (FIGS. 29E-29G). The comparison of scores between groups did not reach statistical difference (p=0.0584 between INO-4800 two dose group and no vaccine group, Mann Whitney test). One outlier animal (10A) in the INO-4800 X1 group scored higher than other animals. However, the level of disease was still considered low and comparable disease burden had been observed in other NHP SARS-CoV-2 challenge studies performed under the same conditions. In summary, CT scanning provides a useful measure of SARS-CoV-2-induced disease in rhesus macaques. Day 5 post SARS-CoV-2 infection, abnormalities where present were reported at low levels (<25% of lung involved). Evidence from CT scans suggested trends for differences in pulmonary disease burden between groups, with disease burden highest in the nonvaccinated control group.

In summary, after high dose SARS-CoV-2 challenge of nonhuman primates the disease burden was reduced in the animals receiving a single of two dose regimen of INO-4800 vaccine. There was no indication of vaccine enhanced disease, even in animals receiving a suboptimal one dose vaccination regimen.

DISCUSSION

This example describes the safety, immunogenicity, and efficacy assessments of the SARS-CoV-2 DNA vaccine INO-4800 in a stringent high dose nonhuman primate challenge model. Intradermal delivery of 1 mg of INO-4800 to rhesus macaques induces both humoral and T cell responses against the SARS-CoV-2 spike antigen in both a 2-dose regimen and a 1 dose regimen. Throughout the study no overt clinical events were recorded in the animals. After a high dose SARS-CoV-2 challenge, a reduction in viral loads was observed and lung disease burden in both the 1 and 2 dose vaccine groups supporting the efficacy of INO-4800. Importantly, vaccine enhanced disease (VED) was not observed, even with the 1 dose group.

The rhesus macaque model has become a widely employed model for assessing medical countermeasures against SARS-CoV-2. Importantly, wildtype non-adapted SARS-CoV-2 replicates in the respiratory tract of rhesus macaques, and the animal presents with some of the characteristics observed in humans with mild COVID-19 symptoms [Salguero, F. J., et al., Comparison of Rhesus and Cynomolgus macaques as an authentic model for COVID-19. 2020: p. 2020.09.17.301093.; Muñoz-Fontela, C., et al., Animal models for COVID-19. Nature, 2020. 586(7830): p. 509-515]. Here, focus was placed on the lung disease burden in SARS-CoV-2 challenged rhesus macaques which had been vaccinated with INO-4800. While the level of lung disease burden measured in the animals was mild, a significant reduction in of histopathology and viral detection scores in the lungs of vaccinated animals was observed (FIG. 29). This suggests the potential for a positive impact on the LRT disease which is observed in COVID-19 patients which progress to severe disease. Interestingly, a significant reduction in viral loads in the throat compartment in the upper respiratory tract was also observed, but only a trend for reduction in the nasal compartment. It may be that differential induction of mucosal immunity exists between the throat and nasal compartment. Interestingly, a significant negative correlation between the RBD targeting and neutralizing antibodies in the serum with throat, but not nasal, viral loads was observed at day 1 post challenge (FIG. 15). However, the levels of these antibodies in either of these URT compartments were not assayed to provide further evidence of the presence of increased levels of functional antibodies in the throat compared to nasal passage. Another possibility could be that viral control in the nasal compartment where the extensive ($5 \times 10^6$ pfu) SARS-CoV-2 challenge dose was directly instilled may be a higher bar than in other mucosal compartments. In support of this, data in the control animals showed nasal swabs yielded higher viral titers than throat swabs, with similar observations being reported in COVID-19 subjects [Mohammadi, A., et al., SARS-CoV-2 detection in different respiratory sites: A systematic review and meta-analysis. EBioMedicine, 2020. 59: p. 102903.]

Importantly, the data indicated that enhanced respiratory disease (ERD) was not associated with INO-4800 immunization in either the 1 dose or 2 dose regimen. In the INO-4800 X1 dose group, one animal (10A) did present with the highest lung histopathology score and CT scan score. However, the multifocal lesions in animal 10A showed a similar histopathological pattern as those observed in the animals from the nonvaccinated group, with no apparent influx of different inflammatory cell subpopulations in the infiltrates. A potential hallmark of vaccine enhanced disease is the increased influx of inflammatory cells such as eosinophils [Bolles, M., et al., A double-inactivated severe acute respiratory syndrome coronavirus vaccine provides incomplete protection in mice and induces increased eosinophilic proinflammatory pulmonary response upon challenge. J Virol, 2011. 85(23): p. 12201-15; Yasui, F., et al., Prior Immunization with Severe Acute Respiratory Syndrome (SARS)-Associated Coronavirus (SARS-CoV) Nucleocapsid Protein Causes Severe Pneumonia in Mice Infected with SARS-CoV. The Journal of Immunology, 2008. 181(9): p. 6337-6348.]. The CT scan and histopathology data for animal 10A are believed not to be associated with ERD, but rather a disease score and pattern similar to that of nonvaccinated animals. Similar lung histopathology inflammation scores ranging from minimal-mild to mild-moderate were reported in samples analyzed 7 or 8 days after challenge in rhesus macaques receiving other vaccine candidates [Corbett, K. S., et al., Evaluation of the mRNA-1273 Vaccine against SARS-CoV-2 in Nonhuman Primates. New England Journal of Medicine, 2020. 383(16): p. 1544-1555]. Currently, VED remains a theoretical concern with SARS-CoV-2 vaccination and attempts to induce enhanced disease using a formalin inactivated whole virus preparation of SARS-CoV-2 have failed to repeat the lung pathology previously reported for other inactivated respiratory viral vaccines [Bewley, K. R., et al., Immunological and pathological outcomes of SARS-CoV-2 challenge after formalin-inactivated vaccine immunization of ferrets and rhesus macaques. 2020: p. 2020.12.21.423746].

This data compliments the NHP SARS-CoV-2 challenge study which demonstrated reduction in LRT viral loads several months after INO-4800 immunization (Example 9). However, there are distinct differences between the studies, including different doses and variants used for the challenge stock, and the timing of the challenge. In the study described in this example, the animal was challenged four weeks after the last vaccination, at a timepoint when high levels of circulating neutralizing antibodies were present. In the other study, the level of serum SARS-CoV-2 neutralizing antibody was low at the time of challenge, protection appeared to be dependent on the recall of a memory response, with a strong humoral and cellular response against SARS-CoV-2 spike antigen detected in the animals. Here, an anamnestic response of a similar magnitude was not observed, suggesting protection may have been mediated by the antibodies present in circulation at time of challenge which is supported by the correlation between serum SARS-CoV-2 targeting antibody levels and reductions in viral loads (FIG. 15).

In conclusion, the results here in a stringent preclinical SARS-CoV-2 animal model provide further support for the efficacy and safety of the DNA vaccine INO-4800 as a prophylactic countermeasure against COVID-19. Importantly, tested as a single dose immunization we observed a positive impact on the lung disease burden and no VED. Taken together with INO-4800 clinical data, INO-4800 has many attributes in terms of safety, efficacy and logistical feasibility due its high stability, negating the need for challenging cold chain distribution requirements for global access. Furthermore, synthetic DNA vaccine technology is amenable to highly accelerated developmental timelines, permitting rapid design and testing of candidates against new SARS-CoV-2 variants which display potential for immune escape [Wibmer, C. K., et al., SARS-CoV-2 501Y.V2 escapes neutralization by South African COVID-19 donor plasma. 2021: p. 2021.01.18.427166.; Moore, J. P. and P. A. Offit, SARS-CoV-2 Vaccines and the Growing Threat of Viral Variants. JAMA, 2021].

Example 9 SARS-CoV-2 DNA Vaccine Induces Humoral and Cellular Immunity Resulting in Memory Responses which Provide Anamnestic Protection in a Rhesus Macaque Challenge The immunogenicity of a synthetic DNA vaccine encoding the SARS-CoV-2 Spike protein was previously demonstrated in both mice and guinea pigs (Example 1). In this example, the durability of INO-4800-induced immune responses in rhesus macaques is demonstrated. ID-EP administration in rhesus macaques induced cellular and humoral responses to SARS-Cov-2 S protein, with additional cross reactivity to the SARS-CoV-1 S protein. Protective efficacy is demonstrated more than 3 months post-final immunization, demonstrating establishment of amamnestic immune responses and reduced viral loads in vaccinated macaques. After viral challenge, a reduction in subgenomic messenger RNA (sgmRNA) BAL viral loads was observed compared to control animals with 1 mg (⅕th the DNA dose) administered via intradermal (ID) delivery. This was associated with induction of a rapid recall response in both cellular and humoral immune arms, supporting the potential for the INO-4800 candidate to moderate disease. No adverse events or evidence of vaccine enhanced disease (VED) were observed in animals in the vaccine group. Reduced viral subgenomic RNA loads in the lower lung and lower VL were observed. In the nose, a trend of lower VL was observed. These data support that immunization with this DNA vaccine candidate limits active viral replication and has the potential to reduce severity of disease, as well as reduced viral shedding in the nasal cavity.

It is important to note that the initial viral loads detected in control animals in this study were on average 1-2 logs higher ($10^9$ PFU/swab in 4/5 NHPs on day 1 post-challenge) than in similar published studies performed under identical conditions (~$10^7$ PFU/swab) (Yu et al., 2020, Science, eabc6284). Only two of the prior reported NHP studies included intranasal delivery as inoculation route for challenge (van Doremalen et al., 2020, bioRxiv 2020.05.13.093195; Yu et al., 2020, Science, eabc6284). High-dose challenge inoculums are frequently employed to ensure take of infection, however non-lethal systems such as this SARS-CoV-2 rhesus macaque model may artificially reduce the impact of potentially protective vaccines and interventions (Durudas et al., 2011, Curr HIV Res 9, 276-288; Innis et al., 2019, Vaccine 37, 4830-4834). Despite these limitations, this study demonstrated significant reduction in peak BAL sgmRNA and overall viral RNA, likely induced by rapid induction of immunological memory mediated by both B and T cell compartments. Wolfel et al reported nasal titers in patients average $6.5 \times 10^5$ copies/swab days 1-5 following onset of symptoms (Wolfel et al., 2020, Nature 581, 465-469). These titers are significantly lower than the challenge dose and support potential for the vaccine candidate to control early during SARS-CoV-2 infection.

This study shows that DNA vaccination with a vaccine candidate targeting the full-length SARS-CoV-2 spike protein likely increases the availability T cell immunodominant epitopes leading to a broader and more potent immune response, compared to partial domains and truncated immunogens. In this study, T cell cross-reactivity was observed to SARS-CoV-1.

In addition to T cells, INO-4800 induced durable antibody responses that rapidly increased following SARS-CoV-2 challenge. It is further demonstrated that INO-4800 induced robust neutralizing antibody responses against both D614 and G614 SARS-CoV-2 variants. While the D/G 614 site is outside the RBD, it has been suggested that this shift has the potential to impact vaccine-elicited antibodies (Korber B et al., 2020, Cell 182:1-16). Other studies report that the G614 variant exhibits increased SARS-CoV-2 infectivity (Hu et al., 2020, bioRxiv 2020.06.20.161323; Ozono S, 2020, bioRxiv 2020.06.15.151779). The data shows induction of comparable neutralization titers between D614 and G614 variants and that these responses are similarly recalled following SARS-CoV-2 challenge.

Materials & Methods

Non-Human Primate Immunizations, IFNγ ELISpot and ELISA

DNA vaccine, INO-4800: The highly optimized DNA sequence encoding SARS-CoV-2 IgE-spike was created using Inovio's proprietary in silico Gene Optimization Algorithm to enhance expression and immunogenicity (Smith et al., 2020, Nat Commun 11, 2601). The optimized DNA sequence was synthesized, digested with BamHI and XhoI, and cloned into the expression vector pGX0001 under the control of the human cytomegalovirus immediate-early promoter and a bovine growth hormone polyadenylation signal.

Animals: All rhesus macaque experiments were approved by the Institutional Animal Care and Use Committee at Bioqual (Rockville, Md.), an Association for Assessment and Accreditation of Laboratory Animal Care (AAALAC) International accredited facility. Blood was collected for blood chemistry, PBMC isolation, serological analysis. BAL was collected on Week 8 to assay lung antibody levels and on Days 1, 2, 4, 7 post challenge to assay lung viral loads.

Immunizations, sample collection and viral challenge. Ten Chinese rhesus macaques (ranging from 4.55 kg-5.55 kg) were randomly assigned in study immunized (3 males and 2 females) or naïve (2 males and 3 females). Immunized macaques received two 1 mg injections of SARS-CoV-2 DNA vaccine, INO-4800 at week 0 and 4 by ID-EP administration using the CELLECTRA 2000® Adaptive Constant Current Electroporation Device with a 3P array (Inovio Pharmaceuticals). Blood was collected at indicated time points to analyse blood chemistry, peripheral blood mononuclear cells (PBMC) isolation, and serum was collected for serological analysis. Bronchoalveolar lavage was collected at Week 8 to assay lung antibody levels. BAL from naïve animals was run as control. At week 17, all animals were challenged with $1.2\times10^8$ VP ($1.1\times10^4$ PFU) SARS-CoV-2. Virus was administered as 1 ml by the intranasal (IN) route (0.5 ml in each nostril) and 1 ml by the intratracheal (IT) route.

Peripheral blood mononuclear cell isolation. Blood was collected from each macaque into sodium citrate cell preparation tubes (CPT, BD Biosciences). The tubes were centrifuged to separate plasma and lymphocytes, according to the manufacturer's protocol. Samples were transported by same-day shipment on cold-packs from Bioqual to The Wistar Institute for PBMC isolation. PBMCs were washed and residual red blood cells were removed using ammonium-chloride-potassium (ACK) lysis buffer. Cells were counted using a ViCell counter (Beckman Coulter) and resuspended in RPMI 1640 (Corning), supplemented with 10% fetal bovine serum (Atlas), and 1% penicillin/streptomycin (Gibco). Fresh cells were then plated for IFNγ ELISpot Assays and flow cytometry.

IFN-γ Enzyme-linked immunospot (ELISpot). Monkey interferon gamma (IFN-γ) ELISpot assay was performed to detect cellular responses. Monkey IFN-γ ELISpotPro (alkaline phosphatase) plates (Mabtech, Sweeden, Cat #3421M-2APW-10) were blocked for a minimum of 2 hours with RPMI 1640 (Corning), supplemented with 10% FBS and 1% perm/strep (R10). Following PBMC isolation, 200 000 cells from macaques were added to each well in the presence of 1) overlapping peptide pools (15-mers with 9-mer overlaps) corresponding to the SARS-CoV-1, SARS-CoV-2, or MERS-CoV Spike proteins (5 μg/mL/well final concentration), 2) R10 with DMSO (negative control), 3) or anti-CD3 positive control (Mabtech, 1:1000 dilution). All samples were plated in triplicate. Plates were incubated overnight at 37° C., 5% $CO_2$. After 18-20 hours, the plates were washed in PBS and spots were developed according to the manufacturer's protocol. Spots were imaged using a CTL Immunospot plate reader and antigen-specific responses were determined by subtracting the number of spots in the R10+DMSO negative control well from the wells stimulated with peptide pools.

Antigen Binding ELISA. Serum and BAL was collected at each time point was evaluated for binding titers as indicated. Ninety-six well immunosorbent plates (NUNC) were coated with 1 ug/mL recombinant SARS-CoV-2 S1+S2 ECD protein (Sino Biological 40589-V08B1), S1 protein (Sino Biological 40591-V08H), S2 protein (Sino Biological 40590-V08B), or receptor-binding domain (RBD) protein (Sino Biological 40595-V05H) in DPBS overnight at 4° C. ELISA plates were also coated with 1 ug/mL recombinant SARS-CoV S1 protein (Sino Biological 40150-V08B1) and RBD protein (Sino Biological 40592-V08B) or MERS-CoV Spike (Sino Biological 40069-V08B). Plates were washed four times with PBS+0.05% Tween20 (PBS-T) and blocked with 5% skim milk in PBS-T (5% SM) for 90 minutes at 37° C. Sera or BAL from INO-4800 vaccinated macaques were serially diluted in 5% SM, added to the washed ELISA plates, and incubated for 1 hour at 37° C. Following incubation, plates were washed 4 times with PBS-T and an anti-monkey IgG conjugated to horseradish peroxidase (Southern Biotech 4700-5). Plates were washed 4 times with PBS-T and one-step TMB solution (Sigma) was added to the plates. The reaction was stopped with an equal volume of 2N sulfuric acid. Plates were read at 450 nm and 570 nm within 30 minutes of development using a Biotek Synergy2 plate reader.

ACE2 Competition ELISA-Non-human primates. 96-well half area plates (Corning) were coated at room temperature for 3 hours with 1 μg/mL PolyRab anti-His antibody (ThermoFisher, PA1-983B), followed by overnight blocking with blocking buffer containing 1×PBS, 5% skim milk, 1% FBS, and 0.2% Tween-20. The plates were then incubated with 10 μg/mL of His6×-tagged SARS-CoV-2 ("His6×" disclosed as SEQ ID NO: 25), S1+S2 ECD (Sinobiological, 40589-V08B1) at room temperature for 1-2 hours. NHP sera (Day0 or Week 6) was serially diluted 3-fold with 1×PBS containing 1% FBS and 0.2% Tween and pre-mixed with huACE2-IgMu at constant concentration of 0.4 ug/ml. The premixture was then added to the plate and incubated at RT for 1-2 hours. The plates were further incubated at room temperature for 1 hour with goat anti-mouse IgG H+L HRP (A90-116P, Bethyl Laboratories) at 1:20,000 dilution followed by addition of one-step TMB ultra substrate (ThermoFisher) and then quenched with 1M 142504. Absorbance at 450 nm and 570 nm were recorded with BioTEK plate reader.

Flow cytometry-based ACE2 receptor binding inhibition assay. HEK-293T cells stably expressing ACE2-GFP were generated using retroviral transduction. Following transduction, the cells were flow sorted based on GFP expression to isolate GFP positive cells. Single cell cloning was done on these cells to generate cell lines with equivalent expression of ACE2-GFP. To detect inhibition of Spike binding to ACE2, S1+S2 ECD-his tagged (Sino Biological, Catalog #40589-V08B1) was incubated with serum collected from vaccinated animals at indicated time points and dilutions at concentration of 2.5 μg/ml on ice for 60 minutes. This mixture was then transferred to 150,000 293T-ACE2-GFP cells and incubated on ice for 90 minutes. Following this, the cells were washed 2× with PBS followed by staining for Surelight® APC conjugated anti-his antibody (Abcam, ab72579) for 30 min on ice. As a positive control, Spike protein was pre-incubated with recombinant human ACE2 before transferring to 293T-Ace2-GFP cells. Data was acquired using a BD LSRII and analyzed by FlowJo (version 10).

Pseudovirus Neutralization Assay. SARS-CoV-2 pseudovirus were produced using HEK293T cells transfected with GeneJammer (Agilent) using IgE-SARS-CoV-2 S plasmid (Genscript) and pNL4-3.Luc.R-E-plasmid (NIH AIDS reagent) at a 1:1 ratio. Forty-eight hours post transfection, transfection supernatant was collected, enriched with FBS to 12% final volume, steri-filtered (Millipore Sigma), and aliquoted for storage at −80° C. SARS-Cov-2 pseudovirus neutralization assay was set up using D10 media (DMEM supplemented with 10% FBS and 1× Penicillin-Streptomycin) in a 96 well format. CHO cells stably expressing Ace2 were used as target cells (Creative Biolabs, Catalog No. VCeL-Wyb019). SARS-Cov-2 pseudovirus were titered to yield greater than 20 times the cells only control relative luminescence units (RLU) after 72 h of infection. For setting up neutralization assay, 10,000 CHO-ACE2 cells were plated in 96-well plates in 100 ul D10 media and rested overnight at 37° C. and 5% CO2 for 24 hours. Following day, Monkey and Rabbit sera from INO-4800 vaccinated and control groups were heat inactivated and serially diluted as desired. Sera were incubated with a fixed amount of SARS-Cov-2 pseudovirus for 90 minutes at RT. 50 ul media was removed from the plated CHO-Ace2 cell containing wells. Post 90 minutes, the mix was added to plated CHO-Ace2 cells and allowed to incubate in a standard incubator (37% humidity, 5% CO2) for 72 h. Post 72 h, cells were lysed using britelite plus luminescence reporter gene assay system (Perkin Elmer Catalog no. 6066769) and RLU were measured using the Biotek plate reader. Neutralization titers (ID50) were calculated using GraphPad Prism 8 and defined as the reciprocal serum dilution at which RLU were reduced by 50% compared to RLU in virus control wells after subtraction of background RLU in cell control wells.

Viral RNA assay. RT-PCR assays were utilized to monitor viral loads, essentially as previously described (Abnink P et al 2019 Science). Briefly, RNA was extracted using a QIAcube HT (Qiagen, Germany) and the Cador pathogen HT kit from bronchoalveolar lavage (BAL) supernatant and nasal swabs. RNA was reverse transcribed using superscript VILO (Invitrogen) and ran in duplicate using the QuantStudio 6 and 7 Flex Real-Time PCR System (Applied Biosystems) according to manufacturer's specifications. Viral loads were calculated of viral RNA copies per mL or per swab and the assay sensitivity was 50 copies. The target for amplification was the SARS-CoV2 N (nucleocapsid) gene. The primers and probes for the targets were: 2019-nCoV_N1-F: 5'-GACCCCAAAATCAGCGAAAT-3' (SEQ ID NO:18); 2019-nCoV_N1-R: 5'-TCTGGTTACTGCCAGTT-GAATCTG-3' (SEQ ID NO:19); 2019-nCoV_N1-P: 5'-FAM-ACCCCGCATTACGTTTGGTGGACC-BHQ1-3' (SEQ ID NO:20).

Subgenomic mRNA assay. SARS-CoV-2 E gene subgenomic mRNA (sgmRNA) was assessed by RT-PCR using an approach similar to previously described (Wolfel R et al. 2020, Nature, 581, 465-469). To generate a standard curve, the SARS-CoV-2 E gene sgmRNA was cloned into a pcDNA3.1 expression plasmid; this insert was transcribed using an AmpliCap-Max T7 High Yield Message Maker Kit (Cellscript) to obtain RNA for standards. Prior to RT-PCR, samples collected from challenged animals or standards were reverse-transcribed using Superscript III VILO (Invitrogen) according to the manufacturer's instructions. A Taqman custom gene expression assay (ThermoFisher Scientific) was designed using the sequences targeting the E gene sgmRNA (18). Reactions were carried out on a QuantStudio 6 and 7 Flex Real-Time PCR System (Applied Biosystems) according to the manufacturer's specifications. Standard curves were used to calculate sgmRNA in copies per ml or per swab; the quantitative assay sensitivity was 50 copies per ml or per swab.

Results

Figure 33A:
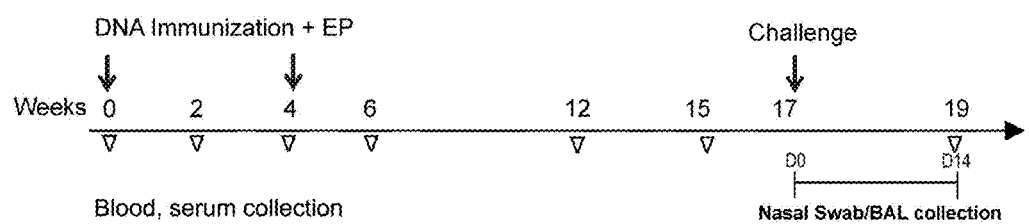
FIGS. 33A through 33H depict humoral and cellular immune responses in rhesus macaques.
Figure 33B:
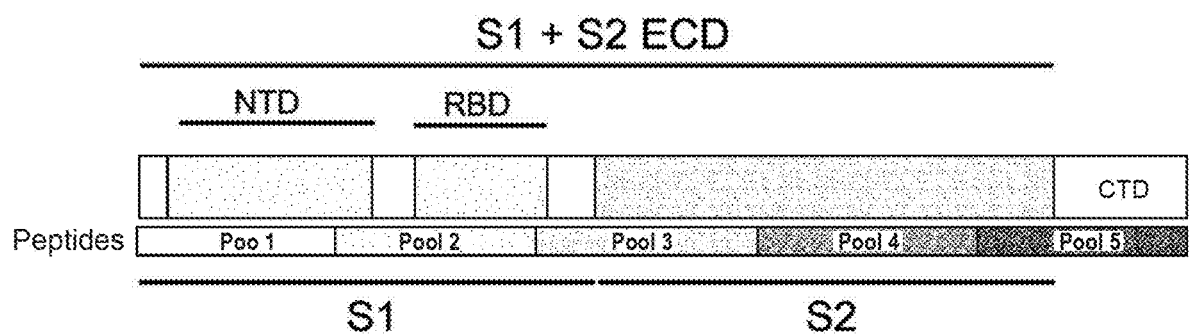
Figure 33C:
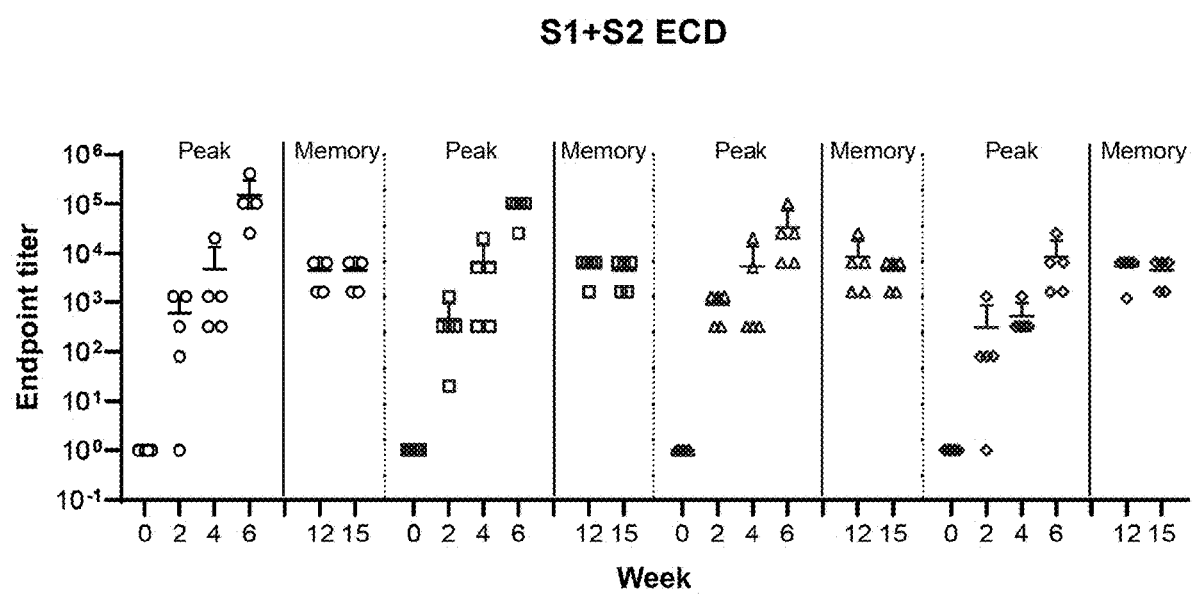
Figure 34:
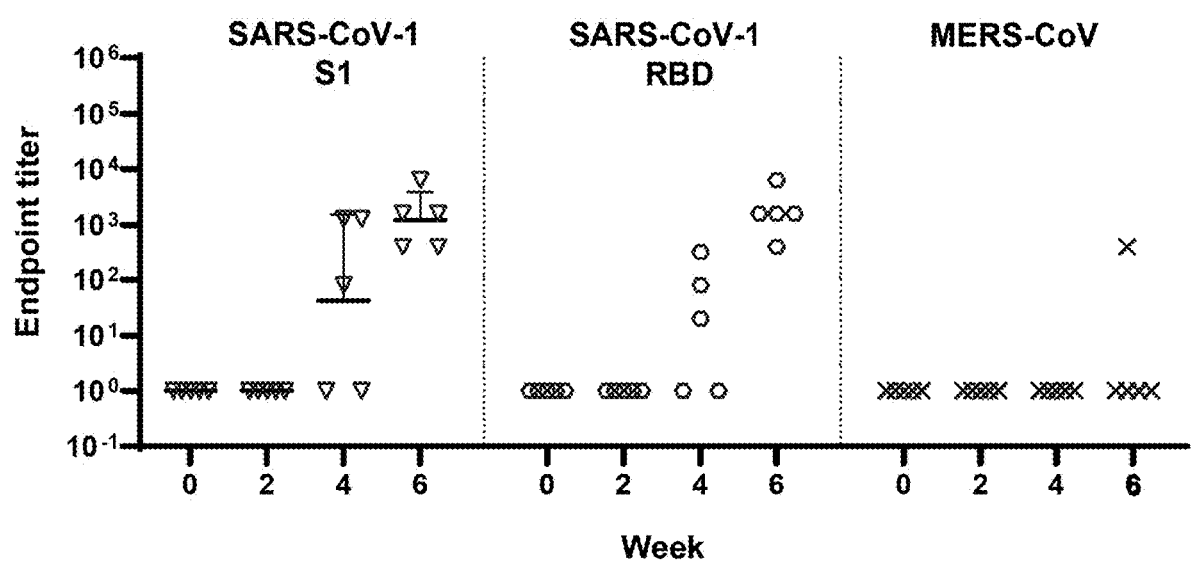
FIG. 34 depicts serum IgG cross-reactivity to SARS-CoV and MERS-CoV spike protein. IgG binding was measured in sera from INO-4800 vaccinated rhesus macaques to SARS-CoV S1 and MERS-CoV S1 protein antigen.
Figure 35:
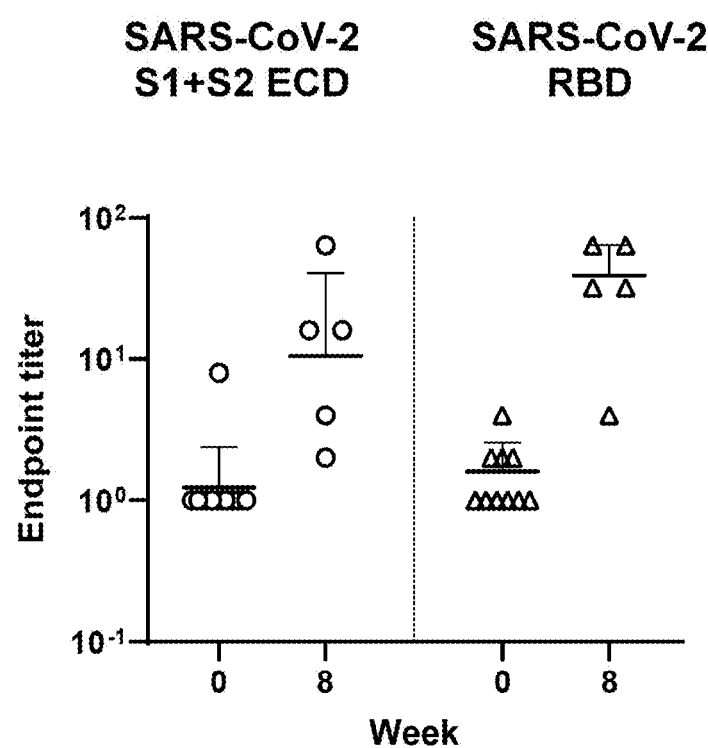
FIG. 35 depicts bronchoalveolar lavage (BAL) IgG reactive to SARS-CoV-2 S protein antigens. BAL samples collected from vaccinated animals were assessed for SARS-CoV-2 reactive IgG binding to the full length SARS-CoV-2 spike protein and the RBD domain.

Induction of memory humoral and cellular immune responses in INO-4800 immunized non-human primates. Non-human primates (NHP) are a valuable model in the development of COVID-19 vaccines and therapeutics as they can be infected with wild-type SARS-CoV-2, and present with similar pathology to humans (Chandrashekar et al., 2020, Science, eabc4776; Qin et al., 2005, J Pathol 206, 251-259; Yao et al., 2014, J Infect Dis 209, 236-242; Yu et al., 2020, Science, eabc6284). Rhesus macaques (n=5) received two immunizations of INO-4800 (1 mg), at Week 0 and Week 4 (FIG. 33A). Naïve control animals (n=5) did not receive vaccine. Humoral and cellular immune responses were monitored for 15 weeks (~4 months) following prime immunization for memory responses. All animals seroconverted following a single INO-4800 immunization, with serum IgG titers detected against the full-length S1+S2 extracellular domain (ECD), S1, S2, and RBD regions of the SARS-CoV-2 S protein (FIG. 33B and FIG. 33C). Cross-reactive antibodies were also detected against SARS-CoV S1 protein and RBD, but not MERS-CoV (FIG. 34). SARS-CoV-2-reactive IgG against the ECD and RBD were detected in bronchoalveolar lavage (BAL) washes at Week 8 following immunization (FIG. 34).

Figure 33D:
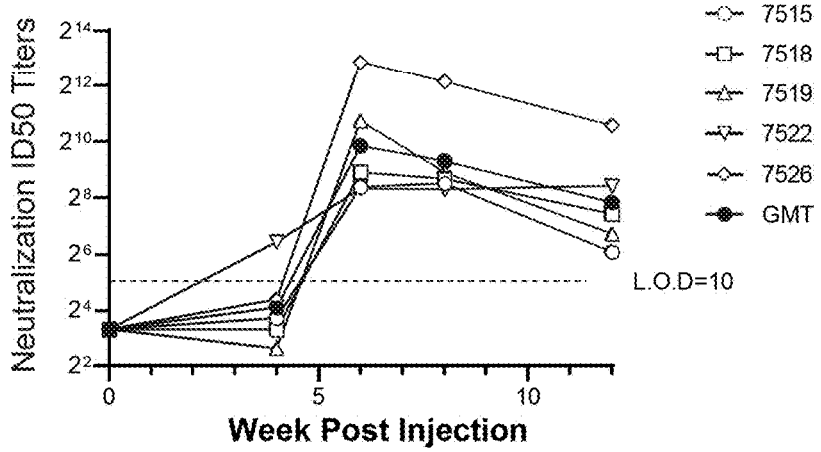
Figure 33E:
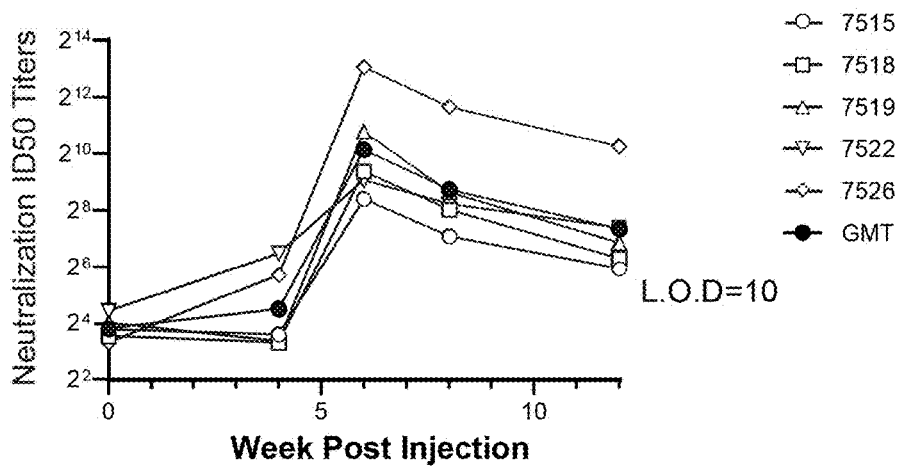

In serum samples of the animals SARS-CoV-2 pseudovirus neutralization activity was detected for >4 months following immunization (FIG. 33D), demonstrating memory titers comparable to those observed in other reported acute protection studies in macaques (Gao et al., 2020, Science 369, 77-81; Tian et al., 2020, Emerg Microbes Infect, 9:382-385; van Doremalen et al., 2020, bioRxiv 2020.05.13.093195; Yu et al., 2020, Science, eabc6284) and reported for convalescent humans (Ni et al., 2020, Immunity 52, 971-977 e973; Robbiani et al., 2020, Nature, s41586-020-2456-9). During the course of the COVID-19 pandemic, a D614G SARS-CoV-2 spike variant has emerged that has potentially greater infectivity, and now accounts for >80% of new isolates (Korber B et al., 2020, Cell 182:1-16). There is concern that vaccines developed prior to this variant's appearance may not neutralize the D614G virus. Therefore, neutralization against this new variant was evaluated using a modified pseudovirus expressing the G614 Spike protein (FIG. 33E). Similar neutralization ID50 titers were observed against both D614 and G614 spikes, supporting induction of functional antibody responses by INO-4800 against the now dominating SARS-CoV-2 variant.

Figure 33F:
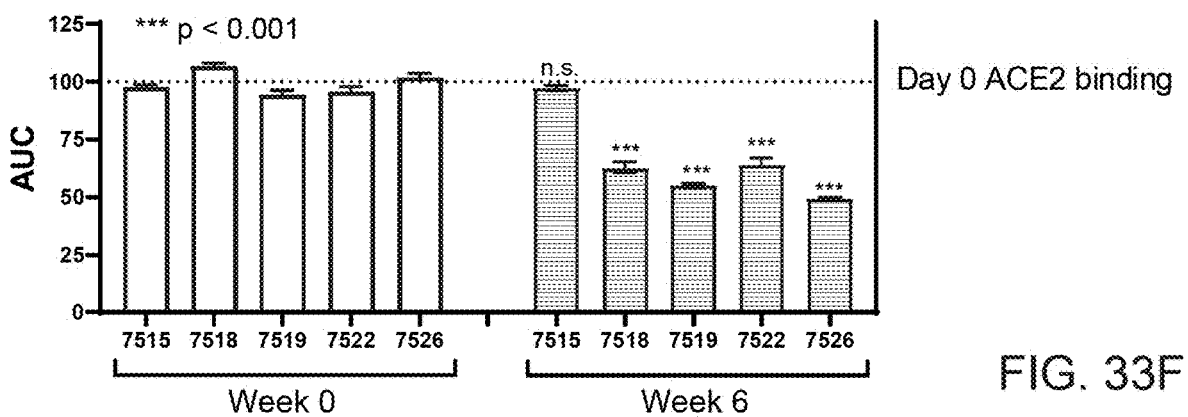
Figure 33G:
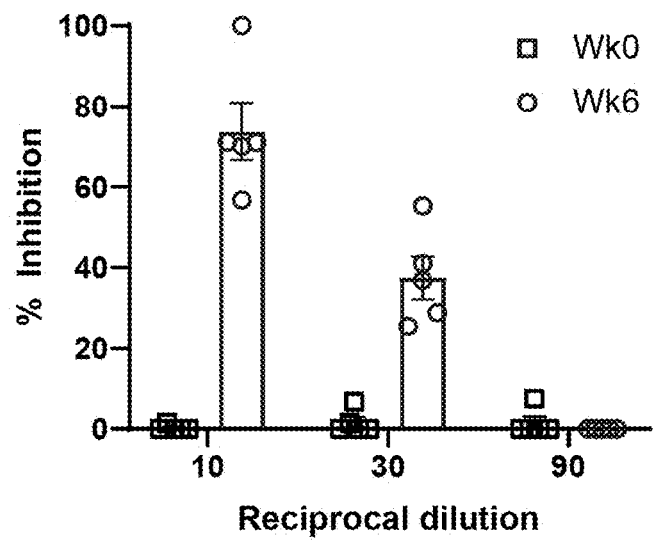

To further investigate the neutralizing activities, the sera was also tested using an ACE2 competition ELISA, where sera from 80% of immunized NHPs inhibited the SARS-CoV-2 Spike-ACE2 interaction (FIG. 33F). 100% of macaques responded in the flow cytometry ACE2-293T inhibition assay, with 53-96% inhibition of the Spike-ACE2 interaction at a 1:10 dilution and 24-53% inhibition at a 1:30 dilution (FIG. 33G).

Figure 33H:
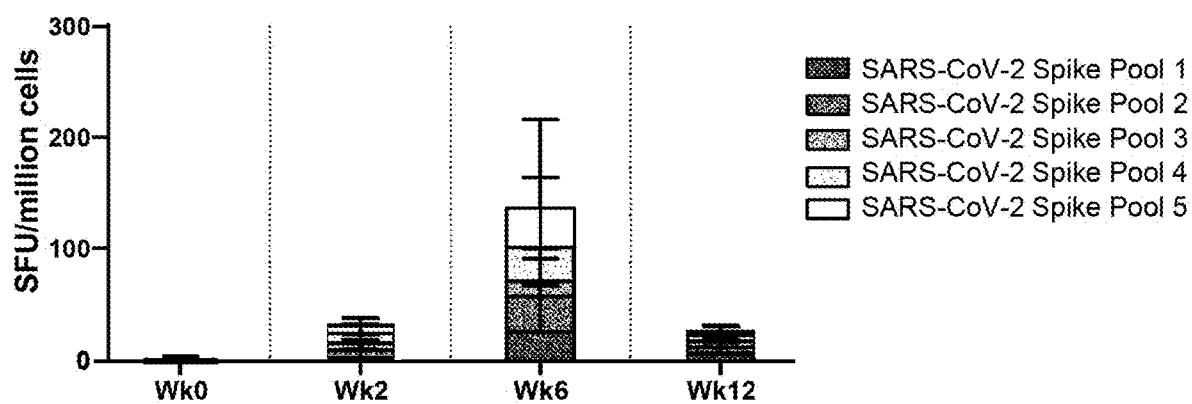
Figure 36A:
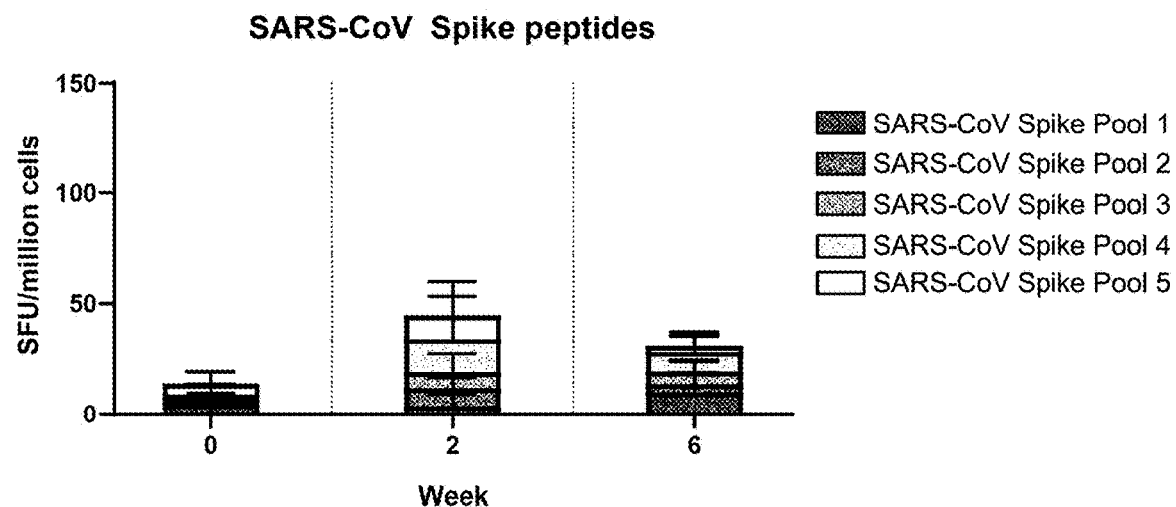
FIG. 36A and FIG. 36B depict exemplary experimental data demonstrating cellular response cross-reactivity to SARS-CoV and MERS-CoV spike protein. PBMC responses were analyzed by IFNγ ELISpot after stimulation with overlapping peptide pools spanning the SARS-CoV-1 spike protein (FIG. 36A) and MERS-CoV spike protein (FIG. 36B). Bars represent the mean+SD.
Figure 36B:
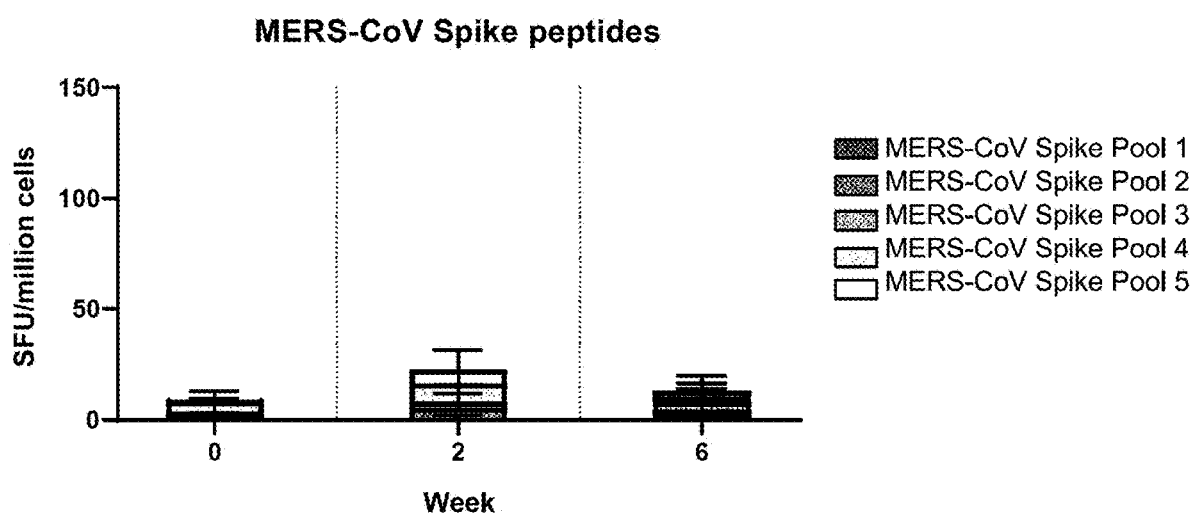

INO-4800 immunization also induced SARS-CoV-2 S antigen reactive T cell responses against all 5 peptide pools with T cells responses peaking at Week 6, two weeks following the second immunization (0-518 SFU/million cells) (FIG. 33H). Distinct immunogenic epitope responses were detected against the RBD and S2 regions (FIG. 33B). Cross-reactive T cells responses were also detected against the SARS-CoV Spike protein (FIG. 36A). However, cross-reactivity was not observed to MERS-CoV Spike peptides, which supports the lower sequence homology between SARS-CoV-2 and MERS-CoV (FIG. 36B).

Figure 37A:
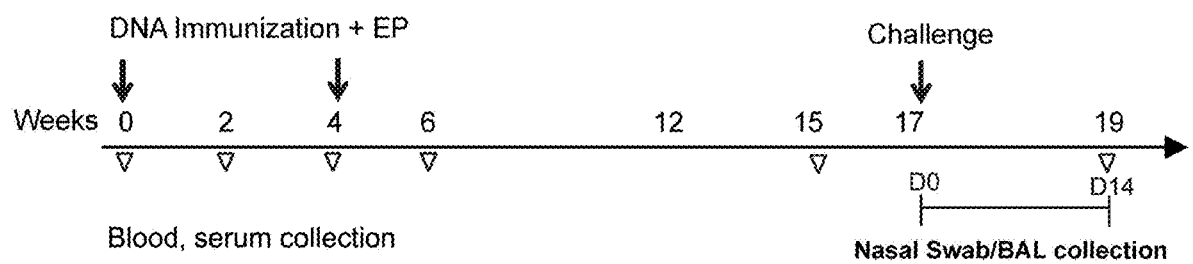
FIG. 37A through FIG. 37C depict exemplary experiments demonstrating recall of humoral immune responses after viral challenge.
Figure 37B:
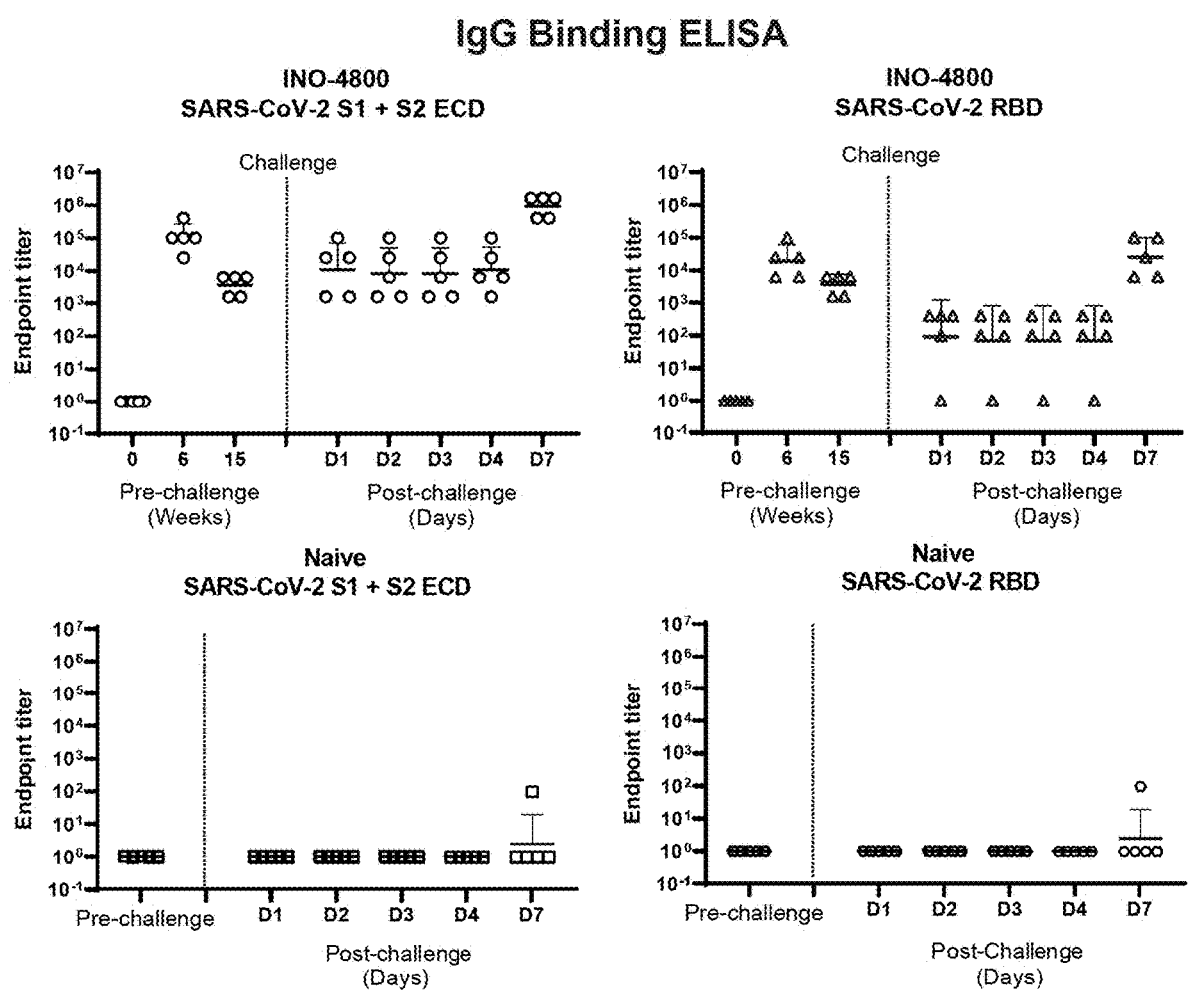
Figure 37C:
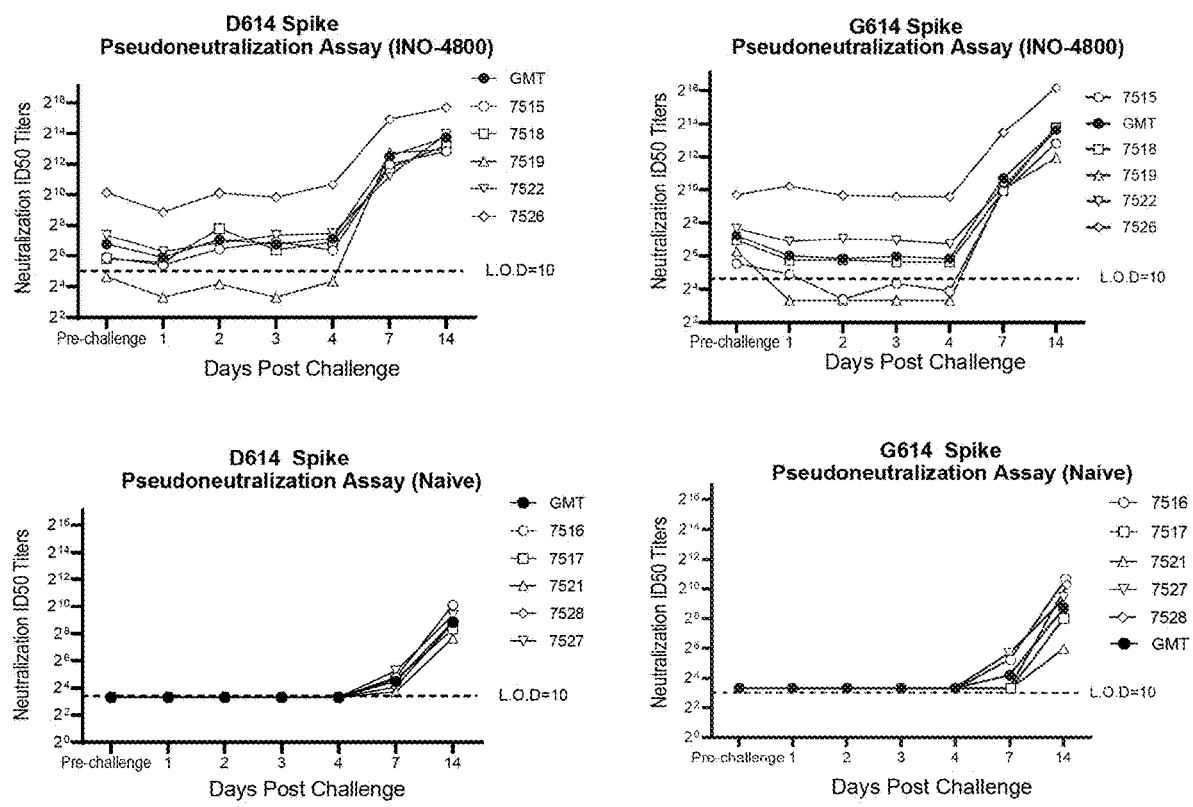

Vaccine induced memory recall responses upon SARS-CoV-2 challenge in non-human primates. Vaccine immunized macaques along with unvaccinated controls were challenged with SARS-CoV-2 13 weeks (~3 months) post-final immunization (Study Week 17, FIG. 37A). NHPs received a challenge dose of $1.1 \times 10^4$ PFU of SARS-CoV-2 Isolate USA-WA1/2020 by intranasal and intratracheal inoculation as previously described (Chandrashekar et al., 2020; Yu et al., 2020). Upon viral challenge, 3/5 of INO-4800 vaccinated animals had an immediate increase in antibody titers against the SARS-CoV-2 full-length ECD. By day 7, 5/5 animals had an increase in antibody titers against both full length ECD and RBD (FIG. 37B). Seven days post-challenge, robust geometric mean endpoint titers ranging from 409,600-1,638,400 were observed in immunized animals, compared with the naïve group which displayed seroconversion of only 1/5 animals (GMT 100) (FIG. 37B). A significant increase in pseudoneutralization titers was observed in all INO-4800 immunized animals against both D614 and G614 Spike variants by day 7 post-challenge (FIG. 37C).

Figure 38:
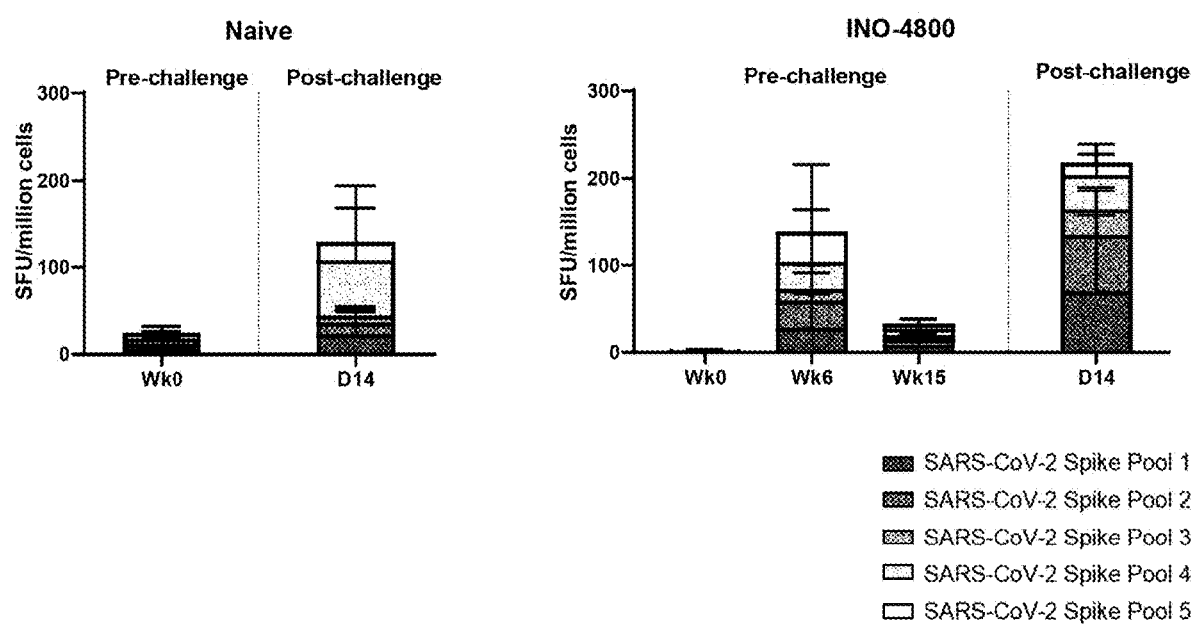
FIG. 38 depicts exemplary experiments demonstrating recall of cellular immune responses after viral challenge. T cells responses were analyzed by IFNγ ELISpot in PBMCs stimulated with overlapping peptide pools spanning the SARS-CoV-2 spike protein. Bars represent the mean+SD. T cell responses analyzed by IFNγ ELISpot in PBMCs isolated pre and post challenge with SARS-CoV-2 virus. Left panel naïve animals, right panel INO-4800 vaccinated animals.
Figure 39:
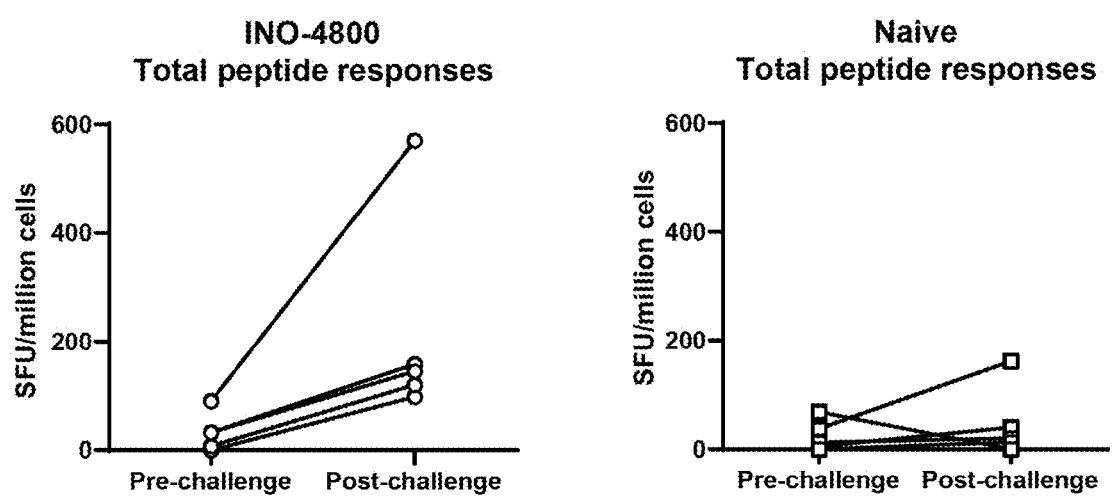
FIG. 39 depicts exemplary experiments demonstrating recall of cellular immune responses after viral challenge in individual rhesus macaques. Cellular responses were analyzed pre and post viral challenge by IFNγ ELISpot in PBMCs stimulated with overlapping peptide pools spanning the SARS-CoV-2 spike protein. Right panel naïve animals, left panel INO-4800 vaccinated animals.

Cellular responses were evaluated before and after challenge. At week 15, IFN-γ ELISpot responses had contracted significantly since the peak responses observed at week 6. T cell responses increased in the vaccinated group following challenge (~218.36 SFU/million cells) implying recall of immunological T cell memory (FIG. 38 and FIG. 39).

Protective efficacy following SARS-CoV-2 challenge. At earlier time points post virus input at challenge, viral mRNA detection does not discriminate between input challenge inoculum and active infection, while sgmRNA levels are more likely representative of active cellular SARS-CoV-2 replication (Wolfel et al., 2020, Nature, 581, 465-469; Yu et al., 2020, Science, eabc6284). SARS-CoV-2 subgenomic mRNA (sgmRNA) was measured in nonvaccinated control and INO-4800 vaccinated macaques following challenge with $1.1 \times 10^4$ PFU of SARS-CoV-2 Isolate USA-WA1/2020 (FIG. 40). Peak viral sgmRNA loads in the BAL were significantly lower in the INO-4800 vaccinated group (FIG. 40A and FIG. 40B), along with significantly lower viral RNA loads at day 7 post-challenge (FIG. 40C), indicating protection from lower respiratory disease. While sgmRNA was detected in the nasal swabs of both the control and INO-4800 vaccinated animals (FIG. 40D through FIG. 40F), viral RNA levels trended downwards in INO-4800 vaccinated animals by more than 2 logs (FIG. 40F). Overall, the reduced viral loads afforded by INO-4800 vaccination are likely due to anamnestic B and T cell responses that are rapidly recalled immediately following exposure to SARS-CoV-2 infection.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

Illustrative Embodiments

Embodiment 1. A nucleic acid molecule encoding a Severe Acute Respiratory Syndrome coronavirus 2 (SARS-CoV-2) spike antigen, the nucleic acid molecule comprising:
  a nucleic acid sequence having at least about 90% identity over an entire length of the nucleic acid sequence set forth in nucleotides 55 to 3837 of SEQ ID NO: 2;
  a nucleic acid sequence having at least about 90% identity over an entire length of SEQ ID NO: 2;
  the nucleic acid sequence of nucleotides 55 to 3837 of SEQ ID NO: 2;
  the nucleic acid sequence of SEQ ID NO: 2;
  a nucleic acid sequence having at least about 90% identity over an entire length of SEQ ID NO: 3;
  the nucleic acid sequence of SEQ ID NO: 3;
  a nucleic acid sequence having at least about 90% identity over an entire length of nucleotides 55 to 3837 of SEQ ID NO: 5;
  a nucleic acid sequence having at least about 90% identity over an entire length of SEQ ID NO: 5;
  the nucleic acid sequence of nucleotides 55 to 3837 of SEQ ID NO: 5;
  the nucleic acid sequence of SEQ ID NO: 5;
  a nucleic acid sequence having at least about 90% identity over an entire length of SEQ ID NO: 6; or
  the nucleic acid sequence of SEQ ID NO: 6.

Embodiment 2. A nucleic acid molecule encoding a SARS-CoV-2 spike antigen, wherein the SARS-CoV-2 spike antigen comprises:
  an amino acid sequence having at least about 90% identity over an entire length of residues 19 to 1279 of SEQ ID NO: 1;
  the amino acid sequence set forth in residues 19 to 1279 of SEQ ID NO: 1;
  an amino acid sequence having at least about 90% identity over an entire length of SEQ ID NO: 1;
  the amino acid sequence of SEQ ID NO: 1;

an amino acid sequence having at least about 90% identity over an entire length of residues 19 to 1279 of SEQ ID NO: 4;

an amino acid sequence having at least about 90% identity over an entire length of SEQ ID NO: 4;

the amino acid sequence set forth in residues 19 to 1279 of SEQ ID NO: 4; or the amino acid sequence of SEQ ID NO: 4.

Embodiment 3. An expression vector comprising the nucleic acid molecule according to Embodiment 1 or Embodiment 2.

Embodiment 4. The expression vector according to Embodiment 3, wherein the nucleic acid molecule is operably linked to a regulatory element selected from a promoter and a poly-adenylation signal.

Embodiment 5. The expression vector according to Embodiment 3 or Embodiment 4, wherein the vector is a plasmid or viral vector.

Embodiment 6. An immunogenic composition comprising an effective amount of the expression vector according to any one of Embodiments 3-5.

Embodiment 7. The immunogenic composition according to Embodiment 6 further comprising a pharmaceutically acceptable excipient.

Embodiment 8. The immunogenic composition according to Embodiment 7 wherein the pharmaceutically acceptable excipient comprises a buffer, optionally saline-sodium citrate buffer.

Embodiment 9. The immunogenic composition of Embodiment 8, wherein the composition is formulated at a concentration of 10 mg per milliliter of a sodium salt citrate buffer.

Embodiment 10. The immunogenic composition according to any one of Embodiments 6-9, further comprising an adjuvant.

Embodiment 11. A SARS-CoV-2 spike antigen comprising:

an amino acid sequence having at least about 90% identity over an entire length of residues 19 to 1279 of SEQ ID NO: 1;

the amino acid sequence set forth in residues 19 to 1279 of SEQ ID NO: 1;

an amino acid sequence having at least about 90% identity over an entire length of SEQ ID NO: 1;

the amino acid sequence of SEQ ID NO: 1;

an amino acid sequence having at least about 90% identity over an entire length of residues 19 to 1279 of SEQ ID NO: 4;

an amino acid sequence having at least about 90% identity over an entire length of SEQ ID NO: 4;

the amino acid sequence set forth in residues 19 to 1279 of SEQ ID NO: 4; or the amino acid sequence of SEQ ID NO: 4.

Embodiment 12. A vaccine for the prevention or treatment of Severe Acute Respiratory Syndrome coronavirus 2 (SARS-CoV-2) infection comprising an effective amount of the nucleic acid molecule of Embodiment 1 or 2, the vector of any one of Embodiments 3-5, or the antigen of Embodiment 11.

Embodiment 13. The vaccine according to Embodiment 12, further comprising a pharmaceutically acceptable excipient.

Embodiment 14. The vaccine according to Embodiment 13, wherein the pharmaceutically acceptable excipient comprises a buffer, optionally sodium salt citrate buffer.

Embodiment 15. The vaccine according to Embodiment 14, formulated at a concentration of 10 mg of nucleic acid per milliliter of a sodium salt citrate buffer.

Embodiment 16. The vaccine according to any one of Embodiments 12 to 15, further comprising an adjuvant.

Embodiment 17. A method of inducing an immune response against Severe Acute Respiratory Syndrome coronavirus 2 (SARS-CoV-2) in a subject in need thereof, the method comprising administering an effective amount of the nucleic acid molecule of Embodiment 1 or 2, the vector of any one of Embodiments 3-5, the immunogenic composition of any one of Embodiments 6-10, the antigen of Embodiment 11, or the vaccine of any one of Embodiments 12-16 to the subject.

Embodiment 18. A method of protecting a subject in need thereof from infection with Severe Acute Respiratory Syndrome coronavirus 2 (SARS-CoV-2), the method comprising administering an effective amount of the nucleic acid molecule of Embodiment 1 or 2, the vector of any one of Embodiments 3-5, the immunogenic composition of any one of Embodiments 6-10, the antigen of Embodiment 11, or the vaccine of any one of Embodiments 12-16 to the subject.

Embodiment 19. A method of protecting a subject in need thereof from a disease or disorder associated with infection with Severe Acute Respiratory Syndrome coronavirus 2 (SARS-CoV-2), the method comprising administering an effective amount of the nucleic acid molecule of Embodiment 1 or 2, the vector of any one of Embodiments 3-5, the immunogenic composition of any one of Embodiments 6-10, the antigen of Embodiment 11, or the vaccine of any one of Embodiments 12-16 to the subject.

Embodiment 20. A method of treating a subject in need thereof against Severe Acute Respiratory Syndrome coronavirus 2 (SARS-CoV-2) infection, the method comprising administering an effective amount of the nucleic acid molecule of Embodiment 1 or 2, the vector of any one of Embodiments 3-5, the immunogenic composition of any one of Embodiments 6-10, the antigen of Embodiment 11, or the vaccine of any one of Embodiments 12-16 to the subject, wherein the subject is thereby resistant to one or more SARS-CoV-2 strains.

Embodiment 21. The method of any one of Embodiments 17 to 20, wherein administering comprises at least one of electroporation and injection.

Embodiment 22. The method of any one of Embodiments 17 to 20, wherein administering comprises parenteral administration followed by electroporation.

Embodiment 23. The method of any one of Embodiments 17 to 22, wherein an initial dose of about 0.5 mg to about 2.0 mg of nucleic acid is administered to the subject, optionally wherein the initial dose is 0.5 mg, 1.0 mg or 2.0 mg of nucleic acid.

Embodiment 24. The method of Embodiment 23, wherein a subsequent dose of about 0.5 mg to about 2.0 mg of nucleic acid is administered to the subject about four weeks after the initial dose, optionally wherein the subsequent dose is 0.5 mg, 1.0 mg or 2.0 mg of nucleic acid.

Embodiment 25. The method of Embodiment 24, wherein one or more further subsequent doses of about 0.5 mg to about 2.0 mg of nucleic acid is administered to the subject at least twelve weeks after the initial dose, optionally wherein the further subsequent dose is 0.5 mg, 1.0 mg, or 2.0 mg of nucleic acid.

Embodiment 26. The method of any one of Embodiments 17 to 25, comprising administering INO-4800 or a biosimilar thereof to the subject.

Embodiment 27. The method of any one of Embodiments 17 to 26, further comprising administering to the subject at least one additional agent for the treatment of SARS-CoV-2 infection or the treatment or prevention of a disease or disorder associated with SARS-CoV-2 infection.

Embodiment 28. The method of Embodiment 27 wherein the nucleic acid molecule, vector, the immunogenic composition, antigen, or vaccine is administered to the subject before, concurrently with, or after the additional agent.

Embodiment 29. Use of the nucleic acid molecule of Embodiment 1 or 2, the vector of any one of Embodiments 3-5, the immunogenic composition of any one of Embodiments 6-10, the antigen of Embodiment 11, or the vaccine of any one of Embodiments 12-16 in a method of inducing an immune response against Severe Acute Respiratory Syndrome coronavirus 2 (SARS-CoV-2) in a subject in need thereof.

Embodiment 30. Use of the nucleic acid molecule of Embodiment 1 or 2, the vector of any one of Embodiments 3-5, the immunogenic composition of any one of Embodiments 6-10, the antigen of Embodiment 11, or the vaccine of any one of Embodiments 12-16 in a method of protecting a subject from infection with Severe Acute Respiratory Syndrome coronavirus 2 (SARS-CoV-2).

Embodiment 31. Use of the nucleic acid molecule of Embodiment 1 or 2, the vector of any one of Embodiments 3-5, the immunogenic composition of any one of Embodiments 6-10, the antigen of Embodiment 11, or the vaccine of any one of Embodiments 12-16 in a method of protecting a subject from a disease or disorder associated with infection with Severe Acute Respiratory Syndrome coronavirus 2 (SARS-CoV-2).

Embodiment 32. Use of the nucleic acid molecule of Embodiment 1 or 2, the vector of any one of Embodiments 3-5, the immunogenic composition of any one of Embodiments 6-10, the antigen of Embodiment 11, or the vaccine of any one of Embodiments 12-16 in a method of treating a subject in need thereof against Severe Acute Respiratory Syndrome coronavirus 2 (SARS-CoV-2) infection.

Embodiment 33. The use of any one of Embodiments 29 to 32 in combination with at least one additional agent for the treatment of SARS-CoV-2 infection or the treatment or prevention of a disease or disorder associated with SARS-CoV-2 infection.

Embodiment 34. The use of any one of Embodiments 29 to 33, wherein the nucleic acid molecule, the vector, the immunogenic composition, the antigen, or the vaccine is administered to the subject by at least one of electroporation and injection.

Embodiment 35. The use of Embodiment 34, wherein the nucleic acid molecule, the vector, the immunogenic composition, the antigen, or the vaccine is administered to the subject by parenteral administration followed by electroporation.

Embodiment 36. The use of any one of Embodiments 29 to 35, wherein an initial dose of about 0.5 mg to about 2.0 mg of nucleic acid is administered to the subject, optionally wherein the initial dose is 0.5 mg, 1.0 mg, or 2.0 mg of nucleic acid.

Embodiment 37. The use of Embodiment 36, wherein a subsequent dose of about 0.5 mg to about 2.0 mg of nucleic acid is administered to the subject about four weeks after the initial dose, optionally wherein the subsequent dose is 0.5 mg, 1.0 mg, or 2.0 mg of nucleic acid.

Embodiment 38. The use of Embodiment 37, wherein a further subsequent dose of about 0.5 mg to about 2.0 mg of nucleic acid is administered to the subject at least twelve weeks after the initial dose, optionally wherein the further subsequent dose is 0.5 mg, 1.0 mg, or 2.0 mg of nucleic acid.

Embodiment 39. The use of any one of Embodiments 29 to 38, wherein the immunogenic composition is INO-4800 or a biosimilar thereof.

Embodiment 40. Use of the nucleic acid molecule of Embodiment 1 or 2, the vector of any one of Embodiments 3-5, or the antigen of Embodiment 11 in the preparation of a medicament.

Embodiment 41. Use of the nucleic acid molecule of Embodiment 1 or 2, the vector of any one of Embodiments 3-5, or the antigen of Embodiment 11 in the preparation of a medicament for treating or protecting against infection with Severe Acute Respiratory Syndrome coronavirus 2 (SARS-CoV-2).

Embodiment 42. Use of the nucleic acid molecule of Embodiment 1 or 2, the vector of any one of Embodiments 3-5, or the antigen of Embodiment 11 in the preparation of a medicament for protecting a subject in need thereof from a disease or disorder associated with infection with Severe Acute Respiratory Syndrome coronavirus 2 (SARS-CoV-2).

Embodiment 43. A method of detecting a persistent cellular immune response in a subject, the method comprising the steps of:
 administering an immunogenic composition for inducing an immune response against a SARS-CoV-2 antigen to a subject in need thereof;
 isolating peripheral mononuclear cells (PBMCs) from the subject;
 stimulating the isolated PBMCs with a SARS-CoV-2 spike antigen comprising an amino acid sequence selected from the group consisting of an amino acid sequence having at least about 90% identity over an entire length of residues 19 to 1279 of SEQ ID NO: 1, the amino acid sequence set forth in residues 19 to 1279 of SEQ ID NO: 1, an amino acid sequence having at least about 90% identity over an entire length of SEQ ID NO: 1, the amino acid sequence of SEQ ID NO: 1, an amino acid sequence having at least about 90% identity over an entire length of residues 19 to 1279 of SEQ ID NO: 4, an amino acid sequence having at least about 90% identity over an entire length of SEQ ID NO: 4, the amino acid sequence set forth in residues 19 to 1279 of SEQ ID NO: 4, the amino acid sequence of SEQ ID NO: 4., and a fragment thereof comprising at least 20 amino acids; and
 detecting at least one of the number of cytokine expressing cells and the level of cytokine expression.

Embodiment 44. The method of Embodiment 43, wherein the step of detecting at least one of the number of cytokine expressing cells and the level of cytokine expression is performed using an assay selected from the group consisting of Enzyme-linked immunospot (ELISpot) and Intracellular Cytokine Staining (ICS) analysis using flow cytometry.

Embodiment 45. The method of Embodiment 43, wherein the subject is administered an immunogenic composition comprising a nucleic acid molecule, wherein the nucleic acid molecule comprises a nucleotide sequence selected from the group consisting of:
 a nucleic acid sequence having at least about 90% identity over an entire length of the nucleic acid sequence set forth in nucleotides 55 to 3837 of SEQ ID NO: 2;
 a nucleic acid sequence having at least about 90% identity over an entire length of SEQ ID NO: 2;
 the nucleic acid sequence of nucleotides 55 to 3837 of SEQ ID NO: 2;
 the nucleic acid sequence of SEQ ID NO: 2;
 a nucleic acid sequence having at least about 90% identity over an entire length of SEQ ID NO: 3;

the nucleic acid sequence of SEQ ID NO: 3;
a nucleic acid sequence having at least about 90% identity over an entire length of nucleotides 55 to 3837 of SEQ ID NO: 5;
a nucleic acid sequence having at least about 90% identity over an entire length of SEQ ID NO: 5;

the nucleic acid sequence of nucleotides 55 to 3837 of SEQ ID NO: 5;
the nucleic acid sequence of SEQ ID NO: 5;
a nucleic acid sequence having at least about 90% identity over an entire length of SEQ ID NO: 6; and
the nucleic acid sequence of SEQ ID NO: 6.

```
SEQUENCE LISTING
SARS-CoV-2 Consensus Spike Antigen amino acid insert sequence of
pGX9501 (SEQ ID NO: 1) (IgE leader sequence underlined):
     1 MDWTWILFLV AAATRVHSSQ CVNLTTRTQL PPAYTNSFTR GVYYPDKVFR SSVLHSTQDL

61 FLPFFSNVTW FHAIHVSGTN GTKRFDNPVL PFNDGVYFAS TEKSNIIRGW IFGTTLDSKT

121 QSLLIVNNAT NVVIKVCEFQ FCNDPFLGVY YHKNNKSWME SEFRVYSSAN NCTFEYVSQP

181 FLMDLEGKQG NFKNLREFVF KNIDGYFKIY SKHTPINLVR DLPQGFSALE PLVDLPIGIN

241 ITRFQTLLAL HRSYLTPGDS SSGWTAGAAA YYVGYLQPRT FLLKYNENGT ITDAVDCALD

301 PLSETKCTLK SFTVEKGIYQ TSNFRVQPTE SIVRFPNITN LCPFGEVFNA TRFASVYAWN

361 RKRISNCVAD YSVLYNSASF STFKCYGVSP TKLNDLCFTN VYADSFVIRG DEVRQIAPGQ

421 TGKIADYNYK LPDDFTGCVI AWNSNNLDSK VGGNYNYLYR LFRKSNLKPF ERDISTEIYQ

481 AGSTPCNGVE GFNCYFPLQS YGFQPTNGVG YQPYRVVVLS FELLHAPATV CGPKKSTNLV

541 KNKCVNFNFN GLTGTGVLTE SNKKFLPFQQ FGRDIADTTD AVRDPQTLEI LDITPCSFGG

601 VSVITPGTNT SNQVAVLYQD VNCTEVPVAI HADQLTPTWR VYSTGSNVFQ TRAGCLIGAE

661 HVNNSYECDI PIGAGICASY QTQTNSPRRA RSVASQSIIA YTMSLGAENS VAYSNNSIAI

721 PTNFTISVTT EILPVSMTKT SVDCTMYICG DSTECSNLLL QYGSFCTQLN RALTGIAVEQ

781 DKNTQEVFAQ VKQIYKTPPI KDFGGFNFSQ ILPDPSKPSK RSFIEDLLFN KVTLADAGFI

841 KQYGDCLGDI AARDLICAQK FNGLTVLPPL LTDEMIAQYT SALLAGTITS GWTFGAGAAL

901 QIPFAMQMAY RFNGIGVTQN VLYENQKLIA NQFNSAIGKI QDSLSSTASA LGKLQDVVNQ

961 NAQALNTLVK QLSSNFGAIS SVLNDILSRL DKVEAEVQID RLITGRLQSL QTYVTQQLIR

1021 AAEIRASANL AATKMSECVL GQSKRVDFCG KGYHLMSFPQ SAPHGVVFLH VTYVPAQEKN

1081 FTTAPAICHD GKAHFPREGV FVSNGTHWFV TQRNFYEPQI ITTDNTFVSG NCDVVIGIVN

1141 NTVYDPLQPE LDSFKEELDK YFKNHTSPDV DLGDISGINA SVVNIQKEID RLNEVAKNLN

1201 ESLIDLQELG KYEQYIKWPW YIWLGFIAGL IAIVMVTIML CCMTSCCSCL KGCCSCGSCC

1261 KFDEDDSEPV LKGVKLHYT

DNA insert sequence of pGX9501 (SEQ ID NO: 2) (IgE leader sequence
underlined):
     1 ATGGATTGGA CTTGGATTCT CTTTCTCGTT GCTGCAGCCA CACGCGTTCA TAGCAGCCAG

61 TGTGTGAACC TGACCACCAG AACACAGCTG CCTCCTGCCT ACACCAACAG CTTCACCAGA

121 GGAGTCTACT ACCCAGACAA AGTCTTCAGA AGCTCTGTGC TGCACAGCAC CCAGGACCTG

181 TTCCTGCCTT TCTTCAGCAA CGTGACCTGG TTCCACGCCA TCCACGTGTC TGGCACCAAC

241 GGCACCAAGA GATTTGACAA CCCTGTTCTT CCTTTCAATG ATGGCGTGTA CTTTGCCAGC

301 ACAGAGAAGA GCAACATCAT CCGAGGCTGG ATCTTTGGCA CCACCCTGGA CAGCAAAACC

361 CAGAGCCTGC TGATCGTGAA CAACGCCACC AACGTGGTCA TCAAGGTGTG TGAGTTCCAG

421 TTCTGCAATG ACCCTTTCCT GGGCGTGTAC TACCACAAGA ACAACAAGTC CTGGATGGAG

481 TCTGAGTTCA GAGTCTACAG CTCTGCCAAC AACTGCACAT TTGAATATGT GTCCCAGCCT

541 TTCCTGATGG ACCTGGAGGG CAAGCAGGGC AACTTTAAGA ACCTGAGAGA ATTTGTGTTC

601 AAGAACATCG ATGGCTACTT CAAGATCTAC AGCAAGCACA CACCCATCAA CCTGGTGAGA
```

```
 661 GACCTGCCTC AGGGCTTCTC TGCCCTGGAG CCTCTGGTGG ACCTGCCCAT CGGCATCAAC

721 ATCACCAGAT TCCAGACCCT GCTGGCCCTG CACAGAAGCT ACCTGACCCC AGGAGACAGC

781 AGCAGCGGCT GGACAGCTGG AGCTGCTGCC TACTACGTGG GCTACCTGCA GCCCAGGACC

841 TTCCTGCTGA AGTACAACGA AAATGGCACC ATCACAGATG CTGTTGACTG TGCCCTGGAC

901 CCTCTTAGCG AGACCAAGTG CACCCTGAAG TCCTTCACAG TGGAGAAAGG CATCTACCAG

961 ACCAGCAACT TCCGAGTGCA GCCAACAGAG AGCATCGTGA GATTTCCAAA CATCACCAAC

1021 CTGTGCCCTT TTGGAGAAGT CTTCAATGCC ACCAGATTTG CTTCTGTGTA CGCCTGGAAC

1081 AGAAAAAGAA TCAGCAACTG TGTGGCTGAC TACTCTGTGC TGTACAACTC TGCCTCCTTC

1141 TCCACCTTCA AGTGCTATGG AGTCTCTCCA ACCAAGCTGA ATGACCTGTG CTTCACCAAC

1201 GTGTATGCTG ACAGCTTTGT GATCAGAGGA GATGAAGTGC GGCAGATTGC TCCTGGCCAG

1261 ACAGGCAAGA TTGCTGACTA CAACTACAAG CTGCCTGATG ACTTCACAGG CTGTGTCATC

1321 GCCTGGAACA GCAACAACCT GGACAGCAAG GTGGGCGGCA ACTACAACTA CCTGTACAGA

1381 CTTTTCAGGA AGAGCAACCT GAAGCCTTTT GAAAGAGACA TCTCCACAGA GATCTACCAG

1441 GCTGGCAGCA CACCCTGCAA TGGTGTGGAA GGCTTCAACT GCTACTTCCC TCTGCAGAGC

1501 TACGGCTTCC AGCCAACAAA TGGCGTGGGC TACCAGCCTT ACAGAGTGGT GGTGCTGTCC

1561 TTTGAGCTGC TGCACGCCCC TGCCACAGTG TGTGGCCCCA AGAAGAGCAC CAACCTGGTG

1621 AAGAACAAAT GTGTGAACTT CAATTTCAAT GGCCTGACAG GCACAGGAGT GCTGACAGAG

1681 AGCAACAAGA AGTTTCTTCC TTTCCAGCAG TTTGGAAGAG ACATTGCTGA CACCACAGAT

1741 GCTGTGAGAG ATCCTCAGAC CCTGGAGATC CTGGATATCA CACCCTGCTC CTTTGGAGGA

1801 GTTTCTGTCA TCACACCTGG CACCAATACC AGCAACCAAG TGGCTGTGCT GTACCAAGAT

1861 GTGAATTGCA CAGAAGTGCC TGTGGCCATC CACGCTGACC AGCTGACACC CACCTGGAGA

1921 GTGTACAGCA CAGGCAGCAA TGTTTTCCAG ACAAGAGCTG GCTGCCTGAT TGGAGCAGAG

1981 CACGTGAACA ACAGCTATGA ATGTGACATC CCTATTGGAG CTGGCATCTG TGCCAGCTAC

2041 CAGACCCAAA CCAACAGCCC AAGAAGAGCC AGATCTGTGG CCAGCCAGAG CATCATCGCC

2101 TACACCATGA GCCTGGGAGC TGAGAACTCT GTGGCCTACA GCAACAACAG CATCGCCATC

2161 CCCACCAACT TCACCATCTC TGTGACCACA GAGATCCTGC CTGTGTCCAT GACCAAGACA

2221 TCTGTGGACT GCACCATGTA CATCTGTGGA GACAGCACAG AATGCAGCAA CCTGCTGCTG

2281 CAGTACGGCT CCTTCTGCAC CCAGCTGAAC AGAGCCCTGA CAGGCATCGC TGTGGAGCAG

2341 GACAAGAACA CACAGGAAGT GTTTGCCCAG GTGAAGCAGA TCTACAAAAC ACCACCCATC

2401 AAGGACTTTG GAGGCTTCAA TTTCTCCCAA ATCCTGCCTG ACCCCAGCAA GCCTTCCAAG

2461 AGAAGCTTCA TTGAAGACCT GCTGTTCAAC AAAGTGACCC TGGCTGATGC TGGCTTCATC

2521 AAGCAGTATG GAGACTGCCT GGGAGACATT GCTGCCAGAG ACCTGATCTG TGCCCAGAAG

2581 TTTAATGGCC TGACTGTGCT GCCTCCTCTG CTGACAGATG AAATGATCGC CCAGTACACA

2641 TCTGCCCTGC TGGCTGGCAC CATCACCAGT GGCTGGACAT TTGGAGCTGG AGCTGCCCTG

2701 CAGATCCCTT TTGCCATGCA GATGGCCTAC AGATTTAATG GCATCGGCGT GACCCAGAAC

2761 GTGCTGTACG AGAACCAGAA GCTGATCGCC AACCAGTTCA ACTCTGCCAT CGGCAAGATC

2821 CAGGACAGCC TGAGCAGCAC AGCCTCTGCC CTGGGCAAGC TGCAGGATGT GGTGAACCAA

2881 AACGCCCAGG CCCTGAACAC CCTGGTGAAG CAGCTGAGCA GCAACTTTGG AGCCATCTCC

2941 TCTGTGCTGA ATGACATCCT GAGCCGGCTG GACAAGGTGG AAGCAGAAGT GCAGATCGAC

3001 AGACTCATCA CAGGCCGCCT GCAGAGCCTG CAGACCTACG TGACCCAGCA GCTGATCAGA
```

-continued

```
3061 GCTGCTGAGA TCCGGGCCTC TGCCAACCTG GCTGCCACCA GATGTCAGA ATGTGTGCTG

3121 GGCCAGAGCA AAAGAGTGGA CTTCTGTGGC AAAGGCTACC ACCTGATGTC CTTCCCTCAG

3181 TCTGCTCCTC ACGGCGTGGT GTTCCTGCAC GTGACCTACG TGCCTGCCCA GGAGAAGAAC

3241 TTCACCACAG CTCCTGCCAT CTGCCACGAT GGCAAGGCCC ACTTCCCAAG AGAAGGTGTC

3301 TTTGTGTCCA ATGGCACCCA CTGGTTCGTG ACCCAGAGAA ACTTCTACGA GCCTCAGATC

3361 ATCACCACAG ACAACACATT TGTGTCTGGC AACTGTGATG TGGTCATCGG CATCGTGAAC

3421 AACACAGTTT ATGACCCTCT GCAGCCTGAG CTGGACAGCT TCAAAGAAGA GCTGGACAAG

3481 TACTTCAAGA ACCACACATC TCCAGATGTG GACCTGGGAG ACATCTCTGG CATCAATGCC

3541 TCTGTGGTGA ACATCCAGAA GGAAATTGAC AGGCTGAACG AAGTGGCCAA GAACCTGAAC

3601 GAAAGCCTCA TCGACCTGCA GGAGCTGGGC AAGTACGAGC AGTACATCAA GTGGCCTTGG

3661 TACATCTGGC TGGGCTTCAT CGCTGGCCTC ATCGCCATCG TGATGGTGAC CATCATGCTG

3721 TGCTGCATGA CCAGCTGCTG CTCTTGCCTG AAGGGCTGCT GCAGCTGTGG CAGCTGCTGC

3781 AAGTTTGATG AAGATGACTC TGAGCCTGTG CTGAAGGGCG TGAAGCTGCA CTACACA
```

Single strand DNA sequence of pGX9501 (SEQ ID NO: 3):

```
   1 gctgcttcgc gatgtacggg ccagatatac gcgttgacat tgattattga ctagttatta 61 atagtaatca attacggggt cattagttca tagcccatat atggagttcc gcgttacata 121 acttacggta aatggcccgc ctggctgacc gcccaacgac ccccgcccat tgacgtcaat 181 aatgacgtat gttcccatag taacgccaat agggactttc cattgacgtc aatgggtgga 241 gtatttacgg taaactgccc acttggcagt acatcaagtg tatcatatgc caagtacgcc 301 ccctattgac gtcaatgacg gtaaatggcc cgcctggcat tatgcccagt acatgacctt 361 atgggacttt cctacttggc agtacatcta cgtattagtc atcgctatta ccatggtgat 421 gcggttttgg cagtacatca atgggcgtgg atagcggttt gactcacggg gatttccaag 481 tctccacccc attgacgtca atgggagttt gttttggcac caaaatcaac gggactttcc 541 aaaatgtcgt aacaactccg ccccattgac gcaaatgggc ggtaggcgtg tacggtggga 601 ggtctatata agcagagctc tctggctaac tagagaaccc actgcttact ggcttatcga 661 aattaatacg actcactata gggagaccca agctggctag cgtttaaact taagcttggt 721 accgagctcg gatccgccac catggattgg acttggattc tctttctcgt tgctgcagcc 781 acacgcgttc atagcagcca gtgtgtgaac ctgaccacca aacacagct gcctcctgcc 841 tacaccaaca gcttcaccag aggagtctac tacccagaca agtcttcag aagctctgtg 901 ctgcacagca cccaggacct gttcctgcct tcttcagca acgtgacctg gttccacgcc 961 atccacgtgt ctggcaccaa cggcaccaag agatttgaca accctgttct tcctttcaat 1021 gatggcgtgt actttgccag cacagagaag agcaacatca tccgaggctg gatctttggc 1081 accaccctgg acagcaaaac ccagagcctg ctgatcgtga caacgccac caacgtggtc 1141 atcaaggtgt gtgagttcca gttctgcaat gacccttttcc tgggcgtgta ctaccacaag 1201 aacaacaagt cctggatgga gtctgagttc agagtctaca gctctgccaa caactgcaca 1261 tttgaatatg tgtcccagcc tttcctgatg gacctggagg gcaagcaggg caactttaag 1321 aacctgagag aatttgtgtt caagaacatc gatggctact tcaagatcta cagcaagcac 1381 acacccatca acctggtgag agacctgcct caggcttct ctgccctgga gcctctggtg 1441 gacctgccca tcggcatcaa catcaccaga ttccagaccc tgctggccct gcacagaagc 1501 tacctgaccc caggagacag cagcagcggc tggacagctg gagctgctgc ctactacgtg 1561 ggctacctgc agcccaggac cttcctgctg aagtacaacg aaaatggcac catcacagat

```

-continued

```
1621 gctgttgact gtgccctgga ccctcttagc gagaccaagt gcaccctgaa gtccttcaca
1681 gtggagaaag gcatctacca gaccagcaac ttccgagtgc agccaacaga gagcatcgtg
1741 agatttccaa acatcaccaa cctgtgccct tttggagaag tcttcaatgc caccagattt
1801 gcttctgtgt acgcctggaa cagaaaaaga atcagcaact gtgtggctga ctactctgtg
1861 ctgtacaact ctgcctcctt ctccaccttc aagtgctatg gagtctctcc aaccaagctg
1921 aatgacctgt gcttcaccaa cgtgtatgct gacagctttg tgatcagagg agatgaagtg
1981 cggcagattg ctcctggcca gacaggcaag attgctgact acaactacaa gctgcctgat
2041 gacttcacag gctgtgtcat cgcctggaac agcaacaacc tggacagcaa ggtgggcggc
2101 aactacaact acctgtacag acttttcagg aagagcaacc tgaagccttt tgaaagagac
2161 atctccacag agatctacca ggctggcagc acaccctgca atggtgtgga aggcttcaac
2221 tgctacttcc ctctgcagag ctacggcttc cagccaacaa atggcgtggg ctaccagcct
2281 tacagagtgg tggtgctgtc ctttgagctg ctgcacgccc ctgccacagt gtgtggcccc
2341 aagaagagca ccaacctggt gaagaacaaa tgtgtgaact tcaatttcaa tggcctgaca
2401 ggcacaggag tgctgacaga gagcaacaag aagtttcttc ctttccagca gtttggaaga
2461 gacattgctg acaccacaga tgctgtgaga gatcctcaga ccctggagat cctggatatc
2521 acaccctgct cctttggagg agtttctgtc atcacacctg caccaatac cagcaaccaa
2581 gtggctgtgc tgtaccaaga tgtgaattgc acagaagtgc ctgtggccat ccacgctgac
2641 cagctgacac ccacctggag agtgtacagc acaggcagca atgtttttcca gacaagagct
2701 ggctgcctga ttggagcaga gcacgtgaac aacagctatg aatgtgacat ccctattgga
2761 gctggcatct gtgccagcta ccagacccaa accaacagcc aagaagagc cagatctgtg
2821 gccagccaga gcatcatcgc ctacaccatg agcctgggag ctgagaactc tgtggcctac
2881 agcaacaaca gcatcgccat ccccaccaac ttcaccatct ctgtgaccac agagatcctg
2941 cctgtgtcca tgaccaagac atctgtggac tgcaccatgt acatctgtgg agacagcaca
3001 gaatgcagca acctgctgct gcagtacggc tccttctgca cccagctgaa cagagccctg
3061 acaggcatcg ctgtggagca ggacaagaac acacaggaag tgtttgccca ggtgaagcag
3121 atctacaaaa caccacccat caaggacttt ggaggcttca atttctccca aatcctgcct
3181 gacccccagca agccttccaa gagaagcttc attgaagacc tgctgttcaa caaagtgacc
3241 ctggctgatg ctggcttcat caagcagtat ggagactgcc tgggagacat tgctgccaga
3301 gacctgatct gtgcccagaa gtttaatggc ctgactgtgc tgcctcctct gctgacagat
3361 gaaatgatcg cccagtacac atctgccctg ctggctggca ccatcaccag tggctggaca
3421 tttggagctg gagctgccct gcagatccct tttgccatgc agatggccta cagatttaat
3481 ggcatcggcg tgacccagaa cgtgctgtac gagaaccaga agctgatcgc caaccagttc
3541 aactctgcca tcggcaagat ccaggacagc ctgagcagca cagcctctgc cctgggcaag
3601 ctgcaggatg tggtgaacca aaacgcccag gccctgaaca ccctggtgaa gcagctgagc
3661 agcaactttg gagccatctc ctctgtgctg aatgacatcc tgagccggct ggacaaggtg
3721 gaagcagaag tgcagatcga cagactcatc acaggccgcc tgcagagcct gcagacctac
3781 gtgacccagc agctgatcag agctgctgag atccgggcct ctgccaacct ggctgccacc
3841 aagatgtcag aatgtgtgct gggccagagc aaaagagtgg acttctgtgg aaaggctac
3901 cacctgatgt ccttccctca gtctgctcct cacggcgtgg tgttcctgca cgtgacctac
3961 gtgcctgccc aggagaagaa cttcaccaca gctcctgcca tctgccacga tggcaaggcc
4021 cacttcccaa gagaaggtgt ctttgtgtcc aatggcaccc actggttcgt gacccagaga
```

-continued

```
4081 aacttctacg agcctcagat catcaccaca gacaacacat ttgtgtctgg caactgtgat
4141 gtggtcatcg gcatcgtgaa caacacagtt tatgaccctc tgcagcctga gctggacagc
4201 ttcaaagaag agctggacaa gtacttcaag aaccacacat ctccagatgt ggacctggga
4261 gacatctctg gcatcaatgc ctctgtggtg aacatccaga aggaaattga caggctgaac
4321 gaagtggcca agaacctgaa cgaaagcctc atcgacctgc aggagctggg caagtacgag
4381 cagtacatca agtggccttg gtacatctgg ctgggcttca tcgctggcct catcgccatc
4441 gtgatggtga ccatcatgct gtgctgcatg accagctgct gctcttgcct gaagggctgc
4501 tgcagctgtg gcagctgctg caagtttgat gaagatgact ctgagcctgt gctgaagggc
4561 gtgaagctgc actacacatg ataactcgag tctagagggc ccgtttaaac ccgctgatca
4621 gcctcgactg tgccttctag ttgccagcca tctgttgttt gcccctcccc cgtgccttcc
4681 ttgaccctgg aaggtgccac tcccactgtc ctttcctaat aaaatgagga aattgcatcg
4741 cattgtctga gtaggtgtca ttctattctg ggggtgggg tggggcagga cagcaagggg
4801 gaggattggg aagacaatag caggcatgct ggggatgcgg tgggctctat ggcttctact
4861 gggcggtttt atggacagca agcgaaccgg aattgccagc tggggcgccc tctggtaagg
4921 ttgggaagcc ctgcaaagta aactggatgg cttcttgcc gccaaggatc tgatggcgca
4981 ggggatcaag ctctgatcaa gagacaggat gaggatcgtt tcgcatgatt gaacaagatg
5041 gattgcacgc aggttctccg gccgcttggg tggagaggct attcggctat gactgggcac
5101 aacagacaat cggctgctct gatgccgccg tgttccggct gtcagcgcag ggcgcccgg
5161 ttcttttttgt caagaccgac ctgtccggtg ccctgaatga actgcaagac gaggcagcgc
5221 ggctatcgtg gctggccacg acgggcgttc cttgcgcagc tgtgctcgac gttgtcactg
5281 aagcgggaag ggactggctg ctattgggcg aagtgccggg gcaggatctc ctgtcatctc
5341 accttgctcc tgccgagaaa gtatccatca tggctgatgc aatgcggcgg ctgcatacgc
5401 ttgatccggc tacctgccca ttcgaccacc aagcgaaaca tcgcatcgag cgagcacgta
5461 ctcggatgga agccggtctt gtcgatcagg atgatctgga cgaagagcat caggggctcg
5521 cgccagccga actgttcgcc aggctcaagg cgagcatgcc cgacggcgag gatctcgtcg
5581 tgacccatgg cgatgcctgc ttgccgaata tcatggtgga aaatggccgc ttttctggat
5641 tcatcgactg tggccggctg ggtgtggcgg accgctatca ggacatagcg ttggctaccc
5701 gtgatattgc tgaagagctt ggcggcgaat gggctgaccg cttcctcgtg ctttacggta
5761 tcgccgctcc cgattcgcag cgcatcgcct ctatcgcct tcttgacgag ttcttctgaa
5821 ttattaacgc ttacaatttc ctgatgcggt attttctcct tacgcatctg tgcggtattt
5881 cacaccgcat caggtggcac ttttcgggga atgtgcgcg aacccctat ttgtttattt
5941 ttctaaatac attcaaatat gtatccgctc atgagacaat aaccctgata aatgcttcaa
6001 taatagcacg tgctaaaact tcattttaa tttaaaagga tctaggtgaa gatcctttt
6061 gataatctca tgaccaaaat cccttaacgt gagttttcgt tccactgagc gtcagacccc
6121 gtagaaaaga tcaaaggatc ttcttgagat cctttttttc tgcgcgtaat ctgctgcttg
6181 caaacaaaaa aaccaccgct accagcggtg gtttgtttgc cggatcaaga gctaccaact
6241 ctttttccga aggtaactgg cttcagcaga gcgcagatac caaatactgt tcttctagtg
6301 tagccgtagt taggccacca cttcaagaac tctgtagcac cgcctacata cctcgctctg
6361 ctaatcctgt taccagtggc tgctgccagt ggcgataagt cgtgtcttac cgggttggac
6421 tcaagacgat agttaccgga taaggcgcag cggtcgggct gaacggggg ttcgtgcaca
```

```
6481 cagcccagct tggagcgaac gacctacacc gaactgagat acctacagcg tgagctatga 6541 gaaagcgcca cgcttcccga agggagaaag gcggacaggt atccggtaag cggcagggtc 6601 ggaacaggag agcgcacgag ggagcttcca gggggaaacg cctggtatct ttatagtcct 6661 gtcgggtttc gccacctctg acttgagcgt cgattttgt gatgctcgtc agggggcgg 6721 agcctatgga aaaacgccag caacgcggcc tttttacggt tcctggcctt ttgctggcct 6781 tttgctcaca tgttctt
```

SARS-CoV-2 Outlier Spike Antigen amino acid insert sequence of pGX9503 (SEQ ID NO: 4) (IgE leader sequence underlined):

```
   1 MDWTWILFLV AAATRVHSSQ CVNLTTRTQL PPAYTNSFTR GVYYPDKVFR SSVLHSTQDL

61 FLPFFSNVTW FHAIHVSGTN GTKRFDNPVL PFNDGVYFAS TEKSNIIRGW IFGTTLDSKT

121 QSLLIVNNAT NVVIKVCEFQ FCNDPFLGVY YHKNNKSWME SEFRVYSSAN NCTFEYVSQP

181 FLMDLEGKQG NFKNLREFVF KNIDGYFKIY SKHTPINLVR DLPQGFSALE PLVDLPIGIN

241 ITRFQTLLAL HRSYLTPGDS SSGWTAGAAA YYVGYLQPRT FLLKYNENGT ITVAVACALD

301 PLSETKCTLK SFTVEKGIYQ TSNFRVQPTE SIVRFPNITN LCPFGEVFNA TRFASVYAWN

361 RKRISNCVAD YSVLYNSASF STFKCYGVSP TKLNDLCFTN VYADSFVIRG DEVRQIAPGQ

421 TGKIADYNYK LPDDFTGCVI AWNSNNLDSK VGGNYNYLYR LFRKSNLKPF ERDISTEIYQ

481 AGSTPCNGVE GFNCYFPLQS YGFQPTNGVG YQPYRVVVLS FELLHAPATV CGPKKSTNLV

541 KNKCVNFNFN GLTGTGVLTE SNKKFLPFQQ FGRDIADTTD AVRDPQTLEI LDITPCSFGG

601 VSVITPGANT SNQVTVLYQD VNCTEVPVAI HADQLTPTWR VYSTGSNVFK TRAGCLIGAE

661 HVNNSYECDI PIGAGICASY QTQTNSPRRA RSTASQSIIA YTMSLGAENS VAYSNNSIVI

721 PTNFTISVTT EILPVSMTKT SVDCTMYICS DSTECSNPLL QYGSFCTQLN RALTGIAVEQ

781 DKNTQEVFAQ VKQIYKTPPI KDFGGFNFSQ ILPDPSKPSK RSFIEDLLFN KVTLADAGFI

841 KQYGDCLGDI AARDLICAQK FNGLTVLPPL LTDEMIAQYT SALLAGTITS GWTFGAGAAL

901 QIPFAMQMAY RFNGIRVTQN VLYENQKLIA NQFNSAIGKI QDSLSSTASA LGKLQDVVNQ

961 NAQALNTLVK QLSSTFSTIS SVLNDILSRL DKVEAEVQID RLITGRLQSL QTYVTQQLIR

1021 AAEIRASANL KATKMSECVL GQSKRVDFCG KGYHLMSFPQ SAPHGVVFLH VTYVPAQEKN

1081 FTTAPATCHD GKAHFPREGV FVSNGTHWFV TQRNFDEPQI ITTDNTFVSG NCDVVIGIVN

1141 NTVYDPLQPE LDSFKEELDK YFKNHTSPDV DLGDISGINA SVVNIQKEID RLNEVAKNLN

1201 ESLIDLQELG KYEQYIKWPW YIWLGFIAGL IAIVMVTIML CCMTSCCSCL KGCCSCGSCC

1261 KFDEDDSEPV LKGVKLHYT
```

DNA insert sequence of pGX9503 (SEQ ID NO: 5) (IgE leader sequence underlined):

```
   1 ATGGATTGGA CCTGGATTCT TTTTCTCGTT GCAGCTGCTA CACGCGTTCA TAGCAGCCAG

61 TGTGTGAACC TGACCACCAG AACACAGCTG CCTCCTGCCT ACACCAACAG CTTCACCAGA

121 GGAGTCTACT ACCCAGACAA GGTGTTCAGA AGCTCTGTGC TGCACAGCAC CCAGGACCTC

181 TTCCTGCCTT TCTTCAGCAA CGTGACCTGG TTCCACGCCA TCCACGTGTC TGGCACCAAC

241 GGCACCAAGA GATTTGACAA CCCTGTGCTG CCTTTCAATG ATGGTGTGTA CTTTGCCAGC

301 ACAGAGAAGA GCAACATCAT CCGAGGCTGG ATCTTTGGCA CCACCCTGGA CAGCAAAACA

361 CAGAGCCTGC TGATCGTGAA TAATGCCACC AACGTGGTCA TCAAGGTGTG TGAGTTCCAG

421 TTCTGCAATG ACCCTTTCCT GGGCGTGTAC TACCACAAGA ACAACAAGTC CTGGATGGAG

481 TCTGAGTTCC GAGTGTACAG CTCTGCCAAC AACTGCACAT TTGAATATGT GTCCCAGCCT

541 TTCCTGATGG ACCTGGAGGG CAAGCAGGGC AATTTCAAGA ACCTGAGAGA ATTTGTGTTC

601 AAGAACATCG ATGGCTACTT CAAGATCTAC AGCAAGCACA CACCCATCAA CCTGGTGAGA
```

-continued

```
 661 GATCTTCCTC AGGGCTTCTC TGCCCTGGAG CCTCTGGTGG ACCTGCCCAT CGGCATCAAC
 721 ATCACCCGCT TTCAGACCCT GCTGGCCCTG CACAGAAGCT ACCTGACCCC AGGAGACAGC
 781 AGCAGCGGCT GGACAGCTGG AGCTGCTGCC TACTACGTGG GCTACCTGCA GCCAAGAACC
 841 TTCCTGCTGA AGTACAACGA AAATGGCACC ATCACTGTGG CTGTGGCCTG TGCCCTGGAC
 901 CCTCTTTCTG AGACCAAGTG CACCCTGAAG TCCTTCACAG TGGAGAAAGG CATCTACCAG
 961 ACCAGCAACT TCAGAGTTCA GCCAACAGAG AGCATCGTGA GATTTCCAAA CATCACCAAC
1021 CTGTGTCCTT TTGGAGAAGT CTTCAATGCC ACCAGATTTG CTTCTGTGTA CGCCTGGAAC
1081 AGAAAAAGAA TCAGCAACTG TGTGGCTGAC TACTCTGTGC TGTACAACTC TGCCTCCTTC
1141 TCCACCTTCA AGTGCTACGG TGTGTCTCCT ACCAAGCTGA ATGACCTGTG CTTCACCAAC
1201 GTGTATGCTG ACAGCTTTGT CATCAGAGGA GATGAAGTGC GGCAGATCGC CCCTGGCCAG
1261 ACAGGCAAGA TTGCTGACTA CAACTACAAG CTGCCTGATG ACTTCACAGG CTGTGTCATC
1321 GCCTGGAACA GCAACAACCT GGACAGCAAG GTGGGCGGCA ACTACAACTA CCTGTACAGA
1381 CTTTTCAGGA AGAGCAACCT GAAGCCTTTT GAAAGAGACA TCTCCACAGA GATCTACCAG
1441 GCTGGCAGCA CACCCTGCAA TGGAGTGGAA GGCTTCAACT GCTACTTCCC TCTGCAGAGC
1501 TACGGCTTCC AGCCCACCAA TGGCGTGGGC TACCAGCCTT ACAGAGTGGT GGTGCTGTCC
1561 TTTGAGCTGC TGCACGCCCC TGCCACAGTG TGTGGCCCCA AGAAGAGCAC CAACCTGGTG
1621 AAGAACAAAT GTGTGAACTT CAATTTCAAT GGCCTGACAG GCACAGGAGT GCTGACAGAG
1681 AGCAACAAGA AGTTCCTGCC TTTCCAGCAG TTTGGAAGAG ACATTGCTGA CACCACAGAT
1741 GCTGTGAGAG ATCCTCAGAC CCTGGAGATC CTGGACATCA CACCCTGCTC CTTTGGAGGA
1801 GTTTCTGTCA TCACACCTGG AGCCAACACC AGCAACCAAG TGACAGTGCT GTACCAAGAT
1861 GTGAACTGCA CAGAAGTTCC TGTGGCCATC CACGCTGACC AGCTGACCCC AACCTGGAGA
1921 GTCTACAGCA CAGGCAGCAA CGTGTTTAAA CAAGAGCTG GCTGCCTGAT TGGAGCAGAG
1981 CACGTGAACA ACAGCTATGA ATGTGACATC CCTATTGGAG CTGGCATCTG TGCCAGCTAC
2041 CAGACCCAAA CCAACAGCCC AAGAAGAGCC AGGAGCACAG CCAGCCAGAG CATCATCGCC
2101 TACACCATGA GCCTGGGAGC AGAGAACTCT GTGGCCTACA GCAACAACAG CATCGTCATC
2161 CCCACCAACT TCACCATCTC TGTGACCACA GAGATCCTGC CTGTGTCCAT GACCAAGACA
2221 TCTGTGGACT GCACCATGTA CATCTGCAGT GACAGCACAG AATGCAGCAA CCCTCTGCTG
2281 CAGTACGGCT CCTTCTGCAC CCAGCTGAAC AGAGCCCTGA CAGGCATCGC TGTGGAGCAG
2341 GACAAGAACA CACAGGAAGT GTTTGCCCAG GTGAAGCAGA TCTACAAAAC ACCACCCATC
2401 AAGGACTTTG GAGGCTTCAA CTTCTCCCAG ATCCTGCCTG ACCCCAGCAA GCCCAGCAAG
2461 AGAAGCTTCA TTGAAGACCT GCTGTTCAAC AAAGTGACCC TGGCTGATGC TGGCTTCATC
2521 AAACAATATG GAGACTGCCT GGGAGACATT GCTGCCAGAG ACCTGATCTG TGCCCAGAAG
2581 TTTAATGGCC TGACTGTGCT GCCTCCTCTG CTGACAGATG AAATGATCGC CCAGTACACA
2641 TCTGCCCTGC TGGCTGGCAC CATCACATCT GGCTGGACAT TTGGAGCTGG AGCTGCCCTG
2701 CAGATCCCTT TTGCCATGCA GATGGCCTAC AGATTTAATG GCATCAGAGT GACCCAGAAC
2761 GTGCTGTATG AAAACCAGAA GCTGATCGCC AACCAGTTCA ACTCTGCCAT CGGCAAGATC
2821 CAGGACAGCC TGAGCAGCAC AGCCTCTGCC CTGGGCAAGC TGCAGGATGT GGTGAACCAA
2881 AATGCCCAGG CCCTGAACAC CCTGGTGAAG CAGCTGAGCA GCAACTTCTC CACCATCTCC
2941 AGCGTGCTGA ATGACATCCT GAGCCGGCTG GACAAGGTGG AAGCTGAGGT GCAGATCGAC
3001 AGACTCATCA CAGGCCGGCT GCAGAGCCTG CAGACCTACG TGACCCAGCA GCTGATCAGA
```

-continued

```
3061 GCTGCTGAGA TCAGAGCTTC TGCCAACCTG AAGGCCACCA AGATGTCAGA ATGTGTGCTG

3121 GGCCAGAGCA AGAGAGTGGA CTTCTGTGGC AAAGGCTACC ACCTGATGTC CTTCCCTCAG

3181 TCTGCTCCTC ACGGCGTGGT GTTCCTGCAC GTGACCTACG TGCCTGCCCA GGAGAAGAAC

3241 TTCACCACAG CTCCTGCCAC CTGCCACGAT GGCAAAGCCC ACTTCCCAAG AGAAGGCGTC

3301 TTTGTGTCCA ATGGCACCCA CTGGTTCGTG ACCCAGAGAA ACTTTGATGA GCCTCAGATC

3361 ATCACCACAG ACAACACATT TGTTTCTGGC AACTGTGATG TGGTCATCGG CATCGTGAAC

3421 AACACAGTTT ATGACCCTCT GCAGCCTGAG CTGGACAGCT TCAAAGAAGA GCTGGACAAG

3481 TACTTCAAGA ACCACACATC TCCAGATGTG GACCTGGGAG ACATCTCTGG CATCAATGCC

3541 TCTGTGGTGA ACATCCAGAA GGAAATTGAC AGGCTGAACG AAGTGGCCAA GAACCTGAAC

3601 GAAAGCCTCA TCGACCTGCA GGAGCTGGGC AAGTACGAGC AGTACATCAA GTGGCCTTGG

3661 TACATCTGGC TGGGCTTCAT TGCTGGCCTC ATCGCCATCG TGATGGTGAC CATCATGCTG

3721 TGCTGCATGA CCAGCTGCTG CTCTTGCCTG AAGGGCTGCT GCAGCTGTGG CAGCTGCTGC

3781 AAGTTTGATG AAGATGACTC TGAGCCTGTG CTGAAGGGCG TGAAGCTGCA CTACACA
```
Single strand DNA sequence of pGX9503 (SEQ ID NO: 6):
```
   1 gctgcttcgc gatgtacggg ccagatatac gcgttgacat tgattattga ctagttatta 61 atagtaatca attacggggt cattagttca tagcccatat atggagttcc gcgttacata 121 acttacggta aatggcccgc ctggctgacc gcccaacgac ccccgcccat tgacgtcaat 181 aatgacgtat gttcccatag taacgccaat agggactttc cattgacgtc aatgggtgga 241 gtatttacgg taaactgccc acttggcagt acatcaagtg tatcatatgc caagtacgcc 301 ccctattgac gtcaatgacg gtaaatggcc cgcctggcat tatgcccagt acatgacctt 361 atgggacttt cctacttggc agtacatcta cgtattagtc atcgctatta ccatggtgat 421 gcggttttgg cagtacatca atgggcgtgg atagcggttt gactcacggg gatttccaag 481 tctccacccc attgacgtca atgggagttt gttttggcac caaaatcaac gggactttcc 541 aaaatgtcgt aacaactccg ccccattgac gcaaatgggc ggtaggcgtg tacggtggga 601 ggtctatata agcagagctc tctggctaac tagagaaccc actgcttact ggcttatcga 661 aattaatacg actcactata gggagaccca agctggctag cgtttaaact taagcttggt 721 accgagctcg gatccgccac catggattgg acctggattc ttttttctcgt tgcagctgct 781 acacgcgttc atagcagcca gtgtgtgaac ctgaccacca gaacacagct gcctcctgcc 841 tacaccaaca gcttcaccag aggagtctac tacccagaca aggtgttcag aagctctgtg 901 ctgcacagca cccaggacct cttcctgcct tcttcagca acgtgacctg gttccacgcc 961 atccacgtgt ctggcaccaa cggcaccaag agatttgaca accctgtgct gccttttcaat 1021 gatggtgtgt actttgccag cacagagaag agcaacatca tccgaggctg gatctttggc 1081 accaccctgg acagcaaaac acagagcctg ctgatcgtga ataatgccac caacgtggtc 1141 atcaaggtgt gtgagttcca gttctgcaat gaccctttcc tgggcgtgta ctaccacaag 1201 aacaacaagt cctggatgga gtctgagttc cgagtgtaca gctctgccaa caactgcaca 1261 tttgaatatg tgtcccagcc tttcctgatg gacctggagg gcaagcaggg caatttcaag 1321 aacctgagag aatttgtgtt caagaacatc gatggctact caagatcta cagcaagcac 1381 acacccatca acctggtgag agatcttcct cagggcttct ctgccctgga gcctctggtg 1441 gacctgccca tcggcatcaa catcacccgc tttcagaccc tgctggccct gcacagaagc 1501 tacctgaccc cagagacag cagcagcggc tggacagctg gagctgctgc ctactacgtg 1561 ggctacctgc agccaagaac cttcctgctg aagtacaacg aaaatggcac catcactgtg
```

-continued

```
1621 gctgtggcct gtgccctgga ccctctttct gagaccaagt gcaccctgaa gtccttcaca 1681 gtggagaaag gcatctacca gaccagcaac ttcagagttc agccaacaga gagcatcgtg 1741 agatttccaa acatcaccaa cctgtgtcct tttggagaag tcttcaatgc caccagattt 1801 gcttctgtgt acgcctggaa cagaaaaaga atcagcaact gtgtggctga ctactctgtg 1861 ctgtacaact ctgcctcctt ctccaccttc aagtgctacg gtgtgtctcc taccaagctg 1921 aatgacctgt gcttcaccaa cgtgtatgct gacagctttg tcatcagagg agatgaagtg 1981 cggcagatcg cccctggcca gacaggcaag attgctgact acaactacaa gctgcctgat 2041 gacttcacag gctgtgtcat cgcctggaac agcaacaacc tggacagcaa ggtgggcggc 2101 aactacaact acctgtacag acttttcagg aagagcaacc tgaagccttt tgaaagagac 2161 atctccacag agatctacca ggctggcagc acaccctgca atggagtgga aggcttcaac 2221 tgctacttcc ctctgcagag ctacggcttc cagcccacca tggcgtggg ctaccagcct 2281 tacagagtgg tggtgctgtc ctttgagctg ctgcacgccc ctgccacagt gtgtggcccc 2341 aagaagagca ccaacctggt gaagaacaaa tgtgtgaact tcaatttcaa tggcctgaca 2401 ggcacaggag tgctgacaga gagcaacaag aagttcctgc ctttccagca gtttggaaga 2461 gacattgctg acaccacaga tgctgtgaga gatcctcaga ccctggagat cctggacatc 2521 acaccctgct cctttggagg agtttctgtc atcacacctg gagccaacac cagcaaccaa 2581 gtgacagtgc tgtaccaaga tgtgaactgc acagaagttc ctgtggccat ccacgctgac 2641 cagctgaccc caacctggag agtctacagc acaggcagca acgtgtttaa acaagagct 2701 ggctgcctga ttggagcaga gcacgtgaac aacagctatg aatgtgacat ccctattgga 2761 gctggcatct gtgccagcta ccagacccaa accaacagcc aagaagagc caggagcaca 2821 gccagccaga gcatcatcgc ctacaccatg agcctgggag cagagaactc tgtggcctac 2881 agcaacaaca gcatcgtcat ccccaccaac ttcaccatct ctgtgaccac agagatcctg 2941 cctgtgtcca tgaccaagac atctgtggac tgcaccatgt acatctgcag tgacagcaca 3001 gaatgcagca accctctgct gcagtacggc tccttctgca cccagctgaa cagagccctg 3061 acaggcatcg ctgtggagca ggacaagaac acacaggaag tgtttgccca ggtgaagcag 3121 atctacaaaa caccacccat caaggacttt ggaggcttca acttctccca gatcctgcct 3181 gacccccagca agcccagcaa gagaagcttc attgaagacc tgctgttcaa caaagtgacc 3241 ctggctgatg ctggcttcat caaacaatat ggagactgcc tgggagacat tgctgccaga 3301 gacctgatct gtgcccagaa gtttaatggc ctgactgtgc tgcctcctct gctgacagat 3361 gaaatgatcg cccagtacac atctgccctg ctggctggca ccatcacatc tggctggaca 3421 tttggagctg gagctgccct gcagatccct tttgccatgc agatggccta cagatttaat 3481 ggcatcagag tgacccagaa cgtgctgtat gaaaaccaga agctgatcgc caaccagttc 3541 aactctgcca tcggcaagat ccaggacagc ctgagcagca cagcctctgc cctgggcaag 3601 ctgcaggatg tggtgaacca aaatgcccag gccctgaaca ccctggtgaa gcagctgagc 3661 agcacctcct ccaccatctc cagcgtgctg aatgacatcc tgagccggct ggacaaggtg 3721 gaagctgagg tgcagatcga cagactcatc acaggccggc tgcagagcct gcagacctac 3781 gtgacccagc agctgatcag agctgctgag atcagagctt ctgccaacct gaaggccacc 3841 aagatgtcag aatgtgtgct gggccagagc aagagagtgg acttctgtgg caagggctac 3901 cacctgatgt ccttccctca gtctgctcct cacggcgtgg tgttcctgca cgtgacctac 3961 gtgcctgcca aggagaagaa cttcaccaca gctcctgcca cctgccacga tggcaaagcc 4021 cacttcccaa gagaaggcgt ctttgtgtcc aatggcaccc actggttcgt gacccagaga
```

```
4081  aactttgatg agcctcagat catcaccaca gacaacacat ttgtttctgg caactgtgat
4141  gtggtcatcg gcatcgtgaa caacacagtt tatgaccctc tgcagcctga gctggacagc
4201  ttcaaagaag agctggacaa gtacttcaag aaccacacat ctccagatgt ggacctggga
4261  gacatctctg gcatcaatgc ctctgtggtg aacatccaga aggaaattga caggctgaac
4321  gaagtggcca agaacctgaa cgaaagcctc atcgacctgc aggagctggg caagtacgag
4381  cagtacatca agtggcttg gtacatctgg ctgggcttca ttgctggcct catcgccatc
4441  gtgatggtga ccatcatgct gtgctgcatg accagctgct gctcttgcct gaagggctgc
4501  tgcagctgtg gcagctgctg caagtttgat gaagatgact ctgagcctgt gctgaagggc
4561  gtgaagctgc actacacatg ataactcgag tctagagggc ccgtttaaac ccgctgatca
4621  gcctcgactg tgccttctag ttgccagcca tctgttgttt gccctcccc cgtgccttcc
4681  ttgaccctgg aaggtgccac tcccactgtc ctttcctaat aaaatgagga aattgcatcg
4741  cattgtctga gtaggtgtca ttctattctg ggggtgggg tggggcagga cagcaagggg
4801  gaggattggg aagacaatag caggcatgct ggggatgcgg tgggctctat ggcttctact
4861  gggcggtttt atggacagca agcgaaccgg aattgccagc tggggcgccc tctggtaagg
4921  ttgggaagcc ctgcaaagta aactggatgg ctttcttgcc gccaaggatc tgatggcgca
4981  ggggatcaag ctctgatcaa gagacaggat gaggatcgtt tcgcatgatt gaacaagatg
5041  gattgcacgc aggttctccg gccgcttggg tggagaggct attcggctat gactgggcac
5101  aacagacaat cggctgctct gatgccgccg tgttccggct gtcagcgcag gggcgcccgg
5161  ttcttttgt caagaccgac ctgtccggtg ccctgaatga actgcaagac gaggcagcgc
5221  ggctatcgtg gctggccacg acgggcgttc cttgcgcagc tgtgctcgac gttgtcactg
5281  aagcgggaag ggactggctg ctattgggcg aagtgccggg gcaggatctc ctgtcatctc
5341  accttgctcc tgccgagaaa gtatccatca tggctgatgc aatgcggcgg ctgcatacgc
5401  ttgatccggc tacctgccca ttcgaccacc aagcgaaaca tcgcatcgag cgagcacgta
5461  ctcggatgga agccggtctt gtcgatcagg atgatctgga cgaagagcat caggggctcg
5521  cgccagccga actgttcgcc aggctcaagg cgagcatgcc cgacggcgag gatctcgtcg
5581  tgacccatgg cgatgcctgc ttgccgaata tcatggtgga aaatggccgc ttttctggat
5641  tcatcgactg tggccggctg ggtgtggcgg accgctatca ggacatagcg ttggctaccc
5701  gtgatattgc tgaagagctt ggcggcgaat gggctgaccg cttcctcgtg ctttacggta
5761  tcgccgctcc cgattcgcag cgcatcgcct ctatcgcct tcttgacgag ttcttctgaa
5821  ttattaacgc ttacaatttc ctgatgcggt attttctcct tacgcatctg tgcggtattt
5881  cacaccgcat caggtggcac ttttcgggga atgtgcgcg gaacccctat tgtttattt
5941  ttctaaatac attcaaatat gtatccgctc atgagacaat aaccctgata aatgcttcaa
6001  taatagcacg tgctaaaact tcatttttaa tttaaaagga tctaggtgaa gatcctttt
6061  gataatctca tgaccaaaat cccttaacgt gagttttcgt tccactgagc gtcagacccc
6121  gtagaaaaga tcaaaggatc ttcttgagat cctttttttc tgcgcgtaat ctgctgcttg
6181  caaacaaaaa aaccaccgct accagcggtg gtttgtttgc cggatcaaga gctaccaact
6241  ctttttccga aggtaactgg cttcagcaga gcgcagatac caaatactgt tcttctagtg
6301  tagccgtagt taggccacca cttcaagaac tctgtagcac cgcctacata cctcgctctg
6361  ctaatcctgt taccagtggc tgctgccagt ggcgataagt cgtgtcttac cgggttggac
6421  tcaagacgat agttaccgga taaggcgcag cggtcgggct gaacgggggg ttcgtgcaca
```

-continued

```
6481 cagcccagct tggagcgaac gacctacacc gaactgagat acctacagcg tgagctatga 6541 gaaagcgcca cgcttcccga agggagaaag gcggacaggt atccggtaag cggcagggtc 6601 ggaacaggag agcgcacgag ggagcttcca gggggaaacg cctggtatct ttatagtcct 6661 gtcgggtttc gccacctctg acttgagcgt cgattttgt gatgctcgtc agggggcgg 6721 agcctatgga aaaacgccag caacgcggcc tttttacggt tcctggcctt tgctggcct 6781 tttgctcaca tgttctt
```

SEQ ID NO: 7 pGX9501 Forward primer
CAGGACAAGAACACACAGGAA

SEQ ID NO: 8 pGX9501 Reverse primer
CAGGCAGGATTTGGGAGAAA

SEQ ID NO: 9 pGX9501 Probe
ACCCATCAAGGACTTTGGAGG

SEQ ID NO: 10 pGX9503 Forward primer
AGGACAAGAACACACAGGAAG;

SEQ ID NO: 11 pGX9503 Reverse primer
CAGGATCTGGGAGAAGTTGAAG

SEQ ID NO: 12 pGX9503 Probe
ACACCACCCATCAAGGACTTTGGA

SEQ ID NO: 13 β-actin Forward primer
GTGACGTGGACATCCGTAAA

SEQ ID NO: 14 β-actin Reverse primer
CAGGGCAGTAATCTCCTTCTG

SEQ ID NO: 15 β-actin Probe
TACCCTGGCATTGCTGACAGGATG

SEQ ID NO: 16
PHGVVFLHV

SEQ ID NO: 17
VVFLHVTVYV

SEQ ID NO: 18: 2019-nCoV_N1-F
5'-GACCCCAAAATCAGCGAAAT-3'

SEQ ID NO: 19: 2019-nCoV_N1-R
5'-TCTGGTTACTGCCAGTTGAATCTG-3'

SEQ ID NO: 20: 2019-nCoV_N1-P
5'-FAM-ACCCCGCATTACGTTTGGTGGACC-BHQ1-3'

SEQ ID NO: 21: 2019-nCoV_sgE-forward
5' CGATCTCTTGTAGATCTGTTCTC 3'

SEQ ID NO: 22: 2019-nCoV_sgE-reverse
5' ATATTGCAGCAGTACGCACACA 3'

SEQ ID NO: 23: 2019-nCoV_sgE-probe
5' FAM- ACACTAGCCATCCTTACTGCGCTTCG-BHQ1 3'

---

What is claimed:

1. A nucleic acid molecule encoding a Severe Acute Respiratory Syndrome coronavirus 2 (SARS-CoV-2) spike antigen, the nucleic acid molecule comprising:
a nucleic acid sequence having at least 99% identity to the nucleic acid sequence set forth from nucleotide 55 to nucleotide 3837 of SEQ ID NO: 2;
the nucleic acid sequence from nucleotide 55 to nucleotide 3837 of SEQ ID NO: 2; or
the nucleic acid sequence of SEQ ID NO: 2.

2. An expression vector comprising a nucleic acid molecule encoding a Severe Acute Respiratory Syndrome coronavirus 2 (SARS-CoV-2) spike antigen, the nucleic acid molecule comprising:
a nucleic acid sequence having at least 99% identity to the nucleic acid sequence set forth from nucleotide 55 to nucleotide 3837 of SEQ ID NO: 2;
the nucleic acid sequence from nucleotide 55 to nucleotide 3837 of SEQ ID NO: 2; or
the nucleic acid sequence of SEQ ID NO: 2.

3. An immunogenic composition comprising an effective amount of an expression vector and a pharmaceutically acceptable excipient, wherein the expression vector comprises a nucleic acid molecule encoding a Severe Acute Respiratory Syndrome coronavirus 2 (SARS-CoV-2) spike antigen, the nucleic acid molecule comprising:
a nucleic acid sequence having at least 99% identity to the nucleic acid sequence set forth from nucleotide 55 to nucleotide 3837 of SEQ ID NO: 2;
the nucleic acid sequence from nucleotide 55 to nucleotide 3837 of SEQ ID NO: 2; or
the nucleic acid sequence of SEQ ID NO: 2.

4. The immunogenic composition according to claim 3, wherein the pharmaceutically acceptable excipient comprises a buffer.

5. The immunogenic composition according to claim 4, wherein the buffer is saline-sodium citrate buffer.

6. The immunogenic composition of claim 5, wherein the composition comprises 10 mg of the vector per milliliter of saline-sodium citrate buffer.

7. The immunogenic composition according to claim 3, further comprising an adjuvant.

8. A method of inducing an immune response against Severe Acute Respiratory Syndrome coronavirus 2 (SARS-CoV-2) in a subject in need thereof, the method comprising administering an effective amount of the immunogenic composition of claim 3.

9. The method of claim 8, wherein administering comprises at least one of electroporation and parenteral administration.

10. The method of claim 9, wherein administering comprises parenteral administration followed by electroporation.

11. The method of claim 9, wherein the parenteral administration is subcutaneous administration, intradermal administration, or intramuscular administration.

12. The method of claim 8, wherein an initial dose of about 0.5 mg to about 2.0 mg of the vector is administered to the subject, optionally wherein the initial dose is 0.5 mg, 1.0 mg or 2.0 mg of the vector.

13. The method of claim 12, wherein a subsequent dose of about 0.5 mg to about 2.0 mg of the vector is administered to the subject about four weeks after the initial dose, optionally wherein the subsequent dose is 0.5 mg, 1.0 mg or 2.0 mg of the vector.

14. The method of claim 13, wherein one or more further subsequent doses of about 0.5 mg to about 2.0 mg of the vector is administered to the subject at least twelve weeks after the initial dose, optionally wherein the further subsequent dose is 0.5 mg, 1.0 mg, or 2.0 mg of the vector.

15. The method of claim 8, wherein the immunogenic composition is INO-4800 or a biosimilar thereof.

16. The method of claim 8, further comprising administering to the subject at least one additional agent for the treatment of SARS-CoV-2 infection or the treatment or prevention of a disease or disorder associated with SARS-CoV-2 infection.

17. The method of claim 16, wherein the immunogenic composition is administered to the subject before, concurrently with, or after the additional agent.

18. The method of claim 8, wherein the subject is thereby treated or protected against one or more SARS-CoV-2 strains.

19. The method of claim 8, wherein the subject is thereby treated or protected against a disease or disorder associated with SARS-CoV-2 infection.

20. The method of claim 19, wherein the disease or disorder associated with SARS-CoV-2 infection is Coronavirus Disease 2019 (COVID-19), Multisystem inflammatory syndrome in adults (MIS-A), or Multisystem inflammatory syndrome in children (MIS-C).

21. The expression vector of claim 2, wherein the vector comprises the nucleic acid sequence of SEQ ID NO: 3.

* * * * *